(12) United States Patent
Atkinson et al.

(10) Patent No.: US 10,583,112 B2
(45) Date of Patent: Mar. 10, 2020

(54) BENZO[B]FURANS AS BROMODOMAIN INHIBITORS

(71) Applicant: GlaxoSmithKline Intellectual Property (No. 2) Limited, Brentford, Middlesex (GB)

(72) Inventors: Stephen John Atkinson, Stevenage (GB); Emmanuel Hubert Demont, Stevenage (GB); Lee Andrew Harrison, Stevenage (GB); Alexander G. Preston, Stevenage (GB); Jonathan Thomas Seal, Stevenage (GB); Ian David Wall, Stevenage (GB); Robert J. Watson, Stevenage (GB); James Michael Woolven, Stevenage (GB)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 16/091,577

(22) PCT Filed: Apr. 5, 2017

(86) PCT No.: PCT/EP2017/058049
§ 371 (c)(1),
(2) Date: Oct. 5, 2018

(87) PCT Pub. No.: WO2017/174620
PCT Pub. Date: Oct. 12, 2017

(65) Prior Publication Data
US 2019/0151279 A1 May 23, 2019

(30) Foreign Application Priority Data
Apr. 7, 2016 (GB) .................................. 1605921.4
Mar. 1, 2017 (GB) .................................. 1703272.3

(51) Int. Cl.
*A61K 31/343* (2006.01)
*A61P 37/00* (2006.01)
*A61P 31/12* (2006.01)
*A61P 19/02* (2006.01)
*A61P 31/04* (2006.01)
*A61P 31/10* (2006.01)
*A61P 35/00* (2006.01)

(52) U.S. Cl.
CPC ............ *A61K 31/343* (2013.01); *A61P 19/02* (2018.01); *A61P 31/04* (2018.01); *A61P 31/10* (2018.01); *A61P 31/12* (2018.01); *A61P 35/00* (2018.01); *A61P 37/00* (2018.01)

(58) Field of Classification Search
CPC .................................................... A61K 31/343
USPC .......................................................... 549/467
See application file for complete search history.

(56) References Cited

FOREIGN PATENT DOCUMENTS

CN 105 085 427 A 11/2015
WO WO 2014/140077 A1 9/2014

*Primary Examiner* — Taofiq A Solola
(74) *Attorney, Agent, or Firm* — Jane F. Djung; Duke M. Fitch; Edward R. Gimmi

(57) ABSTRACT

The present invention relates to compounds of formula (I) and salts thereof, pharmaceutical compositions containing such compounds and to their use in therapy.

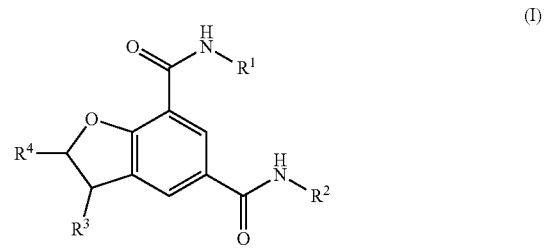

22 Claims, No Drawings

BENZO[B]FURANS AS BROMODOMAIN INHIBITORS

This application is a 371 of International Application No. PCT/EP2017/058049, filed Apr. 5, 2017, which claims the priority of GB Application No. 1605921.4, filed Apr. 7, 2016 and GB Application No. 1703272.3, filed Mar. 1, 2017, which are incorporated herein in their entireties.

FIELD OF THE INVENTION

The present invention is directed to certain compounds which are bromodomain inhibitors, processes for their preparation, pharmaceutical compositions comprising the compounds and the use of the compounds or the compositions in the treatment of various diseases or conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine residues commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem*, 2011, 54, 3827-3838).

Chan et al. report that BET bromodomain inhibition suppresses transcriptional responses to cytokine-Jak-STAT signalling in a gene-specific manner in human monocytes, which suggests that BET inhibition reduces inflammation partially through suppression of cytokine activity. (Chan et al., *Eur. J. Immunol.*, 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., *Ann. Rheum. Dis.*, 2014, 0:1-8).

Park-Min et al. report that I-BET151 that targets bromo and extra-terminal (BET) proteins that 'read' chromatin states by binding to acetylated histones, strongly suppresses osteoclastogenesis. (Park-Min et al. *Nature Communications*, 2014, 5, 5418).

SUMMARY OF THE INVENTION

The invention is directed to compounds of formula (I)

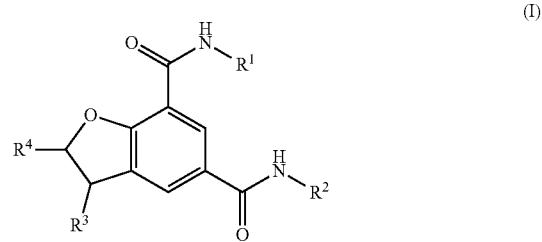

or a salt thereof
wherein:
$R^1$ is —$C_{1-3}$alkyl or cyclopropyl;
$R^2$ is —$C_{0-3}$alkyl-cycloalkyl, wherein the cycloalkyl group is optionally substituted with one, two or three $R^5$ groups which may be the same or different;
$R^2$ is —$C_{0-4}$alkyl-heterocyclyl or —$(CH_2)_pO$-heterocyclyl wherein each heterocyclyl is optionally substituted by one or two $R^9$ groups which may be the same or different; or
$R^2$ is H, —$CH_3$, $C_{2-6}$alkyl optionally substituted by up to five fluoro, —$C_{2-6}$alkylOR$^{13}$, —$C_{2-6}$alkylNR$^{11}$R$^{12}$, —$(CH_2)_mSO_2C_{1-3}$alkyl, —$(CH_2)_mSO_2NR^{11}R^{12}$, —$(CH_2)_mC(O)NR^{11}R^{12}$, —$(CH_2)_mCN$, —$(CH_2)_mCO_2R^{13}$, —$(CH_2)_mNHCO_2C_{1-4}$alkyl —$(CH_2)_mNHC(O)C_{1-4}$alkyl or —$(CH_2)_n$heteroaryl wherein heteroaryl is optionally substituted by one or two $R^{14}$ groups which may be the same or different;
$R^3$ is phenyl optionally substituted with one, two or three $R^7$ groups which may be the same or different;
$R^4$ is —$C_{1-3}$alkyl, —$CH_2OR^6$ or —$CH_2F$;
each $R^5$ is independently halo, —$C_{0-6}$alkyl-$R^8$, —O—$C_{2-6}$alkyl-$R^8$, —CN or —$SO_2C_{1-3}$alkyl;
$R^6$ is —H or $C_{1-3}$alkyl;
each $R^7$ is independently -halo, —$C_{1-4}$alkyl, —$C_{0-3}$alkyl-OR$^{10}$, —$C_{0-3}$alkyl-NR$^{15}$R$^{16}$, —$C_{0-3}$alkyl-CONR$^{15}$R$^{16}$, CN or —$SO_2R^{17}$;
$R^8$ is —H, —OR$^{10a}$, —NR$^{18}$R$^{19}$ or heteroaryl;
each $R^9$ is independently halo, $C_{1-4}$alkyl, cyclopropyl, cyclobutyl, —$CH_2CF_3$, —$CH_2CHF_2$, —$CH_2CH_2F$, —$OCH_2CH_2OR^{13}$, —$C_{0-3}$alkylOR$^{13}$, —$C_{0-3}$alkylNR$^{11}$R$^{12}$, —$NHCH_2CH_2OR^{13}$, —$NHCO_2R^{13}$, oxo, —$C(O)R^{13}$, —$C(O)OR^{13}$ or —$C(O)NR^{11}R^{12}$;

$R^{10a}$ is —H, —$C_{1-3}$alkyl, —$C_{2-3}$alkylNR$^{11}$R$^{12}$ or —$C_{2-3}$alkylOH;

$R^{10}$ is —H, —$C_{1-3}$alkyl, —$C_{2-3}$alkylNR$^{15}$R$^{16}$ or —$C_{2-3}$alkylOH;

$R^{11}$ and $R^{12}$ are each independently selected from —H and —$C_{1-3}$alkyl; or $R^{11}$ and $R^{12}$ may join together with the nitrogen to which they are attached, to form a 4 to 7-membered heterocyclyl group optionally substituted by one or two substituents independently selected from —$C_{1-3}$alkyl, —OH and F;

$R^{13}$ is —H or $C_{1-4}$alkyl;

each $R^{14}$ is independently halo, $C_{1-4}$alkyl, cyclopropyl, cyclobutyl or —OR$^{13}$;

$R^{15}$ and $R^{16}$ are each independently selected from —H and —$C_{1-3}$alkyl; or $R^{15}$ and $R^{16}$ may join together with the nitrogen to which they are attached, to form a 4 to 7-membered heterocyclyl group optionally substituted by one or two substituents independently selected from —$C_{1-3}$alkyl, —OH and F;

$R^{17}$ is —$C_{1-3}$alkyl or —NR$^{15}$R$^{16}$;

$R^{18}$ and $R^{19}$ are each independently selected from —H, —C(O)OC(CH$_3$)$_3$, —$C_{1-6}$alkyl, cycloalkyl, heterocyclyl, —$C_{2-3}$alkylNR$^{13}$COC$_{1-3}$alkyl, $C_{2-3}$alkylNR$^{15}$R$^{16}$ and —$C_{2-3}$alkyl-O—$C_{1-3}$alkyl wherein the —$C_{1-6}$alkyl and cycloalkyl may be optionally substituted by one, two or three fluoro; or $R^{18}$ and $R^{19}$ may join together with the nitrogen to which they are attached, to form a 4 to 7-membered heterocyclyl group optionally substituted by one or two substituents independently selected from —$C_{1-3}$alkyl, —OH and F;

m is an integer selected from 2, 3 and 4;

p is an integer selected from 2, 3 and 4;

n is an integer selected from 0, 1, 2, 3 and 4.

Compounds of the invention have been shown to be bromodomain inhibitors, in particular BD2 selective and may be useful in the treatment of various diseases or conditions, for example acute or chronic auto-immune and/or inflammatory conditions, for example rheumatoid arthritis and cancer. Accordingly, the invention is further directed to pharmaceutical compositions comprising a compound of formula (I), or a pharmaceutically acceptable salt thereof. The invention is still further directed to methods of treatment of diseases or conditions associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

Compounds of formula (I) and salts thereof are referred to herein as "compounds of the invention".

"BD2" refers to Binding Domain 2 of any of the the BET family of proteins BRD2, BRD3, BRD4 or BRDT.

"Alkyl" refers to a saturated hydrocarbon chain having the specified number of carbon atoms. For example, the term "$C_{1-6}$alkyl" as used herein refers to a straight or branched alkyl group having from 1 to 6 carbon atoms, for example 1 to 3 carbon atoms. For example the term "$C_{0-3}$alkyl" refers to a straight or branched alkyl group having from 0 (i.e. is absent) to 3 carbon atoms, for example 0 to 2 carbon atoms. Representative branched alkyl groups have one, two or three branches. An alkyl group may form part of a chain, for example, —$C_{0-4}$alkyl-heterocyclyl refers to a straight or branched alkyl chain having from 0 (i.e. absent) to 4 carbon atoms linked to a heterocyclyl. "Alkyl" includes, but is not limited to, methyl, ethyl, n-propyl, n-butyl, iso-butyl, iso-propyl, t-butyl, pentyl and hexyl.

"Cycloalkyl" refers to a saturated hydrocarbon mono or bicyclic ring or a saturated spiro-linked bicyclic hydrocarbon ring, having 3, 4, 5, 6 or 7 member atoms in the ring. Examples of cycloalkyl groups include, but are not limited to, cyclopropyl, cyclobutyl, cyclopentyl, cyclohexyl, cycloheptanyl and spiro[3.3]heptanyl.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, "enantiomerically enriched" refers to products whose enantiomeric excess is greater than 50% ee, greater than 75% ee, and greater than 90% ee.

"Enantiomerically pure" as used herein refers to products whose enantiomeric excess is 99% or greater.

"Half-life" (or "half-lives") refers to the time required for half of a quantity of a substance to be converted to another chemically distinct species in vitro or in vivo.

"Halo" refers to a halogen radical, for example, fluoro, chloro, bromo, or iodo.

"Heteroaryl" refers to a monocyclic or bicyclic group having 5 or 6 member atoms, including 1, 2 or 3 heteroatoms independently selected from nitrogen, sulphur and oxygen, wherein at least a portion of the group is aromatic. The point of attachment to the rest of the molecule may be by any suitable carbon or nitrogen atom. Examples of "heteroaryl" groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl and triazinyl.

"Heteroatom" refers to a nitrogen, sulfur, or oxygen atom.

"Heterocyclyl" refers to a non-aromatic heterocyclic monocyclic or bicyclic ring system containing 4, 5, 6, 7, 8, 9 or 10 ring member atoms, including one heteroatom and optionally containing a further heteroatom selected from nitrogen, oxygen or sulphur. Examples of "heterocyclyl" groups include, but are not limited to, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, homopiperazinyl, tetra hydropyranyl, dihydropyranyl, tetra hydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, hexahydro-1H-1,4-diazepinyl, azabicylo[3.2.1]octyl, azabicylo[3.3.1]nonyl, azabicylo[4.3.0]nonyl, oxabicylo[2.2.1]heptyl, 1,1-dioxidotetrahydro-2H-thiopyranyl, 1,5,9-triazacyclododecyl, 3-oxabicyclo[3.1.0]hexanyl, 3-azabicyclo[3.1.0]hexanyl, (1r,5s)-3-oxabicyclo[3.1.0]hexanyl and (1r,5s)-3-azabicyclo[3.1.0]hexanyl. "4 to 7-membered heterocyclyl" refers to a non-aromatic heterocyclic monocyclic or bicyclic ring system containing 4, 5, 6 or 7 ring member atoms, including one heteroatom and optionally containing a further heteroatom selected from nitrogen, oxygen or sulphur.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically acceptable e.g. of sufficiently high purity.

"rac" refers to the racemic mixture of the compounds of formula (I).

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds according to formula (I) contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or trans as drawn in the structure. Resolved single enantiomers with unknown absolute stereochemistry but known relative stereochemistry are referred to with (R* or S*) with the appropriate relative stereochemistry depicted.

Where diastereoisomers are represented and only the relative stereochemistry is referred to, the bold or hashed solid bond symbols (—/⸺) are used. Where the absolute stereochemistry is known and the compound is a single enantiomer, the bold or hashed wedges symbols (—/⸺) are used as appropriate.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that included within the scope of the invention are solvates, isomers and polymorphic forms of the compounds of formula (I) and salts thereof.

The present invention also includes isotopically-labeled compounds or a pharmaceutically acceptable salt thereof, which are identical to those recited in Formula (I) above, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulfur, fluorine, chlorine, and iodine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

STATEMENT OF THE INVENTION

In a first aspect there are provided compounds of formula (I):

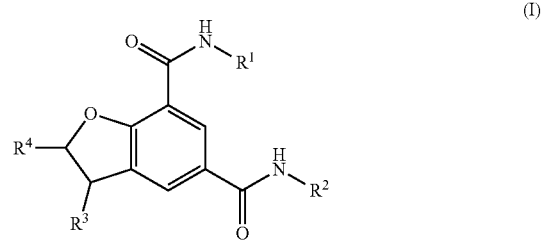

(I)

or a salt thereof
wherein:
$R^1$ is —$C_{1-3}$alkyl or cyclopropyl;
$R^2$ is —$C_{0-3}$alkyl-cycloalkyl, wherein the cycloalkyl group is optionally substituted with one, two or three $R^5$ groups which may be the same or different;
$R^2$ is —$C_{0-4}$alkyl-heterocyclyl or —$(CH_2)_pO$-heterocyclyl wherein each heterocyclyl is optionally substituted by one or two $R^9$ groups which may be the same or different; or
$R^2$ is H, —$CH_3$, $C_{2-6}$alkyl optionally substituted by up to five fluoro, —$C_{2-6}$alkylOR$^{13}$, —$C_{2-6}$alkylNR$^{11}$R$^{12}$; —$(CH_2)_mSO_2C_{1-3}$alkyl, —$(CH_2)_mSO_2NR^{11}R^{12}$, —$(CH_2)_mC(O)NR^{11}R^{12}$; —$(CH_2)_mCN$, —$(CH_2)_mCO_2R^{13}$, —$(CH_2)_mNHCO_2C_{1-4}$alkyl-$(CH_2)_mNHC(O)C_{1-4}$alkyl or —$(CH_2)_n$heteroaryl wherein heteroaryl is optionally substituted by one or two $R^{14}$ groups which may be the same or different;
$R^3$ is phenyl optionally substituted with one, two or three $R^7$ groups which may be the same or different;
$R^4$ is —$C_{1-3}$alkyl, —$CH_2OR^6$ or —$CH_2F$;
each $R^5$ is independently halo, —$C_{0-6}$alkyl-$R^8$, —O—$C_{2-6}$ alkyl-$R^8$, —CN or —$SO_2C_{1-3}$alkyl;
$R^6$ is —H or $C_{1-3}$alkyl;
each $R^7$ is independently -halo, —$C_{1-4}$alkyl, —$C_{0-3}$alkyl-$OR^{10}$, —$C_{0-3}$alkyl-$NR^{15}R^{16}$, —$C_{0-3}$alkyl-$CONR^{15}R^{16}$, CN or —$SO_2R^{17}$;
$R^8$ is —H, —$OR^{10a}$, —$NR^{18}R^{19}$ or heteroaryl;
each $R^9$ is independently halo, $C_{1-4}$alkyl, cyclopropyl, cyclobutyl, —$CH_2CF_3$, —$CH_2CHF_2$, —$CH_2CH_2F$, —$OCH_2CH_2OR^{13}$, —$C_{0-3}$alkylOR$^{13}$, —$C_{0-3}$alkylNR$^{11}R^{12}$, —$NHCH_2CH_2OR^{13}$, —$NHCO_2R^{13}$, oxo, —$C(O)R^{13}$, —$C(O)OR^{13}$ or —$C(O)NR^{11}R^{12}$;
$R^{10a}$ is —H, —$C_{1-3}$alkyl, —$C_{2-3}$alkylNR$^{11}R^{12}$ or —$C_{2-3}$alkylOH;
$R^{11}$ is —H, —$C_{1-3}$alkyl, —$C_{2-3}$alkylNR$^{15}R^{16}$ or —$C_{2-3}$alkylOH;
$R^{11}$ and $R^{12}$ are each independently selected from —H and —$C_{1-3}$alkyl; or $R^{11}$ and $R^{12}$ may join together with the nitrogen to which they are attached, to form a 4 to 7-membered heterocyclyl group optionally substituted by one or two substituents independently selected from —$C_{1-3}$alkyl, —OH and F;

$R^{13}$ is —H or $C_{1-4}$alkyl;

each $R^{14}$ is independently halo, $C_{1-4}$alkyl, cyclopropyl, cyclobutyl or —$OR^{13}$;

$R^{15}$ and $R^{16}$ are each independently selected from —H and —$C_{1-3}$alkyl; or $R^{15}$ and $R^{16}$ may join together with the nitrogen to which they are attached, to form a 4 to 7-membered heterocyclyl group optionally substituted by one or two substituents independently selected from —$C_{1-3}$alkyl, —OH and F;

$R^{17}$ is —$C_{1-3}$alkyl or —$NR^{15}R^{16}$;

$R^{18}$ and $R^{19}$ are each independently selected from —H, —$C(O)OC(CH_3)_3$, —$C_{1-6}$alkyl, cycloalkyl, heterocyclyl, —$C_{2-3}$alkyl$NR^{13}COC_{1-3}$alkyl, $C_{2-3}$alkyl$NR^{15}R^{16}$ and —$C_{2-3}$ alkyl-O—$C_{1-3}$alkyl wherein the —$C_{1-6}$alkyl and cycloalkyl may be optionally substituted by one, two or three fluoro; or $R^{18}$ and $R^{19}$ may join together with the nitrogen to which they are attached, to form a 4 to 7-membered heterocyclyl group optionally substituted by one or two substituents independently selected from —$C_{1-3}$alkyl, —OH and F;

m is an integer selected from 2, 3 and 4;

p is an integer selected from 2, 3 and 4;

n is an integer selected from 0, 1, 2, 3 and 4.

In one embodiment $R^1$ is methyl, ethyl, propyl, iso-propyl or cyclopropyl. In another embodiment $R^1$ is methyl.

In one embodiment $R^2$ is —$C_{0-3}$alkyl-$C_{3-7}$cycloalkyl, wherein the $C_{3-7}$cycloalkyl group is optionally substituted with one, two or three $R^5$ groups which may be the same or different. In another embodiment $R^2$ is —$C_{0-3}$alkyl-$C_{3-7}$cycloalkyl, wherein the $C_{3-7}$cycloalkyl group is cyclopropyl, cyclobutyl or cyclohexyl optionally substituted with one, two or three $R^5$ groups which may be the same or different. In another embodiment $R^2$ is cyclopropyl, cyclobutyl or cyclohexyl optionally substituted with one, two or three $R^5$ groups which may be the same or different. In a further embodiment $R^2$ is selected from:

In one embodiment $R^5$ is —$C_{0-6}$alkyl-$R^8$. In another embodiment $R^5$ is methyl, —$CH_2OH$, —OH or —$CH_2CH_2$morpholinyl.

In one embodiment $R^8$ is OH, methyl or morpholinyl.

In one embodiment $R^2$ is —$C_{0-4}$alkyl-heterocyclyl or —$(CH_2)_pO$-heterocyclyl wherein each heterocyclyl is optionally substituted by one or two $R^9$ groups which may be the same or different. In another embodiment $R^2$ is —$C_{0-4}$alkyl-heterocyclyl wherein the heterocyclyl is optionally substituted by one or two $R^9$ groups which may be the same or different. In another embodiment $R^2$ is —$C_{0-4}$alkyl-heterocyclyl which is -heterocyclyl, —$CH_2CH_2$-heterocyclyl or —$CH_2CH_2CH_2$-heterocyclyl. In another embodiment $R^2$ is —$C_{0-4}$alkyl-heterocyclyl wherein the heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl and (1r,5s)-3-azabicyclo[3.1.0]hexanyl optionally substituted by one or two $R^9$ groups which may be the same or different. In another embodiment $R^2$ is —$C_{0-4}$alkyl-heterocyclyl wherein the heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl and (1r,5s)-3-azabicyclo[3.1.0]hexanyl optionally substituted by one or two $R^9$ groups selected from methyl —$C(O)CH_3$ and fluoro. In a further embodiment $R^2$ is —$C_{0-4}$alkyl-heterocyclyl wherein heterocyclyl, optionally substituted by one or two $R^9$ groups, is selected from:

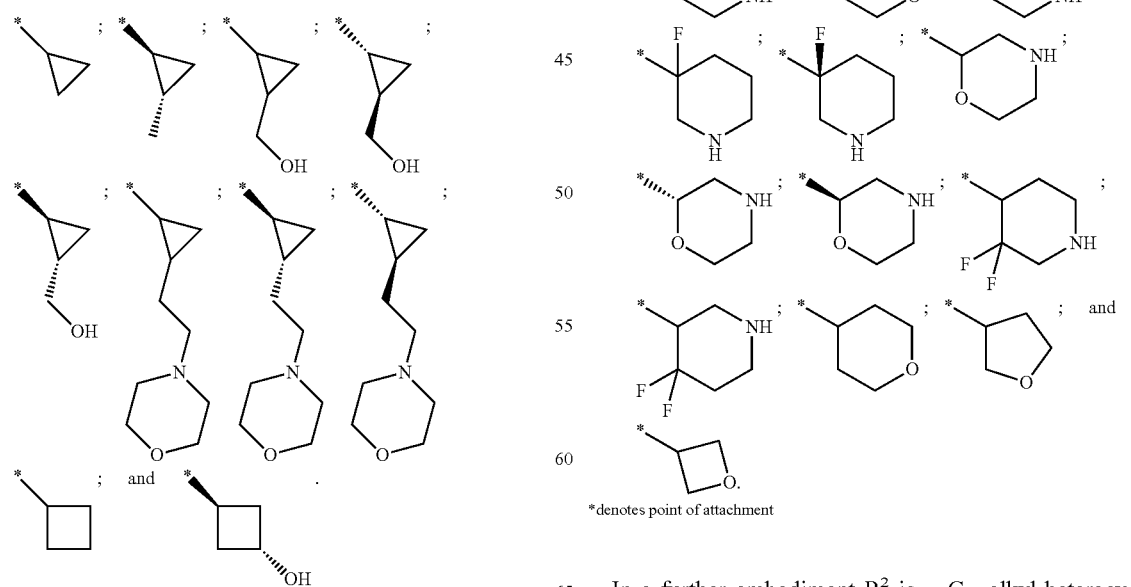

*denotes point of attachment

In a further embodiment $R^2$ is —$C_{0-4}$alkyl-heterocyclyl wherein heterocyclyl, optionally substituted by one or two $R^9$ groups, is:

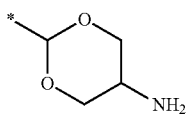
*denotes point of attachment

In one embodiment p is 2 or 3.

In one embodiment $R^2$ is —H, —CH$_3$, C$_{2-6}$alkyl optionally substituted by up to five fluoro, —C$_{2-6}$alkylOR$^{13}$, —C$_{2-6}$alkylNR$^{11}$R$^{12}$, —(CH$_2$)$_m$SO$_2$C$_{1-3}$alkyl, —(CH$_2$)$_m$SO$_2$NR$^{11}$R$^{12}$, —(CH$_2$)$_m$C(O)N$^{11}$R$^{12}$, —(CH$_2$)$_m$CN, —(CH$_2$)$_m$CO$_2$R$^{13}$, —(CH$_2$)$_m$NHCO$_2$C(CH$_3$)$_3$ or —(CH$_2$)$_n$heteroaryl wherein heteroaryl is optionally substituted by one or two $R^{14}$ groups which may be the same or different. In another embodiment $R^2$ is —H, —CH$_3$, C$_{2-6}$alkyl, —C$_{2-6}$alkylOR$^{13}$, —C$_{2-6}$alkylNR$^{11}$R$^{12}$ or —(CH$_2$)$_n$heteroaryl. In a further embodiment $R^2$ is —H, methyl, ethyl, propyl, —CH$_2$CH$_2$OH, —CH$_2$CH$_2$CH$_2$OH, —CH$_2$CH(CH$_3$)OH, —CH$_2$CH$_2$OCH$_3$, —CH$_2$CH$_2$CH$_2$OCH$_3$, —CH$_2$CH$_2$N(CH$_3$)$_2$, —CH$_2$CH$_2$CH$_2$N(CH$_3$)$_2$, —CH$_2$CHF$_2$ or —CH$_2$CH$_2$pyridinyl.

In another embodiment $R^2$ is —(CH$_2$)$_n$heteroaryl wherein heteroaryl is selected from the group consisting of furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl and triazinyl said groups being optionally substituted by one or two $R^{14}$ groups which may be the same or different. In another embodiment there is provided compounds of formula (I) in which $R^2$ is —(CH$_2$)$_n$heteroaryl wherein the heteroaryl is pyrazolyl optionally substituted by C$_{1-4}$alkyl.

In one embodiment n is 0, 2 or 3. In one embodiment n is 0. In another embodiment n is 2.

In one embodiment $R^3$ is phenyl optionally substituted by —OCH$_3$ or —OCH$_2$CH$_2$OH. In another embodiment $R^3$ is phenyl.

In one embodiment $R^4$ is methyl, —CH$_2$F or —CH$_2$OH.

In one embodiment the compound of formula (I) is a compound of formula (IA)

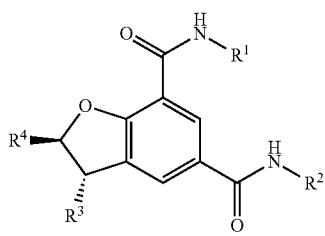

(IA)

or a salt thereof, wherein $R^1$, $R^2$, $R^3$ and $R^4$ are defined according to formula (I).

It is to be understood that the present invention covers all combinations of substituent groups described hereinabove.

Compounds of the invention include the compounds of Examples 1 to 204 and salts thereof.

Compounds of the invention include the compounds of Examples 1 to 108 and salts thereof.

In one embodiment the compound of formula (I) is selected from:
(2R*,3R*)—N$^5$-Cyclobutyl-N$^7$,2-dimethyl-3-phenyl-2,3-dihydrobenzofuran-5,7-dicarboxamide;
(2R*,3S*)—N$^5$-cyclobutyl-N$^7$,2-dimethyl-3-phenyl-2,3-dihydrobenzofuran-5,7-dicarboxamide;
N$^5$-(2-hydroxypropyl)-N$^7$,2-dimethyl-3-phenyl-2,3-dihydrobenzofuran-5,7-dicarboxamide;
N$^5$-cyclopropyl-N$^7$,2-dimethyl-3-phenyl-2,3-dihydrobenzofuran-5,7-dicarboxamide;
N$^5$,N$^7$, 2-trimethyl-3-phenyl-2,3-dihydrobenzofuran-5,7-dicarboxamide;
(2R,3S)—N$^5$-(2-hydroxypropyl)-N$^7$,2-dimethyl-3-phenyl-2,3-dihydrobenzofuran-5,7-dicarboxamide;
(2S,3S)—N$^5$-(2-hydroxypropyl)-N$^7$,2-dimethyl-3-phenyl-2,3-dihydrobenzofuran-5,7-dicarboxamide;
(2R,3S)—N$^5$-cyclopropyl-N$^7$,2-dimethyl-3-phenyl-2,3-dihydrobenzofuran-5,7-dicarboxamide;
(2S,3S)—N$^5$-cyclopropyl-N$^7$,2-dimethyl-3-phenyl-2,3-dihydrobenzofuran-5,7-dicarboxamide;
(2S*,3S*)—N$^5$-cyclopropyl-2-(hydroxymethyl)-N$^7$-methyl-3-phenyl-2,3-dihydrobenzofuran-5,7-dicarboxamide;
(2S*,3S*)—N$^5$-cyclobutyl-2-(hydroxymethyl)-N$^7$-methyl-3-phenyl-2,3-dihydrobenzofuran-5,7-dicarboxamide;
(2S*,3S*)-2-(hydroxymethyl)-N$^7$-methyl-3-phenyl-N$^5$-propyl-2,3-dihydrobenzofuran-5,7-dicarboxamide;
(2S*,3S*)-2-(hydroxymethyl)-N$^7$-methyl-3-phenyl-N$^5$-(2-(piperidin-4-yl)ethyl)-2,3-dihydrobenzofuran-5,7-dicarboxamide;
(2S*,3S*)-2-(hydroxymethyl)-N$^7$-methyl-N$^5$-(3-(4-methylpiperazin-1-yl)propyl)-3-phenyl-2,3-dihydrobenzofuran-5,7-dicarboxamide;
(2S*,3S*)-2-(hydroxymethyl)-N$^7$-methyl-3-phenyl-N$^5$-(3-(piperazin-1-yl)propyl)-2,3-dihydrobenzofuran-5,7-dicarboxamide;
(2S,3S)—N$^5$-cyclopropyl-2-(hydroxymethyl)-N$^7$-methyl-3-phenyl-2,3-dihydrobenzofuran-5,7-dicarboxamide;
(2R*,3S*)—N$^7$,2-dimethyl-3-phenyl-N$^5$-(3-(piperidin-4-yl)propyl)-2,3-dihydrobenzofuran-5,7-dicarboxamide;
(2R,3S)—N$^7$,2-dimethyl-3-phenyl-N$^5$-(3-(piperidin-4-yl)propyl)-2,3-dihydrobenzofuran-5,7-dicarboxamide;
(2R,3S)—N$^5$-ethyl-N$^7$,2-dimethyl-3-phenyl-2,3-dihydrobenzofuran-5,7-dicarboxamide;
(2R,3S)—N$^5$,N$^7$,2-trimethyl-3-phenyl-2,3-dihydrobenzofuran-5,7-dicarboxamide;
(2R,3S)—N$^5$-((1S*,2S*)-2-(hydroxymethyl)cyclopropyl)-N$^7$,2-dimethyl-3-phenyl-2,3-dihydrobenzofuran-5,7-dicarboxamide;
(2S*,3S*)—N$^5$-cyclopropyl-2-(fluoromethyl)-N$^7$-methyl-3-phenyl-2,3-dihydrobenzofuran-5,7-dicarboxamide;
(2S,3S)—N$^5$-cyclopropyl-2-(fluoromethyl)-N$^7$-methyl-3-phenyl-2,3-dihydrobenzofuran-5,7-dicarboxamide;
(2S,3S)-2-(fluoromethyl)-N$^5$,N$^7$-dimethyl-3-phenyl-2,3-dihydrobenzofuran-5,7-dicarboxamide;
(2S,3S)-2-(fluoromethyl)-N$^7$-methyl-N$^5$-((1S,2S)-2-methylcyclopropyl)-3-phenyl-2,3-dihydrobenzofuran-5,7-dicarboxamide;
(2S,3S)—N$^5$-((1R,5S,6r)-3-oxabicyclo[3.1.0]hexan-6-yl)-2-(fluoromethyl)-N$^7$-methyl-3-phenyl-2,3-dihydrobenzofuran-5,7-dicarboxamide;
(2R,3S)—N$^5$-((1S,2S)-2-(hydroxymethyl)cyclopropyl)-N$^7$,2-dimethyl-3-phenyl-2,3-dihydrobenzofuran-5,7-dicarboxamide;
(2R,3S)—N$^5$-((1R,2R)-2-(hydroxymethyl)cyclopropyl)-N$^7$,2-dimethyl-3-phenyl-2,3-dihydrobenzofuran-5,7-dicarboxamide;
(2R,3S)—N$^7$,2-dimethyl-3-phenyl-2,3-dihydrobenzofuran-5,7-dicarboxamide;

(2S*,3S*)—N$^5$-cyclopropyl-2-(hydroxymethyl)-3-(3-methoxyphenyl)-N$^7$-methyl-2,3-dihydrobenzofuran-5,7-dicarboxamide;

(2S*,3S*)-2-(hydroxymethyl)-3-(3-methoxyphenyl)-N$^7$-methyl-N$^5$-((1S,2S)-2-methylcyclopropyl)-2,3-dihydrobenzofuran-5,7-dicarboxamide;

(2S*,3S*)-2-(hydroxymethyl)-3-(3-methoxyphenyl)-N$^5$,N$^7$-dimethyl-2,3-dihydrobenzofuran-5,7-dicarboxamide;

(2S*,3S*)—N$^5$-ethyl-2-(hydroxymethyl)-3-(3-methoxyphenyl)-N$^7$-methyl-2,3-dihydrobenzofuran-5,7-dicarboxamide;

(2S*,3S*)-2-(hydroxymethyl)-N$^5$-(2-methoxyethyl)-3-(3-methoxyphenyl)-N$^7$-methyl-2,3-dihydrobenzofuran-5,7-dicarboxamide;

(2R,3S)—N$^5$-(2-methoxyethyl)-N$^7$,2-dimethyl-3-phenyl-2,3-dihydrobenzofuran-5,7-dicarboxamide;

(2R,3S)—N$^7$,2-dimethyl-3-phenyl-N$^5$-(tetrahydro-2H-pyran-4-yl)-2,3-dihydrobenzofuran-5,7-dicarboxamide;

(2R,3S)—N$^5$-(2-hydroxyethyl)-N$^7$,2-dimethyl-3-phenyl-2,3-dihydrobenzofuran-5,7-dicarboxamide;

(1R,5S,6s)-tert-butyl 6-((2R,3S)-2-methyl-7-(methylcarbamoyl)-3-phenyl-2,3-dihydrobenzofuran-5-carboxamido)-3-azabicyclo[3.1.0]hexane-3-carboxylate;

(2R,3S)—N$^5$-((1R,5S,6s)-3-azabicyclo[3.1.0]hexan-6-yl)-N$^7$,2-dimethyl-3-phenyl-2,3-dihydrobenzofuran-5,7-dicarboxamide;

(2R,3S)—N$^5$-((1R,5S,6s)-3-acetyl-3-azabicyclo[3.1.0]hexan-6-yl)-N$^7$,2-dimethyl-3-phenyl-2,3-dihydrobenzofuran-5,7-dicarboxamide;

(2R,3S)—N$^5$-((1R,5S,6r)-3-oxabicyclo[3.1.0]hexan-6-yl)-N$^7$,2-dimethyl-3-phenyl-2,3-dihydrobenzofuran-5,7-dicarboxamide;

(2R,3S)—N$^5$-(2-(dimethylamino)ethyl)-N$^7$,2-dimethyl-3-phenyl-2,3-dihydrobenzofuran-5,7-dicarboxamide;

(2R,3S)—N$^5$-(3-(dimethylamino)propyl)-N$^7$,2-dimethyl-3-phenyl-2,3-dihydrobenzofuran-5,7-dicarboxamide;

(2R*,3S*)—N$^5$-cyclopropyl-3-(3-methoxyphenyl)-N$^7$,2-dimethyl-2,3-dihydrobenzofuran-5,7-dicarboxamide;

(2R,3S)—N$^7$,2-dimethyl-N$^5$-(oxetan-3-yl)-3-phenyl-2,3-dihydrobenzofuran-5,7-dicarboxamide;

tert-butyl 2-(2-((2R,3S)-2-methyl-7-(methylcarbamoyl)-3-phenyl-2,3-dihydrobenzofuran-5-carboxamido)ethyl)morpholine-4-carboxylate;

(2R,3S)—N$^7$,2-dimethyl-N$^5$-(2-(morpholin-2-yl)ethyl)-3-phenyl-2,3-dihydrobenzofuran-5,7-dicarboxamide;

(2R,3S)—N$^5$-(3-hydroxypropyl)-N$^7$,2-dimethyl-3-phenyl-2,3-dihydrobenzofuran-5,7-dicarboxamide;

(2R,3S)—N$^7$,2-dimethyl-N$^5$-(3-morpholinopropyl)-3-phenyl-2,3-dihydrobenzofuran-5,7-dicarboxamide;

(2R,3S)—N$^5$-(3-methoxypropyl)-N$^7$,2-dimethyl-3-phenyl-2,3-dihydrobenzofuran-5,7-dicarboxamide;

(2R,3S)—N$^7$,2-dimethyl-3-phenyl-N$^5$-(tetrahydrofuran-3-yl)-2,3-dihydrobenzofuran-5,7-dicarboxamide;

(2R,3S)—N$^5$-(2,2-difluoroethyl)-N$^7$,2-dimethyl-3-phenyl-2,3-dihydrobenzofuran-5,7-dicarboxamide;

tert-butyl 2-(3-((2R,3S)-2-methyl-7-(methylcarbamoyl)-3-phenyl-2,3-dihydrobenzofuran-5-carboxamido)propyl)morpholine-4-carboxylate;

(2R,3S)—N$^7$,2-dimethyl-N$^5$-(3-(morpholin-2-yl)propyl)-3-phenyl-2,3-dihydrobenzofuran-5,7-dicarboxamide;

(2S,3S)-ethyl 2-(hydroxymethyl)-3-(3-methoxyphenyl)-7-(methylcarbamoyl)-2,3-dihydrobenzofuran-5-carboxylate;

(2R,3S)—N$^5$-((1R,2S)-2-(hydroxymethyl)cyclopropyl)-3-(3-methoxyphenyl)-N$^7$,2-dimethyl-2,3-dihydrobenzofuran-5,7-dicarboxamide;

(2R,3S)—N$^5$-((1R,5S,6r)-3-oxabicyclo[3.1.0]hexan-6-yl)-3-(3-methoxyphenyl)-N$^7$,2-dimethyl-2,3-dihydrobenzofuran-5,7-dicarboxamide;

(R)-tert-butyl 2-(3-((2R,3S)-3-(3-methoxyphenyl)-2-methyl-7-(methylcarbamoyl)-2,3-dihydrobenzofuran-5-carboxamido)propyl)morpholine-4-carboxylate;

(2R,3S)-3-(3-methoxyphenyl)-N$^7$,2-dimethyl-N$^5$-(3-((R)-morpholin-2-yl)propyl)-2,3-dihydrobenzofuran-5,7-dicarboxamide;

(2R,3S)-3-(3-methoxyphenyl)-N$^7$,2-dimethyl-N$^5$-(3-((S)-morpholin-2-yl)propyl)-2,3-dihydrobenzofuran-5,7-dicarboxamide;

tert-butyl 3-fluoro-3-(3-((2R,3S)-2-methyl-7-(methylcarbamoyl)-3-phenyl-2,3-dihydrobenzofuran-5-carboxamido)propyl)piperidine-1-carboxylate;

(2R,3S)—N$^5$-(3-(3-fluoropiperidin-3-yl)propyl)-N$^7$,2-dimethyl-3-phenyl-2,3-dihydrobenzofuran-5,7-dicarboxamide;

(2R,3S)—N$^5$-((1S*,2R*)-2-(2-hydroxyethyl)cyclopropyl)-N$^7$,2-dimethyl-3-phenyl-2,3-dihydrobenzofuran-5,7-dicarboxamide;

(2R,3S)—N$^7$,2-dimethyl-N$^5$-((1S*,2S*)-2-(2-morpholinoethyl)cyclopropyl)-3-phenyl-2,3-dihydrobenzofuran-5,7-dicarboxamide;

(2R,3S)—N$^7$,2-dimethyl-N$^5$-((1S,2S)-2-(2-morpholinoethyl)cyclopropyl)-3-phenyl-2,3-dihydrobenzofuran-5,7-dicarboxamide;

(2S,3S)—N$^7$,2-dimethyl-N$^5$-((1S,2S)-2-(2-morpholinoethyl)cyclopropyl)-3-phenyl-2,3-dihydrobenzofuran-5,7-dicarboxamide;

(2R*,3S*)-3-(3-(2-hydroxyethoxy)phenyl)-N$^7$,2-dimethyl-N$^5$-((1S,2S)-2-methylcyclopropyl)-2,3-dihydrobenzofuran-5,7-dicarboxamide;

(S)-tert-butyl 3-fluoro-3-(3-((2R*,3S*)-3-(3-(2-hydroxyethoxy)phenyl)-2-methyl-7-(methylcarbamoyl)-2,3-dihydrobenzofuran-5-carboxamido)propyl)piperidine-1-carboxylate;

(2R*,3S*)—N$^5$-(3-((R)-3-fluoropiperidin-3-yl)propyl)-3-(3-(2-hydroxyethoxy)phenyl)-N$^7$,2-dimethyl-2,3-dihydrobenzofuran-5,7-dicarboxamide;

(R)-tert-butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate;

(2S,3S)-2-(fluoromethyl)-N$^5$-(2-((R)-3-fluoropiperidin-3-yl)ethyl)-N$^7$-methyl-3-phenyl-2,3-dihydrobenzofuran-5,7-dicarboxamide;

(2S,3S)-2-(fluoromethyl)-N$^5$-(3-((R)-3-fluoropiperidin-3-yl)propyl)-N$^7$-methyl-3-phenyl-2,3-dihydrobenzofuran-5,7-dicarboxamide;

(R)-tert-butyl 3-fluoro-3-(2-((2R,3S)-2-methyl-7-(methylcarbamoyl)-3-phenyl-2,3-dihydrobenzofuran-5-carboxamido)ethyl)piperidine-1-carboxylate;

(2R,3S)—N$^5$-(2-((R)-3-fluoropiperidin-3-yl)ethyl)-N$^7$,2-dimethyl-3-phenyl-2,3-dihydrobenzofuran-5,7-dicarboxamide;

(R)-tert-butyl 2-(3-((2S,3S)-2-(fluoromethyl)-7-(methylcarbamoyl)-3-phenyl-2,3-dihydrobenzofuran-5-carboxamido)propyl)morpholine-4-carboxylate;

(2S,3S)-2-(fluoromethyl)-N$^7$-methyl-N$^5$-(3-((R)-morpholin-2-yl)propyl)-3-phenyl-2,3-dihydrobenzofuran-5,7-dicarboxamide;

(2R*,3S*)—N$^5$-((1R,5S,6r)-3-oxabicyclo[3.1.0]hexan-6-yl)-3-(3-(2-hydroxyethoxy)phenyl)-N$^7$,2-dimethyl-2,3-dihydrobenzofuran-5,7-dicarboxamide;

(R)-tert-butyl 2-(2-((2S,3S)-2-(fluoromethyl)-7-(methylcarbamoyl)-3-phenyl-2,3-dihydrobenzofuran-5-carboxamido)ethyl)morpholine-4-carboxylate;

(2S,3S)-2-(fluoromethyl)-N⁷-methyl-N⁵-(2-((R)-morpholin-2-yl)ethyl)-3-phenyl-2,3-dihydrobenzofuran-5,7-dicarboxamide;
(2R,3S)—N⁵-(2-(4,4-difluoropiperidin-3-yl)ethyl)-N⁷,2-dimethyl-3-phenyl-2,3-dihydrobenzofuran-5,7-dicarboxamide;
tert-butyl 4,4-difluoro-3-(2-((2R,3S)-2-methyl-7-(methylcarbamoyl)-3-phenyl-2,3-dihydrobenzofuran-5-carboxamido)ethyl)piperidine-1-carboxylate;
(2R,3S)—N⁵-(2-(3,3-difluoropiperidin-4-yl)ethyl)-N⁷,2-dimethyl-3-phenyl-2,3-dihydrobenzofuran-5,7-dicarboxamide;
tert-butyl 3,3-difluoro-4-(2-((2R,3S)-2-methyl-7-(methylcarbamoyl)-3-phenyl-2,3-dihydrobenzofuran-5-carboxamido)ethyl)piperidine-1-carboxylate;
(2S*,3S*)-2-(fluoromethyl)-N⁵-((1R,4S)-4-hydroxycyclohexyl)-N⁷-methyl-3-phenyl-2,3-dihydrobenzofuran-5,7-dicarboxamide;
(2R,3S)—N⁵-((1R,5S,6R)-3-oxabicyclo[3.1.0]hexan-6-yl)-3-(3-(2-hydroxyethoxy)phenyl)-N⁷,2-dimethyl-2,3-dihydrobenzofuran-5,7-dicarboxamide;
(2S*,3S*)-2-(fluoromethyl)-N⁵-((1R,3S)-3-hydroxycyclobutyl)-N⁷-methyl-3-phenyl-2,3-dihydrobenzofuran-5,7-dicarboxamide;
(2S,3S)-2-(fluoromethyl)-N⁵-((1R,2R)-2-(hydroxymethyl)cyclopropyl)-N⁷-methyl-3-phenyl-2,3-dihydrobenzofuran-5,7-dicarboxamide;
(2S,3S)—N⁵-((1R,5S,6s)-3-azabicyclo[3.1.0]hexan-6-yl)-2-(fluoromethyl)-N⁷-methyl-3-phenyl-2,3-dihydrobenzofuran-5,7-dicarboxamide;
(1R,5S,6S)-tert-butyl 6-((2S,3S)-2-(fluoromethyl)-7-(methylcarbamoyl)-3-phenyl-2,3-dihydrobenzofuran-5-carboxamido)-3-azabicyclo[3.1.0]hexane-3-carboxylate;
(2S,3S)-2-(fluoromethyl)-N⁷-methyl-3-phenyl-N⁵-(tetrahydrofuran-3-yl)-2,3-dihydrobenzofuran-5,7-dicarboxamide;
(2S,3S)-2-(fluoromethyl)-N⁵-(2-hydroxyethyl)-N⁷-methyl-3-phenyl-2,3-dihydrobenzofuran-5,7-dicarboxamide;
(2S*,3S*)—N⁵-((1R,5S,6S)-3-acetyl-3-azabicyclo[3.1.0]hexan-6-yl)-2-(fluoromethyl)-N⁷-methyl-3-phenyl-2,3-dihydrobenzofuran-5,7-dicarboxamide;
(2R,3S)-3-(3-(2-hydroxyethoxy)phenyl)-N⁷,2-dimethyl-N⁵-(2-(pyridin-3-yl)ethyl)-2,3-dihydrobenzofuran-5,7-dicarboxamide;
(2R*,3S*)—N⁵-((1R,5S,6s)-3-acetyl-3-azabicyclo[3.1.0]hexan-6-yl)-3-(3-(2-hydroxyethoxy)phenyl)-N⁷,2-dimethyl-2,3-dihydrobenzofuran-5,7-dicarboxamide;
(2R*,3S*)—N⁵-((1R,5S,6s)-3-azabicyclo[3.1.0]hexan-6-yl)-3-(3-(2-hydroxyethoxy)phenyl)-N⁷,2-dimethyl-2,3-dihydrobenzofuran-5,7-dicarboxamide;
(1R,5S,6r)-tert-butyl 6-((2R*,3S*)-3-(3-(2-hydroxyethoxy)phenyl)-2-methyl-7-(methylcarbamoyl)-2,3-dihydrobenzofuran-5-carboxamido)-3-azabicyclo[3.1.0]hexane-3-carboxylate;
(R)-tert-butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate;
(2S,3S)-2-(fluoromethyl)-N⁵-(2-((R)-3-fluoropiperidin-3-yl)ethyl)-N⁷-methyl-3-phenyl-2,3-dihydrobenzofuran-5,7-dicarboxamide;
(2S,3R)—N⁷,2-dimethyl-3-phenyl-N⁵-(3-(piperidin-4-yl)propyl)-2,3-dihydrobenzofuran-5,7-dicarboxamide;
(2S,3R)—N⁵,N⁷,2-trimethyl-3-phenyl-2,3-dihydrobenzofuran-5,7-dicarboxamide;
(2S,3R)—N⁵-ethyl-N⁷,2-dimethyl-3-phenyl-2,3-dihydrobenzofuran-5,7-dicarboxamide;
(2S,3R)—N⁵-cyclopropyl-N⁷,2-dimethyl-3-phenyl-2,3-dihydrobenzofuran-5,7-dicarboxamide;
(2R,3R)—N⁵-cyclopropyl-N⁷,2-dimethyl-3-phenyl-2,3-dihydrobenzofuran-5,7-dicarboxamide;
(2R,3R)—N⁵-cyclopropyl-2-(hydroxymethyl)-N⁷-methyl-3-phenyl-2,3-dihydrobenzofuran-5,7-dicarboxamide;
(2R,3R)—N⁵-((1R,5S,6r)-3-oxabicyclo[3.1.0]hexan-6-yl)-2-(fluoromethyl)-N⁷-methyl-3-phenyl-2,3-dihydrobenzofuran-5,7-dicarboxamide;
(2S,3R)—N⁵-(2-hydroxypropyl)-N⁷,2-dimethyl-3-phenyl-2,3-dihydrobenzofuran-5,7-dicarboxamide; and
(2R,3R)—N⁵-(2-hydroxypropyl)-N⁷,2-dimethyl-3-phenyl-2,3-dihydrobenzofuran-5,7-dicarboxamide or a salt thereof.

In another embodiment the compound is selected from
(2R,3S)—N⁵-((1R,5S,6r)-3-oxabicyclo[3.1.0]hexan-6-yl)-3-(3-(2-hydroxyethoxy)phenyl)-N⁷,2-dimethyl-2,3-dihydrobenzofuran-5,7-dicarboxamide;
(trans)-2-(fluoromethyl)-N⁷-methyl-N⁵-(1-methyl-1H-pyrazol-4-yl)-3-phenyl-2,3-dihydrobenzofuran-5,7-dicarboxamide;
(2S,3S)-2-(fluoromethyl)-N⁵-((1R,2R)-2-(hydroxymethyl)cyclopropyl)-N⁷-methyl-3-phenyl-2,3-dihydrobenzofuran-5,7-dicarboxamide;
(trans) tert-butyl 3,3-difluoro-4-(2-2-(fluoromethyl)-7-(methylcarbamoyl)-3-phenyl-2,3-dihydrobenzofuran-5-carboxamido)ethyl)piperidine-1-carboxylate;
(2R,3S)—N⁵-(2-((S*)-3,3-difluoropiperidin-4-yl)ethyl)-N⁷,2-dimethyl-3-phenyl-2,3-dihydrobenzofuran-5,7-dicarboxamide;
(2S,3S)—N⁵-(3-((2r,5S)-5-Amino-1,3-dioxan-2-yl)propyl)-2-(fluoromethyl)-N⁷-methyl-3-phenyl-2,3-dihydrobenzofuran-5,7-dicarboxamide;
(2S,3S)—N⁵-(2-((2r,5S)-5-amino-1,3-dioxan-2-yl)ethyl)-2-(fluoromethyl)-N⁷-methyl-3-phenyl-2,3-dihydrobenzofuran-5,7-dicarboxamide;
(trans)-N⁵-((1R,5S,6r)-3,3-difluorobicyclo[3.1.0]hexan-6-yl)-2-(fluoromethyl)-N⁷-methyl-3-phenyl-2,3-dihydrobenzofuran-5,7-dicarboxamide; and
(trans)-2-(fluoromethyl)-N⁷-methyl-N⁵-(1S,2S)-2-methylcyclopropyl)-3-phenyl-2,3-dihydrobenzofuran-5,7-dicarboxamide
or a salt thereof.

In one embodiment there is provided a compound of formula (I) or (Ia) in which R¹ is methyl, R² is 3-oxabicyclo[3.1.0]hexanyl, R³ is phenyl and R⁴ is —CH₂F.

In one embodiment the compound of formula (I) is

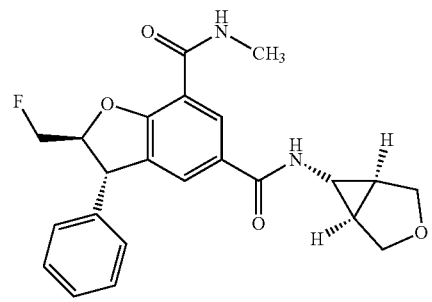

or a salt thereof.

In one embodiment the compound of formula (I) is

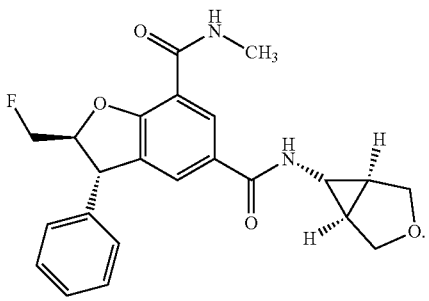

In a second aspect of the present invention, there is provided a pharmaceutical composition comprising a compound of formula (I) or a pharmaceutically acceptable salt thereof and one or more pharmaceutically acceptable excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

Statement of Use

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement, acute rejection of transplanted organs and systemic sclerosis.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), pulmonary arterial hypertension, cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, pulmonary fibrosis, cystic fibrosis, progressive massive fibrosis, renal fibrosis, liver fibrosis, liver cirrhosis, non-alcoholic steatohepatitis (NASH), non-alcoholic fatty liver disease (NAFLD), post-operative stricture, keloid scar formation, scleroderma (including morphea and systemic sclerosis), cardiac fibrosis, atrial fibrosis, endomyocardial fibrosis, old myocardial infarction, arthrofibrosis, Dupuytren's contracture, mediastinal, myelofibrosis, Peyronie's disease, nephrogenic systemic fibrosis, retroperitoneal fibrosis and adhesive capsulitis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer. In another embodiment the cancer is prostate cancer. In another embodiment the cancer is castration resistant prostate cancer.

Bromodomain inhibitors may be useful in the treatment of diseases associated with systemic inflammatory response syndrome, such as sepsis, burns, pancreatitis, major trauma, haemorrhage and ischaemia. In this embodiment, the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders. In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain containing protein which comprises contacting the bromodomain containing protein with a compound of formula (I) or a pharmaceutically acceptable salt thereof.

As used herein the reference to the "treatment" of a particular disease or condition includes the prevention or prophylaxis of such a disease or condition.

Pharmaceutical Compositions/Routes of Administration/Dosages

Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and one or more pharmaceutically acceptable excipients. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable excipients. The pharmaceutical composition can be used in the treatment of any of the conditions described herein.

In a further aspect the invention is directed to pharmaceutical compositions for the treatment or prophylaxis of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The pharmaceutical compositions of the invention typically contain one compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subject compliance.

Suitable pharmaceutically-acceptable excipients include the following types of excipients: carriers, diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents). The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral administration, the compound of formula (I) or a pharmaceutically acceptable salt thereof, may be in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situgellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

Aerosol formulations, e.g. for inhaled administration, can comprise a solution or fine suspension of the active substance in a pharmaceutically acceptable aqueous or nonaqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in Internation Patent Application WO-A-2005/044354.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents (such as PD-1 inhibitors including nivolumab and pembrolizumab, and CTLA-4 inhibitors, including ipilimumab); proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic agent(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic agent. It will be clear also that, where appropriate, the therapeutic agents may be used in optically pure form.

The combinations referred to above may conveniently be presented for use in the form of a pharmaceutical composition and thus pharmaceutical compositions comprising a combination as defined above together with a pharmaceutically acceptable excipient represent a further aspect of the invention.

Synthetic Routes

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in any of the Schemes below:

Scheme 1:

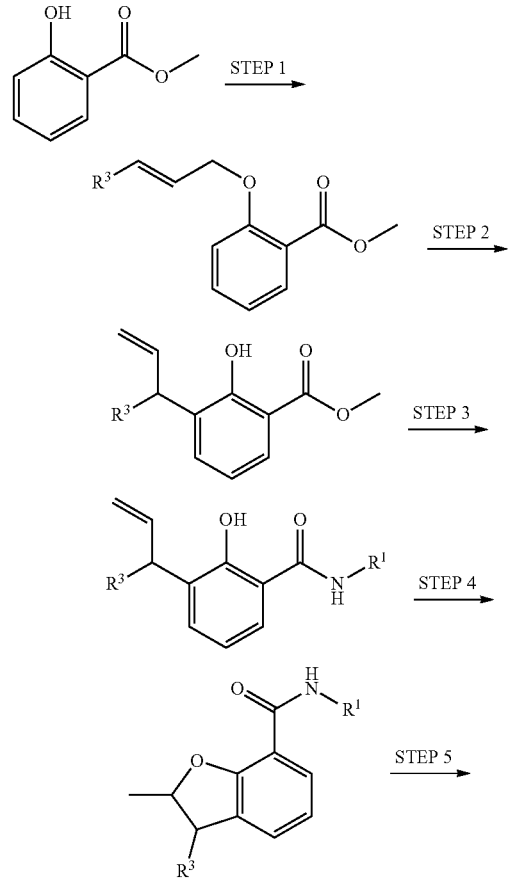

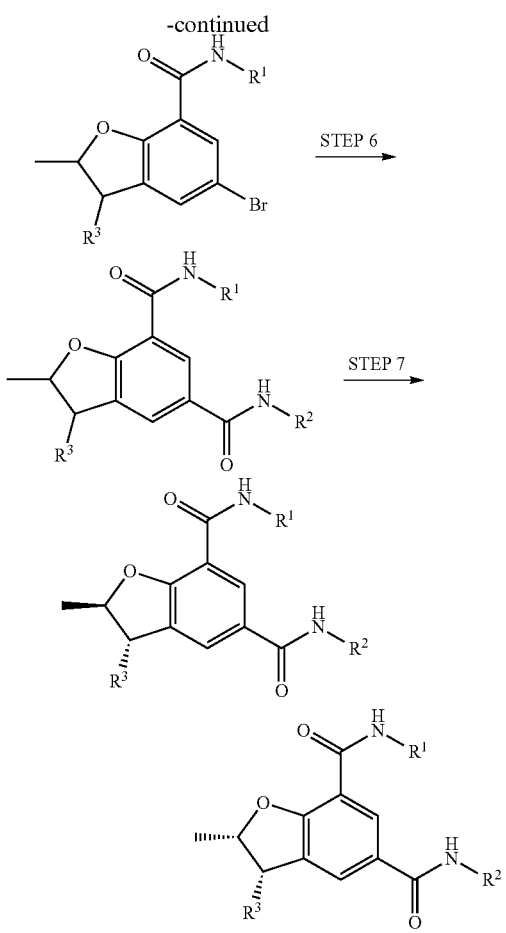

In respect of the steps shown in Scheme 1 above the following reaction conditions may be utilised to access Compounds of Formula (I) wherein $R^4$ is methyl:

Step 1: is an alkylation and may be carried out using cinnamyl halide of formula $R^3$—CH═CH—CH$_2$Hal, such as cinnamyl chloride, in the presence of a suitable base, such as potassium carbonate, and a suitable catalyst such as potassium iodide, in a suitable solvent such as acetone, at a suitable temperature, such as reflux temperature.

Step 2: is a Claisen rearrangement which can be conducted in a suitable high boiling solvent such as N,N-dimethylaniline, at a suitable temperature such as reflux temperature.

Step 3: is an amide formation and can be carried out using an appropriate primary amine $R^1NH_2$, such as methanamine, in a suitable solvent such as a mixture of THF and water, at a suitable temperature such as room temperature.

Step 4: is a cyclisation and can be carried out in a suitable acid such as trifluoroacetic acid, as a suitable temperature such as reflux temperature. In these conditions, the product is typically obtained as a mixture of cis and trans isomers, such as a 1:1 mixture of cis and trans isomers.

Step 5: is a bromination which can be carried out using a suitable brominating agent such as NBS, in a suitable solvent such as dichloromethane, at a suitable temperature such as room temperature.

Step 6: is an aminocarbonylation and can be carried out using an appropriate carbon monoxide source, such as dicobalt octacarbonyl, in the presence of a suitable primary amine of formula $R^2NH_2$, using an appropriate catalyst such as palladium(II)acetate and a suitable ligand such as di((3S,5S,7S)-adamantan-1-yl)(butyl)phosphine, in the presence of a suitable tertiary amine such as DMAP, in a suitable solvent such as 2-methyltetrahydrofuran, at a suitable temperature such as between 100° C. and 120° C., under microwave irradiation.

Step 7: is a an optional separation of isomers, which can be carried out using the appropriate chromatographic system (solid or liquid phase). This step can be performed as the last step of the synthesis of compounds of Formula (I) but can also be performed after Step 4 or Step 5. In this case, the bromination and/or the aminocarbonylation will be carried out with the cis and trans isomers separately. Alternatively this step may be performed chirally.

It should be understood as well that the products from steps 4 to 6 can be separated by method known to one skilled in the art, such as purification by chromatography on chiral column, into single enantiomers. In this case, all the subsequent intermediates and example are obtained as a single enantiomer, using the same procedure as for the racemates.

Scheme 2:

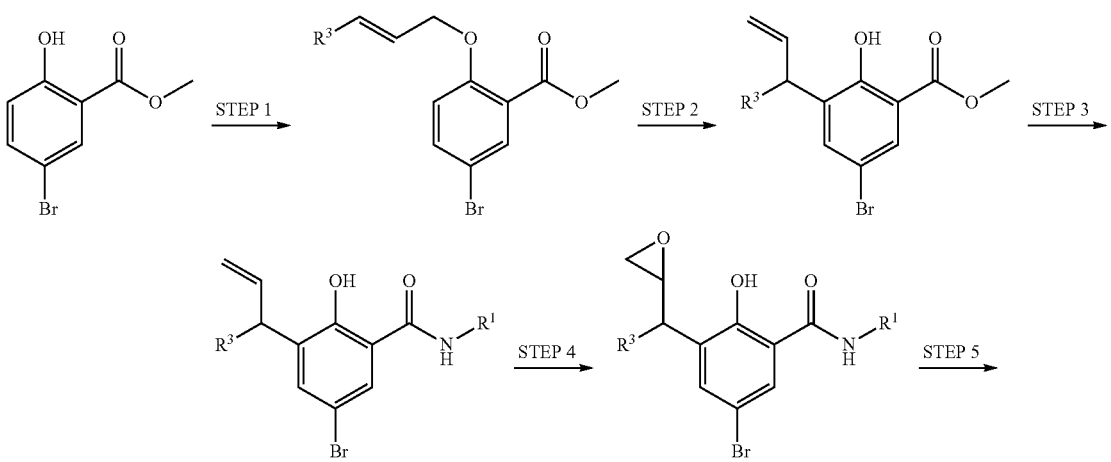

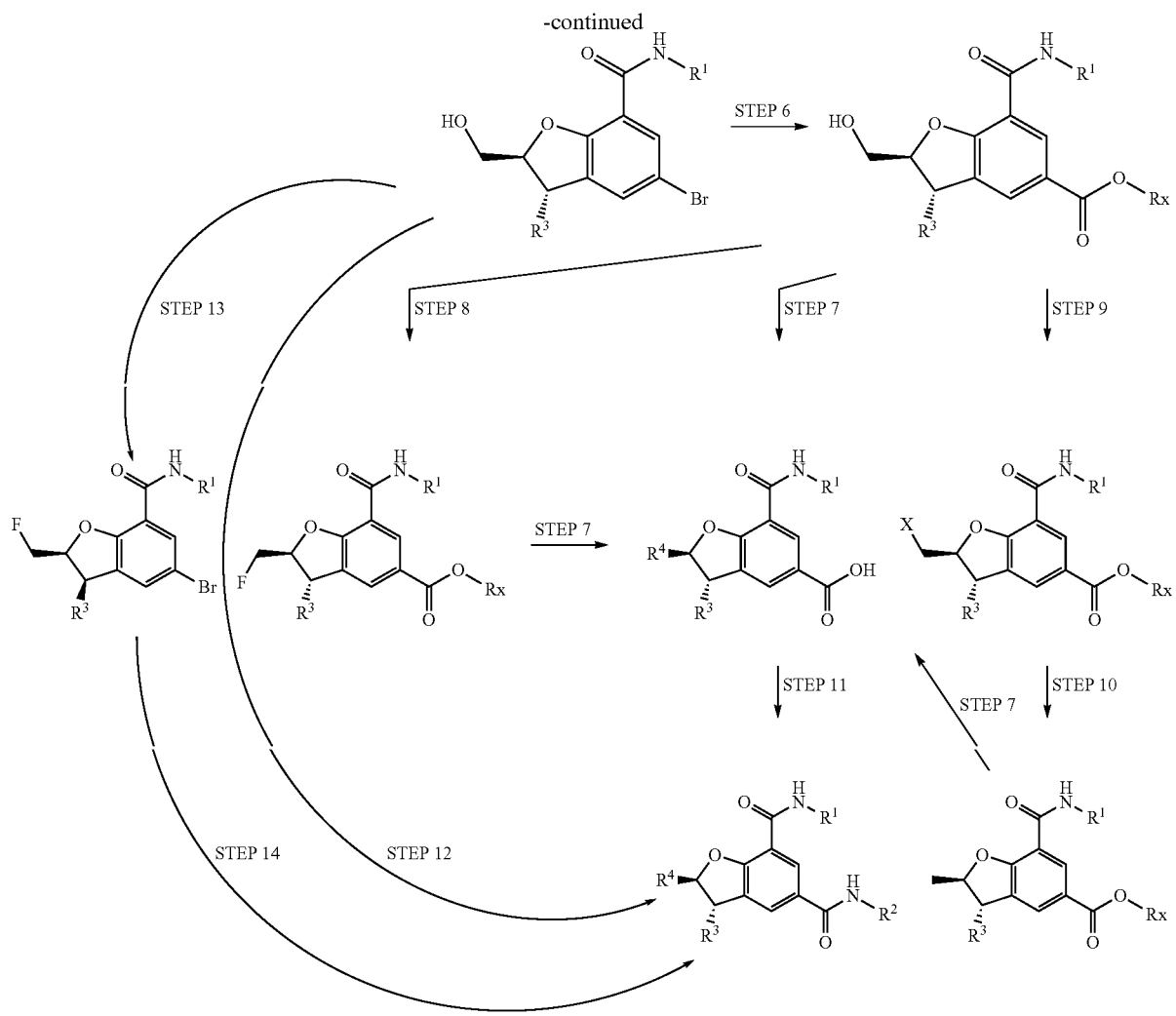

In respect of the steps shown in Scheme 2 above, the following reaction conditions may be utilised to access Compounds of Formula (1):

Step 1: is an alkylation and may be carried out using cinnamyl halide of formula $R^3$—CH=CH—$CH_2$Hal, such as cinnamyl chloride, in the presence of a suitable base, such as potassium carbonate, and a suitable catalyst such as potassium iodide, in a suitable solvent such as acetone, at a suitable temperature, such as reflux temperature Step 2: is a Claisen rearrangement which can be conducted in a suitable high boiling solvent such as N,N-dimethylaniline, at a suitable temperature such as reflux temperature.

Step 3: is an amide formation and can be carried out using an appropriate primary amine $R^1NH_2$, such as methanamine, in a suitable solvent such as a mixture of THF and water, at a suitable temperature such as room temperature.

Step 4: is an epoxidation and can be carried out using the appropriate oxidising agent, such as m-CPBA, in a suitable solvent such as dichloromethane, at a suitable temperature such as room temperature. In these conditions, the product is typically obtained as a mixture of diastereoisomers, such as a 1:1 mixture of diastereoisomers. Alternatively this step may be performed chirally.

Step 5: is a cyclisation via epoxide opening followed by the epimerisation of the benzylic position, leading to a mixture of isomers where the more thermodynamically stable trans isomer is present in equal or higher proportion than the cis isomer. This ratio of trans/cis isomer can be superior to 95/5. This reaction can be carried out using an appropriate base, such as potassium hydroxide, in a suitable solvent such as a mixture of DMSO and water, at a suitable temperature such as 0° C.

Step 6: is a carbonylation reaction. This can be carried out using an appropriate source of carbon monoxide, such as carbon monoxide gas, in the presence of an appropriate catalyst, such as palladium(II) acetate, a suitable ligand, such as Xantphos, an appropriate tertiary amine, such as triethylamine, in an appropriate solvent such as a mixture of DMF and alcohol RxOH, wherein Rx is $C_{1-6}$alkyl (in a suitable ratio such as 2:1), at an appropriate temperature such as 70° C.

Step 7: is a saponification which can be carried out using the appropriate hydroxide salt such as sodium hydroxide, in an appropriate solvent such as a mixture of alcohol (such as ethanol) and water, at an appropriate temperature such as room temperature.

Step 8: is a substitution of an hydroxyl group by a fluorine atom. This can be carried out using the appropriate fluorinating agent, such as deoxofluor, in a suitable solvent such as dichloromethane, at a suitable temperature, such as between 0° c. and 40° C.

Step 9: is either: 1) a substitution of an hydroxyl by an halogen, such as iodine, which can be carried out using the appropriate source of halogen, such as diodine, in the presence of a trisubstituted phosphine such as triphenylphosphine and a mild base such as imidazole, in a suitable solvent such as dichloromethane, at a suitable temperature such as room temperature; 2) formation of a sulfonate such as methylsulfonate. This can be carried out using an appropriate source of sulfonylating agent, such as methanesulfonyl chloride, in the presence of a tertiary amine, such as triethylamine, in a suitable solvent such as dichloromethane, at a suitable temperature such as room temperature.

Step 10: is a reduction. This can be carried out using an appropriate reducing agent, such as lithium borohydride (wherein X is $RSO_2O-$ in which X is $C_{1-6}$alkyl), in a suitable solvent such as THF, at a suitable temperature such as between 0° C. and room temperature. It can also be performed (wherein X is halogen such as iodine) using an appropriate source of hydrogen, such as hydrogen gas, in the presence of an appropriate catalyst such as palladium on carbonyl, and an adequate base such as a trialkyl amine (such as triethylamine) in an appropriate solvent, such as an alcohol (such as methanol) at an appropriate temperature such as room temperature.

Step 11: is an amide formation of, which can be carried out using an appropriate activating agent such as HATU, in the presence of an adequate base, such as a trialkylamine (for example triethylamine or diisopropylethylamine) or pyridine, and using the appropriate primary amine $R^2NH_2$, in an appropriate solvent such as dichloromethane or DMF, at an adequate temperature such as room temperature.

Step 12: is an aminocarbonylation and can be carried out using an appropriate carbon monoxide source, such as dicobalt octacarbonyl, in the presence of a suitable primary amine of formula $R^2NH_2$, using an appropriate catalyst such as palladium(II) acetate and a suitable ligand such as di((3S,5S,7S)-adamantan-1-yl)(butyl)phosphine, in the presence of a suitable tertiary amine such as DMAP, in a suitable solvent such as 2-methyltetrahydrofuran, at a suitable temperature such as between 100° C. and 120° C., under microwave irradiation.

Step 13: is a substitution of an hydroxyl group by a fluorine atom. This can be carried out using the appropriate fluorinating agent, such as perfluoro-1-butanesulfonyl fluoride and triethylamine trihydrofluoride, in a suitable solvent such as dichloromethane, with a suitable base such as DIPEA and at a suitable temperature, such as room temperature.

Step 14: is an aminocarbonylation and can be carried out using an appropriate carbon monoxide source, such as CO(g), in the presence of a suitable primary amine of formula $R^2NH_2$, using an appropriate catalyst such as palladium(II) acetate and a suitable ligand such as 4,5-Bis(diphenylphosphino)-9,9-dimethylxanthene, in the presence of a suitable amine such as 2,6, lutidine, in a suitable solvent such as 1,4,Dioxan, at a suitable temperature such as between 80° C. and 100° C. at between 1 and 2 bar of pressure.

It is to be understood that compounds obtained from steps 11 or 12 can be further modified if necessary. In particular, it may be desired to remove protecting groups from amines present in $R^2$, such as a tert-butyl carbamate protecting group. This can be achieved by the use of an appropriate strong acid, such as trifluoroacetic acid, in a suitable solvent such as dichloromethane, at a suitable temperature such as room temperature. It may also be desired to deprotect $R^7$ substituent such as a benzyloxy derivatives to generate the corresponding phenol. This can be achieved, for example by the use of an hydrogen source (such as hydrogen gas) in the presence of an adequate catalyst such as palladium on carbon, in an appropriate solvent such as alcohol, methanol for example, at an appropriate temperature such as room temperature.

It will be appreciated that all derivatives obtained from step 5 onwards are racemic and can be separated into their two enantiomers by techniques known to one skilled in the art, such as purification by chromatography on a chiral column.

Scheme 3:

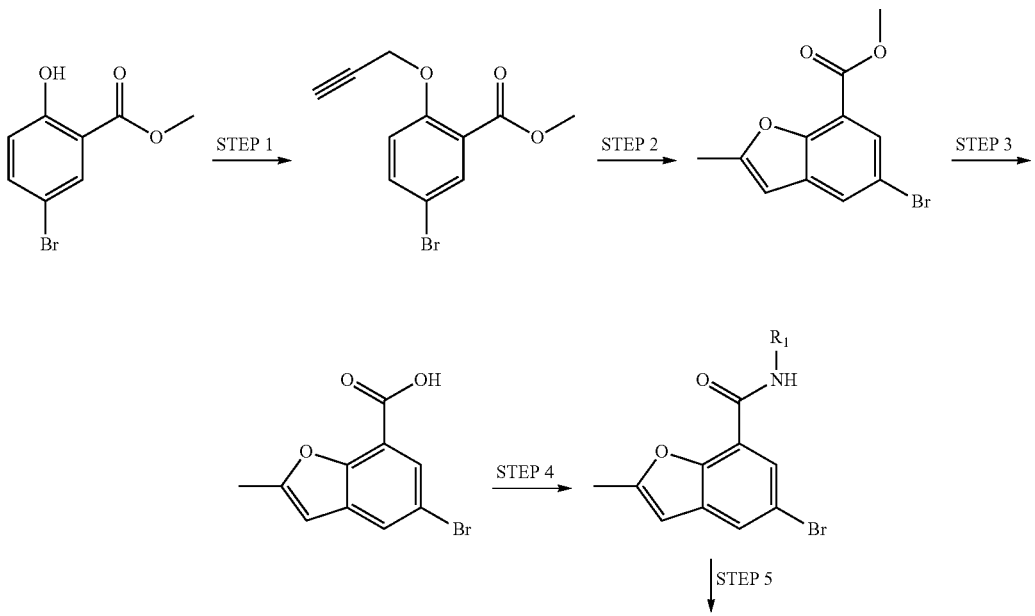

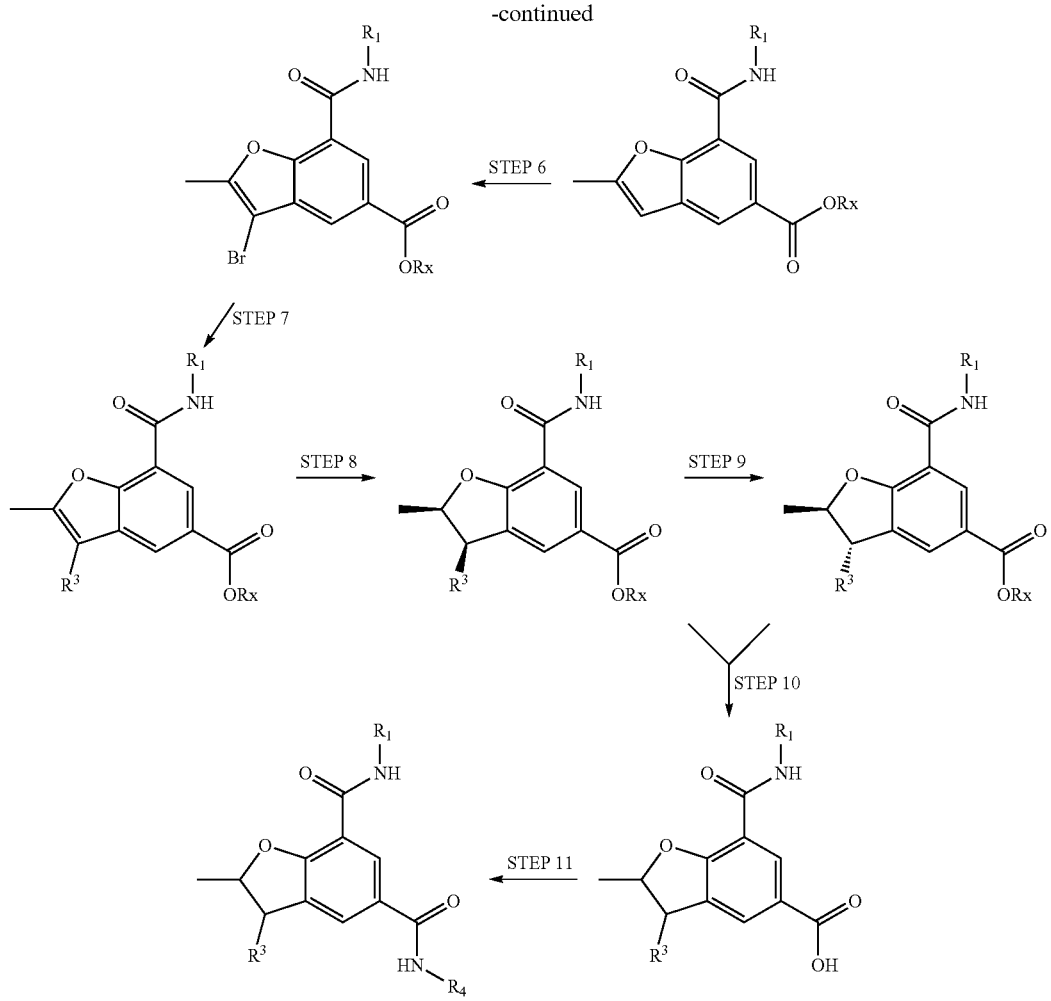

In respect of the steps shown in Scheme 3 above, the following reaction conditions may be utilised to access Compounds of Formula (I):

Step 1: is an alkylation and can be carried out using the appropriate alkylating agent such as propargyl bromide, with an appropriate base, such as potassium carbonate, in an adequate solvent such as DMF, at an appropriate temperature such as room temperature.

Step 2: is a cyclisation and can be carried out using an appropriate catalyst, such as (acetonitrile)[(2-biphenyl)di-tert-butylphosphine]gold(I) hexafluoroantimonate, in an adequate solvent such as dichloromethane, at an appropriate temperature such as room temperature.

Step 3: is a saponification and can be carried out using an appropriate hydroxide salt such as sodium hydroxide, in an adequate solvent such as a mixture of THF, methanol and water, at an appropriate temperature such as room temperature.

Step 4: is an amide formation. This can be carried out by the reaction of an acylating agent such as an acyl chloride with an appropriate amine $R^1NH_2$. The acyl chloride can be prepared from the corresponding acid using an appropriate chloride source such as oxalyl chloride, in the presence of a catalytic quantity of DMF, in an adequate solvent such as dichloromethane, at the appropriate temperature such as room temperature. The acid chloride and the amine $R^1NH_2$ can be reacted in the presence of an appropriate tertiary amine such as DIPEA, in an adequate solvent such as dichloromethane, at an appropriate temperature such as room temperature.

Step 5: is a carbonylation. This can be carried out using an appropriate source of carbon monoxide, such as carbon monoxide gas, in the presence of an appropriate alcohol RxOH, wherein Rx is $C_{1-6}$alkyl, an appropriate catalyst, such as palladium(II) acetate, an appropriate ligand, such as Xantphos, an appropriate tertiary amine, such as triethylamine, in an adequate solvent, such as DMF, and at an adequate temperature such as 70° C.

Step 6: is a bromination. This can be carried out using an appropriate source of bromine, such as dibromine, in an adequate solvent such as dichloromethane, at an adequate temperature such as between room temperature and reflux temperature.

Step 7: is an aryl-aryl coupling. This can be carried out using the appropriate boronic acid or ester $R_3PhB(ORy)_2$, Ry being H or alkyl, such as (3-(benzyloxy)phenyl)boronic acid, in the presence of an adequate catalyst, such as palladium(II) acetate, an adequate ligand, such as di((3S,5S,7S)-adamantan-1-yl)(butyl)phosphine, and an appropriate base, such as potassium carbonate, in an adequate solvent such as THF, at an appropriate temperature such as room temperature.

Step 8: is an hydrogenation, which can be carried out using an adequate source of hydrogen, such as dihydrogen gas, at an appropriate pressure, such as 70 bar, in the presence of an adequate catalyst, such as palladium on carbonyl, at an appropriate temperature such as 70° C., in an adequate solvent such as MeOH.

Step 9: is an epimerisation step and can be carried out in the presence of an appropriate base, such as DBU, in the appropriate solvent, such as $CH_3CN$ and at an adequate temperature such as 100° C.

Step 10: is a saponification which can be carried out using an appropriate hydroxide salt such as sodium hydroxide, in an appropriate solvent such as a mixture of alcohol (such as ethanol) and water, at an appropriate temperature such as room temperature.

Step 11: is a formation of an amide, which can be carried out using an appropriate activating agent such as HATU, in the presence of an adequate base, such as a trialkylamine (triethylamine or diisopropylethylamine for example) or pyridine, and of an appropriate primary amine $R^2NH_2$, in an adequate solvent such as dichloromethane or DMF, at an adequate temperature such as room temperature.

EXAMPLES

General Methods
General Experimental Details
All temperatures referred to are in ° C.
As used herein the symbols and conventions used in these processes, schemes and examples are consistent with those used in the contemporary scientific literature, for example, the *Journal of the American Chemical Society*. Unless otherwise noted, all starting materials were obtained from commercial suppliers and used without further purification. Specifically, the following abbreviations may be used in the examples and throughout the specification:

Abbreviations

AcOH acetic acid
$BBr_3$ boron tribromide
BOC/Boc tert-butyloxycarbonyl
$Boc_2O$ di-tert-butyl dicarbonate
BuLi butyllithium
$Cs_2CO_3$ cesium carbonate
$CHCl_3$ chloroform
Cobalt carbonyl dicobalt octacarbonyl
CV column volume
DMSO-$d_6$ deuterated dimethylsulfoxide
DCM dichloromethane
DIAD diisopropyl azodicarboxylate
DIBAL-H diisobutylaluminum hydride
DIPEA diisopropylethylamine
DMAP 4-dimethylaminopyridine
DMF dimethylformamide
DMSO dimethylsulfoxide
DMSO-$d_6$ deuterated dimethylsulfoxide
DPPA diphenylphosphoryl azide
dppb 1,4-bis(diphenylphosphino)butane
EDC 1-ethyl-3-(3-dimethylaminopropyl)carbodiimide
$Et_3N$ triethylamine
$Et_2O$ diethyl ether
EtOAc ethyl acetate
EtOH ethanol
h hour(s)
HATU O-(7-azabenzotriazol-1-yl)-N,N,N',N'-tetramethyluronium hexafluorophosphate
HCl hydrochloric acid
$HCO_2H$ formic acid
IPA isopropyl alcohol
Isolera Biotage Flash purification system
KCN potassium cyanide
$K_2CO_3$ potassium carbonate
KI potassium iodide
KOH potassium hydroxide
LCMS liquid chromatography-mass spectrometry
$LiBH_4$ lithium borohydride
LiOH lithium hydroxide
M molar (concentration)
mCPBA meta-chloroperoxybenzoic acid
MDAP mass directed autoprep
MeCN acetonitrile
MeI methyl iodide
MeOH methanol
2-MeTHF 2-methyl tetrahydrofuran
$MgSO_4$ magnesium sulphate
min minute (s)
MsCl methanesulfonyl chloride
MTBE methyl tert-butyl ether
N normal (concentration)
$N_2$ nitrogen
$Na_2CO_3$ sodium carbonate
NaI sodium iodide
NaH sodium hydride
NaOH sodium hydroxide
$Na(OAc)_3BH$ sodium triacetoxy borohydride
$Na_2SO_4$ sodium sulphate
NBS N-bromosuccinimide
$NEt_3$ triethylamine
NMP M-methyl-2-pyrrolidone
NUT nuclear protein in testis
Pd/C palladium on carbon
$PPh_3$ triphenylphosphine
$Ph_3PO$ triphenylphosphine oxide
RBF round bottomed flask
Rt retention time
rt room temperature
sat saturated
SCX Isolute strong cation exchange sorbent SPE
$SiO_2$ silicon dioxide
SNAP Biotage (silica) flash chromatography cartridge
SP4 Biotage Flash purification system
SPE solid phase extraction
TBME tert-butyl methyl ether
$Tf_2O$ trifluoromethanesulfonic anhydride
TFA trifluoroacetic acid
THF tetrahydrofuran
TMSCl/TMS-Cl trimethylsilyl chloride
TLC Thin layer chromatography
Ts tosyl
UPLC ultra performance liquid chromatography
XantPhos 1,1'-(9,9-dimethyl-9H-xanthene-4,5-diyl)bis[1,1-diphenylphosphine
The names of the following compounds have been obtained using the compound naming programme "ACD Name Pro 6.02" or using the naming functionality of ChemDraw Ultra 12.0.
LCMS Methodology
Formic Method
LC Conditions
The UPLC analysis was conducted on an Acquity UPLC CSH C18 column (50 mm×2.1 mm, i.d. 1.7 μm packing diameter) at 40° C.

The solvents employed were:
A=0.1% v/v solution of formic acid in water
B=0.1% v/v solution of formic acid in acetonitrile
The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
High pH Method
LC Conditions
The UPLC analysis was conducted on an Acquity UPLC CSH C18 column (50 mm×2.1 mm, i.d. 1.7 µm packing diameter) at 40° C.
The solvents employed were:
A=10 mM ammonium hydrogen carbonate in water adjusted to pH10 with ammonia solution
B=acetonitrile
The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
TFA Method
LC Conditions
The UPLC analysis was conducted on an Acquity UPLC CSH C18 column (50 mm×2.1 mm, i.d. 1.7 µm packing diameter) at 40° C.
The solvents employed were:
A=0.1% v/v solution of trifluoroacetic acid in water
B=0.1% v/v solution of trifluoroacetic acid in acetonitrile
The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
General MDAP Purification Methods
Listed below are examples of mass-directed autopreparative chromatography (MDAP) methods that have been used or may be used in compound purification.
MDAP (High pH).
The HPLC analysis was conducted on an Xselect CSH C18 column (150 mm×30 mm i.d. 5 µm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 minutes.
The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.
MDAP (Formic).
The HPLC analysis was conducted on an Xselect CSH C18 column (150 mm×30 mm i.d. 5 µm packing diameter) at ambient temperature, eluting with 0.1% formic acid in water (Solvent A) and 0.1% formic acid in acetonitrile (Solvent B) using an elution gradient of between 0 and 100% solvent B over 15 or 25 minutes.
The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.
MDAP (TFA).
The HPLC analysis was conducted on an Xselect CSH C18 column (150 mm×30 mm i.d. 5 µm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 minutes.
The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.
NMR
Spectra were run on either a 400 MHz or 600 MHz NMR machine at 302 K.
GLOBAL gradient for chromatography are as follows (solvent B polar component, CV=column volume): 10% GLOBAL: 3% B for 2 CV, 3 to 13% B over 10 CV then 13% B for 5 CV; 20% GLOBAL: 5% B for 2 CV, 5 to 20% B over 10 CV then 20% B for 5 CV; 30% GLOBAL: 8% B for 2

CV, 8 to 38% B over 10 CV then 38% B for 5 CV; 40% GLOBAL: 10% B for 2 CV, 10 to 50% B over 10 CV then 50% B for 5 CV; 50% GLOBAL: 13% B for 2 CV, 13 to 63% B over 10 CV then 63% B for 5 CV. 100% GLOBAL: 25% B for 2 CV, 25 to 100% B over 10 CV then 100% B for 10 CV.

Intermediate 1: Methyl 2-(cinnamyloxy)benzoate

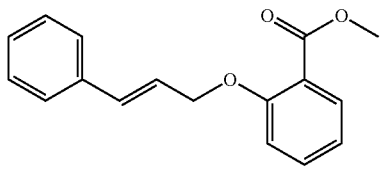 [SMILES: COC(=O)c1ccccc1OC/C=C/c1ccccc1]

A solution of methyl 2-hydroxybenzoate (commercially available from, for example, Aldrich, 3.8 mL, 30 mmol) in acetone (100 mL) was treated with K$_2$CO$_3$ (8.29 g, 60.0 mmol), KI (0.1 g, 0.6 mmol) and (E)-(3-chloroprop-1-en-1-yl)benzene (commercially available from, for example, Aldrich, 3.47 mL, 36.0 mmol) and the resulting mixture was stirred at reflux for 11 h then was cooled to room temperature. The insolubles were filtered off, rinsed with EtOAc and the combined organics were concentrated in vacuo. The residue was partitioned between Et$_2$O and water and the layers were separated. The aqueous phase was extracted twice with Et$_2$O and the combined organics were washed with brine, dried over MgSO$_4$ and concentrated in vacuo to give methyl 2-(cinnamyloxy)benzoate (7.12 g, 88%) as a pale yellow solid which was used in the next step without further purification.

LCMS (method high pH): Retention time 1.29 min, [M+H]$^+$=269

Intermediate 2: Methyl 2-hydroxy-3-(1-phenylallyl)benzoate

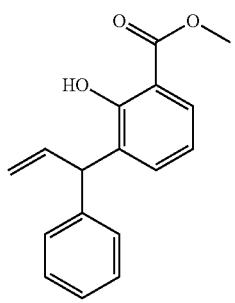 [SMILES: C=CC(c1ccccc1)c1cccc(C(=O)OC)c1O]

A solution of methyl 2-(cinnamyloxy)benzoate (0.8 g, 3 mmol) in N,N-dimethylaniline (7 mL) was refluxed for 2 h then was cooled to room temperature and partitioned between Et$_2$O and a 24-26% w/w HCl aqueous solution. The layers were separated and the aqueous phase was extracted with Et$_2$O. The combined organics were washed with a 2N NaOH aqueous solution, dried over MgSO$_4$ and concentrated in vacuo. Purification of the residue obtained by flash chromatography on silica gel (100 g column, 10% GLOBAL gradient, EtOAc in cyclohexane) gave methyl 2-hydroxy-3-(1-phenylallyl)benzoate (440 mg, 55%) as a colourless oil.

LCMS (method high pH): Retention time 1.46 min, [M+H]$^+$=269

Intermediate 3: 2-Hydroxy-N-methyl-3-(1-phenylallyl)benzamide

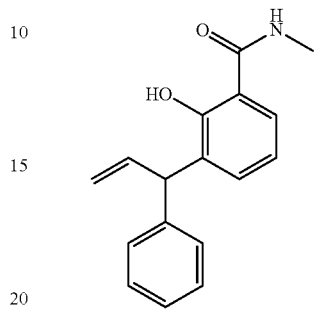

A solution of methyl 2-hydroxy-3-(1-phenylallyl)benzoate (5.0 g, 19 mmol) in THF (25 mL) at room temperature was treated with methylamine (48% w/w in water, 1 mL) and the resulting mixture was stirred at this temperature for 2 h then was concentrated in vacuo. The residue was partitioned between DCM and water and the layers were separated. The aqueous phase was extracted twice with DCM. The combined organics were dried using a phase separator and concentrated in vacuo to give 2-hydroxy-N-methyl-3-(1-phenylallyl)benzamide (4.4 g, 88%) as a yellow solid which was used in the next step without purification.

LCMS (method high pH): Retention time 1.20 min, [M+H]$^+$=268

Intermediate 4: N,2-Dimethyl-3-phenyl-2,3-dihydrobenzofuran-7-carboxamide

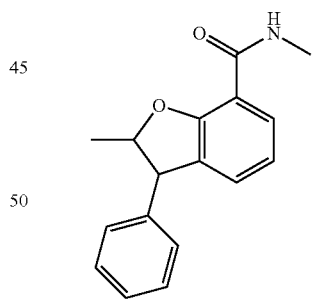

A solution of 2-hydroxy-N-methyl-3-(1-phenylallyl)benzamide (4.4 g, 16 mmol) in trifluoroacetic acid (60 mL) was stirred at 80° C. for 5 h then was cooled to room temperature and concentrated in vacuo. The residue was co-evaporated with DCM. Purification of the residue (6 g) by flash chromatography on silica gel (100 g column, 50% GLOBAL gradient, AcOEt in hexanes) gave N,2-dimethyl-3-phenyl-2,3-dihydrobenzofuran-7-carboxamide (3 g, 68%) as a 1:1 mixture of stereoisomers.

LCMS (method high pH): Retention time 1.10 and 1.12 min, [M+H]$^+$=268

Intermediate 5: 5-Bromo-N,2-dimethyl-3-phenyl-2,3-dihydrobenzofuran-7-carboxamide

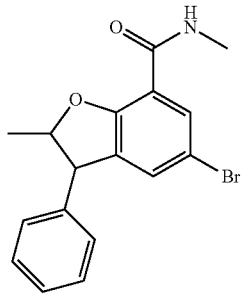 [SMILES: CNC(=O)c1cc(Br)cc2c1OC(C)C2c1ccccc1]

A solution of N,2-dimethyl-3-phenyl-2,3-dihydrobenzofuran-7-carboxamide (0.103 g, 0.385 mmol) in DCM (3 mL) at room temperature was treated with NBS (0.082 g, 0.46 mmol) and the resulting yellow solution was stirred at this temperature. NBS (0.082 g, 0.46 mmol) was added after 30 min and the resulting mixture was stirred at room temperature for 16 h then was diluted with DCM and treated with of a 10% w/w sodium thiosulfate aqueous solution (20 mL). The biphasic mixture was vigorously stirred for 10 min then the layers were separated. The aqueous phase was extracted twice with DCM and the combined organics were dried using a phase separator and concentrated in vacuo to give 5-bromo-N,2-dimethyl-3-phenyl-2,3-dihydrobenzofuran-7-carboxamide (130 mg, 97%) as a pale orange foam which was used in the next step without further purification.

LCMS (method high pH): Retention time 1.25 and 1.27 min, [M+H]$^+$=346 and 348 (1 Br)

Intermediate 6: Methyl 5-bromo-2-(cinnamyloxy)benzoate

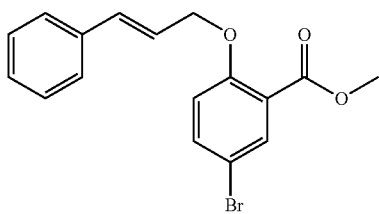 [SMILES: COC(=O)c1cc(Br)ccc1OC/C=C/c1ccccc1]

A flask was charged with methyl 5-bromo-2-hydroxybenzoate (commercially available from, for example, Aldrich, 52.3 g, 226 mmol), potassium carbonate (50.1 g, 362 mmol), potassium iodide (1.879 g, 11.32 mmol) and then was filled with acetone (500 mL). The resulting suspension was treated with (E)-(3-chloroprop-1-en-1-yl)benzene (26.2 mL, 272 mmol) before being stirred at reflux for 6 h. At this stage, potassium carbonate (20.0 g, 145 mmol) and (E)-(3-chloroprop-1-en-1-yl)benzene (12.0 mL, 124 mmol) were added and the mixture was refluxed for 8 h then was cooled to room temperature. The solid residue was filtered off and washed with acetone. The combined organics were concentrated in vacuo.

The solid residue filtered off was partitioned between water and EtOAc and the layers were separated. EtOAc obtained was used to dissolve the residue from the mother liquors (acetone). This organic phase was washed with water then brine, dried over MgSO$_4$ and concentrated in vacuo to give a solid residue which was dried under house vacuum at 40° C. for 16 h to give methyl 5-bromo-2-(cinnamyloxy)benzoate (80 g, 102%) as a yellow solid which was used in the next step without further purification.

LCMS (method high pH): Retention time 1.42 min, [M+H]$^+$=346 and 348 (1 Br)

$^1$H NMR (400 MHz, CDCl$_3$) δ 7.95 (d, J=2.7 Hz, 1H), 7.56 (dd, J=2.4, 8.8 Hz, 1H), 7.39-7.46 (m, 2H), 7.25-7.38 (m, 3H), 6.94 (d, J=9.0 Hz, 1H), 6.81 (d, J=16.1 Hz, 1H), 6.41 (td, J=5.5, 16.1 Hz, 1H), 4.80 (d, J=5.5 Hz, 2H), 3.93 (s, 3H).

Intermediate 7: Methyl 5-bromo-2-hydroxy-3-(1-phenylallyl)benzoate

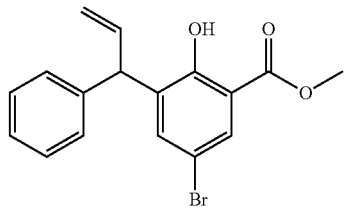 [SMILES: C=CC(c1ccccc1)c1cc(Br)cc(C(=O)OC)c1O]

2 Flasks were charged each with methyl 5-bromo-2-(cinnamyloxy)benzoate (39.5 g, 114 mmol) then filled with N,N-dimethylaniline (250 mL). The resulting solutions were stirred at reflux for 3 h then were cooled to room temperature and combined. The resulting mixture was added to a ice cold mixture of Et$_2$O (1000 mL) and 24-26% w/w HCl aqueous solution (900 mL). Once the addition was complete, EtOAc (500 mL) was added and the layers were separated. The aqueous phase was extracted twice with EtOAc. The combined organics were washed consecutively with a 2N HCl aqueous solution, water then brine, and then were dried over MgSO$_4$ and concentrated in vacuo to give methyl 5-bromo-2-hydroxy-3-(1-phenylallyl)benzoate (72 g, 90%) as a yellow oil which was used in the next step without further purification.

LCMS (method high pH): Retention time 1.57 min, [M+H]$^+$=346 and 348 (1 Br)

Intermediate 8: 5-Bromo-2-hydroxy-N-methyl-3-(1-phenylallyl)benzamide

A solution of methyl 5-bromo-2-hydroxy-3-(1-phenylallyl)benzoate (72.0 g, 207 mmol) in THF (250 mL) at room temperature was treated with methanamine (40% w/w in water, 90 mL, 1.0 mol) and the resulting mixture was stirred at this temperature for 16 h then was concentrated in vacuo. The residue was partitioned between DCM and water and the layers were separated. The aqueous phase was extracted twice with DCM and the combined organics were dried over MgSO₄ and concentrated in vacuo. Purification of the residue by flash chromatography on silica gel (780 g column, gradient (EtOAc in hexanes): 5% (2CV), 5 to 35% (over 10 CV), 35% (5 CV)) gave 5-bromo-2-hydroxy-N-methyl-3-(1-phenylallyl)benzamide (44.6 g, 62%) as a brown foam.

LCMS (method high pH): Retention time 1.26 min, [M+H]⁺=345 and 347 (1 Br)

Intermediate 9: 5-Bromo-2-hydroxy-N-methyl-3-(oxiran-2-yl(phenyl)methyl)benzamide

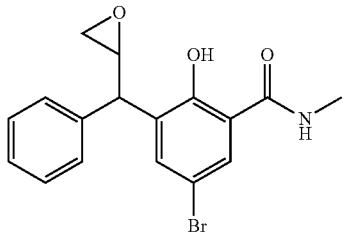 [SMILES: CNC(=O)c1cc(Br)cc(C(c2ccccc2)C2CO2)c1O]

A solution of 5-bromo-2-hydroxy-N-methyl-3-(1-phenylallyl)benzamide (36.6 g, 106 mmol) in DCM (300 mL) at room temperature was treated with mCPBA (<77% w/w, 52.1 g, 211 mmol) and the resulting mixture was stirred at this temperature for 48 h. The mixture was then partitioned between DCM and a mixture of saturated NaHCO₃ aqueous solution (200 mL) and sodium thiosulfate pentahydrate (52.5 g, 211 mmol) in water (100 mL). The biphasic mixture was vigorously stirred for 20 min then the layers were separated. The aqueous phase was extracted twice with DCM and the combined organics were washed three times with a saturated NaHCO₃ aqueous solution, then with water, and then were dried over MgSO₄ and concentrated in vacuo to give 5-bromo-2-hydroxy-N-methyl-3-(oxiran-2-yl(phenyl)methyl)benzamide (1:1 mixture of diastereoisomers, 37.4 g, 98%) as a pale yellow foam which was used in the next step without purification.

LCMS (method high pH): Retention time 1.02 and 1.04 min, [M+H]⁺=362 and 364 (1 Br)

Intermediate 10: (Trans)-5-Bromo-2-(hydroxymethyl)-N-methyl-3-phenyl-2,3-dihydrobenzofuran-7-carboxamide

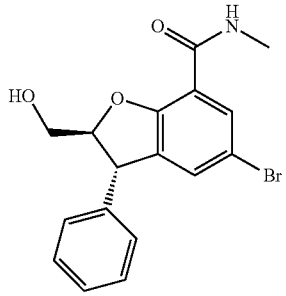 [SMILES: CNC(=O)c1cc(Br)cc2c1O[C@H](CO)[C@H]2c1ccccc1]

A solution of 5-bromo-2-hydroxy-N-methyl-3-(oxiran-2-yl(phenyl)methyl)benzamide (37.4 g, 103 mmol) in DMSO (150 mL) and water (40 mL) was cooled to 0° C. using an ice bath then was treated with an ice-cooled solution of potassium hydroxide (11.6 g, 207 mmol) in water (40 mL). The resulting black solution was stirred at this temperature for 7 h then was left still in a freezer (−20° C.) for 16 h. The mixture was then warmed to 0° C. and stirred for a further 2 h before being treated with acetic acid (13.6 mL, 237 mmol). The mixture was then diluted with water and EtOAc and the layers were separated. The aqueous phase was extracted three times with EtOAc and the combined organics were washed with water then brine, dried over MgSO₄ and concentrated in vacuo. The residue obtained was triturated with Et₂O and the precipitate formed was filtered off, rinsed with Et₂O and dried at 40° C. under house vacuum for 2 h to give (trans)-5-bromo-2-(hydroxymethyl)-N-methyl-3-phenyl-2,3-dihydrobenzofuran-7-carboxamide (25 g, 67%) as a white solid.

LCMS (method high pH): Retention time 1.04 min, [M+H]⁺=362 and 364 (1 Br)

¹H NMR (400 MHz, DMSO-d₆) δ 7.96 (q, J=4.6 Hz, 1H), 7.73 (dd, J=0.7, 2.2 Hz, 1H), 7.15-7.42 (m, 6H), 5.50 (br. s., 1H), 4.82 (ddd, J=3.5, 4.9, 7.1 Hz, 1H), 4.61 (d, J=7.1 Hz, 1H), 3.63-3.82 (m, 2H), 2.86 (d, J=4.6 Hz, 3H).

Intermediate 11: (Trans)-Methyl 2-(hydroxymethyl)-7-(methylcarbamoyl)-3-phenyl-2,3-dihydrobenzofuran-5-carboxylate

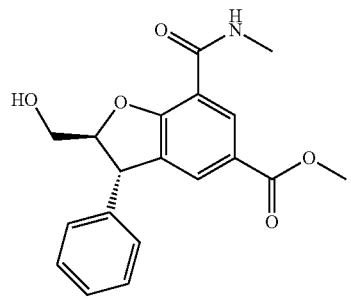 [SMILES: CNC(=O)c1cc(C(=O)OC)cc2c1O[C@H](CO)[C@H]2c1ccccc1]

(Trans)-5-Bromo-2-(hydroxymethyl)-N-methyl-3-phenyl-2,3-dihydrobenzofuran-7-carboxamide (22.5 g, 62.1 mmol) was dissolved in a mixture of DMF (200 mL) and MeOH (100 mL), then Xantphos (3.6 g, 6.2 mmol) was added. The solution was degassed with nitrogen and Pd(OAc)₂ (1.4 g, 6.2 mmol) and Et₃N (26.0 mL, 186 mmol) were added. The mixture was purged with carbon monoxide, then a balloon full of carbon monoxide was fitted and the mixture heated at 70° C. for 16 h. The mixture was cooled to room temperature, diluted with water (600 mL) and then was extracted with EtOAc (2×300 mL). The combined organics were washed with water (2×200 mL), dried over MgSO₄ and concentrated in vacuo Purification of the residue by chromatography on silica gel (340 g column, gradient: 0-25% EtOH in EtOAc) gave (2S*,3S*)-methyl 2-(hydroxymethyl)-7-(methylcarbamoyl)-3-phenyl-2,3-dihydrobenzofuran-5-carboxylate (10.4 g, 49%) as a pale yellow solid.

LCMS (method formic): Retention time 0.89 min, [M+H]⁺=342

¹H NMR (400 MHz, DMSO-d₆) δ 8.34 (d, J=1.2 Hz, 1H), 7.91 (q, J=4.6 Hz, 1H), 7.54-7.58 (m, 1H), 7.24-7.41 (m, 5H), 5.26 (t, J=6.1 Hz, 1H), 4.93 (ddd, J=3.4, 4.6, 7.6 Hz, 1H), 4.65 (d, J=7.6 Hz, 1H), 3.80-3.88 (m, 1H), 3.78 (s, 3H), 3.68-3.76 (m, 1H), 2.89 (d, J=4.6 Hz, 3H).

Intermediate 12: (2S,3S)-Methyl 2-(hydroxymethyl)-7-(methylcarbamoyl)-3-phenyl-2,3-dihydrobenzofuran-5-carboxylate

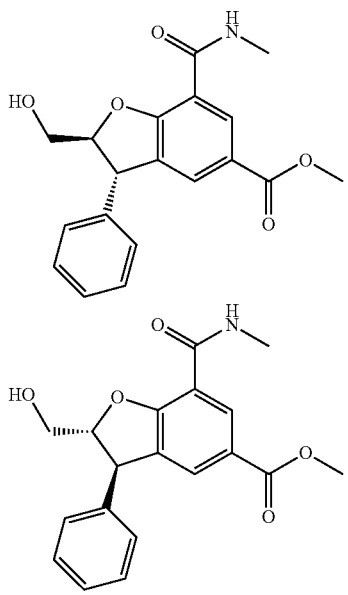

52 g of (Trans)-methyl 2-(hydroxymethyl)-7-(methylcarbamoyl)-3-phenyl-2,3-dihydrobenzofuran-5-carboxylate were dissolved in batches in EtOH, and purified on a Chiralpak IC 30 mm×25 cm column, eluting with 50% EtOH/heptane (200 mg/1.5 mL injection). The first eluting isomer was collected and bulked together to give (2S,3S)-methyl 2-(hydroxymethyl)-7-(methylcarbamoyl)-3-phenyl-2,3-dihydrobenzofuran-5-carboxylate as a pale yellow solid (21.28 g, 82%).

LCMS (method formic): Retention time 0.89 min, [M+H]$^+$=342

Intermediate 13: (2S,3S)-2-(Hydroxymethyl)-7-(methylcarbamoyl)-3-phenyl-2,3-dihydrobenzofuran-5-carboxylic Acid

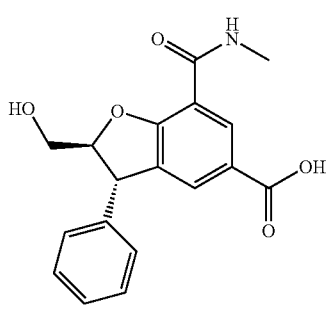 [SMILES: CNC(=O)c1cc(C(=O)O)cc2c1O[C@H](CO)[C@H]2c1ccccc1]

Lithium hydroxide (191 mg, 7.99 mmol) was added to a solution of (2S,3S)-methyl 2-(hydroxymethyl)-7-(methylcarbamoyl)-3-phenyl-2,3-dihydrobenzofuran-5-carboxylate (682 mg, 2.00 mmol) in water (5 mL), THF (5 mL) and MeOH (5 mL) at room temperature. The resulting suspension was stirred 3 h at this temperature then most of the solvent was removed in vacuo. The solid residue was dissolved in a minimum amount of water, and the solution was treated with a 25% w/w HCl aqueous solution (5 mL), forming a thick white suspension. The solid was filtrated over Celite®, washed several times with water and dried under house vacuum to give (2S,3S)-2-(hydroxymethyl)-7-(methylcarbamoyl)-3-phenyl-2,3-dihydrobenzofuran-5-carboxylic acid (700 mg, 107%) which was used in the next step without further purification.

LCMS (method formic): Retention time 0.75 min, [M+H]$^+$=328

Intermediate 14: (2S,3S)-Methyl 2-(iodomethyl)-7-(methylcarbamoyl)-3-phenyl-2,3-dihydrobenzofuran-5-carboxylate

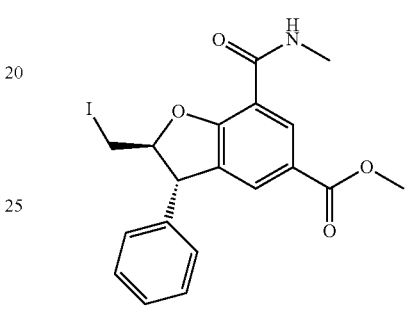

A solution of iodine (178 mg, 0.703 mmol) in DCM (10 mL) under nitrogen was treated with triphenylphosphine (200 mg, 0.762 mmol) and 1H-imidazole (51.9 mg, 0.762 mmol). The resulting suspension was stirred 10 min at room temperature, then was treated with (2S,3S)-methyl 2-(hydroxymethyl)-7-(methylcarbamoyl)-3-phenyl-2,3-dihydrobenzofuran-5-carboxylate (200 mg, 0.586 mmol). The resulting suspension was stirred at room temperature for 14 h then was washed with water (2×10 mL), dried using a phase separator and concentrated in vacuo. Purification of the residue by flash chromatography on silica gel (25 g column, gradient: 0 to 100% EtOAc in hexane) gave (2S,3S)-methyl 2-(iodomethyl)-7-(methylcarbamoyl)-3-phenyl-2,3-dihydrobenzofuran-5-carboxylate (210 mg, 79%) as a colourless solid.

LCMS (method high pH): Retention time 1.23 min, [M+H]$^+$=452

Intermediate 15: (2R,3S)-Methyl 2-methyl-7-(methylcarbamoyl)-3-phenyl-2,3-dihydrobenzofuran-5-carboxylate

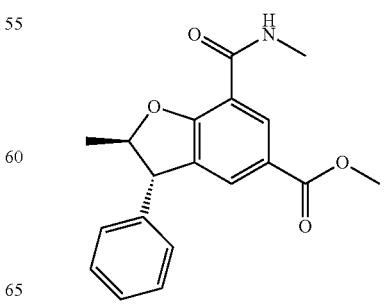

A solution of (2S,3S)-methyl 2-(iodomethyl)-7-(methylcarbamoyl)-3-phenyl-2,3-dihydrobenzofuran-5-carboxylate (220 mg, 0.488 mmol) in MeOH (50 mL), was treated with Et₃N (0.136 mL, 0.975 mmol) and the resulting mixture was hydrogenated in an H-Cube over a Pd/C catcart on full mode at 1 mL/min. The eluant was then concentrated in vacuo. Purification of the residue by flash chromatography on silica gel (25 g column, gradient: 0 to 100% EtOAc in hexane) gave (2R,3S)-methyl 2-methyl-7-(methylcarbamoyl)-3-phenyl-2,3-dihydrobenzofuran-5-carboxylate (89 mg, 56%).

LCMS (method high pH): Retention time 1.15 min, [M+H]⁺=326

Intermediate 16: (2R,3S)-2-Methyl-7-(methylcarbamoyl)-3-phenyl-2,3-dihydrobenzofuran-5-carboxylic Acid

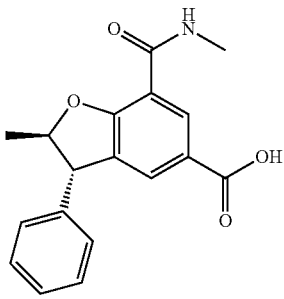

A solution of (2R,3S)-methyl 2-methyl-7-(methylcarbamoyl)-3-phenyl-2,3-dihydrobenzofuran-5-carboxylate (1.4 g, 4.3 mmol) in EtOH (20 mL) was treated at room temperature with a 2N NaOH aqueous solution (10 mL, 20 mmol) and the resulting mixture was stirred at this temperature for 16 h. The solvent was then evaporated to half volume, and the mixture was treated with a 2N HCl aqueous solution (11 mL, 22 mmol) and then was extracted with DCM (2×30 mL). The combined organics were dried using a phase separator and concentrated in vacuo to give (2R,3S)-2-methyl-7-(methylcarbamoyl)-3-phenyl-2,3-dihydrobenzofuran-5-carboxylic acid (1.3 g, 97%) as a colourless solid.

LCMS (method high pH): Retention time 0.69 min, [M+H]⁺=312

Intermediate 17: (2S,3S)-Methyl 2-(fluoromethyl)-7-(methylcarbamoyl)-3-phenyl-2,3-dihydrobenzofuran-5-carboxylate

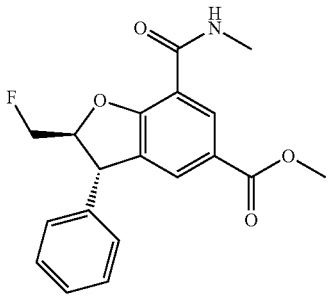 [SMILES: CNC(=O)c1cc(C(=O)OC)cc2c1O[C@H](CI)[C@H]2c1ccccc1]

A solution of (2S,3S)-methyl 2-(hydroxymethyl)-7-(methylcarbamoyl)-3-phenyl-2,3-dihydrobenzofuran-5-carboxylate (3.10 g, 9.08 mmol) in DCM (50 mL) was cooled under nitrogen using an ice bath, then was treated with deoxofluor (8.40 mL, 22.7 mmol) dropwise. The resulting mixture was stirred at 0° C. for 2 h, at 40° C. for 18 h, then was cooled to room temperature. The mixture was diluted with DCM (50 mL) and then cautiously added to a saturated NaHCO₃ aqueous solution (200 mL). The biphasic mixture was stirred for 30 min at room temperature and the layers were separated. The aqueous phase was extracted with DCM (50 mL) and the combined organics were dried over MgSO₄ and concentrated in vacuo. Purification of the residue by chromatography on silica gel (50 g column, gradient: 0 to 100% EtOAc in hexane) gave (2S,3S)-methyl 2-(fluoromethyl)-7-(methylcarbamoyl)-3-phenyl-2,3-dihydrobenzofuran-5-carboxylate (2.2 g, 71%) as a colourless solid.

LCMS (method high pH): Retention time 1.07 min, [M+H]⁺=344

¹H NMR (400 MHz, DMSO-d₆) δ 8.32 (d, J=2.0 Hz, 1H), 7.93 (q, J=4.6 Hz, 1H), 7.57-7.61 (m, 1H), 7.27-7.42 (m, 5H), 5.13-5.27 (m, 1H), 4.97 (dd, J=2.4, 11.0 Hz, 1H), 4.80-4.89 (m, 1H), 4.66-4.76 (m, 1H), 3.79 (s, 3H), 2.88 (d, J=4.6 Hz, 3H)

Intermediate 18: (2S,3S)-2-(Fluoromethyl)-7-(methylcarbamoyl)-3-phenyl-2,3-dihydrobenzofuran-5-carboxylic Acid

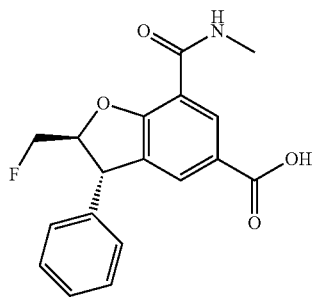 [SMILES: CNC(=O)c1cc(C(=O)O)cc2c1O[C@H](CF)[C@H]2c1ccccc1]

A solution of (2S,3S)-methyl 2-(fluoromethyl)-7-(methylcarbamoyl)-3-phenyl-2,3-dihydrobenzofuran-5-carboxylate (2.2 g, 6.4 mmol) in EtOH (20 mL) and THF (20 mL) at room temperature was treated with a 2N NaOH aqueous solution (10 mL, 20 mmol) and the resulting mixture was stirred at this temperature for 18 h, then was concentrated in vacuo. The residue was dissolved in water (50 mL), and the solution was then acidified with a 2N HCl aqueous solution to pH 2. The resulting mixture was extracted with DCM (2×50 mL) and the combined organics were dried using a phase separator and concentrated in vacuo to give (2S,3S)-2-(fluoromethyl)-7-(methylcarbamoyl)-3-phenyl-2,3-dihydrobenzofuran-5-carboxylic acid (2.1 g, 100%) as a colourless solid, which was used in the next step without further purification.

LCMS (method formic): Retention time 0.91 min, [M+H]⁺=330

¹H NMR (400 MHz, CDCl₃) δ 8.85 (q, J=14.6 Hz, 1H), 7.82-7.85 (m, 1H), 7.31-7.48 (m, 4H), 7.17-7.24 (m, 2H), 5.01-5.12 (m, 1H), 4.87-4.93 (m, 0.5H), 4.73-4.81 (m, 1H), 4.65 (dd, J=5.0, 10.9 Hz, 0.5H), 4.58 (d, J=8.1 Hz, 1H), 3.09 (d, J=4.6 Hz, 3H), OH not seen.

Intermediate 19: (E)-Methyl 3-(3-methoxyphenyl)acrylate

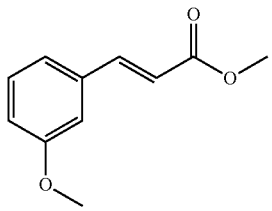

A suspension of methyl 2-(triphenylphosphoranylidene) acetate (36.8 g, 110 mmol) in toluene (300 mL) at room temperature was treated with 3-methoxybenzaldehyde (commercially available from, for example, Aldrich, 12.2 mL, 100 mmol) and the resulting mixture was stirred at 100° C. for 3.5 h then was cooled to room temperature and left still for 60 h. The crystals formed (Ph$_3$PO) were filtered off and most of the solvent was removed in vacuo. The residue was suspended in Et$_2$O and stirred for 30 min. The insolubles (Ph$_3$PO) were filtered off and the organics were concentrated in vacuo. Purification of the residue obtained by flash chromatography on silica gel (330 g column, 20% GLOBAL gradient (AcOEt in hexanes)) gave (E)-methyl 3-(3-methoxyphenyl)acrylate (17.3 g, 90%) as a colourless oil.

LCMS (method high pH): Retention time 1.08 min, [M+H]$^+$=193

Intermediate 20: (E)-3-(3-Methoxyphenyl)prop-2-en-1-ol

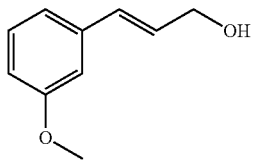

A solution of (E)-methyl 3-(3-methoxyphenyl)acrylate (12.6 g, 65.6 mmol) in toluene (250 mL) at −78° C. under nitrogen was treated with DIBAL-H (25% w/w in toluene, 97 mL, 144 mmol) over 15 min. The solution was stirred at −78° C. for 1 h then at −50° C. for 1 h. The solution was then treated with EtOAc (20 mL) and the resulting mixture was allowed to warm to room temperature after 10 min. The mixture was then added to an aqueous solution of Rochelle's salt (150 g in 400 mL) and the biphasic mixture was vigorously stirred for 2 h then the layers were separated. The aqueous phase was extracted twice with EtOAc and the combined organics were washed with brine, dried over MgSO$_4$ and concentrated in vacuo to give a colourless oil (residue A, 11 g).

In parallel, a second experiment was performed: A solution of (E)-methyl 3-(3-methoxyphenyl)acrylate (4.8 g, 25 mmol) in toluene (100 mL) at −78° C. under nitrogen was treated with DIBAL-H (25% w/w in toluene, 37.0 mL, 55.0 mmol) over 5 min. The solution was stirred at −78° C. for 20 min then at −50° C. for 30 min. The solution was then treated with EtOAc (10 mL) and the resulting mixture was allowed to warm to room temperature after 15 min. The mixture was then added to an aqueous solution of Rochelle's salt (50 g in 150 mL) and the biphasic mixture was vigorously stirred for 2 h then the layers were separated. The aqueous phase was extracted twice with EtOAc and the combined organics were washed with brine, dried over MgSO$_4$ and concentrated in vacuo to give a colourless oil (residue B, 3.96 g).

Residues A and B were combined and purified by flash chromatography on silica gel (100 g column, 50% GLOBAL gradient, EtOAc in hexanes) to give (E)-3-(3-methoxyphenyl)prop-2-en-1-ol (13.85 g, 93%) as a colourless oil.

LCMS (method high pH): Retention time 0.82 min, [M+H]$^+$=165

Intermediate 21: (E)-1-(3-Chloroprop-1-en-1-yl)-3-methylbenzene

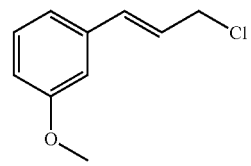

A solution of (E)-3-(3-methoxyphenyl)prop-2-en-1-ol (7.63 g, 46.5 mmol) in EtOH (30 mL) at 0° C. was treated with acetyl chloride (4.96 mL, 69.7 mmol) and the resulting mixture was allowed to warm to room temperature and stirred for 20 h. Acetyl chloride (4.96 mL, 69.7 mmol) was further added at room temperature and the resulting mixture was stirred for 24 h then was concentrated in vacuo. The residue was dissolved in DCM and the organic phase was washed with water, dried using an hydrophobic frit and concentrated in vacuo to give (E)-1-(3-chloroprop-1-en-1-yl)-3-methoxybenzene (8.29 g, 98%) as a pale yellow oil which was used in the next step without further purification.

LCMS (method high pH): Retention time 1.23 min, [M+H]$^+$=183

Intermediate 22: (E)-Methyl 5-bromo-2-((3-(3-methoxyphenyl)allyl)oxy)benzoate

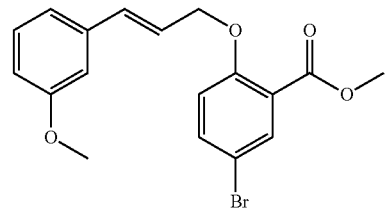 [SMILES: COC(=O)c1cc(Br)ccc1OC/C=C/c1cccc(OC)c1]

A flask was charged with methyl 5-bromo-2-hydroxybenzoate (18.6 g, 80.0 mmol), K$_2$CO$_3$ (16.7 g, 121 mmol) and KI (0.667 g, 4.02 mmol) then was filled with acetone (150 mL) and the resulting suspension was treated with (E)-1-(3-chloroprop-1-en-1-yl)-3-methoxybenzene (14.7 g, 80.0 mmol) in acetone (50 mL and 20 mL rinse). The resulting mixture was refluxed for 9 h then was cooled to room temperature and concentrated in vacuo to give a residue A.

In parallel, a second experiment was performed: A flask was charged with methyl 5-bromo-2-hydroxybenzoate (10.5 g, 45.4 mmol), K$_2$CO$_3$ (9.41 g, 68.1 mmol) and KI (0.377 g, 2.27 mmol) then was filled with acetone (120 mL) and the resulting suspension was treated with (E)-1-(3-chloroprop-1-en-1-yl)-3-methoxybenzene (8.29 g, 45.4 mmol) in acetone (50 mL and 20 mL rinse). The resulting mixture was refluxed for 9 h then was cooled to room temperature and concentrated in vacuo to give a residue B.

Residues A and B were mixed together and partitioned between EtOAc and water and the layers were separated. The aqueous phase was extracted twice with EtOAc and the combined organics were washed with brine, dried over MgSO$_4$ and concentrated in vacuo. Purification of the residue obtained by flash chromatography on silica gel (750 g column, 20% GLOBAL gradient, EtOAc in hexanes) gave (E)-methyl 5-bromo-2-((3-(3-methoxyphenyl)allyl)oxy)benzoate (30 g, 63%) as a pale yellow oil.

LCMS (method high pH): Retention time 1.43 min, [M+H]$^+$=377 and 379 (1 Br)

Intermediate 23: Methyl5-bromo-2-hydroxy-3-(1-(3-methoxyphenyl)allyl)benzoate

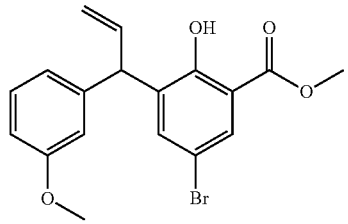 [SMILES: C=CC(c1cccc(OC)c1)c1cc(Br)cc(C(=O)OC)c1O]

A solution of methyl 5-bromo-2-(cinnamyloxy)benzoate (32 g, 92 mmol) in N,N-dimethylaniline (200 mL) was refluxed for 2.5 h then was cooled to room temperature and added over 2 min onto a ice-cold mixture of a HCL aqueous solution (25% w/w, 400 mL) and EtOAc (500 mL). The layers were separated and the aqueous phase was extracted 3 times with EtOAc. The combined organics were washed with brine, dried over MgSO$_4$ and concentrated in vacuo. Purification of the residue obtained by flash chromatography on silica gel (330 g column, 20% GLOBAL gradient, EtOAc in hexanes) gave methyl 5-bromo-2-hydroxy-3-(1-(3-methoxyphenyl)allyl)benzoate (26.3 g, 88%) as a pale yellow oil, which was used in the next step without further purification.

LCMS (method high pH): Retention time 1.57 min, [M+H]$^+$=377 and 379 (1 Br)

Intermediate 24: 5-Bromo-2-hydroxy-3-(1-(3-methoxyphenyl)allyl)-N-methylbenzamide

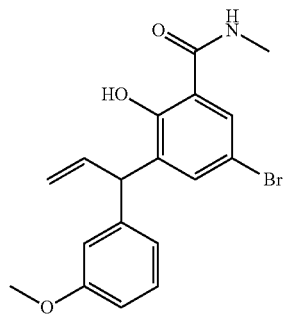

A solution of methyl 5-bromo-2-hydroxy-3-(1-(3-methoxyphenyl)allyl)benzoate (26.3 g, 69.7 mmol) in THF (120 mL) at room temperature was treated with methanamine (40% w/w in water, 30.2 mL, 349 mmol) and the resulting mixture was stirred at this temperature for 16 h then was concentrated in vacuo. The residue was partitioned between EtOAc and water and the layers were separated. The organics were dried over MgSO$_4$ and concentrated in vacuo to give 5-bromo-2-hydroxy-3-(1-(3-methoxyphenyl)allyl)-N-methylbenzamide (26.2 g, 100%) as a pale yellow oil which was used in the next step without further purification.

LCMS (method high pH): Retention time 1.27 min, [M+H]$^+$=376 and 378 (1 Br)

Intermediate 25: 5-Bromo-2-hydroxy-3-((3-methoxyphenyl)(oxiran-2-yl)methyl)-N-methylbenzamide

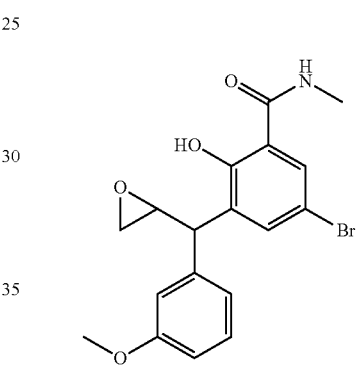

A solution of 5-bromo-2-hydroxy-3-(1-(3-methoxyphenyl)allyl)-N-methylbenzamide (26.2 g, 69.7 mmol) in DCM (400 mL) at room temperature was treated with mCPBA (<77% w/w, 30 g, 122 mmol) and the resulting solution was stirred for 16 h. mCPBA (<77% w/w, 30 g, 122 mmol) was further added and the resulting mixture was stirred for another 16 h. mCPBA (<77% w/w, 15 g, 61 mmol) was added again and the mixture was stirred for 60 h. mCPBA (<77%, 10 g, 40 mmol) was finally added and the mixture was stirred for 24 h at room temperature. The mixture was then treated with a solution of sodium thiosulfate pentahydrate (51.9 g, 209 mmol) and NaHCO$_3$ (17.6 g, 209 mmol) in water (200 mL) and the biphasic mixture was stirred for 15 min then the layers were separated. The aqueous phase was diluted with a saturated NaHCO$_3$ aqueous solution (200 mL) then was extracted twice with DCM. The combined organics were washed with a saturated NaHCO$_3$ aqueous solution then with water, dried over MgSO$_4$ and concentrated in vacuo to give 5-bromo-2-hydroxy-3-((3-methoxyphenyl)(oxiran-2-yl)methyl)-N-methylbenzamide (15.6 g, 57%) as an orange foam which was used in the next step without further purification.

LCMS (method high pH): Retention time 1.03 and 1.05 min, [M+H]$^+$=392 and 394 (1 Br)

Intermediate 26: (Trans)-5-Bromo-2-(hydroxymethyl)-3-(3-methoxyphenyl)-N-methyl-2,3-dihydrobenzofuran-7-carboxamide

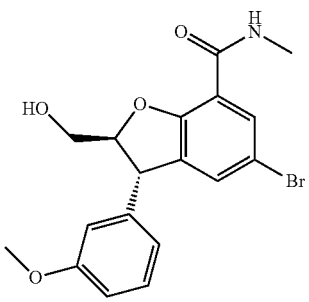

A solution of 5-bromo-2-hydroxy-3-((3-methoxyphenyl)(oxiran-2-yl)methyl)-N-methyl benzamide (7.23 g, 18.4 mmol) in DMSO (40 mL) and water (10 mL) was cooled using an ice bath then was treated by the dropwise addition of KOH (2.07 g, 36.9 mmol) in water (10 mL). The resulting dark red mixture was stirred at this temperature for 7 h then was treated with acetic acid (2.22 mL, 38.7 mmol). A precipitate formed and the mixture was extracted 3 times with EtOAc. The combined organics were washed with brine, dried over MgSO$_4$ and concentrated in vacuo. Purification of the residue by flash chromatography on silica gel (50 g column, 100% GLOBAL gradient (AcOEt in hexanes)) gave (trans)-5-bromo-2-(hydroxymethyl)-3-(3-methoxyphenyl)-N-methyl-2,3-dihydrobenzofuran-7-carboxamide (2.9 g, 40%) as a white foam.

LCMS (method high pH): Retention time 1.05 min, [M+H]$^+$=392 and 394 (1 Br)

Intermediate 27: (Trans)-ethyl 2-(hydroxymethyl)-3-(3-methoxyphenyl)-7-(methylcarbamoyl)-2,3-dihydrobenzofuran-5-carboxylate

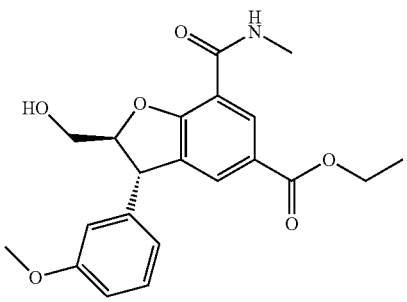 [SMILES: CCOC(=O)c1cc(C(=O)NC)c2c(c1)[C@H](c1cccc(OC)c1)[C@@H](CO)O2]

A solution of (trans)-5-bromo-2-(hydroxymethyl)-3-(3-methoxyphenyl)-N-methyl-2,3-dihydrobenzofuran-7-carboxamide (0.67 g, 1.7 mmol) in DMF (10 mL) and EtOH (10 mL) at room temperature was treated with NEt$_3$ (0.476 mL, 3.42 mmol), Pd(OAc)$_2$ (0.038 g, 0.17 mmol) and Xantphos (0.099 g, 0.17 mmol). The mixture was purged with carbon monoxide, then was stirred at 70° C. under a CO atmosphere (using a balloon) for 2 h, and then was cooled to room temperature and diluted with EtOAc (50 mL). The organic phase was washed with water (2×30 mL), dried over MgSO$_4$ and concentrated in vacuo. Purification of the residue obtained by flash chromatography on silica gel (gradient: 0-25% EtOH in EtOAc) gave (trans)-ethyl 2-(hydroxymethyl)-3-(3-methoxyphenyl)-7-(methylcarbamoyl)-2,3-dihydrobenzofuran-5-carboxylate (370 mg, 56%) as a pale yellow oil.

LCMS (method high pH): Retention time 1.00 min, [M+H]$^+$=386

Intermediate 28: (Trans)-2-(hydroxymethyl)-3-(3-methoxyphenyl)-7-(methylcarbamoyl)-2,3-dihydrobenzofuran-5-carboxylic Acid

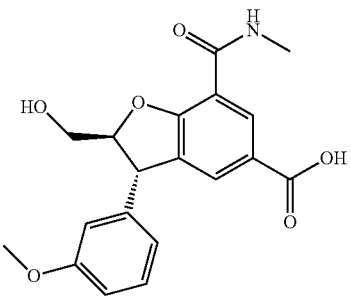 [SMILES: CNC(=O)c1cc(C(=O)O)cc2c1O[C@H](CO)[C@H]2c1cccc(OC)c1]

A solution of (trans)-ethyl 2-(hydroxymethyl)-3-(3-methoxyphenyl)-7-(methylcarbamoyl)-2,3-dihydrobenzofuran-5-carboxylate (360 mg, 0.934 mmol) in EtOH (5 mL) at room temperature was treated with a 2N NaOH aqueous solution (2.33 mL, 4.66 mmol) and the resulting solution was stirred at this temperature for 2 h then was concentrated to approximatively half its original volume and was diluted with water (10 mL). This solution was washed with Et$_2$O (10 mL) then was acidified to pH 2 using a 2N HCl aqueous solution. The precipitate formed was collected by filtration and dried under house vacuum at 40° C. for 16 h to give (trans)-2-(hydroxymethyl)-3-(3-methoxyphenyl)-7-(methylcarbamoyl)-2,3-dihydrobenzofuran-5-carboxylic acid (320 mg, 96%) as a colourless solid.

LCMS (method high pH): Retention time 0.57 min, [M+H]$^+$=358

Intermediate 29: Methyl 5-bromo-2-(prop-2-yn-1-yloxy)benzoate

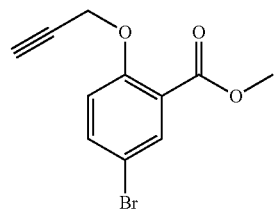

A solution of methyl 5-bromo-2-hydroxybenzoate (25.0 g, 108 mmol) in DMF (100 mL) at room temperature was treated with potassium carbonate (23.9 g, 173 mmol) then 3-bromoprop-1-yne (80% w/w in toluene, 14.0 mL, 130 mmol) and the resulting brown mixture was stirred at this temperature for 16 h. The mixture was then diluted with water (100 mL) and the aqueous phase was extracted three times with Et$_2$O. The combined organics were washed twice with water, dried over MgSO$_4$ and concentrated in vacuo to give a yellow oil which rapidly crystallized. This residue was triturated with Et$_2$O to give methyl 5-bromo-2-(prop-2-yn-1-yloxy)benzoate (13.8 g, 47%) as a white solid. The mother liquors were concentrated in vacuo. A second trituration of the residue obtained with Et₂O/pentane gave methyl 5-bromo-2-(prop-2-yn-1-yloxy)benzoate (9.81 g, 34%) as a very pale yellow solid. The mother liquors were concentrated in vacuo. Purification of the residue obtained by flash chromatography on silica gel (50 g column, 20% GLOBAL gradient (AcOEt in hexanes)) gave methyl 5-bromo-2-(prop-2-yn-1-yloxy)benzoate (3.91 g, 13%) as a yellow solid.

LCMS (method high pH): Retention time 1.12 min, [M+H]⁺=269 and 271 (1 Br)

Intermediate 30: Methyl 5-bromo-2-methylbenzofuran-7-carboxylate

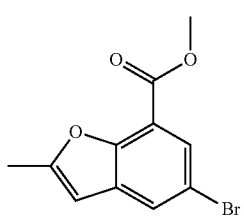

A solution of methyl 5-bromo-2-(prop-2-yn-1-yloxy)benzoate (17.6 g, 65.4 mmol) in DCM (150 mL) at room temperature was treated with (acetonitrile)[(2-biphenyl)di-tert-butylphosphine]gold(I) hexafluoroantimonate (0.759 g, 0.981 mmol) and the resulting mixture was stirred at this temperature for 23 h. (acetonitrile)[(2-biphenyl)di-tert-butylphosphine]gold(I) hexafluoroantimonate (0.100 g, 0.129 mmol) was added and the mixture was stirred for 60 h at room temperature then was concentrated in vacuo to give residue A.

A solution of methyl 5-bromo-2-(prop-2-yn-1-yloxy)benzoate (9.80 g, 36.4 mmol) in DCM (100 mL) at room temperature was treated with (acetonitrile)[(2-biphenyl)di-tert-butylphosphine]gold(I) hexafluoroantimonate (0.422 g, 0.546 mmol) and the resulting mixture was stirred at this temperature for 23 h. (acetonitrile)[(2-biphenyl)di-tert-butylphosphine]gold(I) hexafluoroantimonate (0.100 g, 0.129 mmol) was added and the mixture was stirred for 60 h at room temperature then was concentrated in vacuo to give residue B.

Residues A and B were combined and purified by flash chromatography on silica gel (330 g column, 20% GLOBAL gradient, AcOEt in hexanes) to give methyl 5-bromo-2-methylbenzofuran-7-carboxylate (17.0 g, 62%) as a white solid.

LCMS (method high pH): Retention time 1.26 min, [M+H]⁺=269 and 271 (1 Br)

Intermediate 31: 5-Bromo-2-methylbenzofuran-7-carboxylic Acid

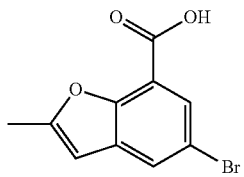

A flask was charged with methyl 5-bromo-2-methylbenzofuran-7-carboxylate (17.0 g, 63.2 mmol) then THF (120 mL) was added followed by MeOH (20 mL). The solution was then treated at room temperature with sodium hydroxide (2N in water, 45 mL, 90 mmol) and the resulting yellow mixture was stirred at this temperature for 2 h then most of the solvent was removed in vacuo. The residue was dissolved in water (100 mL) and the solution was treated with HCl (2N in water, 45 mL, 90 mmol). After 5 min, the white solid formed was filtered off, rinsed with water and dried under house vacuum at 40° C. for 16 h to give 5-bromo-2-methylbenzofuran-7-carboxylic acid (16.92 g, 105%) as a white solid. The aqueous phase was extracted with AcOEt. The organic phase was washed with brine, dried over MgSO₄ and concentrated in vacuo to give 5-bromo-2-methylbenzofuran-7-carboxylic acid (0.443 g, 3%) as a white solid.

LCMS (method high pH): Retention time 0.61 min, [M+H]⁺=255 and 257 (1 Br)

Intermediate 32: 5-Bromo-N,2-dimethylbenzofuran-7-carboxamide

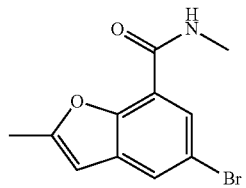

A suspension of 5-bromo-2-methylbenzofuran-7-carboxylic acid (16.1 g, 63.2 mmol) in DCM (200 mL) at 0° C. was treated with DMF (0.400 mL, 5.17 mmol) then with oxalyl chloride (11.1 mL, 126 mmol) dropwise and the mixture was stirred at this temperature for 2 h. DMF (0.400 mL, 5.17 mmol) was added again followed by oxalyl chloride (1.0 mL, 11 mmol). After another 2 h at room temperature, the mixture was concentrated in vacuo. The residue was co-evaporated with toluene then dried under vacuum before being dissolved in DCM (200 mL). The resulting solution was cooled to 0° C. then was treated with DIPEA (16.6 mL, 95.0 mmol) then methanamine (2N in THF, 63.2 mL, 126 mmol). The resulting mixture was stirred for 30 min at this temperature then was dissolved with DCM and washed with water. The layers were separated and the aqueous phase was extracted with DCM. The combined organics were dried over MgSO₄ and concentrated in vacuo to give 5-bromo-N,2-dimethylbenzofuran-7-carboxamide (17.35 g, 102%) as a brown solid which was used in the next step without further purification.

LCMS (method high pH): Retention time 1.03 min, [M+H]⁺=268 and 270 (1 Br)

Intermediate 33: Ethyl 2-methyl-7-(methylcarbamoyl)benzofuran-5-carboxylate

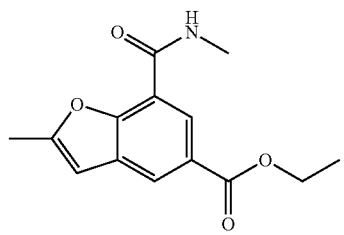 [SMILES: CCOC(=O)c1cc(C(=O)NC)c2oc(C)cc2c1]

A solution of 5-bromo-N,2-dimethylbenzofuran-7-carboxamide (7.00 g, 26.1 mmol) in DMF (50 mL) and EtOH (50 mL) a room temperature was treated with Et₃N (10.9 mL, 78 mmol), and the resulting mixture was degassed with nitrogen then was treated with Xantphos (1.5 g, 2.6 mmol) and Pd(OAc)₂ (0.59 g, 2.6 mmol). The resulting mixture was purged with carbon monoxide, then a balloon full of carbon monoxide was fitted and the mixture was heated at 70° C. for 16 h then was cooled to room temperature. The mixture was then diluted with water (150 mL) and extracted with EtOAc (2×200 mL). The combined organics were washed with water (2×200 mL), dried over MgSO₄ and concentrated in vacuo. Purification of the residue obtained by flash chromatography on silica gel (100 g column, gradient: 0-100% EtOAc in cyclohexane) gave ethyl 2-methyl-7-(methylcarbamoyl)benzofuran-5-carboxylate (5.6 g, 82%) as a colourless solid.

LCMS (method formic): Retention time 0.96 min, [M+H]⁺=262

Intermediate 34: Ethyl 3-bromo-2-methyl-7-(methylcarbamoyl)benzofuran-5-carboxylate

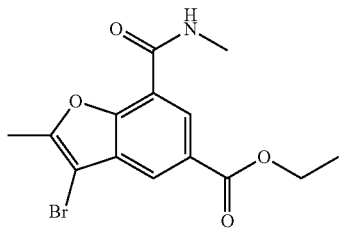 [SMILES: CCOC(=O)c1cc(C(=O)NC)c2oc(C)c(Br)c2c1]

Bromine (1.50 mL, 28.3 mmol) was added at room temperature to a solution of ethyl 2-methyl-7-(methylcarbamoyl)benzofuran-5-carboxylate (7.40 g, 28.3 mmol) in DCM (50 mL) and the resulting mixture was stirred at this temperature under nitrogen for 16 h. Bromine (0.20 mL, 3.8 mmol) was added and the mixture was heated at reflux for 24 h then was cooled to room temperature and added to a 10% w/w aqueous sodium thiosulphate solution (200 mL). The biphasic mixture was vigorously stirred for 20 min, then was diluted with DCM (100 mL) and the layers were separated. The organic phase was washed with water, dried over sodium sulphate and concentrated in vacuo to give ethyl 3-bromo-2-methyl-7-(methylcarbamoyl)benzofuran-5-carboxylate (9.3 g, 97%) as an off white solid which was used in the next step without further purification.

LCMS (method formic): Retention time 1.11 min, [M+H]⁺=340 and 342 (1 Br)

Intermediate 35: Ethyl 3-(3-(benzyloxy)phenyl)-2-methyl-7-(methylcarbamoyl)benzofuran-5-carboxylate

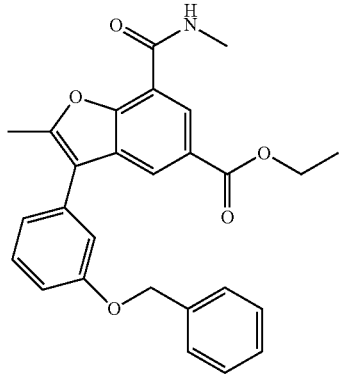 [SMILES: CCOC(=O)c1cc(C(=O)NC)c2oc(C)c(-c3cccc(OCc4ccccc4)c3)c2c1]

A solution of ethyl 3-bromo-2-methyl-7-(methylcarbamoyl)benzofuran-5-carboxylate (140 mg, 0.412 mmol) in THF (2 mL) at room temperature was treated with (3-(benzyloxy)phenyl)boronic acid (113 mg, 0.494 mmol), di((3S,5S,7S)-adamantan-1-yl)(butyl)phosphine (14.8 mg, 0.040 mmol), Pd(OAc)₂ (9.24 mg, 0.0410 mmol) and K₂CO₃ (171 mg, 1.23 mmol) in water (1 mL) and the resulting mixture was stirred at this temperature under nitrogen for 2 h then was diluted with EtOAc (5 mL) and washed with water (5 mL). The organic phase was dried over MgSO₄ and concentrated in vacuo Purification of the residue obtained by flash chromatography on silica gel (10 g column, gradient: 0-100% EtOAc in cyclohexane) gave ethyl 3-(3-(benzyloxy)phenyl)-2-methyl-7-(methylcarbamoyl)benzofuran-5-carboxylate (90 mg, 49%) as a dark brown gum.

LCMS (method formic): Retention time 1.44 min, [M+H]⁺=444

Intermediate 36: Ethyl 3-(3-hydroxyphenyl)-2-methyl-7-(methylcarbamoyl)benzofuran-5-carboxylate

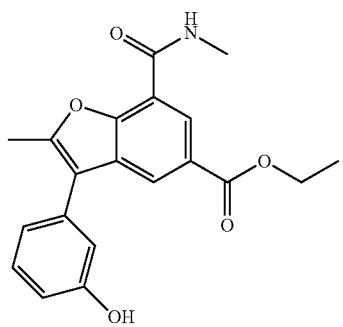 [SMILES: CCOC(=O)c1cc(C(=O)NC)c2oc(C)c(-c3cccc(O)c3)c2c1]

Ethyl 3-(3-(benzyloxy)phenyl)-2-methyl-7-(methylcarbamoyl)benzofuran-5-carboxylate (90 mg, 0.20 mmol) was dissolved in EtOH (30 mL) and hydrogenated in an H-Cube over a Pd/C cartridge at 70 bar and 50° C., using the machine on a loop so that the eluant was added back into the feed flask. After 4 h, the machine was washed through with MeOH and the combined eluant were concentrated in vacuo to give a pale yellow solid. This residue was partitioned between DCM and a 0.5N HCl aqueous solution and the layers were separated. The organic phase was dried using a phase separator and concentrated in vacuo to give ethyl 3-(3-hydroxyphenyl)-2-methyl-7-(methylcarbamoyl)benzofuran-5-carboxylate (0.35 g, 88%) as a pale pink solid which was used in the next step without further purification.

LCMS (method formic): Retention time 1.07 min, [M+H]⁺=354

Intermediate 37: Ethyl 3-(3-(2-hydroxyethoxy)phenyl)-2-methyl-7-(methylcarbamoyl)benzofuran-5-carboxylate

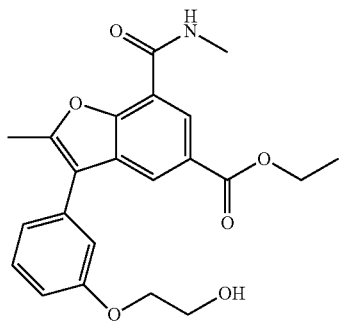 [SMILES: CCOC(=O)c1cc(C(=O)NC)c2oc(C)c(-c3cccc(OCCO)c3)c2c1]

A solution of ethyl 3-(3-hydroxyphenyl)-2-methyl-7-(methylcarbamoyl)benzofuran-5-carboxylate (0.35 g, 0.99 mmol) in DMF (5 mL) at room temperature was treated with 1,3-dioxolan-2-one (0.174 g, 1.98 mmol) and K$_2$CO$_3$ (0.274 g, 1.98 mmol). The resulting mixture was stirred at 80° C. for 2 h then was cooled to room temperature, diluted with water (20 mL) and extracted with EtOAc (20 mL). The layers were separated and the organic phase was washed with water (20 mL), dried over MgSO$_4$ and concentrated in vacuo to give a pale yellow gum. Purification of the residue obtained by flash chromatography on silica gel (25 g column, gradient: 0-100% EtOAc in cyclohexane) gave ethyl 3-(3-(2-hydroxyethoxy)phenyl)-2-methyl-7-(methylcarbamoyl)benzofuran-5-carboxylate (0.32 g, 81%) as a pale yellow gum.

LCMS (method high pH): Retention time 1.05 min, [M+H]$^+$=398

Intermediate 38: (Cis)-Ethyl 3-(3-(2-hydroxyethoxy)phenyl)-2-methyl-7-(methylcarbamoyl)-2,3-dihydrobenzofuran-5-carboxylate

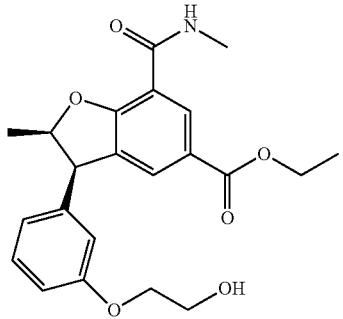 [SMILES: CCOC(=O)c1cc(C(=O)NC)c2c(c1)[C@@H](c1cccc(OCCO)c1)[C@@H](C)O2]

Ethyl 3-(3-(2-hydroxyethoxy)phenyl)-2-methyl-7-(methylcarbamoyl)benzofuran-5-carboxylate (200 mg, 0.503 mmol) was dissolved in MeOH (100 mL) with heating, then the solution was cooled and hydrogenated in an H-Cube at 70 bar and 70° C. eluting at 1 mL/min for 6 h. The eluant was evaporated in vacuo to give (2R*,3R*)-ethyl 3-(3-(2-hydroxyethoxy)phenyl)-2-methyl-7-(methylcarbamoyl)-2,3-dihydrobenzofuran-5-carboxylate (181 mg, 90%) as a colourless solid which was used in the next step without further purification.

LCMS (method high pH): Retention time 0.98 min, [M+H]$^+$=400

Intermediate 39: (Trans)-ethyl 3-(3-(2-hydroxyethoxy)phenyl)-2-methyl-7-(methylcarbamoyl)-2,3-dihydrobenzofuran-5-carboxylate

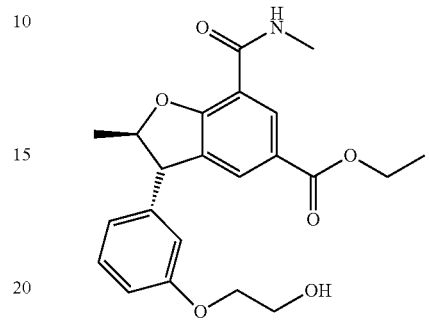

A solution of (2R*,3R*)-ethyl 3-(3-(2-hydroxyethoxy)phenyl)-2-methyl-7-(methylcarbamoyl)-2,3-dihydrobenzofuran-5-carboxylate (45 mg, 0.11 mmol) in DMF (2 mL) at room temperature was treated with DBU (0.051 mL, 0.34 mmol) and the resulting mixture was stirred at 90° C. for 1 h then was cooled to room temperature and concentrated in vacuo. Purification of the residue by MDAP (method high pH) gave (2R*,3S*)-ethyl 3-(3-(2-hydroxyethoxy)phenyl)-2-methyl-7-(methylcarbamoyl)-2,3-dihydrobenzofuran-5-carboxylate (19 mg, 42%) as a colourless gum.

LCMS (method high pH): Retention time 1.00 min, [M+H]$^+$=400

Intermediate 39 (Alternative Procedure): (Trans)-Ethyl 3-(3-(2-hydroxyethoxy)phenyl)-2-methyl-7-(methylcarbamoyl)-2,3-dihydrobenzofuran-5-carboxylate

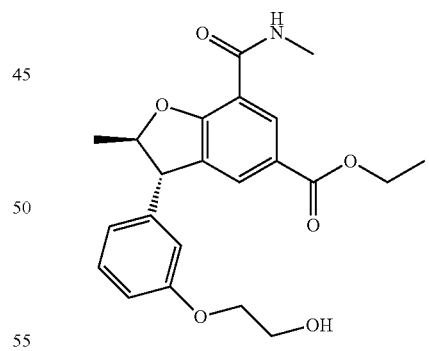

A solution of ethyl 3-(3-hydroxyphenyl)-2-methyl-7-(methylcarbamoyl)-2,3-dihydrobenzofuran-5-carboxylate (90 mg, 0.25 mmol) in DMF (3 mL) at room temperature was treated with K$_2$CO$_3$ (70.0 mg, 0.506 mmol) and 1,3-dioxolan-2-one (66.9 mg, 0.760 mmol) and the resulting mixture was stirred at 80° C. for 4 h, then was cooled to room temperature and allowed to stand still for 60 h. The mixture was then diluted with water (10 mL) and the aqueous phase was extracted with EtOAc (2×10 mL). The combined organics were washed with brine (10 mL), dried over MgSO$_4$ and concentrated in vacuo. Purification of the residue obtained by MDAP (method high pH) gave (2R*, 3S*)-ethyl 3-(3-(2-hydroxyethoxy)phenyl)-2-methyl-7-(methylcarbamoyl)-2,3-dihydrobenzofuran-5-carboxylate (13 mg, 13%).

LCMS (method high pH): Retention time 1.02 min, [M+H]$^+$=400

Intermediate 40: (cis)-Ethyl 3-(3-hydroxyphenyl)-2-methyl-7-(methylcarbamoyl)-2,3-dihydrobenzofuran-5-carboxylate

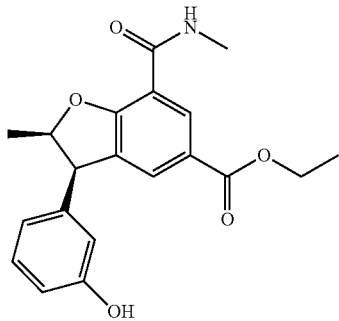 [SMILES: CCOC(=O)c1cc(C(=O)NC)c2c(c1)[C@@H](c1cccc(O)c1)[C@@H](C)O2]

A solution of ethyl 3-(3-(benzyloxy)phenyl)-2-methyl-7-(methylcarbamoyl)benzofuran-5-carboxylate (90 mg, 0.20 mmol) in EtOH (30 mL) was hydrogenated in an H-Cube over a Pd/C cartridge at 70 bar and 50° C., using the machine on a loop so that the eluant was added back into the feed flask. After 4 h, the machine was washed through with MeOH and the combined eluant were concentrated in vacuo to give (2R*,3R*)-ethyl 3-(3-hydroxyphenyl)-2-methyl-7-(methylcarbamoyl)-2,3-dihydrobenzofuran-5-carboxylate (75 mg, 104%) as a pale yellow solid which was used in the next step without purification.

LCMS (method high pH): Retention time 1.01 min, [M+H]$^+$=356

Intermediate 41: (trans)-3-(3-(2-Hydroxyethoxy)phenyl)-2-methyl-7-(methylcarbamoyl)-2,3-dihydrobenzofuran-5-carboxylic Acid

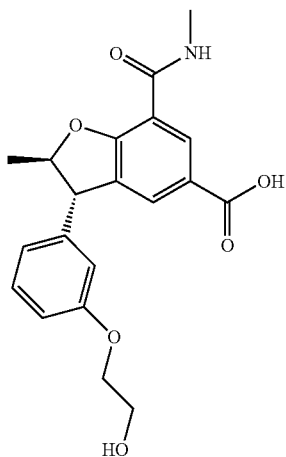 [SMILES: CNC(=O)c1cc(C(=O)O)cc2c1O[C@H](C)[C@H]2c1cccc(OCCO)c1]

A solution of (2R*,3S*)-ethyl 3-(3-(2-hydroxyethoxy)phenyl)-2-methyl-7-(methylcarbamoyl)-2,3-dihydrobenzofuran-5-carboxylate (120 mg, 0.150 mmol) in EtOH (1.5 mL) at room temperature was treated with NaOH (2N in water, 0.075 mL, 0.15 mmol) and the resulting solution was stirred at this temperature for 3 h after which EtOH (1 mL) was added. The mixture was stirred at room temperature for 2 h then was treated with NaOH (2N in water, 0.075 mL, 0.150 mmol). The resulting mixture was stirred at room temperature for 1 h then EtOH (1 mL) was added. The reaction mixture was then stirred at room temperature for 16 h then was treated with NaOH (2N in water, 0.150 mL, 0.300 mmol). The reaction mixture was then stirred at room temperature for 3 h then was concentrated in vacuo. The residue was dissolved in water (3 mL) and the aqueous phase was acidified with a 2N HCl aqueous solution to pH 3 and the precipitate formed was filtered off. The filtrate was extracted with EtOAc (3×20 mL) and the combined organics were dried via a hydrophobic frit and concentrated in vacuo. The residue obtained from the extraction was combined with the precipitate to give (trans)-3-(3-(2-hydroxyethoxy)phenyl)-2-methyl-7-(methylcarbamoyl)-2,3-dihydrobenzofuran-5-carboxylic acid (67 mg, 60%), as a white solid which was used in the next step without further purification.

LCMS (method formic): Retention time 0.81 min, [M+H]$^+$=372

Intermediate 42: ((Trans)-5-(Cyclopropylcarbamoyl)-3-(3-methoxyphenyl)-7-(methylcarbamoyl)-2,3-dihydrobenzofuran-2-yl)methyl Methanesulfonate

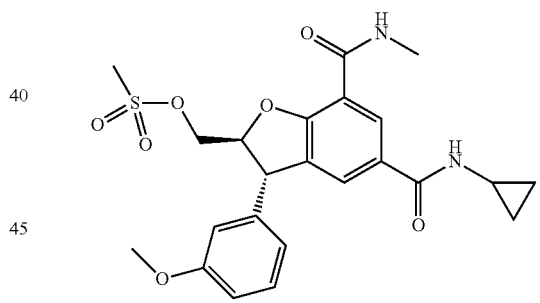

A solution of (2S*,3S*)—N$^5$-cyclopropyl-2-(hydroxymethyl)-3-(3-methoxyphenyl)-N$^7$-methyl-2,3-dihydrobenzofuran-5,7-dicarboxamide (80 mg, 0.20 mmol) and Et$_3$N (0.042 mL, 0.30 mmol) in DCM (5 mL) at room temperature was treated with MsCl (0.024 mL, 0.30 mmol) and the resulting mixture was stirred at this temperature for 2 h, then was washed with water (5 mL), dried using an hydrophobic frit and concentrated in vacuo to give ((trans)-5-(cyclopropylcarbamoyl)-3-(3-methoxyphenyl)-7-(methylcarbamoyl)-2,3-dihydrobenzofuran-2-yl)methyl methanesulfonate (90 mg, 94%) as a colourless gum which was used in the next step without further purification.

LCMS (method high pH): Retention time 1.01 min, [M+H]$^+$=475

Intermediate 43: (2S,3S)-Ethyl 2-(hydroxymethyl)-3-(3-methoxyphenyl)-7-(methylcarbamoyl)-2,3-dihydrobenzofuran-5-carboxylate

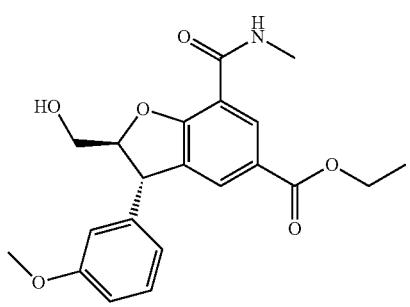 [SMILES: CCOC(=O)c1cc(C(=O)NC)c2c(c1)[C@H](c1cccc(OC)c1)[C@@H](CI)O2]

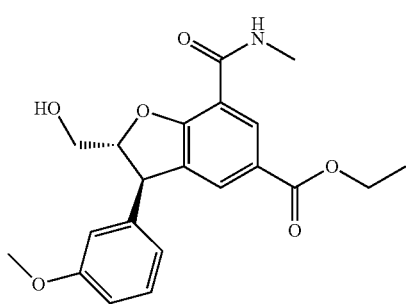

3.9 g of (trans)-ethyl 2-(hydroxymethyl)-3-(3-methoxyphenyl)-7-(methylcarbamoyl)-2,3-dihydrobenzofuran-5-carboxylate were purified by chiral chromatography to deliver the two enantiomers:

Analytical method: Approximately 0.5 mg of material were dissolved in 50% EtOH in heptane (1 mL). Injection: 20 uL of solution were injected on column, eluting with 40% EtOH (+0.2% isopropylamine) in heptane, flow=1.0 mL/min, wavelength 215 nm. Column 4.6 mmid×25 cm Chiralpak IC.

Preparative method: Approximatively 250 mg of material were dissolved in EtOH (2 mL, with heating). Injections (18 in total); 2 mL of the solution was injected onto the column, eluting with 40% EtOH (+0.2% isopropylamine) in heptane (+0.2% isopropylamine), flow=30 mL/min, wavelength 215 nm. Column 30 mm×25 cm Chiralpak IC (5 um)

This purification gave (2S,3S)-ethyl 2-(hydroxymethyl)-3-(3-methoxyphenyl)-7-(methylcarbamoyl)-2,3-dihydrobenzofuran-5-carboxylate (1.47 g, 75%) as the fast running enantiomer and (2R,3R)-ethyl 2-(hydroxymethyl)-3-(3-methoxyphenyl)-7-(methylcarbamoyl)-2,3-dihydrobenzofuran-5-carboxylate (1.38 g, 71%) as slow running enantiomer.

LCMS (method high pH): Retention time 1.00 min, [M+H]$^+$=386

Intermediate 44: (2S,3S)-Ethyl 2-(iodomethyl)-3-(3-methoxyphenyl)-7-(methylcarbamoyl)-2,3-dihydrobenzofuran-5-carboxylate

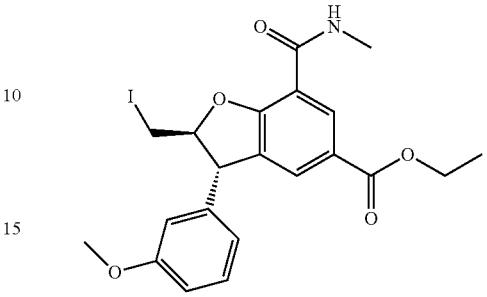

A solution of iodine (1.26 g, 4.96 mmol) in DCM (30 mL) at room temperature was treated with 1H-imidazole (0.519 g, 7.63 mmol) and triphenylphosphine (1.30 g, 4.96 mmol) and the resulting mixture was stirred at this temperature for 30 min. (2S,3S)-Ethyl 2-(hydroxymethyl)-3-(3-methoxyphenyl)-7-(methylcarbamoyl)-2,3-dihydrobenzofuran-5-carboxylate (1.47 g, 3.81 mmol) was then added to the solution. The resulting mixture was stirred at room temperature for 16 h, then was washed with water (30 mL), dried using an hydrophobic frit and concentrated in vacuo. Purification of the residue by flash chromatography on silica gel (50 g column, gradient: 0-60% EtOAc in cyclohexane) gave (2S,3S)-ethyl 2-(iodomethyl)-3-(3-methoxyphenyl)-7-(methylcarbamoyl)-2,3-dihydrobenzofuran-5-carboxylate (1.5 g, 79%) as a colourless solid.

LCMS (method high pH): Retention time 1.28 min, [M+H]$^+$=496

Intermediate 45: (2R,3S)-Ethyl 3-(3-methoxyphenyl)-2-methyl-7-(methylcarbamoyl)-2,3-dihydrobenzofuran-5-carboxylate

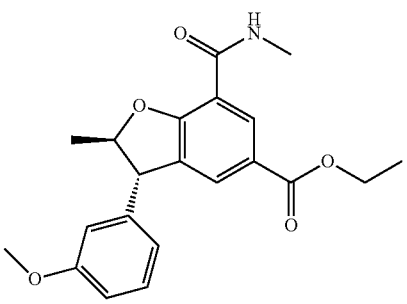 [SMILES: CCOC(=O)c1cc(C(=O)NC)c2c(c1)[C@H](c1cccc(OC)c1)[C@@H](C)O2]

A solution of (2S,3S)-ethyl 2-(iodomethyl)-3-(3-methoxyphenyl)-7-(methylcarbamoyl)-2,3-dihydrobenzofuran-5-carboxylate (1.4 g, 2.8 mmol) in EtOAc (50 mL) and MeOH (50 mL) was treated with Et$_3$N (0.394 mL, 2.83 mmol) and the resulting solution was hydrogenated in an H-cube at atmospheric pressure eluting at 1 mL/min. The eluant was concentrated in vacuo and the residue obtained was purified by flash chromatography on silica gel (25 g column, gradient: 0-100% EtOAc in cyclohexane) to give (2R,3S)-ethyl 3-(3-methoxyphenyl)-2-methyl-7-(methylcarbamoyl)-2,3-dihydrobenzofuran-5-carboxylate (0.95 g, 91%) as a colourless solid.

LCMS (method high pH): Retention time 1.21 min, [M+H]⁺=370

Intermediate 46: (2R,3S)-3-(3-Methoxyphenyl)-2-methyl-7-(methylcarbamoyl)-2,3-dihydrobenzofuran-5-carboxylic Acid

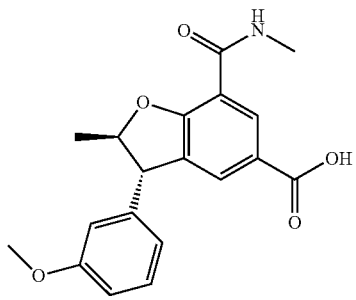 [SMILES: CNC(=O)c1cc(C(=O)O)cc2c1O[C@H](C)[C@H]2c1cccc(OC)c1]

A solution of (2R,3S)-ethyl 3-(3-methoxyphenyl)-2-methyl-7-(methylcarbamoyl)-2,3-dihydrobenzofuran-5-carboxylate (0.90 g, 2.4 mmol) in EtOH (10 mL) at room temperature was treated with a 2N NaOH aqueous solution (5.0 mL, 10 mmol) and the resulting mixture was stirred at this temperature for 16 h then was concentrated in vacuo. The residue was dissolved in water (10 mL), and the aqueous phase was acidified with a 2N HCl aqueous solution (pH 2), and then was extracted with DCM (20 mL). The organic phase was dried using an hydrophobic frit and concentrated in vacuo to give (2R,3S)-3-(3-methoxyphenyl)-2-methyl-7-(methylcarbamoyl)-2,3-dihydrobenzofuran-5-carboxylic acid (750 mg, 90%) as a colourless foam.

LCMS (method high pH): Retention time 0.69 min, [M+H]⁺=342

Intermediate 47: (1R,5S,6R)-3-Oxabicyclo[3.1.0]hexane-6-carboxylic Acid

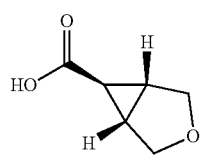

Lithium hydroxide (751 mg, 31.4 mmol) was added at room temperature to a solution of (1R,5S,6r)-ethyl 3-oxabicyclo[3.1.0]hexane-6-carboxylate (1.00 g, 6.27 mmol, commercially available from, for example, Pharmablock) in water (10 mL), THF (10 mL) and MeOH (10 mL). The resulting suspension was stirred 3 h at this temperature then was concentrated in vacuo. The residue was dissolved in a minimum amount of water, and treated with hydrochloric acid (5 mL, 25% w/w in water). The aqueous phase was extracted 4 times with MeOH/DCM and the combined organic phases were dried over a hydrophobic frit, concentrated in vacuo, to give (1R,5S,6r)-3-oxabicyclo[3.1.0]hexane-6-carboxylic acid (750 mg, 93%) which was used in the next step without further purification.

¹H NMR (400 MHz, DMSO-d₆) δ ppm 12.13 (s, 1H) 3.80 (d, J=8.6 Hz, 2H) 3.62 (d, J=8.6 Hz, 2H) 2.00-2.15 (m, 2H) 1.32 (t, J=3.1 Hz, 1H)

Intermediate 48: Benzyl (1R,5S,6R)-3-oxabicyclo[3.1.0]hexan-6-ylcarbamate

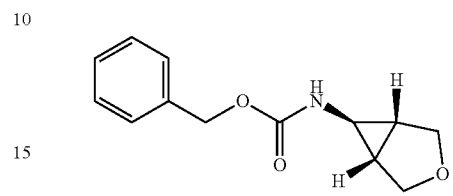

A solution of (1R,5S,6r)-3-Oxabicyclo[3.1.0]hexane-6-carboxylic acid (340 mg, 2.65 mmol) in toluene (12 mL) at room temperature was treated with NEt₃ (1.11 mL, 7.96 mmol), diphenyl phosphorazidate (0.686 mL, 3.18 mmol) and benzyl alcohol (0.552 mL, 5.31 mmol) and the resulting mixture was heated at reflux for 2 h then was cooled to room temperature. The solution was diluted with EtOAc (10 mL) and washed with water (10 mL) and a saturated NaHCO₃ aqueous solution (10 mL). The organic phase was dried and evaporated and the residue purified by chromatography on a 25 g silica column eluting with 0-50% EtOAc/cyclohexane and the product-containing fractions were evaporated in vacuo to give benzyl (1R,5S,6r)-3-oxabicyclo[3.1.0]hexan-6-ylcarbamate (460 mg, 74%) as a white solid.

LCMS (Formic): Retention time 0.83 min, [M+H]⁺=234.3.

Intermediate 49: (1R,5S,6R)-3-Oxabicyclo[3.1.0]hexan-6-amine, Hydrochloride

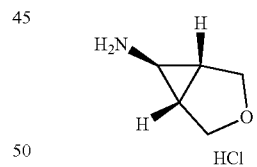

Benzyl (1R,5S,6r)-3-oxabicyclo[3.1.0]hexan-6-ylcarbamate (460 mg, 1.97 mmol) was dissolved in EtOH (20 mL) and the reaction was hydrogenated using an H-cube (settings: room temperature, 1 bar, 1 mL/min flow rate) and 10% Pd/C CatCart 30 as the catalyst. The reaction was cycled though the H-Cube for 1.5 h before acidifying the mixture with HCl (7M aqueous, 1.33 mL, 9.86 mmol) and evaporating in vacuo to yield an oily solid. The solid was dried in vacuo over 2 days to yield the desired product (1R,5S,6r)-3-oxabicyclo[3.1.0]hexan-6-amine, hydrochloride (262 mg, 93%) as an off-white solid.

¹H NMR (400 MHz, DMSO-d6) δ ppm 8.48 (br. s., 3H) 3.80 (d, J=8.8 Hz, 2H) 3.59 (d, J=8.6 Hz, 2H) 2.24 (t, J=2.3 Hz, 1H) 2.07 (t, J=2.6 Hz, 2H).

Intermediate 50: (+/−)-Ethyl 2-(4-benzylmorpholin-2-yl)acetate

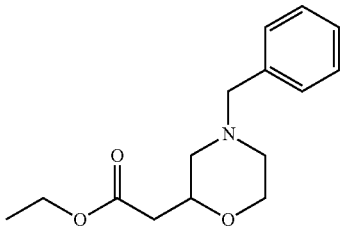 [SMILES: CCOC(=O)CC1CN(Cc2ccccc2)CCO1]

A mixture of 2-(benzylamino)ethanol (6.57 mL, 46.3 mmol, commercially available from, for example, Sigma-Aldrich) and NEt$_3$ (6.45 mL, 46.3 mmol) in water (40 mL) was heated to 105° C. (E)-Ethyl 4-bromobut-3-enoate (8.50 mL, 49.4 mmol, commercially available from, for example, Fluorochem) was added dropwise and the reaction mixture was heated at 105° C. for 2 h. The reaction mixture was cooled to room temperature and sodium hydroxide (2N solution in water, 10 mL, 20 mmol) was added. The reaction mixture was partitioned between ethyl acetate and water. The layers were separated and the aqueous phase was further extracted with ethyl acetate (2×30 mL). The combined organic layers were dried (Na$_2$SO$_4$) and concentrated in vacuo to give ~11 g of brown oil. This was purified by chromatography on SiO$_2$ (Biotage SNAP 340 g cartridge, eluting with 5-50% ethyl acetate/cyclohexane). The appropriate fractions were combined and concentrated in vacuo to give the desired product (4.17 g, 29%) as a pale yellow oil.

LCMS (method formic): Retention time 0.43 min, [M+H]$^+$=264.2.

Intermediate 51: (+/−)-Ethyl 2-(morpholin-2-yl)acetate

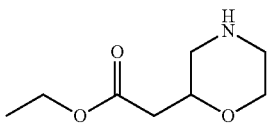

To a solution of ethyl 2-(4-benzylmorpholin-2-yl)acetate (3.15 g, 12.0 mmol) in EtOH (70 mL) was added ammonium formate (3.77 g, 59.8 mmol) and 10% Pd/C (3.82 g, 35.9 mmol). The reaction mixture was stirred at room temperature under N$_2$ for 16 h.

Separately, to a solution of ethyl 2-(4-benzylmorpholin-2-yl)acetate (375 mg, 1.42 mmol) in EtOH (10 mL) was added ammonium formate (449 mg, 7.12 mmol) and 10% Pd/C (555 mg, 5.21 mmol). The reaction mixture was stirred at room temperature under N$_2$ for 16 h.

The two reaction mixtures were combined and filtered though Celite®. The filtrate was concentrated in vacuo to give ethyl 2-(morpholin-2-yl)acetate (2.45 g) as an off-white gummy solid which was used as is in subsequent reactions.

$^1$H NMR (400 MHz, DMSO-d$_6$) δ ppm 4.05 (q, J=7.1 Hz, 2H) 3.67-3.82 (m, 2H) 3.46 (td, J=11.3, 2.8 Hz, 1H) 2.87 (br. d, J=12.2 Hz, 1H) 2.75 (br. d, J=12.5 Hz, 1H) 2.60-2.70 (m, 1H) 2.40-2.48 (m, 2H) 2.34 (dd, J=15.7, 8.6 Hz, 1H) 1.17 (t, J=7.1 Hz, 3H)

Intermediate 52: (+/−)-tert-Butyl 2-(2-ethoxy-2-oxoethyl)morpholine-4-carboxylate

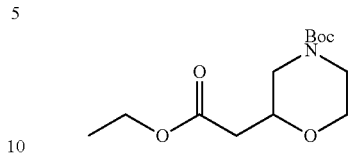

To a solution of ethyl 2-(morpholin-2-yl)acetate (2.45 g, 14.1 mmol) in DCM (30 mL) was added Et$_3$N (3.94 mL, 28.3 mmol), Boc-anhydride (4.93 mL, 21.2 mmol) and DMAP (0.086 g, 0.71 mmol) and the reaction mixture stirred under N$_2$ at room temperature for 16 h. The reaction mixture was partitioned between DCM and a 1N HCl aqueous solution. The layers were separated, the organic phase was washed with a saturated NaHCO$_3$ aqueous solution, dried (Na$_2$SO$_4$) and then concentrated in vacuo to give (+/−)-tert-Butyl 2-(2-ethoxy-2-oxoethyl)morpholine-4-carboxylate (3.03 g, 85%) as an orange oil.

$^1$H NMR (400 MHz, MeOH-d$_4$) δ ppm 4.14 (q, J=7.1 Hz, 2H) 3.95 (dt, J=13.0, 1.9 Hz, 1H) 3.71-3.87 (m, 3H) 3.49 (td, J=11.7, 2.8 Hz, 1H) 2.86-3.00 (m, 1H) 2.60-2.77 (m, 1H) 2.49 (dd, J=6.6, 1.5 Hz, 2H) 1.47 (s, 9H) 1.25 (t, J=7.1 Hz, 3H)

Intermediate 53: (+/−)-tert-Butyl 2-(2-hydroxyethyl)morpholine-4-carboxylate

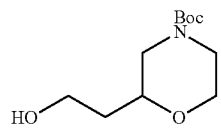 [SMILES: CC(C)(C)OC(=O)N1CCOC(CCO)C1]

tert-Butyl 2-(2-ethoxy-2-oxoethyl)morpholine-4-carboxylate (2.8 g, 10 mmol) was dissolved in THF (50 mL) and LiBH$_4$ (0.893 g, 41.0 mmol) was added, then the mixture was stirred at room temperature for 65 h. The reaction mixture was cooled in an ice bath and quenched with a saturated ammonium chloride aqueous solution (50 mL), then stirred for 1 h and extracted with EtOAc (2×100 mL). The combined organics were dried over sodium sulphate and evaporated in vacuo to give tert-butyl 2-(2-hydroxyethyl)morpholine-4-carboxylate (2.2 g, 93%) as a colourless gum.

$^1$H NMR (400 MHz, CDCl$_3$) δ ppm 3.74-4.02 (m, 5H) 3.44-3.65 (m, 2H) 2.84-3.01 (m, 1H) 2.56-2.76 (m, 1H) 1.63-1.83 (m, 2H) 1.47 (s, 9H)

Intermediate 54: (+/−)-tert-Butyl 2-(2-((methylsulfonyl)oxy)ethyl)morpholine-4-carboxylate

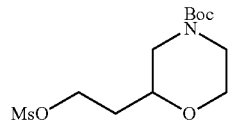 [SMILES: CC(C)(C)OC(=O)N1CCOC(CCOS(C)(=O)=O)C1]

MsCl (0.815 mL, 10.5 mmol) was added to a solution of tert-butyl 2-(2-hydroxyethyl)morpholine-4-carboxylate (2.2 g, 9.5 mmol) and Et₃N (1.458 mL, 10.46 mmol) in DCM (50 mL) at 0° C. The resulting mixture was stirred at 0° C. for 1 h, then washed with water (50 mL). The organic layer was dried using an hydrophobic frit and evaporated in vacuo to give tert-butyl 2-(2-((methylsulfonyl)oxy)ethyl)morpholine-4-carboxylate (3.0 g, 102%) as a pale yellow gum which was used in the next step without further purification.

¹H NMR (400 MHz, CDCl₃) δ ppm 4.30-4.44 (m, 2H) 3.78-4.00 (m, 3H) 3.45-3.57 (m, 2H) 3.01 (s, 3H) 2.85-2.98 (m, 1H) 2.56-2.72 (m, 1H) 1.78-1.98 (m, 2H) 1.47 (s, 9H)

Intermediate 55: (+/−)-tert-Butyl 2-(2-cyanoethyl)morpholine-4-carboxylate

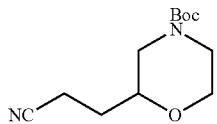 [SMILES: CC(C)(C)OC(=O)N1CCOC(CCC#N)C1]

tert-Butyl 2-(2-((methylsulfonyl)oxy)ethyl)morpholine-4-carboxylate (3.0 g, 9.7 mmol) was dissolved in DMSO (30 mL), then KI (1.61 g, 9.70 mmol) and KCN (0.947 g, 14.5 mmol) were added and the mixture was heated at 80° C. for 1 h then cooled to room temperature. The resulting brown suspension was diluted with water (100 mL) and extracted with EtOAc (2×50 mL). The combined organics were washed with water (2×100 mL), dried and evaporated in vacuo and the resulting oil was purified on a 50 g silica column eluting with 0-50% EtOAc/cyclohexane. The product-containing fractions (visualised by ninhydrin) were combined and evaporated in vacuo to give tert-butyl 2-(2-cyanoethyl)morpholine-4-carboxylate (1.42 g, 61%) as a colourless oil.

¹H NMR (400 MHz, CDCl₃) δ ppm 3.80-4.00 (m, 3H) 3.39-3.58 (m, 2H) 2.83-3.01 (m, 1H) 2.56-2.71 (m, 1H) 2.50 (t, J=7.2 Hz, 2H) 1.69-1.87 (m, 2H) 1.47 (s, 9H)

Intermediate 56: (+/−)-tert-Butyl 2-(3-aminopropyl)morpholine-4-carboxylate

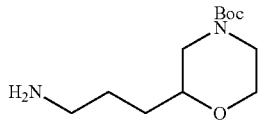 [SMILES: CC(C)(C)OC(=O)N1CCOC(CCCN)C1]

tert-Butyl 2-(2-cyanoethyl)morpholine-4-carboxylate (1.40 g, 5.83 mmol) was dissolved in THF (20 mL) and borane.THF (1M in THF, 23.30 mL, 23.30 mmol) was added, then the mixture was heated at 70° C. for 2 h. The solution was then cooled in an ice bath and quenched by the cautious addition of MeOH (20 mL) (effervescence) then evaporated in vacuo. The residue was dissolved in MeOH (20 mL), acetic acid (2 mL) was added and the solution was stirred for 2 h, then evaporated in vacuo and the residue was purified by chromatography on a 25 g silica column eluting with 0-15% 2N methanolic ammonia/DCM to give two main ninhydrin-active components. The more polar component was collected to give tert-butyl 2-(3-aminopropyl)morpholine-4-carboxylate (180 mg, 13%) as a colourless oil. The earlier running component was suspected to be a borane complex. This was collected and evaporated in vacuo to give a colourless oil (0.20 g). The material was dissolved in methanol (10 mL) and a 2N NaOH aqueous solution (10 mL), then the mixture was stirred at reflux for 6 h, then cooled to room temperature and evaporated in vacuo and the residue partitioned between water (10 mL) and DCM (10 mL). The organic layer was dried and evaporated in vacuo to give a colourless oil, which was purified by chromatography on a 10 g snap ultra cartridge, eluting with 0-20% 2N methanolic ammonia/DCM to give further desired product (100 mg)

¹H NMR (400 MHz, CDCl₃) δ ppm 3.70-3.97 (m, 3H) 3.44-3.55 (m, 1H) 3.26-3.40 (m, 1H) 2.92 (br. t, J=10.8, 10.8 Hz, 1H) 2.67-2.77 (m, 2H) 2.49-2.66 (m, 1H) 1.39-1.68 (m, 13H).

Intermediate 57: (S)-tert-Butyl 2-(3-ethoxy-3-oxo-prop-1-en-1-yl)morpholine-4-carboxylate, 77:23 Mix of E/Z Isomers

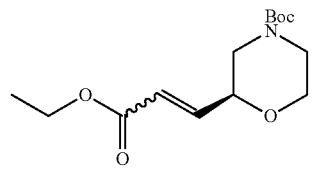 [SMILES: CCOC(=O)C=C[C@H]1CN(C(=O)OC(C)(C)C)CCO1]

(R)-tert-Butyl 2-(hydroxymethyl)morpholine-4-carboxylate (0.50 g, 2.3 mmol, commercially available from, for example, Activate Scientific) was dissolved in DCM (10 mL) and Dess-Martin periodinane (1.17 g, 2.76 mmol) was added, then the solution was stirred at room temperature for 2 h. The mixture was washed with a saturated sodium bicarbonate aqueous solution (20 mL) and the organic layer dried and evaporated to give a colourless solid—NMR shows presence of desired aldehyde. The crude intermediate was dissolved in toluene (20 mL) and ethyl 2-(triphenylphosphoranylidene)acetate (1.04 g, 2.99 mmol) was added, then the mixture was heated at 90° C. for 16 h before being cooled to room temperature. The resulting suspension was filtered and the filtrate washed with water, then the organic layer was dried and evaporated in vacuo. The residue was purified by chromatography on a 25 g silica column eluting with 0-50% EtOAc/cyclohexane and product-containing fractions were evaporated in vacuo to give (S)-tert-butyl 2-(3-ethoxy-3-oxoprop-1-en-1-yl)morpholine-4-carboxylate (0.45 g, 69%) as a colourless gum and as a mixture of Z and E isomers which was used in the next step.

¹H NMR (400 MHz, CDCl₃) δ ppm 6.83 (dd, J=15.8, 4.3 Hz, 1H) 6.06-6.18 (m, 1.3H) 5.87 (dd, J=11.7, 1.5 Hz, 0.3H) 4.15-4.30 (m, 2.6H) 3.78-4.12 (m, 5.2H) 3.51-3.65 (m, 1.3H) 2.97 (br. t, J=10.6, 10.6 Hz, 1.3H) 2.56-2.77 (m, 1.3H) 1.48 (s, 11.7H) 1.22-1.36 (m, 3.9H)

Intermediate 58: (S)-tert-Butyl 2-(3-ethoxy-3-oxopropyl)morpholine-4-carboxylate

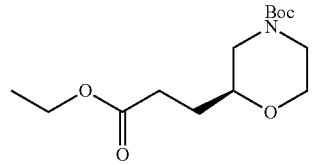 [SMILES: CCOC(=O)CC[C@H]1CN(C(=O)OC(C)(C)C)CCO1]

(S)-tert-Butyl 2-(3-ethoxy-3-oxoprop-1-en-1-yl)morpholine-4-carboxylate (0.450 g, 1.58 mmol) was dissolved in EtOH (50 mL) and hydrogenated in an H-Cube on full mode using a Pd/C cat cart at 1 mL/min flow rate. The eluant was evaporated in vacuo to give (S)-tert-butyl 2-(3-ethoxy-3-oxopropyl)morpholine-4-carboxylate (0.40 g, 88%) as a colourless gum.

¹H NMR (400 MHz, CDCl₃) δ ppm 4.14 (q, J=7.3 Hz, 2H) 3.74-3.98 (m, 3H) 3.48 (td, J=11.7, 2.8 Hz, 1H) 3.36 (dddd, J=10.4, 7.8, 4.8, 2.7 Hz, 1H) 2.92 (br. t, J=11.1, 11.1 Hz, 1H) 2.60 (br. t, J=9.5, 9.5 Hz, 1H) 2.35-2.53 (m, 2H) 1.70-1.86 (m, 2H) 1.47 (s, 9H) 1.26 (t, J=7.1 Hz, 3H)

Intermediate 59: (S)-tert-Butyl 2-(3-hydroxypropyl)morpholine-4-carboxylate

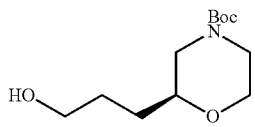 [SMILES: CC(C)(C)OC(=O)N1CCO[C@@H](CCCO)C1]

LiBH₄ (0.121 g, 5.57 mmol) was added to a solution of (S)-tert-butyl 2-(3-ethoxy-3-oxopropyl)morpholine-4-carboxylate (0.40 g, 1.39 mmol) in THF (10 mL) at 0° C., then the mixture was stirred for 16 h, allowing it to warm to room temperature. The reaction mixture was quenched by the very cautious addition of a saturated ammonium chloride aqueous solution (20 mL) and extracted with EtOAc (2×20 mL). The combined organics were dried and evaporated in vacuo to give (S)-tert-butyl 2-(3-hydroxypropyl)morpholine-4-carboxylate (0.30 g, 88%).

¹H NMR (400 MHz, CDCl₃) δ ppm 3.73-3.99 (m, 3H) 3.58-3.69 (m, 2H) 3.49 (td, J=11.7, 2.8 Hz, 1H) 3.30-3.40 (m, 1H) 2.91 (br. t, J=10.8, 10.8 Hz, 1H) 2.49-2.68 (m, 1H) 2.16-2.40 (m, 1H) 1.62-1.76 (m, 2H) 1.48-1.60 (m, 2H) 1.45 (s, 9H)

Intermediate 60: (S)-tert-Butyl 2-(3-((methylsulfonyl)oxy)propyl)morpholine-4-carboxylate

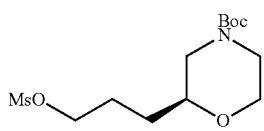 [SMILES: CC(C)(C)OC(=O)N1CCO[C@@H](CCCOS(C)(=O)=O)C1]

(S)-tert-Butyl 2-(3-hydroxypropyl)morpholine-4-carboxylate (0.30 g, 1.22 mmol) was dissolved in DCM (10 mL) and Et₃N (0.256 mL, 1.83 mmol) and Ms-Cl (0.124 mL, 1.59 mmol) were added. The solution was stirred for 2 h, then washed with water and the organic layer dried and evaporated in vacuo to give (S)-tert-butyl 2-(3-((methylsulfonyl)oxy)propyl)morpholine-4-carboxylate (0.39 g, 99%) which was used in the next step immediately.

¹H NMR (400 MHz, CDCl₃) δ ppm 4.20-4.33 (m, 2H) 3.76-3.97 (m, 3H) 3.44-3.57 (m, 1H) 3.30-3.41 (m, 1H) 3.01 (s, 3H) 2.84-2.97 (m, 1H) 2.53-2.67 (m, 1H) 1.78-2.01 (m, 2H) 1.53-1.61 (m, 2H) 1.47 (s, 9H)

Intermediate 61: (S)-tert-Butyl 2-(3-azidopropyl)morpholine-4-carboxylate

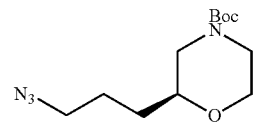 [SMILES: CC(C)(C)OC(=O)N1CCO[C@@H](CCCN=[N+]=[N-])C1]

(S)-tert-Butyl 2-(3-((methylsulfonyl)oxy)propyl)morpholine-4-carboxylate (0.39 g, 1.2 mmol) was dissolved in DMF (5 mL) and sodium azide (0.235 g, 3.62 mmol) was added, then the mixture was heated at 80° C. for 2 h. The mixture was cooled to room temperature and diluted with water (20 mL) and extracted with EtOAc (20 mL), the organic layer was washed with water (2×10 mL), dried and evaporated in vacuo to give (S)-tert-butyl 2-(3-azidopropyl)morpholine-4-carboxylate (300 mg, 92%) as a colourless gum. The crude product was carried on to the next step without purification.

1H NMR (400 MHz, CDCl₃) δ ppm 3.74-3.99 (m, 3H) 3.49 (td, J=11.7, 2.8 Hz, 1H) 3.24-3.40 (m, 3H) 2.85-3.00 (m, 1H) 2.49-2.68 (m, 1H) 1.61-1.85 (m, 2H) 1.45-1.58 (m, 11H)

Intermediate 62: (S)-tert-Butyl 2-(3-aminopropyl)morpholine-4-carboxylate

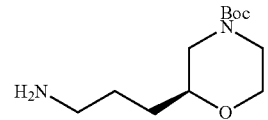 [SMILES: CC(C)(C)OC(=O)N1CCO[C@@H](CCCN)C1]

(S)-tert-Butyl 2-(3-azidopropyl)morpholine-4-carboxylate (300 mg, 1.11 mmol) was dissolved in EtOH (30 mL) and was hydrogenated in an H-Cube on full mode at 1 mL/min flow rate over a Pd/C cat cart. The eluant was evaporated in vacuo to give (S)-tert-butyl 2-(3-aminopropyl)morpholine-4-carboxylate (190 mg, 70%) which was used in subsequent chemistry.

¹H NMR (400 MHz, CDCl₃) δ ppm 3.73-3.99 (m, 3H) 3.44-3.57 (m, 1H) 3.27-3.40 (m, 1H) 2.84-3.00 (m, 1H) 2.73 (t, J=6.7 Hz, 2H) 2.51-2.65 (m, 1H) 1.38-1.67 (m, 13H)

Intermediate 63: (R,E)-tert-Butyl 2-(3-ethoxy-3-oxoprop-1-en-1-yl)morpholine-4-carboxylate

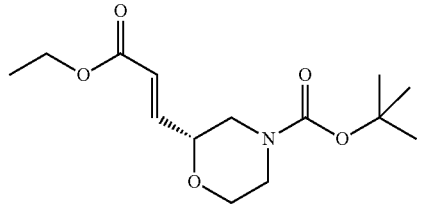 [SMILES: CCOC(=O)/C=C/[C@@H]1CN(C(=O)OC(C)(C)C)CCO1]

(S)-tert-Butyl 2-(hydroxymethyl)morpholine-4-carboxylate (5.0 g, 23 mmol, commercially available from, for example, AOK Chem) was dissolved in DCM (10 mL) and Dess-Martin periodinane (11.7 g, 27.6 mmol) was added, then the solution was stirred at room temperature for 2 h.

The mixture was washed with a saturated sodium bicarbonate aqueous solution (20 mL) and the organic layer dried and evaporated to give a colourless solid. NMR shows the presence of the desired aldehyde. The crude intermediate was dissolved in toluene (20 mL) and ethyl 2-(triphenylphosphoranylidene)acetate (10.4 g, 29.9 mmol) was added, then the mixture was heated at 90° C. for 16 h and then was cooled to room temperature. The resulting suspension was filtered and the filtrate washed with water, then the organic layer was dried and evaporated in vacuo. The residue was purified by chromatography on a 25 g silica column eluting with 0-50% EtOAc/cyclohexane and product-containing fractions were evaporated in vacuo to give (R,E)-tert-butyl 2-(3-ethoxy-3-oxoprop-1-en-1-yl)morpholine-4-carboxylate (1.9 g, 29%) as a colourless gum.

$^1$H NMR (400 MHz, CDCl$_3$) δ ppm 6.84 (dd, J=15.9, 4.2 Hz, 1H) 6.02-6.24 (m, 1H) 4.15-4.34 (m, 2H) 4.02-4.12 (m, 1H) 3.80-3.99 (m, 2H) 3.49-3.67 (m, 1H) 2.98 (t, J=10.6 Hz, 1H) 2.70 (br. s., 1H) 1.49 (s, 9H) 1.26-1.36 (m, 4H)

Intermediate 64: (R)-tert-Butyl 2-(3-ethoxy-3-oxopropyl)morpholine-4-carboxylate

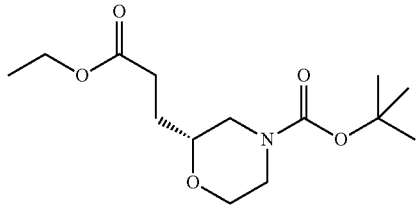 [SMILES: CCOC(=O)CC[C@@H]1CN(C(=O)OC(C)(C)C)CCO1]

(R,E)-tert-Butyl 2-(3-ethoxy-3-oxoprop-1-en-1-yl)morpholine-4-carboxylate (1.8 g, 6.3 mmol) was dissolved in EtOH (60 mL) and hydrogenated in an H-Cube on full mode at 1 mL/min flow rate over a Pd/C cat cart. The eluant was evaporated in vacuo to give (R)-tert-butyl 2-(3-ethoxy-3-oxopropyl)morpholine-4-carboxylate (1.7 g, 94%) as a colourless gum.

$^1$H NMR (400 MHz, CDCl$_3$) δ ppm 4.14 (q, J=7.1 Hz, 2H), 3.73-3.95 (m, 3H), 3.43-3.53 (m, 1H), 3.26-3.40 (m, 1H), 2.86-2.97 (m, 1H), 2.56-2.65 (m, 1H), 2.44 (spt, J=7.5 Hz, 2H), 1.72-1.82 (m, 2H), 1.44-1.48 (m, 9H), 1.26 (t, J=7.1 Hz, 3H).

Intermediate 65: (R)-tert-Butyl 2-(3-hydroxypropyl)morpholine-4-carboxylate

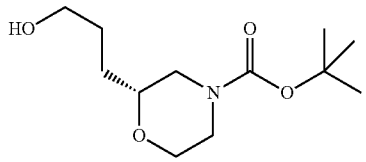 [SMILES: CC(C)(C)OC(=O)N1CCO[C@H](CCCO)C1]

LiBH$_4$ (0.121 g, 5.57 mmol) was added to a solution of (S)-tert-butyl 2-(3-ethoxy-3-oxopropyl)morpholine-4-carboxylate (0.400 g, 1.39 mmol) in THF (10 mL) at 0° C., then the mixture was stirred for 16 h, allowing it to warm to room temperature. The reaction mixture was quenched by very cautious addition of a saturated ammonium chloride aqueous solution (20 mL) and extracted with EtOAc (2×20 mL). The combined organics were dried and evaporated in vacuo to give (S)-tert-butyl 2-(3-hydroxypropyl)morpholine-4-carboxylate (0.30 g, 88%).

$^1$H NMR (400 MHz, CDCl$_3$-d) δ ppm 5.32 (s, 1H) 3.88 (br. s., 3H) 3.75-3.80 (m, 1H) 3.67 (br. d, J=2.2 Hz, 1H) 3.53 (td, J=11.0, 3.0 Hz, 1H) 3.34-3.43 (m, 1H) 2.88-2.99 (m, 1H) 2.57-2.68 (m, 1H) 1.71 (q, J=6.6 Hz, 2H) 1.53-1.62 (m, 2H) 1.48 (s, 9H)

Intermediate 66: (R)-tert-Butyl 2-(3-(methylsulfonyl)oxy)propyl)morpholine-4-carboxylate

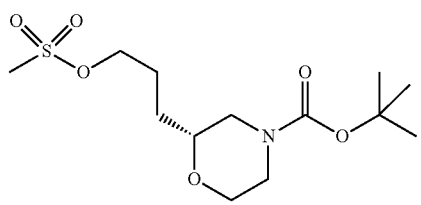 [SMILES: CC(C)(C)OC(=O)N1CCO[C@H](CCCOS(C)(=O)=O)C1]

(R)-tert-Butyl 2-(3-hydroxypropyl)morpholine-4-carboxylate (1.34 g, 5.46 mmol) was dissolved in DCM (10 mL) and Et$_3$N (1.14 mL, 8.19 mmol) and MsCl (0.553 mL, 7.10 mmol) were added. The solution was stirred for 2 h at room temperature, then washed with water and the organic layer dried and evaporated in vacuo to give a pale yellow oil. This was purified by chromatography on a 50 g silica column, eluting with 0-100% EtOAc/cyclohexane and the product-containing fractions were evaporated in vacuo to give (R)-tert-butyl 2-(3-((methylsulfonyl)oxy)propyl)morpholine-4-carboxylate (1.22 g, 69%).

$^1$H NMR (400 MHz, CDCl$_3$-d) δ ppm 4.21-4.35 (m, 2H) 3.76-3.95 (m, 3H) 3.45-3.55 (m, 1H) 3.32-3.41 (m, 1H) 3.02 (s, 3H) 2.84-2.97 (m, 1H) 2.55-2.66 (m, 1H) 1.91-2.02 (m, 1H) 1.78-1.90 (m, 1H) 1.52-1.65 (m, 2H) 1.48 (s, 9H)

Intermediate 67: (R)-tert-Butyl 2-(3-azidopropyl)morpholine-4-carboxylate

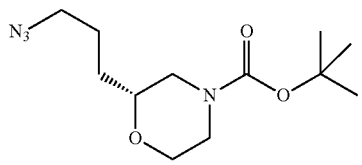 [SMILES: CC(C)(C)OC(=O)N1CCO[C@H](CCCN=[N+]=[N-])C1]

(R)-tert-Butyl 2-(3-((methylsulfonyl)oxy)propyl)morpholine-4-carboxylate (1.2 g, 3.7 mmol) was dissolved in DMF (5 mL) and sodium azide (0.724 g, 11.1 mmol) was added, then the mixture was heated at 80° C. for 2 h before being cooled to room temperature. The mixture was diluted with water (20 mL) and extracted with EtOAc (20 mL). The organic layer was washed with water (2×10 mL), dried and evaporated in vacuo to give (R)-tert-butyl 2-(3-azidopropyl)morpholine-4-carboxylate (0.96 g, 96%) as a colourless gum.

¹H NMR (400 MHz, CDCl₃) δ ppm 4.12 (q, J=7.3 Hz, 1H) 3.74-3.97 (m, 3H) 3.49 (td, J=11.7, 2.8 Hz, 1H) 3.20-3.41 (m, 2H) 2.89-2.95 (m, 1H) 2.59 (br. s., 1H) 1.60-1.85 (m, 2H) 1.49-1.56 (m, 2H) 1.47 (s, 9H)

Intermediate 68: (R)-tert-Butyl 2-(3-aminopropyl)morpholine-4-carboxylate

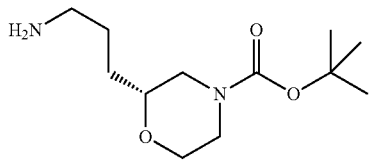 [SMILES: CC(C)(C)OC(=O)N1CCO[C@H](CCCN)C1]

(R)-tert-Butyl 2-(3-azidopropyl)morpholine-4-carboxylate (0.96 g, 3.5 mmol) was dissolved in EtOH (30 mL) and was hydrogenated in the H-Cube on full mode at 1 mL/min flow rate over a Pd/C cat cart. The eluant was evaporated in vacuo to give (R)-tert-butyl 2-(3-aminopropyl)morpholine-4-carboxylate (0.81 g, 93%).

¹H NMR (400 MHz, CDCl₃) δ ppm 3.70-4.00 (m, 3H), 3.41-3.56 (m, 1H), 3.23-3.40 (m, 2H), 2.79-3.12 (m, 2H), 2.47-2.69 (m, 1H), 1.80-1.98 (m, 1H), 1.25-1.72 (m, 12H).

Intermediate 69: 1-tert-Butyl 3-ethyl 3-fluoropiperidine-1,3-dicarboxylate

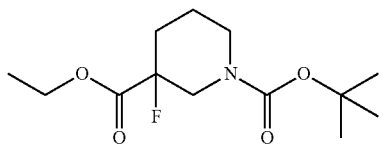 [SMILES: CCOC(=O)C1(F)CCCN(C(=O)OC(C)(C)C)C1]

1-tert-Butyl 3-ethyl piperidine-1,3-dicarboxylate (5.0 g, 19 mmol, commercially available form, for example, Sigma Aldrich) in THF (20 mL) was added dropwise to a solution of lithium bis(trimethylsilyl)amide (1N in THF, 38.9 mL, 38.9 mmol) in THF (20 mL) at −78° C. under nitrogen, then the solution was allowed to warm to −20° C. over 1 h, then recooled to −78° C. A solution of N-fluoro-N-(phenylsulfonyl)benzenesulfonamide (12.2 g, 38.9 mmol) in THF (30 mL) was added dropwise, then the mixture was stirred for 2 h, allowing it to warm gradually to room temperature. The reaction mixture was quenched with a saturated ammonium chloride aqueous solution (100 mL) and extracted with EtOAc (100 mL). The organic layer was washed with 1N NaOH aqueous solution (100 mL) and brine, then dried and evaporated to give a yellow oil. The crude product was dissolved in DCM and loaded onto a 50 g silica column, then eluted with 0-50% EtOAc/cyclohexane to give 1-tert-butyl 3-ethyl 3-fluoropiperidine-1,3-dicarboxylate (3.5 g, 65%) as a colourless oil.

¹H NMR (400 MHz, CDCl₃) δ ppm 4.27 (q, J=7.3 Hz, 2H) 3.17-3.44 (m, 1H) 2.70-2.92 (m, 1H) 1.98-2.21 (m, 2H) 1.78-1.96 (m, 2H) 1.60-1.72 (m, 2H) 1.45-1.51 (m, 9H) 1.33 (s, 3H)

Intermediate 70: tert-Butyl 3-fluoro-3-(hydroxymethyl)piperidine-1-carboxylate

1-tert-Butyl 3-ethyl 3-fluoropiperidine-1,3-dicarboxylate (3.50 g, 12.7 mmol) was dissolved in THF (50 mL) and LiBH₄ (0.831 g, 38.1 mmol) was added, then the mixture was stirred for 4 h at room temperature. A saturated ammonium chloride aqueous solution (50 mL) was added, initially very cautiously, dropwise, then the mixture was stirred for 20 min before extraction with EtOAc (2×100 mL). The combined organics were dried over sodium sulphate and evaporated in vacuo to give tert-butyl 3-fluoro-3-(hydroxymethyl)piperidine-1-carboxylate (2.2 g, 74%) as a colourless oil.

¹H NMR (400 MHz, CDCl₃) δ ppm 3.54-3.74 (m, 3H) 1.92 (br. s., 2H) 1.72-1.82 (m, 2H) 1.58-1.62 (m, 1H) 1.51-1.57 (m, 2H) 1.48 (s, 9H)

Intermediate 71: (E)-tert-Butyl 3-(3-ethoxy-3-oxoprop-1-en-1-yl)-3-fluoropiperidine-1-carboxylate

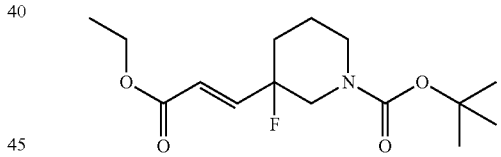

tert-Butyl 3-fluoro-3-(hydroxymethyl)piperidine-1-carboxylate (2.2 g, 9.4 mmol) was dissolved in DCM (60 mL) and Dess-Martin periodinane (4.80 g, 11.3 mmol) was added and the mixture was stirred at room temperature for 18 h, then washed with water and the organic layer dried over sodium sulphate and decanted into a clean, dry flask. Ethyl 2-(triphenylphosphoranylidene)acetate (4.93 g, 14.1 mmol) was added and the mixture was stirred for 16 h, then washed with water and the organic layer dried and evaporated in vacuo. The residue was purified on a 50 g silica column, eluting with 0-50% EtOAc/cyclohexane and the product-containing fractions were evaporated in vacuo to give (E)-tert-butyl 3-(3-ethoxy-3-oxoprop-1-en-1-yl)-3-fluoropiperidine-1-carboxylate (2.2 g, 77%) as a colourless oil.

¹H NMR (400 MHz, CDCl₃) δ ppm 6.89 (dd, J=19.4, 15.8 Hz, 1H) 6.15 (d, J=15.9 Hz, 1H) 4.22 (q, J=7.1 Hz, 2H) 3.76-4.13 (m, 2H) 3.01-3.29 (m, 1H) 2.90-3.01 (m, 1H) 1.63-2.01 (m, 4H) 1.54-1.62 (m, 2H) 1.45-1.52 (m, 10H) 1.31 (t, J=7.1 Hz, 3H)

Intermediate 72: tert-Butyl 3-(3-ethoxy-3-oxopropyl)-3-fluoropiperidine-1-carboxylate

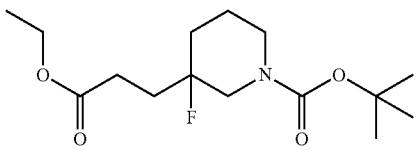 [SMILES: CCOC(=O)CCC1(F)CCCN(C(=O)OC(C)(C)C)C1]

(E)-tert-Butyl 3-(3-ethoxy-3-oxoprop-1-en-1-yl)-3-fluoropiperidine-1-carboxylate (2.00 g, 6.64 mmol) was dissolved in EtOH (50 mL) and hydrogenated over 5% Pd/C at atmospheric pressure for 16 h. The mixture was then filtered though Celite under nitrogen and the filtrate evaporated in vacuo to give tert-butyl 3-(3-ethoxy-3-oxopropyl)-3-fluoropiperidine-1-carboxylate (2.0 g, 99%) as a colourless oil. NMR showed a significant amount of remaining starting material, therefore the crude product was dissolved in EtOH (50 mL) and hydrogenated in the H-Cube on full mode over a Pd/C cartridge. The eluant was evaporated in vacuo to give a colourless oil. NMR showed some remaining starting material and the solution was hydrogenated in the H-Cube again, then the eluant was evaporated in vacuo to give tert-butyl 3-(3-ethoxy-3-oxopropyl)-3-fluoropiperidine-1-carboxylate (2.0 g, 99%).

$^1$H NMR (400 MHz, CDCl$_3$) δ ppm 4.14 (q, J=6.9 Hz, 2H) 3.70-3.99 (m, 2H) 2.91-3.24 (m, 2H) 2.47 (t, J=7.9 Hz, 2H) 1.71-2.04 (m, 4H) 1.42-1.66 (m, 11H) 1.26 (t, J=7.1 Hz, 3H).

Intermediate 73: tert-Butyl 3-fluoro-3-(3-hydroxypropyl)piperidine-1-carboxylate

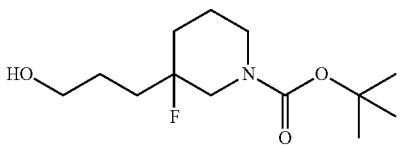 [SMILES: CC(C)(C)OC(=O)N1CCCC(F)(CCCO)C1]

LiBH$_4$ (0.431 g, 19.78 mmol) was added to a solution of tert-butyl 3-(3-ethoxy-3-oxopropyl)-3-fluoropiperidine-1-carboxylate (2.0 g, 6.6 mmol) in THF (30 mL) at room temperature under nitrogen and the mixture was stirred for 16 h, then quenched by very cautious, initially dropwise addition of a saturated ammonium chloride aqueous solution (50 mL). The mixture was stirred vigorously for 30 min, then extracted with EtOAc (2×50 mL) and the combined organics dried and evaporated in vacuo to give a colourless oil. This was dissolved in DCM and loaded onto a 50 g silica column, then eluted with 0-100% EtOAc/cyclohexane and the product-containing fractions were then evaporated in vacuo to give tert-butyl 3-fluoro-3-(3-hydroxypropyl)piperidine-1-carboxylate (1.6 g, 93%) as a colourless oil.

$^1$H NMR (400 MHz, CDCl$_3$-d) δ ppm 3.59-3.93 (m, 4H) 2.93-3.17 (m, 2H) 1.86-2.01 (m, 1H) 1.48-1.85 (m, 9H) 1.43-1.48 (m, 9H)

Intermediate 74: tert-Butyl 3-fluoro-3-(3-((methylsulfonyl)oxy)propyl)piperidine-1-carboxylate

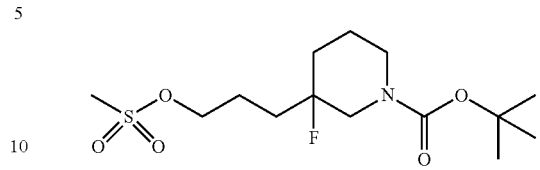

tert-Butyl 3-fluoro-3-(3-hydroxypropyl)piperidine-1-carboxylate (1.6 g, 6.1 mmol) was dissolved in DCM (50 mL) and Et$_3$N (1.28 mL, 9.18 mmol) was added, then the mixture was stirred at room temperature for 2 h. The solvent was washed with water (20 mL), dried and evaporated in vacuo to give the product (2.5 g, 120%) as a yellow oil which was used in the next step without further purification.

$^1$H NMR (400 MHz, CDCl$_3$) δ ppm 4.20-4.32 (m, 2H) 3.70-3.97 (m, 2H) 3.07-3.19 (m, 1H) 2.97-3.06 (m, 4H) 1.86-2.00 (m, 3H) 1.58-1.85 (m, 4H) 1.49-1.57 (m, 1H) 1.46 (s, 9H).

Intermediate 75: tert-Butyl 3-(3-azidopropyl)-3-fluoropiperidine-1-carboxylate

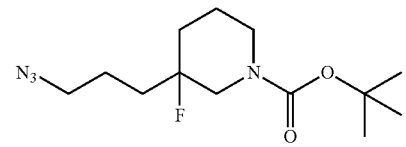 [SMILES: CC(C)(C)OC(=O)N1CCCC(F)(CCCN=[N+]=[N-])C1]

tert-Butyl 3-fluoro-3-(3-((methylsulfonyl)oxy)propyl)piperidine-1-carboxylate (2.5 g, 7.4 mmol) was dissolved in DMF (30 mL) then sodium azide (0.958 g, 14.7 mmol) was added and the mixture was heated at 80° C. for 2 h then was cooled to room temperature. The resulting suspension was diluted with water (100 mL) and extracted with EtOAc (2×50 mL). The combined organics were washed with water (2×50 mL), dried and evaporated in vacuo to give tert-butyl 3-(3-azidopropyl)-3-fluoropiperidine-1-carboxylate (2.8 g, 133%) as a pale yellow oil which was used in the next step without further purification.

$^1$H NMR (400 MHz, CDCl$_3$) δ ppm 3.75 (dt, J=13.1, 4.1 Hz, 2H) 3.32 (t, J=6.5 Hz, 2H) 2.97-3.06 (m, 2H) 1.86-2.00 (m, 1H) 1.58-1.85 (m, 6H) 1.43-1.57 (m, 10H).

Intermediate 76: tert-Butyl 3-(3-aminopropyl)-3-fluoropiperidine-1-carboxylate

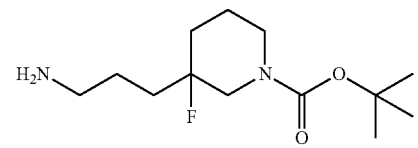 [SMILES: CC(C)(C)OC(=O)N1CCCC(F)(CCCN)C1]

tert-Butyl 3-(3-azidopropyl)-3-fluoropiperidine-1-carboxylate (2.8 g, 5.9 mmol) was dissolved in EtOH (60 mL) and hydrogenated in an H-Cube on full mode over a Pd/C cat cart. The eluant was evaporated in vacuo to give a pale yellow oil. The crude material was dissolved in DCM and loaded onto a 25 g silica column, then eluted with 0-20% 2N methanolic ammonia/DCM to give tert-butyl 3-(3-aminopropyl)-3-fluoropiperidine-1-carboxylate (1.2 g, 79%) as a colourless oil.

$^1$H NMR (400 MHz, CDCl$_3$) δ ppm 3.72-4.03 (m, 2H) 2.90-3.13 (m, 2H) 2.72 (t, J=6.5 Hz, 2H) 1.87-1.98 (m, 1H) 1.72-1.87 (m, 1H) 1.33-1.69 (m, 17H).

Intermediate 77: (R,E)-tert-Butyl 3-(3-ethoxy-3-oxoprop-1-en-1-yl)-3-fluoropiperidine-1-carboxylate

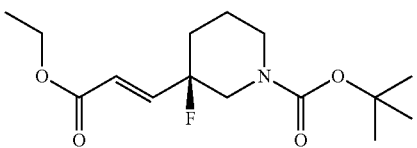

(S)-tert-Butyl 3-fluoro-3-(hydroxymethyl)piperidine-1-carboxylate (10 g, 43 mmol, preparation described in the literature: Org. Process Res. Dev. 2015, 19, 7, 865-871)) was dissolved in DCM (60 mL) and Dess-Martin periodinane (23.6 g, 55.7 mmol) was added and the mixture was stirred at room temperature for 18 h, then was washed with water. The organic layer was dried over sodium sulphate and decanted into a clean, dry flask. Ethyl 2-(triphenylphosphoranylidene)acetate (19.4 g, 55.7 mmol) was added and the mixture was stirred at room temperature for 16 h, then was washed with water. The organic layer was then dried and concentrated in vacuo. The residue obtained was purified on a 50 g silica column eluting with 0-50% EtOAc/cyclohexane and the product-containing fractions were evaporated in vacuo to give (R,E)-tert-butyl 3-(3-ethoxy-3-oxoprop-1-en-1-yl)-3-fluoropiperidine-1-carboxylate (10.5 g, 81%) as a colourless oil.

$^1$H NMR (400 MHz, CDCl$_3$) δ ppm 6.89 (dd, J=19.6, 15.7 Hz, 1H) 6.15 (d, J=15.7 Hz, 1H) 4.13-4.28 (m, 2H) 3.80-4.10 (m, 2H) 2.86-3.25 (m, 2H) 1.52-2.04 (m, 4H) 1.46 (s, 9H) 1.30 (t, J=7.1 Hz, 3H)

Intermediate 78: (R)-tert-Butyl 3-(3-ethoxy-3-oxopropyl)-3-fluoropiperidine-1-carboxylate

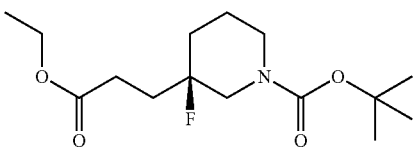 [SMILES: CCOC(=O)CC[C@]1(F)CCCN(C(=O)OC(C)(C)C)C1]

(R,E)-tert-Butyl 3-(3-ethoxy-3-oxoprop-1-en-1-yl)-3-fluoropiperidine-1-carboxylate (10 g, 33 mmol) was dissolved in EtOH (100 mL) and added to 5% Pd—C (2 g, 18.79 mmol) under nitrogen. The mixture was then hydrogenated at atmospheric pressure for 6 h, giving the expected uptake of hydrogen. The mixture was filtered though Celite® under nitrogen and the filtrate evaporated in vacuo to give (R)-tert-butyl 3-(3-ethoxy-3-oxopropyl)-3-fluoropiperidine-1-carboxylate (9.5 g, 94%) as a pale yellow oil.

$^1$H NMR (400 MHz, CDCl$_3$) δ ppm 4.05-4.22 (m, 2H) 3.66-4.01 (m, 2H) 2.88-3.23 (m, 2H) 2.47 (t, J=8.1 Hz, 2H) 1.84-2.12 (m, 3H) 1.71-1.84 (m, 1H) 1.47-1.71 (m, 2H) 1.45 (s, 9H) 1.21-1.32 (m, 3H)

Intermediate 79: (R)-3-(1-(tert-Butoxycarbonyl)-3-fluoropiperidin-3-yl)propanoic Acid

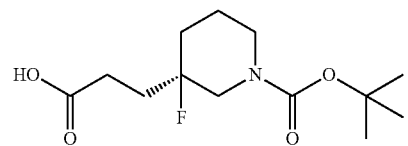 [SMILES: CC(C)(C)OC(=O)N1CCC[C@@](F)(CCC(=O)O)C1]

(R)-tert-Butyl 3-(3-ethoxy-3-oxopropyl)-3-fluoropiperidine-1-carboxylate (9.60 g, 31.6 mmol) was dissolved in EtOH (50 mL) and NaOH (2N in water, 47.5 mL, 95.0 mmol) was added, then the solution was stirred at room temperature for 4 h. The solvent was evaporated in vacuo and the residue was partitioned between water (100 mL) and ether (100 mL). The aqueous layer was acidified with 2M HCl aqueous solution to pH ~2 then extracted with EtOAc (2×100 mL). The organic layer was washed with water (100 mL), then dried and evaporated in vacuo to give (R)-3-(1-(tert-butoxycarbonyl)-3-fluoropiperidin-3-yl)propanoic acid (8.6 g, 99%) as a colourless solid.

$^1$H NMR (400 MHz, CDCl$_3$) δ ppm 3.76 (dt, J=13.4, 4.2 Hz, 1H) 3.06 (d, J=8.6 Hz, 1H) 2.55 (t, J=7.8 Hz, 2H) 1.98-2.08 (m, 2H) 1.88-1.97 (m, 2H) 1.68-1.81 (m, 2H) 1.51-1.60 (m, 2H) 1.45-1.50 (m, 9H)

Intermediate 80: (R)-tert-Butyl 3-(2-(((benzyloxy)carbonyl)amino)ethyl)-3-fluoropiperidine-1-carboxylate

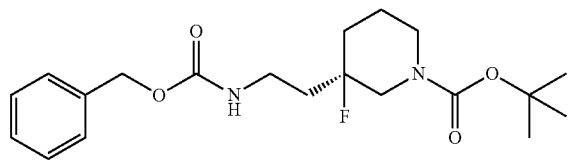 [SMILES: CC(C)(C)OC(=O)N1CCC[C@@](F)(CCNC(=O)OCc2ccccc2)C1]

Diphenyl phosphorazidate (8.08 mL, 37.5 mmol) was added to a mixture of (R)-3-(1-(tert-butoxycarbonyl)-3-fluoropiperidin-3-yl)propanoic acid (8.6 g, 31 mmol) and Et$_3$N (13 mL, 94 mmol) in toluene (50 mL), then the solution was stirred for 30 min at room temperature. Benzyl alcohol (6.50 mL, 62.5 mmol) was added and the mixture was heated at reflux for 3 h then was cooled to room temperature. The reaction mixture was diluted with EtOAc (100 mL) and washed with water (100 mL), the organic layer dried and evaporated in vacuo and the residue purified by chromatography on a 340 g silica column eluting with 0-50% EtOAc/cyclohexane. The product-containing fractions were combined and evaporated in vacuo to give (k)-tert-butyl 3-(2-(((benzyloxy)carbonyl)amino)ethyl)-3-fluoropiperidine-1-carboxylate (8.9 g, 75%) as a colourless gum.

$^1$H NMR (400 MHz, 393 K, DMSO-d$_6$) δ ppm 7.25-7.43 (m, 5H) 6.69 (br. s., 1H) 5.05 (s, 2H) 3.74-3.82 (m, 1H) 3.70 (dt, J=13.1, 4.2 Hz, 1H) 3.16-3.24 (m, 2H) 3.01-3.15 (m, 1H) 2.90-3.00 (m, 1H) 1.75-1.90 (m, 3H) 1.56-1.74 (m, 2H) 1.40-1.54 (m, 10H).

Intermediate 81: (R)-tert-Butyl 3-(2-aminoethyl)-3-fluoropiperidine-1-carboxylate

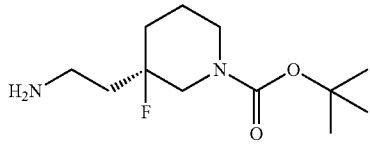 [SMILES: CC(C)(C)OC(=O)N1CCC[C@@](F)(CCN)C1]

(R)-tert-butyl 3-(2-(((benzyloxy)carbonyl)amino)ethyl)-3-fluoropiperidine-1-carboxylate (8.9 g, 23 mmol) was dissolved in EtOH (100 mL) and added to 5% Pd/C (2 g) under vacuum, then hydrogenated at atmospheric pressure over 60 h. The mixture was filtered though Celite under nitrogen and the filtrate evaporated in vacuo to give (R)-tert-butyl 3-(2-aminoethyl)-3-fluoropiperidine-1-carboxylate (6.0 g, 104%) as a colourless oil which was used in the next step without further purification.

$^1$H NMR (400 MHz, DMSO-$d_6$) δ ppm 3.80 (ddd, J=13.7, 9.8, 1.5 Hz, 1H) 3.69-3.75 (m, 1H) 3.01-3.13 (m, 1H) 2.90-2.99 (m, 1H) 2.74 (t, J=7.5 Hz, 2H) 1.80-1.87 (m, 1H) 1.66-1.76 (m, 3H) 1.56-1.64 (m, 1H) 1.46-1.53 (m, 1H) 1.43 (s, 9H)

Intermediate 82: (±)-tert-Butyl 3,3-difluoro-4-(2-hydroxyethyl)piperidine-1-carboxylate

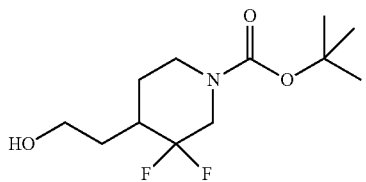 [SMILES: CC(C)(C)OC(=O)N1CCC(CCO)C(F)(F)C1]

To a stirred solution of (±)-2-(1-(tert-butoxycarbonyl)-3,3-difluoropiperidin-4-yl)acetic acid (1.99 g, 7.13 mmol, commercially available from Activate Scientific) in THF (50 mL) at room temperature was added portionwise (5 mL aliquots) borane tetrahydrofuran complex (1.0 M in THF, 29.0 mL, 29.0 mmol). The mixture was stirred at room temperature under nitrogen for 15.5 h before MeOH (50 mL) was carefully added. After stirring for a further 20 min the mixture was evaporated in vacuo and the residue partitioned between ethyl acetate (50 mL) and water (50 mL). Saturated aqueous brine solution (10 mL) was added to aid phase separation and the phases were separated. The aqueous phase was extracted with further ethyl acetate (3×40 mL), the combined organic extracts dried by passing through a cartridge fitted with a hydrophobic frit, the solvent evaporated under a stream of nitrogen and the residue dried in vacuo to give a pale yellow viscous oil; (±)-tert-butyl 3,3-difluoro-4-(2-hydroxyethyl)piperidine-1-carboxylate (1.942 g, 103%).

$^1$H NMR (400 MHz, DMSO-$d_6$) δ ppm 4.50 (t, J=5.5 Hz, 1H) 4.06 (br s, 1H) 3.89 (br d, 1H) 3.38-3.54 (m, 2H) 3.18 (br s, 1H) 2.87 (br s, 1H) 2.02-2.19 (m, 1H) 1.79-1.87 (m, 2H) 1.40 (s, 9H) 1.19-1.34 (m, 2H).

Intermediate 83: (±)-tert-Butyl 3,3-difluoro-4-(2-((methylsulfonyl)oxy)ethyl)piperidine-1-carboxylate

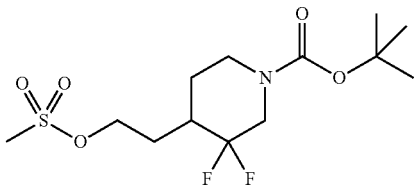 [SMILES: CC(C)(C)OC(=O)N1CCC(CCOS(C)(=O)=O)C(F)(F)C1]

(±)-tert-Butyl 3,3-difluoro-4-(2-hydroxyethyl)piperidine-1-carboxylate (1.88 g, 7.10 mmol) was dissolved in DCM (60 mL) and triethylamine (1.48 mL, 10.6 mmol) and methanesulfonyl chloride (0.719 mL, 9.23 mmol) were added. The solution was stirred at room temperature for 2.75 h, then washed with water (100 mL) and the aqueous phase extracted with DCM (2×100 mL). The combined organic phases were dried by passing them through a cartridge fitted with a hydrophobic frit and the solvent evaporated in vacuo to give a clear oil which crystallized to give a white solid; (±)-tert-butyl 3,3-difluoro-4-(2-((methylsulfonyl)oxy)ethyl)piperidine-1-carboxylate (2.467 g, 101%)

$^1$H NMR (400 MHz, DMSO-$d_6$) δ ppm 4.23-4.33 (m, 2H) 4.09 (br s, 1H) 3.91 (br d, 1H) 3.21 (br s, 1H) 3.19 (s, 3H) 2.89 (br s, 1H) 2.02-2.23 (m, 2H) 1.85 (br dt, 1H) 1.56-1.66 (m, 1H) 1.40 (s, 9H) 1.24-1.38 (m, 2H).

Intermediate 84: (±)-tert-Butyl 4-(2-azidoethyl)-3,3-difluoropiperidine-1-carboxylate

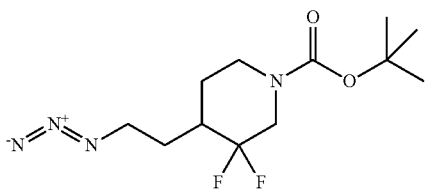

(±)-tert-Butyl 3,3-difluoro-4-(2-((methylsulfonyl)oxy)ethyl)piperidine-1-carboxylate (1.33 g, 3.88 mmol) was dissolved in DMF (10 mL) and sodium azide (301 mg, 4.64 mmol) was added. The mixture was stirred under nitrogen at 80° C. for 4 h. After cooling, the mixture was diluted with 1M aqueous sodium carbonate solution (50 mL) and extracted with EtOAc (3×30 mL) [Note that 3 phases were observed in the separation, the ethyl acetate extracts being the least dense; on the 2nd and 3rd extractions some salting out of solid occurred in the lower phase and water (ca. ~10 mL) was added to help with this]. The combined organics were washed with water (2×40 mL) [Note that the 2nd water wash caused emusification of the layers and saturated brine solution (ca. ~10 mL) was added to help the phases to separate], then dried and evaporated in vacuo to give a pale yellow oil; (±)-tert-butyl 4-(2-azidoethyl)-3,3-difluoropiperidine-1-carboxylate (1.23 g, 109%) containing approximately 0.33 equivalents of DMF.

$^1$H NMR (400 MHz, DMSO-$d_6$) δ ppm 4.08 (br s, 1H) 3.89 (br d, 1H) 3.36-3.53 (m, 2H) 3.19 (br s, 1H) 2.88 (br s, 1H) 2.01-2.17 (m, 1H) 1.79-1.94 (m, 1H) 1.42-1.51 (m, 1H) 1.40 (s, 9H) 1.22-1.33 (m, 1H).

Intermediate 85: (±)-tert-Butyl 4-(2-aminoethyl)-3,3-difluoropiperidine-1-carboxylate

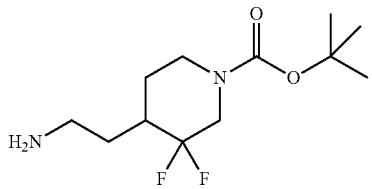 [SMILES: CC(C)(C)OC(=O)N1CCC(CCN)C(F)(F)C1]

A solution of (±)-tert-butyl 4-(2-azidoethyl)-3,3-difluoropiperidine-1-carboxylate (1.22 g, 4.20 mmol) in ethyl acetate (50 mL) was hydrogenated over a 10% Pd/C catalyst cartridge using a Thales 'H-Cube' flow apparatus in full hydrogen mode at 20° C. The solvent was evaporated from the collected solution in vacuo to give a colourless oil which by NMR analysis was determined to be a 6:5 mixture of starting azide to product amine. The residue was re-dissolved in EtOH (50 mL) and was again hydrogenated over a 10% Pd/C catalyst cartridge using a Thales 'H-Cube' flow apparatus in full hydrogen mode but this time at 40° C. The solvent was evaporated from the collected solution in vacuo to give a colourless oil (982.1 mg, 88%).

$^1$H NMR (400 MHz, DMSO-d$_6$) δ ppm 4.06 (br s, 1H) 3.88 (br d, 1H) 3.16 (br s, 1H) 2.86 (br s, 1H) 2.50-2.68 (m, 2H) 2.00-2.14 (m, 1H) 1.66-1.82 (m, 2H) 1.40 (s, 9H) 1.17-1.29 (m, 2H).

Intermediate 86: (±)-tert-Butyl 4,4-difluoro-3-(2-hydroxyethyl)piperidine-1-carboxylate

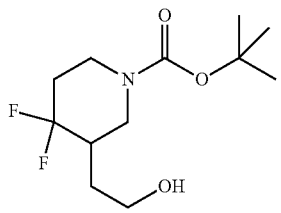 [SMILES: CC(C)(C)OC(=O)N1CCC(F)(F)C(CCO)C1]

To a stirred solution of (±)-2-(1-(tert-butoxycarbonyl)-4,4-difluoropiperidin-3-yl)acetic acid (197.0 mg, 0.705 mmol, commercially available from Activate Scientific) in THF (5 mL) at room temperature was added borane tetrahydrofuran complex (1.0 M in THF, 2.8 mL, 2.8 mmol). The mixture was stirred at room temperature under nitrogen for 2.5 h before MeOH (5 mL) was carefully added. After stirring for a further 10 min the mixture was evaporated in vacuo and the residue partitioned between ethyl acetate (5 mL) and water (5 mL). The aqueous phase was extracted with further ethyl acetate (3×4 mL), the combined organic extracts dried by passing through a cartridge fitted with a hydrophobic frit and the solvent evaporated under a stream of nitrogen to give a colourless gum; (±)-tert-butyl 4,4-difluoro-3-(2-hydroxyethyl)piperidine-1-carboxylate (162 mg, 87%)

$^1$H NMR (400 MHz, DMSO-d$_6$) δ ppm 4.56 (t, J=5.0 Hz, 1H) 3.69 (br s, 2H) 3.42-3.53 (m, 2H) 3.20 (br s, 1H) 2.97 (br s, 1H) 1.94-2.09 (m, 2H) 1.69-1.92 (m, 2H) 1.41 (s, 9H) 1.24-1.32 (m, 1H).

Intermediate 87: (±)-tert-Butyl 4,4-difluoro-3-(2-((methylsulfonyl)oxy)ethyl)piperidine-1-carboxylate

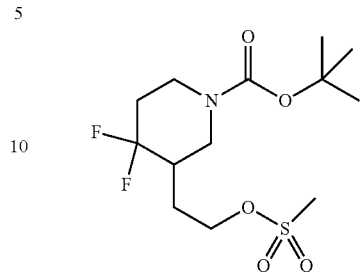

(±)-tert-Butyl 4,4-difluoro-3-(2-hydroxyethyl)piperidine-1-carboxylate (883 mg, 3.33 mmol) was dissolved in DCM (30 mL) and triethylamine (0.70 mL, 5.0 mmol) and methanesulfonyl chloride (0.337 mL, 4.33 mmol) were added. The solution was stirred at room temperature for 2.75 h, then washed with water (50 mL) and the aqueous phase extracted with DCM (2×50 mL). The combined organic phases were dried by passing them through a cartridge fitted with a hydrophobic frit and the solvent evaporated in vacuo to give a white solid; (±)-tert-butyl 4,4-difluoro-3-(2-((methylsulfonyl)oxy)ethyl)piperidine-1-carboxylate (1.141 g, 100%).

$^1$H NMR (400 MHz, DMSO-d$_6$) δ ppm 4.30 (dt, J=6.5 Hz, 2H) 3.81 (br s, 1H) 3.71 (br d, 1H) 3.20 (s, 3H) 3.15-3.22 (m, 1H) 2.99 (br s, 1H) 1.81-2.14 (m, 4H) 1.56-1.64 (m, 1H) 1.42 (s, 9H).

Intermediate 88: (±)-tert-Butyl 3-(2-azidoethyl)-4,4-difluoropiperidine-1-carboxylate

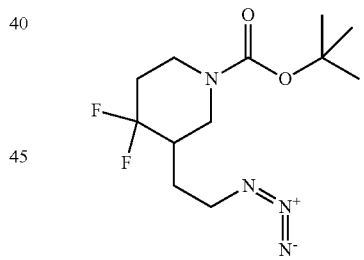

(±)-tert-Butyl 4,4-difluoro-3-(2-((methylsulfonyl)oxy)ethyl)piperidine-1-carboxylate (1.14 g, 3.31 mmol) was dissolved in DMF (20 mL) and sodium azide (263 mg, 4.05 mmol) was added. The mixture was stirred under nitrogen at 80° C. for 4 h. After cooling, the mixture was diluted with 1M aqueous sodium carbonate solution (50 mL) and extracted with EtOAc (3×30 mL) [Note that 3 phases were observed in the separation, the ethyl acetate extracts being the least dense]. The combined organics were washed with water (2×40 mL), then dried and evaporated in vacuo to give a pale yellow oil; (±)-tert-butyl 3-(2-azidoethyl)-4,4-difluoropiperidine-1-carboxylate (0.980 g, 102%) containing approximately 0.2 equivalents of DMF.

$^1$H NMR (400 MHz, DMSO-d$_6$) δ ppm 3.75 (br s, 1H) 3.68 (br d, 1H) 3.39-3.55 (m, 2H) 3.20 (br t, 1H) 2.99 (br s, 1H) 1.77-2.09 (m, 4H) 1.42 (s, 9H) 1.36-1.49 (m, 1H).

Intermediate 89: (±)-tert-Butyl 3-(2-aminoethyl)-4,4-difluoropiperidine-1-carboxylate

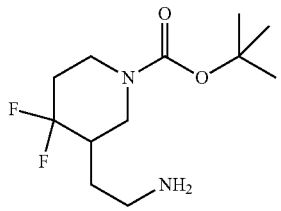 [SMILES: CC(C)(C)OC(=O)N1CCC(F)(F)C(CCN)C1]

A solution of (±)-tert-butyl 3-(2-azidoethyl)-4,4-difluoropiperidine-1-carboxylate (978 mg, 3.37 mmol) in ethyl acetate (50 mL) was hydrogenated over a 10% Pd/C catalyst cartridge using a Thales 'H-Cube' flow apparatus in full hydrogen mode at 20° C. The solvent was evaporated from the collected solution in vacuo to give a colourless oil which by NMR analysis was determined to be a 5:4 mixture of starting azide to product amine. The residue was re-dissolved in EtOH (50 mL) and was again hydrogenated over a 10% Pd/C catalyst cartridge using a Thales 'H-Cube' flow apparatus in full hydrogen mode but this time at 40° C. The solvent was evaporated from the collected solution in vacuo to give a colourless oil, (±)-tert-butyl 3-(2-aminoethyl)-4,4-difluoropiperidine-1-carboxylate (796.3 mg, 89%).

$^1$H NMR (400 MHz, DMSO-$d_6$) δ ppm 3.65 (br s, 2H) 3.23 (br s, 1H) 2.95 (br s, 1H) 2.63-2.69 (m, 1H) 2.52-2.59 (m, 1H) 1.93-2.08 (m, 2H) 1.76-1.91 (m, 1H) 1.56-1.65 (m, 1H) 1.47 (br s 1H) 1.41 (s, 9H) 1.15-1.27 (m, 1H).

Intermediate 90: (R,E)-tert-Butyl 3-(3-ethoxy-3-oxoprop-1-en-1-yl)-3-fluoropiperidine-1-carboxylate

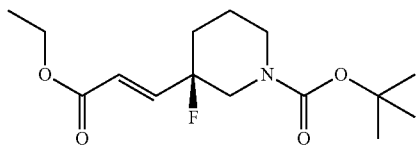 [SMILES: CCOC(=O)/C=C/[C@]1(F)CCCN(C(=O)OC(C)(C)C)C1]

(S)-tert-Butyl 3-fluoro-3-(hydroxymethyl)piperidine-1-carboxylate (10 g, 43 mmol, preparation described in the literature: *Org. Process Res. Dev.* 2015, 19, 7, 865-871)) was dissolved in DCM (60 mL) and Dess-Martin periodinane (23.6 g, 55.7 mmol) was added and the mixture was stirred at room temperature for 18 h, then was washed with water. The organic layer was dried over sodium sulphate and decanted into a clean, dry flask. Ethyl 2-(triphenylphosphoranylidene)acetate (19.4 g, 55.7 mmol) was added and the mixture was stirred at room temperature for 18 h, then was washed with water and the organic layer dried and evaporated in vacuo. The residue was purified on a 50 g silica column eluting with 0-50% EtOAc/cyclohexane and the product-containing fractions were evaporated in vacuo to give (R,E)-tert-butyl 3-(3-ethoxy-3-oxoprop-1-en-1-yl)-3-fluoropiperidine-1-carboxylate (10.5 g, 81%) as a colourless oil.

$^1$H NMR (400 MHz, CDCl$_3$) δ ppm 6.89 (dd, J=19.6, 15.7 Hz, 1H) 6.15 (d, J=15.7 Hz, 1H) 4.13-4.28 (m, 2H) 3.80-4.10 (m, 2H) 2.86-3.25 (m, 2H) 1.52-2.04 (m, 4H) 1.46 (s, 9H) 1.30 (t, J=7.1 Hz, 3H)

Intermediate 91: (R)-tert-Butyl 3-(3-ethoxy-3-oxopropyl)-3-fluoropiperidine-1-carboxylate

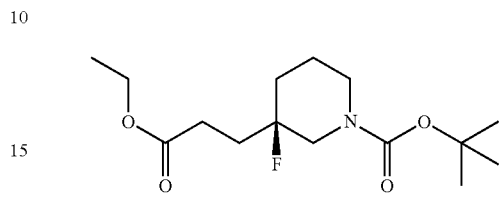

(R,E)-tert-Butyl 3-(3-ethoxy-3-oxoprop-1-en-1-yl)-3-fluoropiperidine-1-carboxylate (10 g, 33 mmol) was dissolved in EtOH (100 mL) and added to 5% Pd—C (2.0 g, 19 mmol) under nitrogen, then the mixture was hydrogenated at atmospheric pressure for 6 h, giving the expected uptake of hydrogen. The mixture was filtered though Celite under nitrogen and the filtrate evaporated in vacuo to give (R)-tert-butyl 3-(3-ethoxy-3-oxopropyl)-3-fluoropiperidine-1-carboxylate (9.5 g, 94%) as a pale yellow oil.

$^1$H NMR (400 MHz, CDCl$_3$) δ ppm 4.05-4.22 (m, 2H) 3.66-4.01 (m, 2H) 2.88-3.23 (m, 2H) 2.47 (t, J=8.1 Hz, 2H) 1.84-2.12 (m, 3H) 1.71-1.84 (m, 1H) 1.47-1.71 (m, 2H) 1.45 (s, 9H) 1.21-1.32 (m, 3H)

Intermediate 92: (R)-tert-Butyl 3-fluoro-3-(3-hydroxypropyl)piperidine-1-carboxylate

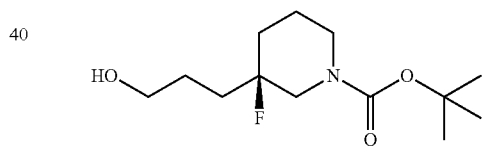

LiBH$_4$ (2.05 g, 94.0 mmol) was added to a solution of (R)-tert-butyl 3-(3-ethoxy-3-oxopropyl)-3-fluoropiperidine-1-carboxylate (9.5 g, 31 mmol) in THF (100 mL) and the mixture was stirred at room temperature under nitrogen for 48 h, then was cooled in an ice bath and quenched by very cautious, initially dropwise addition of a saturated ammonium chloride aqueous solution (100 mL) (strong effervescence on addition). The mixture was stirred for 20 min, diluted with EtOAc (100 mL) and the combined organics separated, dried over sodium sulphate and evaporated in vacuo to give a pale yellow oil. The crude material was dissolved in DCM and loaded onto a 100 g silica column, then eluted with 0-100% EtOAc/cyclohexane and the product-containing fractions were evaporated in vacuo to give (R)-tert-butyl 3-fluoro-3-(3-hydroxypropyl)piperidine-1-carboxylate (6.0 g, 73%) which was carried though to the next step immediately.

$^1$H NMR (400 MHz, CDCl$_3$) δ ppm 3.61-3.93 (m, 4H) 2.94-3.14 (m, 2H) 1.87-1.99 (m, 1H) 1.48-1.86 (m, 7H) 1.45 (s, 9H)

Intermediate 93: (R)-tert-Butyl 3-fluoro-3-(3-((methylsulfonyl)oxy)propyl)piperidine-1-carboxylate

(R)-tert-Butyl 3-fluoro-3-(3-hydroxypropyl)piperidine-1-carboxylate (6.0 g, 23 mmol) was dissolved in DCM (100 mL), Et₃N (4.80 mL, 34.4 mmol) was added and the mixture was cooled in an ice bath, then Ms-Cl (2.33 mL, 29.8 mmol) was added dropwise (exotherm!) and the mixture was stirred for 2 h, allowing it to warm to room temperature. The solution was washed with water (100 mL) and brine (100 mL). The organic layer was dried and evaporated in vacuo to give (R)-tert-butyl 3-fluoro-3-(3-((methylsulfonyl)oxy)propyl)piperidine-1-carboxylate (7.2 g, 92%) as a colourless oil which was used in the next step.

$^1$H NMR (400 MHz, CDCl$_3$) δ ppm 4.20-4.32 (m, 2H) 3.70-3.96 (m, 2H) 3.68 (s, 1H) 3.04-3.15 (m, 1H) 3.00-3.03 (m, 3H) 1.88-1.99 (m, 3H) 1.49-1.83 (m, 5H) 1.43-1.48 (m, 9H)

Intermediate 94: (R)-tert-Butyl 3-(3-azidopropyl)-3-fluoropiperidine-1-carboxylate

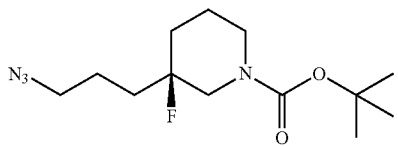

Sodium azide (2.68 g, 41.2 mmol) was added to a solution of (R)-tert-butyl 3-fluoro-3-(3-((methylsulfonyl)oxy)propyl)piperidine-1-carboxylate (7.00 g, 20.6 mmol) in DMF (50 mL) and the mixture was heated at 70° C. for 2 h, then cooled to room temperature, diluted with water (200 mL) and extracted with EtOAc (2×100 mL). The combined organics were washed with water (2×100 mL), dried and evaporated in vacuo to give (R)-tert-butyl 3-(3-azidopropyl)-3-fluoropiperidine-1-carboxylate as a colourless oil. The crude product was dissolved in DCM (10 mL) and loaded onto a 100 g silica column, then eluted with 0-50% EtOAc/cyclohexane and the product-containing fractions (visualised by ninhydrin) were evaporated in vacuo to give (R)-tert-butyl 3-(3-azidopropyl)-3-fluoropiperidine-1-carboxylate (5.2 g, 88%) as a colourless oil which was carried though to the next step without further purification.

$^1$H NMR (400 MHz, CDCl$_3$) δ ppm 3.69-3.99 (m, 2H) 3.33 (t, J=6.5 Hz, 2H) 2.96-3.17 (m, 2H) 1.86-1.98 (m, 1H) 1.58-1.83 (m, 6H) 1.49-1.58 (m, 1H) 1.47 (s, 9H).

Intermediate 95: (S)-tert-Butyl 3-(3-aminopropyl)-3-fluoropiperidine-1-carboxylate

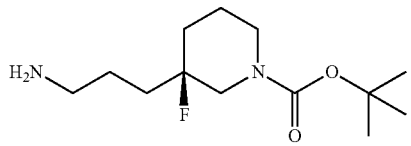 [SMILES: CC(C)(C)OC(=O)N1CCC[C@@](F)(CCCN)C1]

(R)-tert-Butyl 3-(3-azidopropyl)-3-fluoropiperidine-1-carboxylate (5.00 g, 17.4 mmol) was dissolved in THF (50 mL) and triphenylphosphine (5.50 g, 20.9 mmol) was added, then the mixture was stirred at room temperature for 60 h. Water (50 mL) was added and the mixture stirred vigorously for 2 h, then diluted with EtOAc (100 mL) and brine (50 mL) and the organic layer separated, dried and evaporated in vacuo to give a pale yellow oil. The crude product was dissolved in DCM (20 mL) and loaded onto a 100 g silica column, then eluted with 0-20% 2N methanoic ammonia/DCM and the product-containing fractions (visualised by ninhydrin) were evaporated in vacuo to give (S)-tert-butyl 3-(3-aminopropyl)-3-fluoropiperidine-1-carboxylate (4.0 g, 88%) as a colourless oil.

$^1$H NMR (400 MHz, CDCl$_3$) δ ppm 3.72-4.02 (m, 2H) 2.89-3.12 (m, 2H) 2.72 (t, J=6.6 Hz, 2H) 1.86-1.98 (m, 1H) 1.72-1.85 (m, 1H) 1.48-1.70 (m, 6H) 1.46 (s, 9H)

Intermediate 96: (S)-tert-Butyl 2-(((methylsulfonyl)oxy)methyl)morpholine-4-carboxylate

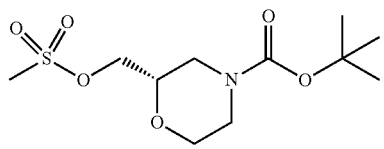 [SMILES: CC(C)(C)OC(=O)N1CCO[C@H](COS(C)(=O)=O)C1]

(S)-tert-Butyl 2-(hydroxymethyl)morpholine-4-carboxylate (commercially available from, for example, Activate Scientific) (3.00 g, 13.8 mmol) and triethylamine (3.85 mL, 27.6 mmol) were stirred in DCM (30 mL) at 0° C. Mesyl-Cl (1.614 mL, 20.71 mmol) was added portionwise over 5 min and the reaction was stirred at room temperature for 4 h. The reaction was then diluted with further DCM and was washed with a 1N HCl aqueous solution, a saturated NaHCO₃ aqueous solution and water, dried using a hydrophobic frit and concentrated in vacuo to give (S)-tert-butyl 2-(((methylsulfonyl)oxy)methyl)morpholine-4-carboxylate (4.242 g, 104%) as a yellow oil which was used crude in next step.

$^1$H NMR (400 MHz, DMSO-d$_6$) δ ppm 4.13-4.35 (m, 2H) 3.76-3.95 (m, 2H) 3.71 (br. d, J=13.2 Hz, 1H) 3.62 (br. ddt, J=10.6, 5.9, 3.1, 3.1 Hz, 1H) 3.43 (td, J=11.6, 2.7 Hz, 1H) 3.14-3.31 (m, 3H) 2.62-2.99 (m, 2H) 1.31-1.52 (m, 9H).

Intermediate 97: (R)-tert-Butyl 2-(cyanomethyl)morpholine-4-carboxylate

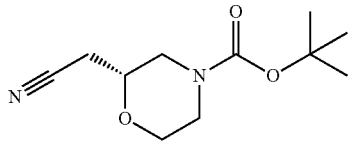 [SMILES: CC(C)(C)OC(=O)N1CCO[C@H](CC#N)C1]

(S)-tert-Butyl 2-(((methylsulfonyl)oxy)methyl)morpholine-4-carboxylate (4.2 g, 14 mmol), KCN (0.972 g, 14.9 mmol) and KI (3.54 g, 21.3 mmol) were stirred at 100° C. in DMSO (30 mL) for 4 h. The reaction was then cooled to room temperature, diluted with water and extracted with EtOAc. The organic layer was washed with water and brine, dried using a hydrophobic frit and concentrated in vacuo to a yellow oil. This oil was purified using a SP4 flash chromatography, using a SNAP 50 g Si column and eluting with 0-50% EtOAc:cyclohexane to give (R)-tert-butyl 2-(cyanomethyl)morpholine-4-carboxylate (2.393 g, 74%) as a white solid.

$^1$H NMR (400 MHz, DMSO-d$_6$) δ ppm 3.85 (br. dd, J=11.5, 2.2 Hz, 2H) 3.70 (br. d, J=13.2 Hz, 1H) 3.52-3.63 (m, 1H) 3.44 (td, J=11.6, 2.9 Hz, 1H) 2.79-2.93 (m, 2H) 2.67-2.79 (m, 1H) 2.57-2.67 (m, 1H) 1.41 (s, 9H).

Intermediate 98: (R)-tert-Butyl 2-(2-aminoethyl)morpholine-4-carboxylate

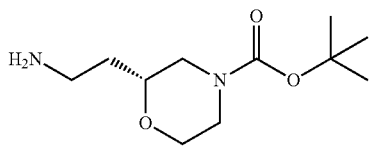 [SMILES: CC(C)(C)OC(=O)N1CCO[C@H](CCN)C1]

(R)-tert-Butyl 2-(cyanomethyl)morpholine-4-carboxylate (2.39 g, 10.6 mmol) was taken up in THF (20 mL) and stirred at room temperature, borane tetrahydrofuran complex (1M in THF, 15.84 mL, 15.84 mmol) was added over 10 min and the reaction stirred at room temperature for 2 h. The reaction was quenched by the careful addition of MeOH until all effervescence had stopped. The reaction was concentrated in vacuo and the residue was dissolved in MeOH and the resulting solution was treated with 1M NaOH (50 mL) and stirred at room temperature for 2 h, a precipitate resulted. The reaction was concentrated in vacuo to remove the MeOH and was diluted with water and extracted with EtOAc. The combined organics were washed with water, dried using a hydrophobic frit and concentrated in vacuo to give the crude product as a colourless oil. This was further purified using SP4 flash chromatography, using a SNAP 50 g Si column and eluting with 0-8% 2N NH$_3$ in MeOH:DCM to give (R)-tert-butyl 2-(2-aminoethyl)morpholine-4-carboxylate (965 mg, 40%) as a colourless oil.

$^1$H NMR (400 MHz, DMSO-d$_6$) δ ppm: 3.56-3.90 (m, 3H) 3.23-3.46 (m, 2H) 2.01-3.11 (obs m, 6H) 1.28-1.62 (m, 11H).

Intermediate 99: (Trans)-methyl 2-(2-(tert-butoxy)-2-oxoethyl)cyclopropanecarboxylate

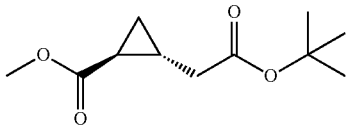

A solution of diisopropylamine (6.27 mL, 44.0 mmol) in THF (40 mL) at −78° C. under nitrogen was treated with n-butyllithium (1.6 N in hexanes, 27.5 mL, 44.0 mmol). After 5 min, the mixture was warmed using an ice bath and stirred at 0° C. for 30 min before being cooled again to −78° C. and treated with tert-butyl acetate (5.90 mL, 44.0 mmol) in THF (15 mL). The yellow mixture was stirred at this temperature for 30 min then was treated with (E)-methyl 4-bromobut-2-enoate (4.70 mL, 40 mmol) in THF (15 mL). The yellow mixture was stirred at this temperature for 2.5 h then was treated with a saturated NH$_4$Cl aqueous solution (50 mL) and warmed to room temperature. The mixture was partitioned between AcOEt and water and the layers were separated. The aqueous phase was extracted twice with EtOAc and the combined organics were washed with brine, dried over MgSO$_4$ and concentrated in vacuo Purification of the residue by flash chromatography on silica gel (50 g column, 40% GLOBAL gradient (AcOEt in hexanes)) gave (Trans)-methyl 2-(2-(tert-butoxy)-2-oxoethyl)cyclopropanecarboxylate (6.95 g, 81%) as a colourless oil.

$^1$H NMR (400 MHz, CDCl$_3$) δ ppm 3.69 (s, 3H), 2.24 (d, J=7.1 Hz, 2H), 1.62-1.73 (m, 1H), 1.42-1.53 (m, 1H), 1.47 (s, 9H) 1.22-1.32 (m, 1H), 0.75-0.87 (m, 1H)

Intermediate 100: 2-((trans)-2-(Methoxycarbonyl)cyclopropyl)acetic Acid

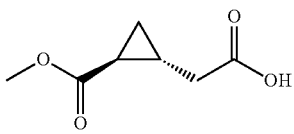

A solution of (trans)-methyl 2-(2-(tert-butoxy)-2-oxoethyl)cyclopropanecarboxylate (6.95 g, 32.4 mmol) in DCM (30 mL) at 0° C. was treated with TFA (30 mL) and the resulting mixture was stirred at this temperature for 2 h then was concentrated in vacuo and the residue was co-evaporated four times with toluene to give 2-((trans)-2-(methoxycarbonyl)cyclopropyl)acetic acid (5.28 g, 103%) as a colourless oil which was used in the next step without further purification.

$^1$H NMR (400 MHz, CDCl$_3$) δ ppm 3.68-3.73 (m, 1H), 2.40 (d, J=6.85 Hz, 1H), 1.69-1.79 (m, 1H), 1.53-1.58 (m, 1H), 1.27-1.35 (m, 1H), 0.86 (ddd, J=4.6, 6.2, 8.4 Hz, 1H)

Intermediate 101: (1S*,2R*)-Methyl 2-(2-hydroxyethyl)cyclopropanecarboxylate

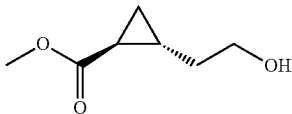

A solution of 2-((trans)-2-(methoxycarbonyl)cyclopropyl)acetic acid (5.22 g, 33.0 mmol) in THF (35 mL) at 0° C. was slowly treated with borane tetrahydrofuran complex (1N in THF, 72.6 mL, 72.6 mmol) and the resulting solution was stirred at this temperature for 2 h then was very slowly quenched with MeOH (26.7 mL, 660 mmol) and concentrated in vacuo. Purification of the residue by flash chromatography on silica gel (50 g column, 40% GLOBAI gradient (AcOEt in hexanes)) gave (Trans)-methyl 2-(2-hydroxyethyl)cyclopropanecarboxylate (3.36 g, 71%) as a colourless oil.

$^1$H NMR (400 MHz, CDCl$_3$) δ ppm 3.75 (t, J=6.4 Hz, 1H), 3.69 (s, 3H), 1.54-1.66 (m, 2H), 1.40-1.52 (m, 3H), 1.17-1.26 (m, 1H), 0.71-0.83 (m, 1H)

Intermediate 102: (trans)-Methyl 2-(2-((tert-butyldimethylsilyl)oxy)ethyl)cyclopropanecarboxylate

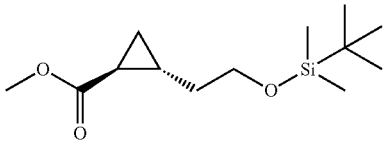 [SMILES: COC(=O)[C@H]1C[C@@H]1CCO[Si](C)(C)C(C)(C)C]

A solution of (trans)-methyl 2-(2-hydroxyethyl)cyclopropanecarboxylate (3.36 g, 23.3 mmol) in DCM (60 mL) at room temperature was treated with imidazole (2.38 g, 35.0 mmol), then TBDMS-Cl (4.22 g, 28.0 mmol) and finally DMAP (0.285 g, 2.33 mmol) and the resulting mixture was stirred at this temperature for 16 h. The mixture was diluted with DCM and water and the layers were separated. The aqueous phase was extracted with DCM and the combined organics were dried using a phase separator then were concentrated in vacuo to give (trans)-methyl 2-(2-((tert-butyldimethylsilyl)oxy)ethyl)cyclopropanecarboxylate (6.5 g, 108%) as a colourless oil which was used in the next step without further purification.

Intermediate 103: (Trans)-2-(2-((tert-Butyldimethylsilyl)oxy)ethyl)cyclopropanecarboxylic Acid

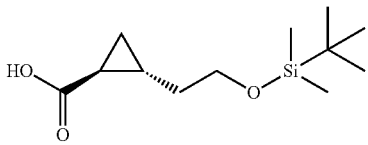 [SMILES: CC(C)(C)[Si](C)(C)OCC[C@H]1C[C@@H]1C(=O)O]

A solution of (trans)-methyl 2-(2-((tert-butyldimethylsilyl)oxy)ethyl)cyclopropanecarboxylate (6.02 g, 23.3 mmol) in MeOH (50 mL) at room temperature was treated with sodium hydroxide (2N in water, 23.30 mL, 46.60 mmol) and the resulting mixture was stirred at this temperature for 16 h then most of MeOH was removed in vacuo and the residue was diluted with water. The mixture was then treated with HCl (2N in water, 23.30 mL, 46.6 mmol) and the precipitate formed was extracted 3 times with AcOEt. The combined organics were dried over MgSO$_4$ and concentrated in vacuo to give (trans)-2-(2-((tert-butyldimethylsilyl)oxy)ethyl)cyclopropanecarboxylic acid (5 g, 88%) as a yellow solid.

$^1$H NMR (400 MHz, CDCl$_3$) δ ppm 3.68 (s, 3H), 1.39-1.61 (m, 4H), 1.14-1.22 (m, 1H), 0.89-0.93 (m, 1H), 0.91 (s, 9H), 0.71-0.78 (m, 1H), 0.07 (s, 6H)

Intermediate 104: Benzyl((trans)-2-(2-Hydroxyethyl)cyclopropyl)carbamate

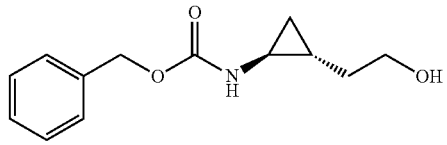 [SMILES: O=C(N[C@H]1C[C@@H]1CCO)OCc1ccccc1]

A solution of (trans)-2-(2-((tert-butyldimethylsilyl)oxy)ethyl)cyclopropanecarboxylic acid (5.00 g, 20.5 mmol) in toluene (80 mL) at room temperature was successively treated with triethylamine (8.55 mL, 61.4 mmol), diphenyl phosphorazidate (5.29 mL, 24.5 mmol) then benzyl alcohol (4.25 mL, 40.9 mmol) and the resulting mixture was refluxed for 6 h then cooled to room temperature and concentrated in vacuo to give a yellow solid The residue was dissolved in AcOEt and the organic phase was washed with water and brine, dried over MgSO$_4$ and concentrated in vacuo. Purification of the residue by flash chromatography on silica gel (100 g column, 50% GLOBAL gradient (EtOAc in hexanes)) gave benzyl ((trans)-2-(2-((tert-butyldimethylsilyl)oxy)ethyl)cyclopropyl)carbamate (1.34 g, 19%) as very pale yellow oil, then benzyl ((trans)-2-(2-hydroxyethyl)cyclopropyl)carbamate (1.69 g, 35%) as a pale yellow oil.

LCMS (method high pH): Retention time 0.85 min, [M+H]$^+$=236

Intermediate 105: 2-((Trans)-2-Aminocyclopropyl)ethanol

A solution of benzyl ((1S*,2R*)-2-(2-hydroxyethyl)cyclopropyl)carbamate (1.34 g, 5.70 mmol) in MeOH (30 mL) was treated with palladium on carbon (50% wet, 10% w/w, 300 mg) and the resulting mixture was stirred under hydrogen (1 atm) for 3 h. The catalyst was filtered off using a pad of Celite® (2.5 g) and rinsed with MeOH. The combined organics were concentrated in vacuo to give 2-((1R*,2S*)-2-aminocyclopropyl)ethanol (576 mg, 100% yield) as a very pale grey solid.

$^1$H NMR (400 MHz, CDCl$_3$) δ ppm 3.61-3.76 (m, 2H), 2.29-2.56 (m, 3H), 2.05-2.17 (m, 1H), 1.36-1.56 (m, 2H), 0.70-0.86 (m, 1H), 0.54 (m, 1H), 0.31-0.39 (m, 1H).

Intermediate 106: 2-((1S,2S)-2-(Hydroxymethyl)cyclopropyl)isoindoline-1,3-dione

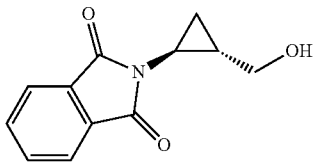 [SMILES: O=C1c2ccccc2C(=O)N1[C@H]1C[C@@H]1CO]

(+/−)-((trans)-2-Aminocyclopropyl)methanol (10 g, 115 mmol, commercially available from, for example, Enamine) was dissolved in toluene (156 mL), phthalic anhydride (22 g, 149 mmol) was added and the reaction heated at 110° C. under nitrogen. The reaction was stirred for 5 h. The solution was then cooled to room temperature and partitioned between EtOAc (50 mL) and water (50 mL), and the layers were separated. The aqueous phase was extracted with EtOAc (2×50 mL), and the combined organics were washed with brine (60 mL), dried over a hydrophobic frit and concentrated to give 34.0 g as a black oil. This was purified by chromatography on $SiO_2$ (Biotage SNAP 750 g, eluting with 0-100% ethyl acetate/cyclohexane). The desired fractions were concentrated to give 26 g of a colourless oil. This was further purified by chromatography on $SiO_2$ (Biotage SNAP 750 g, eluting with 10-60% DCM/diethylether). The desired fractions were concentrated to give 19.5 g as a colourless oil. This was suspended in diethyl ether (600 mL) and filtered under vacuum. The filtrate was concentrated to give (+/−)-2-((trans)-2-(hydroxymethyl)cyclopropyl)isoindoline-1,3-dione (16.4 g, 42%) as a colourless oil.

LCMS (method formic): Retention time 1.07 min, $[M+H]^+$=218.2

(+/−)-2-((trans)-2-(hydroxymethyl)cyclopropyl)isoindoline-1,3-dione (16.4 g) was purified by chiral HPLC. The racemate was dissolved in EtOH (100 mL). Injection: 2.5 mL of the solution was injected onto the column (50% EtOH/Heptane, flow rate=30 mL/min, detection wavelength=215 nm, 4. Ref 550, 100, Column 30 mm×25 cm Chiralpak AD-H (5 µm) Lot No ADH12143-01). Total number of injections=40. Fractions from 12-14.5 min were bulked and labelled peak 1. Fractions from 19.5-26 min were bulked and labelled peak 2. The bulked fractions were concentrated in vacuo and then transferred to weighed flasks. The final compounds were recovered from DCM and heptane in order to obtain a solid The fractions corresponding to peak 1 were collected to afford 2-((1S,2S)-2-(hydroxymethyl)cyclopropyl)isoindoline-1,3-dione, intermediate 106 (5.74 g)

The fractions corresponding to peak 2 were collected to afford the enantiomeric product (7.24 g)

Intermediate 107: ((1S,2S)-2-Aminocyclopropyl)methanol, Hydrochloride

Hydrazine hydrate (0.466 mL, 9.65 mmol, 65% wt.) was added slowly to a suspension of 2-((1S,2S)-2-(hydroxymethyl)cyclopropyl)isoindoline-1,3-dione (2.0 g, 9.21 mmol) in EtOH (46 mL). The reaction mixture was heated to 50° C. under nitrogen for 16 h. The resulting white precipitate was filtered under vacuum. The filtrate was acidified with HCl (4M in dioxane, 57.5 mL, 230 mmol) and evaporated in vacuo to give the crude product. The residue was suspended in MeOH and purified by SPE on sulphonic acid (SCX) 20 g using sequential solvents: methanol followed by 2N ammonia in MeOH. The appropriate fractions were combined and acidified with HCl (4N in dioxane, 6 mL, 24 mmol), before evaporating in vacuo to yield a white slurry. Concerned that salt formation had not completed successfully, the residue was taken up in EtOH (30 mL) and treated with aqueous 2N HCl aqueous solution (10 mL) and evaporated in vacuo once more to yield a white slurry (1540 mg).

The sample was dried in vacuo over 3 days to yield a white paste ((1S,2S)-2-aminocyclopropyl)methanol, hydrochloride (1035 mg, 73%).

$^1$H NMR (400 MHz, DMSO-$d_6$) δ ppm 8.40 (br. s., 3H) 4.07-6.59 (obs., 1H) 3.36 (dd, J=11.2, 5.9 Hz, 1H) 3.27 (dd, J=10.8, 5.9 Hz, 1H) 2.37 (dsxt, J=7.9, 4.2, 4.2, 4.2, 4.2, 4.2 Hz, 1H) 1.34-1.46 (m, 1H) 0.88 (ddd, J=9.7, 5.6, 4.0 Hz, 1H) 0.65 (dt, J=7.6, 6.0 Hz, 1H)

Intermediate 108: tert-Butyl 4,4-difluoro-3-(2-((2R,3S)-2-methyl-7-(methylcarbamoyl)-3-phenyl-2,3-dihydrobenzofuran-5-carboxamido)ethyl)piperidine-1-carboxylate (1:1 Diasteroemeric Mixture)

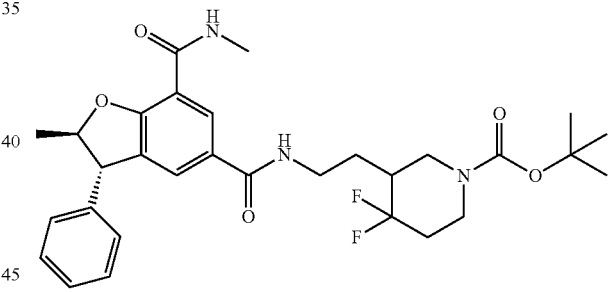

(2R,3S)-2-Methyl-7-(methylcarbamoyl)-3-phenyl-2,3-dihydrobenzofuran-5-carboxylic acid (50 mg, 0.161 mmol), HATU (73.3 mg, 0.193 mmol) and DIPEA (0.084 mL, 0.482 mmol) were dissolved in DMF (3 mL) with stirring at rt for 5 min. tert-Butyl 3-(2-aminoethyl)-4,4-difluoropiperidine-1-carboxylate (59.4 mg, 0.225 mmol) was dissolved in DMF (1 mL) and added to the reaction mixture, which was then stirred at rt for 2 h. Further tert-butyl 3-(2-aminoethyl)-4,4-difluoropiperidine-1-carboxylate (20 mg, 0.076 mmol) was added and the reaction mixture was stirred at rt for 1 h. The reaction mixture was diluted with water and extracted with DCM. The organics were washed with 10% LiCl (aq) dried using hydrophobic frit and concentrated in vacuo. The residue was purified using silica gel column chromatography eluting with a gradient of 0-10% 2M $NH_3$ in MeOH:DCM to give tert-butyl 4,4-difluoro-3-(2-((2R,3S)-2-methyl-7-(methylcarbamoyl)-3-phenyl-2,3-dihydrobenzofuran-5-carboxamido)ethyl)piperidine-1-carboxylate (1:1 diastereomeric mixture) (79 mg, 0.142 mmol, 88% yield) as a yellow oil.

LCMS (2 min high pH): Rt 1.28 min, $[MH]^+$=558

Intermediate 110: (+/−)-5-Bromo-2-(iodomethyl)-N-methyl-3-phenyl-2,3-dihydrobenzofuran-7-carboxamide

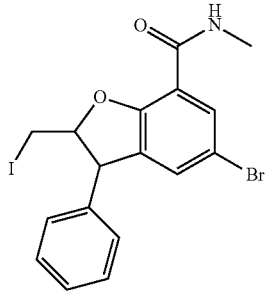 [SMILES: CNC(=O)c1cc(Br)cc2c1OC(CI)C2c1ccccc1]

(+/−)-5-Bromo-2-hydroxy-N-methyl-3-(1-phenylallyl)benzamide (500 mg, 1.444 mmol) was dissolved in DCM (20 ml) and sodium bicarbonate (243 mg, 2.89 mmol) and iodine (513 mg, 2.022 mmol) were added, then the mixture was stirred at rt overnight. The mixture was quenched with sat. sodium thiosulphate solution(aq) and extracted with DCM. The organics were dried and evaporated in vacuo to give (+/−)-5-bromo-2-(iodomethyl)-N-methyl-3-phenyl-2,3-dihydrobenzofuran-7-carboxamide (0.67 g, 1.419 mmol, 98% yield) as a pale yellow foam.

LCMS (2 min formic): Rt 1.35 min, $[M+H]^+=474$

Intermediate 111: (trans)-5-Bromo-2-(fluoromethyl)-N-trideuteromethyl-3-phenyl-2,3-dihydrobenzofuran-7-carboxamide

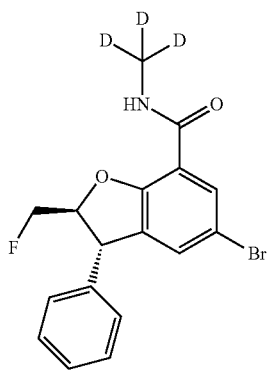 [SMILES: [2H]C([2H])([2H])NC(=O)c1cc(Br)cc2c1O[C@H](CF)[C@H]2c1ccccc1]

(trans)-5-Bromo-2-(hydroxymethyl)-N-trideuteromethyl-3-phenyl-2,3-dihydrobenzofuran-7-carboxamide (3 g, 8.21 mmol) was suspended in DCM (50 mL) and cooled in an ice bath under $N_2$, then Deoxo-Fluor (7.57 mL, 20.53 mmol) was added dropwise over 30 min and the mixture was then warmed to 40° C. overnight under Nz. The solution was added to rapidly stirred sat $NaHCO_3$ (aq) and stirred for 30 min, then the organic layer was separated, dried and evaporated in vacuo. The residue was purified by silica gel column chromatography eluting with a gradient of 0-100% EtOAc/cyclohexane to give (trans)-5-bromo-2-(fluoromethyl)-N-trideuteromethyl-3-phenyl-2,3-dihydrobenzofuran-7-carboxamide (2.25 g, 6.13 mmol, 75% yield) as a colourless solid.

LCMS (2 min Formic): Rt=1.19 min, [MH]+=369

Intermediate 112: (trans)-5-Bromo-2-(hydroxymethyl)-N-trideuteromethyl-3-phenyl-2,3-dihydrobenzofuran-7-carboxamide

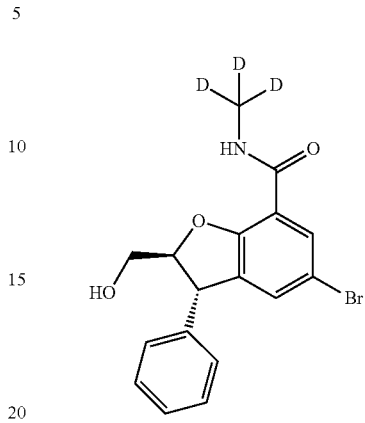

A solution of (trans)-5-bromo-2-hydroxy-N-trideuterated methyl-3-(oxiran-2-yl(phenyl)methyl)benzamide (15.1 g, 41.3 mmol) in DMSO (150 mL) and water (40 mL) was cooled to 0° C. and was treated with an ice-cold solution of potassium hydroxide (4.64 g, 83 mmol) in water (40 mL). The resulting black solution was stirred at this temperature for 7 h, then the mixture was left in the freezer for 16 h. The resulting solution was warmed and stirred at 0° C. for 1 h and then was treated with acetic acid (5.44 mL, 95 mmol). The aqueous phase as extracted with EtOAc and the combined organics were washed with water, then brine, dried over $MgSO_4$ and concentrated in vacuo. Trituration of the residue with $Et_2O$ gave a white solid which was filtered off and dried under vacuum to give (trans)-5-bromo-2-(hydroxymethyl)-N-trideuterated methyl-3-phenyl-2,3-dihydrobenzofuran-7-carboxamide (11.18 g, 30.6 mmol, 74% yield).

LCMS (2 min High pH): Rt=1.03 min, [MH]+=367

Intermediate 113: (+/−)-(5-Bromo-2-hydroxy-N-trideuterated methyl-3-(oxiran-2-yl(phenyl)methyl)benzamide

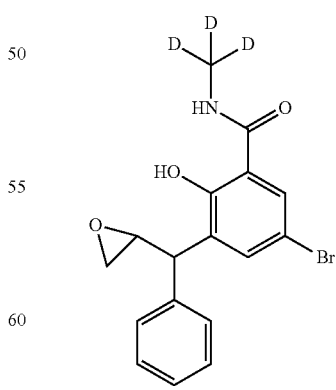

A solution of (+/−)-5-bromo-2-hydroxy-N-methyl-3-(1-phenylallyl)benzamide (14.65 g, 41.9 mmol) in DCM (200 mL) at rt was treated with mCPBA (18.80 g, 84 mmol) (50% w/w) and the resulting mixture was stirred at rt for 48 h. The mixture was then partitioned between DCM and a mixture of sat. NaHCO₃(aq) (100 mL) and sodium thiosulfate pentahydrate (15.62 g, 62.9 mmol) in water (100 mL). The mixture was stirred for 20 min then the layers were separated. The aqueous phase was extracted with DCM and the combined organics were washed with sat. NaHCO₃(aq), water, dried over MgSO₄ and concentrated in vacuo to give crude (+/−)-5-bromo-2-hydroxy-N-trideuterated methyl-3-(oxiran-2-yl(phenyl)methyl)benzamide (15.4 g, 42.2 mmol, 101% yield) as a white/pale yellow solid.

LCMS (2 min High pH): Rt=1.01 min, [MH]+=367

Intermediate 114: (+/−)-5-Bromo-2-hydroxy-N-trideuterated-methyl-3-(1-phenylallyl)benzamide

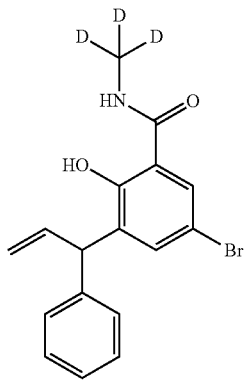 [SMILES: [2H]C([2H])([2H])NC(=O)c1cc(Br)cc(C(C=C)c2ccccc2)c1O]

A solution of (+/−)-methyl 5-bromo-2-hydroxy-3-(1-phenylallyl)benzoate (28 g, 81 mmol) in Water (100 mL) at rt was treated with C-trideuterated methylamine (416 mL). The resulting mixture was stirred at rt for 16 h and was then concentrated in vacuo. The residue was partitioned between water and EtOAc. The aqueous phase was extracted with EtOAc and the combined organics were washed with brine, dried over MgSO₄ and concentrated in vacuo. The residue was purified using silica gel column chromatography eluting with a gradient of 5-35% AcOEt:hexanes to give (+/−)-5-bromo-2-hydroxy-N-trideuterated-methyl-3-(1-phenylallyl)benzamide (14.65 g, 41.9 mmol, 52% yield) as a orange foam.

LCMS (2 min High pH): Rt=1.26 min, [MH]+=351

Intermediate 115: (trans)-5-Bromo-2-(fluoromethyl)-N-methyl-3-phenyl-2,3-dihydrobenzofuran-7-carboxamide

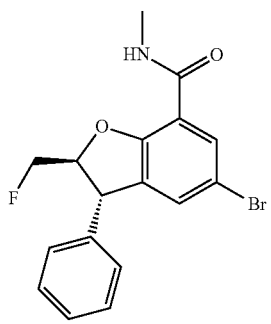 [SMILES: CNC(=O)c1cc(Br)cc2c1O[C@H](CF)[C@H]2c1ccccc1]

Deoxo-Fluor (100 mL, 271 mmol) was added dropwise to a suspension of (trans)-5-bromo-2-(hydroxymethyl)-N-methyl-3-phenyl-2,3-dihydrobenzofuran-7-carboxamide (49 g, 135 mmol) in DCM (400 mL) at 0° C. under N₂ over 1 h and the mixture was then stirred at 0° C. for 30 min, allowed to warm to rt over 1 h, then heated to 35° C. overnight under N₂. The mixture was poured into rapidly stirred sat. NaHCO₃ (aq) (2 L) in small portions, then the mixture was stirred for 30 min before separation of the phases. The organics were washed with sat. NaHCO₃ (aq), then dried and evaporated in vacuo to give a pale yellow solid. This was triturated with ether and the solid collected by filtration and washed with ether to give (trans)-5-bromo-2-(fluoromethyl)-N-methyl-3-phenyl-2,3-dihydrobenzofuran-7-carboxamide (26.5 g, 72.8 mmol, 54% yield) as a colourless solid.

LCMS (2 min Formic): Rt=1.19 min, [MH]+=366

Intermediate 116: (+/−)-(tert-Butyl 4,4-difluoro-3-(2-((trans)-2-methyl-7-(methylcarbamoyl)-3-phenyl-2,3-dihydrobenzofuran-5-carboxamido)ethyl)piperidine-1-carboxylate

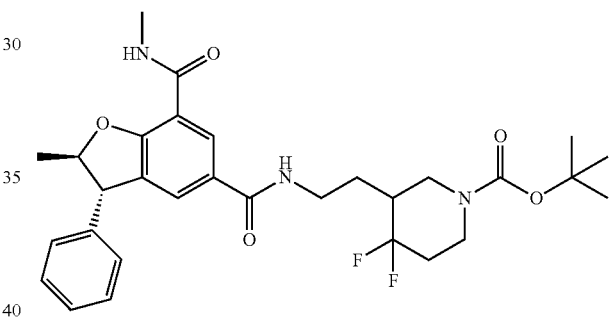

(+/−)-(trans)-2-Methyl-7-(methylcarbamoyl)-3-phenyl-2,3-dihydrobenzofuran-5-carboxylic acid (50 mg, 0.161 mmol), HATU (73.3 mg, 0.193 mmol) and DIPEA (0.084 mL, 0.482 mmol) were dissolved in DMF (3 mL) with stirring at rt for 5 min. tert-Butyl 3-(2-aminoethyl)-4,4-difluoropiperidine-1-carboxylate (59.4 mg, 0.225 mmol) was dissolved in DMF (1.00 mL) and added to the reaction mixture, which was then stirred at rt for 2 h further and tert-butyl 3-(2-aminoethyl)-4,4-difluoropiperidine-1-carboxylate (20 mg, 0.076 mmol) was added. The reaction mixture was stirred at rt for 1 h. The reaction mixture was diluted with water and extracted with DCM. The organics were washed with 10% LiCl (aq) and brine was added. The organic layers were dried via a hydrophobic frit and concentrated in vacuo. The residue was purified using silica gel column chromatography eluting with a gradient of 0-7% MeOH:DCM to give (+/−)-tert-butyl 4,4-difluoro-3-(2-((trans)-2-methyl-7-(methylcarbamoyl)-3-phenyl-2,3-dihydrobenzofuran-5-carboxamido)ethyl)piperidine-1-carboxylate (79 mg, 0.142 mmol, 88% yield), a yellow oil.

LCMS (2 min High pH): Rt=1.28 min, [MH]+=558

Intermediate 117: (trans)-N⁵-((1R,5S,6s)-3-azabicyclo[3.1.0]hexan-6-yl)-N⁷,2-dimethyl-3-phenyl-2,3-dihydrobenzofuran-5,7-dicarboxamide

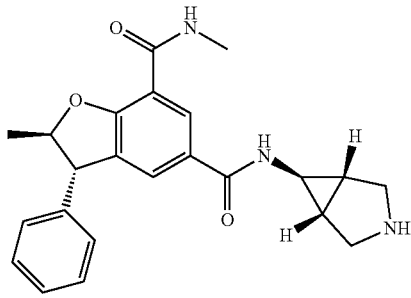 [SMILES: CNC(=O)c1cc(C(=O)N[C@H]2[C@@H]3CNC[C@@H]32)cc2c1O[C@H](C)[C@H]2c1ccccc1]

(1R,5S,6s)-tert-butyl 6-((trans)-2-methyl-7-(methylcarbamoyl)-3-phenyl-2,3-dihydrobenzofuran-5-carboxamido)-3-azabicyclo[3.1.0]hexane-3-carboxylate (240 mg, 0.462 mmol) was taken up in DCM (5 mL) and treated with TFA (0.107 mL, 1.386 mmol) and stirred at rt for 16 h. The reaction was concentrated and dried to give (trans)-N⁵-(1R,5S,6s)-3-azabicyclo[3.1.0]hexan-6-yl)-N⁷,2-dimethyl-3-phenyl-2,3-dihydrobenzofuran-5,7-dicarboxamide (168 mg, 0.429 mmol, 93% yield) as a yellow gum.

LCMS (2 min formic): Rt 0.63 min, [MH]⁺=392

Intermediate 118: (2S,3S)—N⁵-((1R,5S,6s)-3-Azabicyclo[3.1.0]hexan-6-yl)-2-(fluoromethyl)-N⁷-methyl-3-phenyl-2,3-dihydrobenzofuran-5,7-dicarboxamide

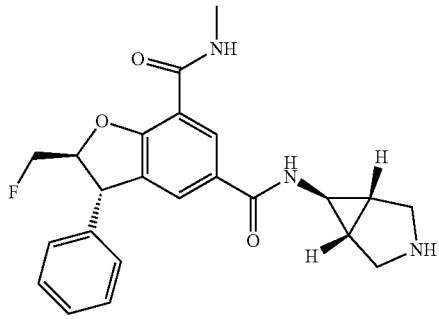 [SMILES: CNC(=O)c1cc(C(=O)N[C@H]2[C@@H]3CNC[C@@H]32)cc2c1O[C@H](CF)[C@H]2c1ccccc1]

(1R,5S,6s)-tert-Butyl 6-((2S,3S)-2-(fluoromethyl)-7-(methylcarbamoyl)-3-phenyl-2,3-dihydrobenzofuran-5-carboxamido)-3-azabicyclo[3.1.0]hexane-3-carboxylate (133 mg, 0.261 mmol) and TFA (0.201 mL, 2.61 mmol) were stirred in DCM (10 mL) at rt for 2 h. The reaction was concentrated to a brown gum, which was eluted through a SCX SPE (1 g) with MeOH followed by NH₃ solution (2M in MeOH). The ammonia fraction was concentrated to give (2S,3S)—N⁵-((1R,5S,6s)-3-azabicyclo[3.1.0]hexan-6-yl)-2-(fluoromethyl)-N⁷-methyl-3-phenyl-2,3-dihydrobenzofuran-5,7-dicarboxamide (85 mg, 0.208 mmol, 80% yield) as a yellow gum.

LCMS (2 min formic): Rt 0.55 min, [MH]⁺=410

Intermediate 119: (1R,5S,6s)-tert-Butyl 6-((trans)-2-(fluoromethyl)-7-(methylcarbamoyl)-3-phenyl-2,3-dihydrobenzofuran-5-carboxamido)-3-azabicyclo[3.1.0]hexane-3-carboxylate

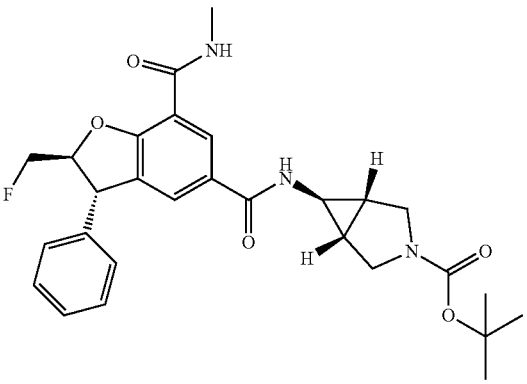 [SMILES: CNC(=O)c1cc(C(=O)N[C@H]2[C@@H]3CN(C(=O)OC(C)(C)C)C[C@@H]32)cc2c1O[C@H](CF)[C@H]2c1ccccc1]

(1R,5S,6s)-Tert-butyl 6-amino-3-azabicyclo[3.1.0]hexane-3-carboxylate (212 mg, 1.071 mmol) (available from, for example, Astatech), (trans)-5-bromo-2-(fluoromethyl)-N-methyl-3-phenyl-2,3-dihydrobenzofuran-7-carboxamide (130 mg, 0.357 mmol), palladium(II) acetate (40.1 mg, 0.178 mmol), xantphos (103 mg, 0.178 mmol), DMAP (65.4 mg, 0.535 mmol) and Cobalt Carbonyl (61.0 mg, 0.178 mmol) were placed in a microwave vial and the cap added. 1,4-Dioxane (4 mL) was added and the reaction was irradiated in a biotage microwave at 90° C. for 1 h. The reaction was diluted with water and extracted with EtOAc. The organic phase was washed with brine, dried using a hydrophobic frit and concentrated to a black oil. This oil was purified using using silica gel column chromatography eluting with a gradient of 0-40% (25% EtOH in EtOAc):Etoac to give (1R,5S,6s)-tert-butyl 6-((trans)-2-(fluoromethyl)-7-(methylcarbamoyl)-3-phenyl-2,3-dihydrobenzofuran-5-carboxamido)-3-azabicyclo[3.1.0]hexane-3-carboxylate (133 mg, 0.261 mmol, 73.1% yield) as a brown oil.

LCMS (method formic): Rt=1.11 min, [MH]⁺=510

Intermediate 120: (2R,3R)-2-(Fluoromethyl)-7-(methylcarbamoyl)-3-phenyl-2,3-dihydrobenzofuran-5-carboxylic Acid

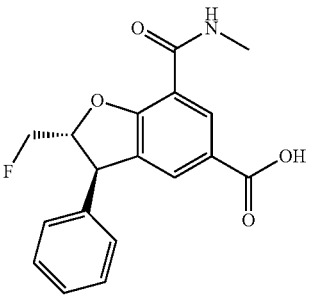 [SMILES: CNC(=O)c1cc(C(=O)O)cc2c1O[C@@H](CF)[C@@H]2c1ccccc1]

Methyl (2R,3R)-2-(fluoromethyl)-7-(methylcarbamoyl)-3-phenyl-2,3-dihydrobenzofuran-5-carboxylate (2.2 g, 6.41 mmol) and lithium hydroxide (0.307 g, 12.81 mmol) were stirred in water (30 mL) and THF (30 mL) at 50° C. for 16 h. The reaction was concentrated to remove the THF and was then diluted with water before being acidified to pH 3 with 2N HCl (aq). A precipitate formed which was removed by filtration and dried to give (2R,3R)-2-(fluoromethyl)-7-(methylcarbamoyl)-3-phenyl-2,3-dihydrobenzofuran-5-carboxylic acid (2.010 g, 6.10 mmol, 95% yield) as a white solid.

LCMS (method formic): Rt 0.89 min, [M+H]$^+$=330

Intermediate 121: (2S,3S)-5-Bromo-2-(fluoromethyl)-N-methyl-3-phenyl-2,3-dihydrobenzofuran-7-carboxamide

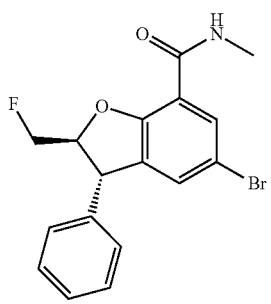 [SMILES: CNC(=O)c1cc(Br)cc2c1O[C@H](CF)[C@H]2c1ccccc1]

(trans)-5-bromo-2-(fluoromethyl)-N-methyl-3-phenyl-2,3-dihydrobenzofuran-7-carboxamide (320 mg, 0.879 mmol) (320 mg) was purified by chiral HPLC. The racemate was dissolved in EtOH (5 mL). Injection: 0.5 mL of the solution was injected onto the column (20% EtOH/heptane, flow rate=20 mL/min, detection wavelength=215 nm, 4. Ref 550, 100, Column 2 cm×25 cm Chiralcel OJ (10 µm), lot no. OJ00CJ-FD022). Total number of injections=12. Fractions from 5.75-6.5 min were bulked and labelled peak 1. Fractions from 6.5-7.5 min were bulked and labelled mix, Fractions from 7.5-9.5 min were bulked and labelled peak 2. The bulked mixed fractions were concentrated in vacuo and reprocessed using the above method. The bulked pure fractions were concentrated in vacuo and then transferred to weighed flasks.

The fractions corresponding to peak 1 were collected to afford (2S,3S)-5-Bromo-2-(fluoromethyl)-N-methyl-3-phenyl-2,3-dihydrobenzofuran-7-carboxamide (145 mg)

LCMS (2 min Formic): Rt=1.17 min, [MH]+=364, 366.

Intermediate 122: N$^5$-((1R,5S,6r)-3-Oxabicyclo[3.1.0]hexan-6-yl)-3-bromo-N$^7$,2-dimethylbenzofuran-5,7-dicarboxamide

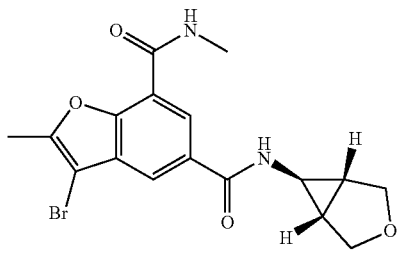 [SMILES: CNC(=O)c1cc(C(=O)N[C@H]2[C@@H]3COC[C@@H]32)cc2c(Br)c(C)oc12]

A flask was charged with 3-bromo-2-methyl-7-(methylcarbamoyl)benzofuran-5-carboxylic acid (713 mg, 2.28 mmol) and (1R,5S,6r)-3-oxabicyclo[3.1.0]hexan-6-amine (226 mg, 2.28 mmol) then was filled with DCM (17 mL). The resulting mixture was treated at rt with DIPEA (1.20 mL, 6.85 mmol) and the resulting solution was stirred at this temperature for 5 min. T3P (1.63 mL, 2.74 mmol) was added and the reaction mixture was stirred at rt for 3 h. (1R,5S,6r)-3-Oxabicyclo[3.1.0]hexan-6-amine (45.3 mg, 0.457 mmol) was then added and the reaction mixture was stirred for 30 min at rt. T3P (0.680 mL, 1.14 mmol) was then added and the reaction mixture was stirred at rt for 16 h. DIPEA (0.399 mL, 2.28 mmol) was then added, followed by T3P (0.680 mL, 1.14 mmol) and the reaction mixture was stirred at rt for 2 h. The mixture was then treated with a sat. NaHCO$_3$ (aq) and the layers were separated. The aqueous phase was extracted with DCM and the combined organics were washed with brine, dried using a hydrophobic frit and concentrated in vacuo to give N$^5$-((1R,5S,6r)-3-oxabicyclo[3.1.0]hexan-6-yl)-3-bromo-N$^7$,2-dimethylbenzofuran-5,7-dicarboxamide (583 mg, 65%) as a cream coloured solid.

LCMS (2 min high pH): Rt 0.84 min, [M+H]$^+$=395 (1 Br).

Intermediate 123: N$^5$-((1R,5S,6r)-3-Oxabicyclo[3.1.0]hexan-6-yl)-3-(3-hydroxyphenyl)-N$^7$,2-dimethylbenzofuran-5,7-dicarboxamide

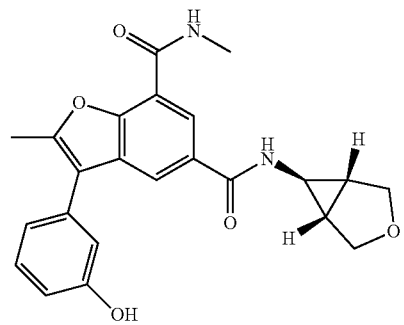 [SMILES: CNC(=O)c1cc(C(=O)N[C@H]2[C@@H]3COC[C@@H]32)cc2c(-c3cccc(O)c3)c(C)oc12]

A flask was charged with N$^5$-((1R,5S,6r)-3-oxabicyclo[3.1.0]hexan-6-yl)-3-bromo-N$^7$,2-dimethylbenzofuran-5,7-dicarboxamide (653 mg, 1.66 mmol), (3-hydroxyphenyl)boronic acid (275 mg, 1.99 mmol), palladium(II) acetate (37.3 mg, 0.166 mmol), CatacXium A (59.5 mg, 0.166 mmol) and K$_2$CO$_3$ (136 mg, 0.984 mmol) was then filled with 1,4-dioxane (9 mL) and water (3 mL) and the reaction mixture was stirred at 70° C. under N$_2$ for 1 h. (3-Hydroxyphenyl)boronic acid (275 mg, 1.99 mmol), palladium(II) acetate (37.3 mg, 0.166 mmol), CatacXium A (59.5 mg, 0.166 mmol) and K$_2$CO$_3$ (229 mg, 1.66 mmol) were added and the reaction mixture was stirred under N$_2$ at 70° C. for 16 h, then was cooled to rt. The reaction mixture was eluted through a 10 g celite column with MeOH and EtOAc and the fractions were concentrated in vacuo. The residue was diluted with water and the aqueous phase was extracted with EtOAc. The organics were washed with brine, dried via a hydrophobic frit and concentrated in vacuo. The residue was dissolved in DCM and MeOH, Florisil® was added and the mixture was concentrated in vacuo. The resulting free flowing solid was charged onto a 50 g silica column and eluted with a gradient of 0-80% [25% EtOH in EtOAc]:cyclohexane. The relevant fractions were concentrated in vacuo to give N$^5$-((1R,5S,6r)-3-oxabicyclo[3.1.0]hexan-6-yl)-3-(3-hydroxyphenyl)-N$^7$,2-dimethylbenzofuran-5,7-dicarboxamide (270 mg, 40%), a white solid.

LCMS (2 min high pH): Rt 0.84 min, [M+H]$^+$=407.

Intermediate 124: N⁵-((1R,5S,6r)-3-Oxabicyclo[3.1.0]hexan-6-yl)-3-(3-(2-methoxyethoxy)phenyl)-N⁷,2-dimethylbenzofuran-5,7-dicarboxamide

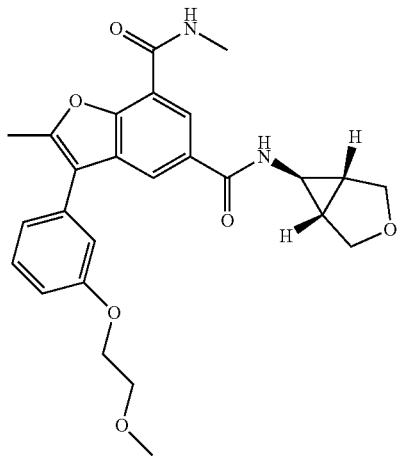 [SMILES: CNC(=O)c1cc(C(=O)N[C@H]2[C@@H]3COC[C@@H]32)cc2c(-c3cccc(OCCOC)c3)c(C)oc12]

A flask was charged with N⁵-((1R,5S,6r)-3-oxabicyclo[3.1.0]hexan-6-yl)-3-(3-hydroxyphenyl)-N⁷,2-dimethylbenzofuran-5,7-dicarboxamide (200 mg, 0.492 mmol) and K₂CO₃ (136 mg, 0.984 mmol) and DMF (5 ml) was added. The resulting mixture was treated at rt with 1-chloro-2-methoxyethane (0.054 mL, 0.59 mmol) and was then stirred at 70° C. for 2 h, further 1-chloro-2-methoxyethane (0.135 mL, 1.48 mmol) was added and the reaction mixture was stirred at 70° C. for 16h. Further 1-chloro-2-methoxyethane (0.135 mL, 1.48 mmol) and K₂CO₃ (136 mg, 0.984 mmol) were added and the reaction mixture stirred at 70° C. for 3 h and then at 90° C. for 3 h. The reaction was cooled to rt and diluted with water, the aqueous phase was extracted with DCM, the organics were washed with 10% w/w LiCl (aq) dried using a hydrophobic frit and concentrated in vacuo to give N⁵-((1R,5S,6r)-3-oxabicyclo[3.1.0]hexan-6-yl)-3-(3-(2-methoxyethoxy)phenyl)-N⁷,2-dimethylbenzofuran-5,7-dicarboxamide (224 mg, 98%) as an orange oil.

LCMS (2 min formic): Rt=0.96 min, [MH]⁺=465

Intermediate 125: (cis)-N⁵-((1R,5S,6r)-3-Oxabicyclo[3.1.0]hexan-6-yl)-3-(3-(2-methoxyethoxy)phenyl)-N⁷,2-dimethyl-2,3-dihydrobenzofuran-5,7-dicarboxamide

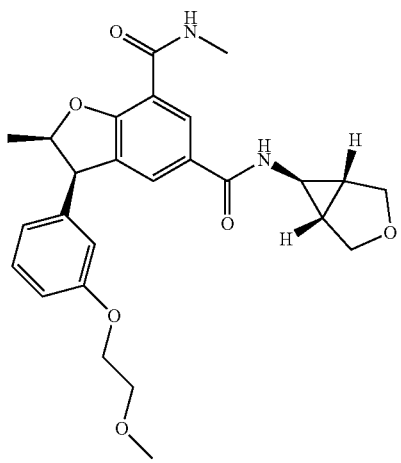 [SMILES: CNC(=O)c1cc(C(=O)N[C@H]2[C@@H]3COC[C@@H]32)cc2c1O[C@H](C)[C@@H]2c1cccc(OCCOC)c1]

A mixture of N⁵-((1R,5S,6r)-3-oxabicyclo[3.1.0]hexan-6-yl)-3-(3-(2-methoxyethoxy)phenyl)-N⁷,2-dimethylbenzofuran-5,7-dicarboxamide (224 mg, 0.482 mmol) and Pd—C 424 (commercially available from, for example, Johnson Matthey, 100 mg) in EtOH (10 mL) was stirred at rt under an atmosphere of H₂ (1 atm) for 4 days. The reaction was filtered through Celite to remove the catalyst and was then concentrated in vacuo to give (cis)-N⁵-((1R,5S,6r)-3-oxabicyclo[3.1.0]hexan-6-yl)-3-(3-(2-methoxyethoxy)phenyl)-N⁷,2-dimethyl-2,3-dihydrobenzofuran-5,7-dicarboxamide (198 mg, 88%) as a colourless gum.

LCMS (2 min formic): Rt 0.92 min, [M+H]⁺=467.

Intermediate 126: (+/−)tert-Butyl 3,3-difluoro-4-(3-((trans)-2-methyl-7-(methylcarbamoyl)-3-phenyl-2,3-dihydrobenzofuran-5 carboxamido)propyl)piperidine-1-carboxylate

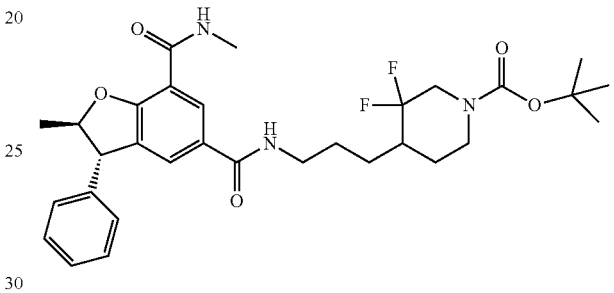

(+/−)(trans)-2-Methyl-7-(methylcarbamoyl)-3-phenyl-2,3-dihydrobenzofuran-5-carboxylic acid (80 mg, 0.26 mmol), tert-butyl 4-(3-aminopropyl)-3,3-difluoropiperidine-1-carboxylate (71.5 mg, 0.257 mmol), DIPEA (0.134 mL, 0.771 mmol) and HATU (147 mg, 0.385 mmol) were dissolved in DMF (5 mL) and the resulting mixture was stirred for 15 min at rt then was left still overnight (16 h). The mixture was then diluted with EtOAc and the organic phase was washed with water (20 mL) then with a sat. NaHCO₃ (aq), passed through a hydrophobic frit and concentrated in vacuo Purification of the residue by flash chromatography on silica gel (10 g column, gradient: 0-100% EtOAc in hexanes) gave (+/−) tert-butyl 3,3-difluoro-4-(3-((trans)-2-methyl-7-(methylcarbamoyl)-3-phenyl-2,3-dihydrobenzofuran-5-carboxamido)propyl)piperidine-1-carboxylate (91 mg, 95%).

LCMS (2 min formic): Rt 1.27 min, [M+H]⁺=572.

Intermediate 127: (+/−)(trans)-N⁵-(3-(3,3-difluoropiperidin-4-yl)propyl)-N⁷,2-dimethyl-3-phenyl-2,3-dihydrobenzofuran-5,7-dicarboxamide

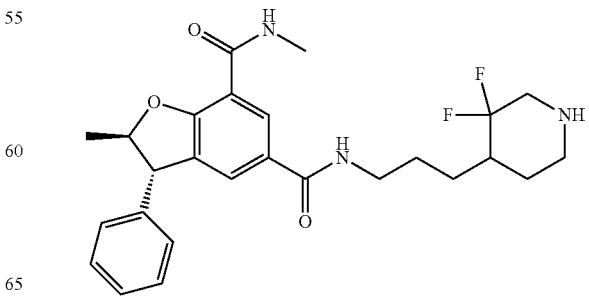

A solution of (+/−) tert-butyl 3,3-difluoro-4-(3-(((trans)-2-methyl-7-(methylcarbamoyl)-3-phenyl-2,3-dihydrobenzofuran-5-carboxamido)propyl)piperidine-1-carboxylate (91 mg, 0.159 mmol) in DCM (4 mL) at rt was treated with TFA (0.5 mL, 6.49 mmol) and the resulting mixture was stirred for 15 min at this temperature then this was concentrated in vacuo and was further dried under a stream of nitrogen for 2 h to give (+/−) (trans)-$N^5$-(3-(3,3-difluoropiperidin-4-yl)propyl)-$N^7$,2-dimethyl-3-phenyl-2,3-dihydrobenzofuran-5,7-dicarboxamide trifluoroacetate (75 mg, 76%) as a white solid.

LCMS (2 min high pH): Rt 1.03 min, [M+H]$^+$=472

Intermediate 128: (2S,3S)—$N^5$-(4,4-Diethoxybutyl)-2-(fluoromethyl)-$N^7$-methyl-3-phenyl-2,3-dihydrobenzofuran-5,7-dicarboxamide

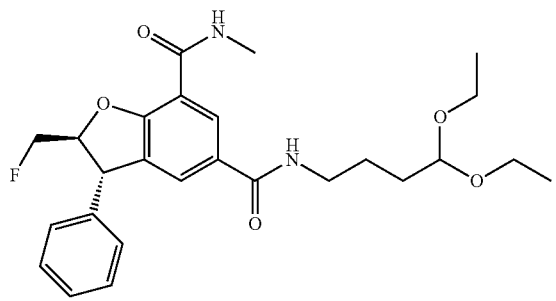 [SMILES: CCOC(CCCNC(=O)c1cc(C(=O)NC)c2c(c1)[C@H](c1ccccc1)[C@@H](CF)O2)OCC]

(2S,3S)-2-(Fluoromethyl)-7-(methylcarbamoyl)-3-phenyl-2,3-dihydrobenzofuran-5-carboxylic acid (200 mg, 0.607 mmol), HATU (277 mg, 0.729 mmol) and DIPEA (0.318 mL, 1.822 mmol) were dissolved in DMF (1 mL) and left to mix at rt for 5 min. 4,4-Diethoxybutan-1-amine (0.109 mL, 0.607 mmol) was added and the resulting mixture was stirred at rt for 1.5 h. Further 4,4-diethoxybutan-1-amine (0.109 mL, 0.607 mmol) was added and the reaction was stirred for 5 min then left to stand overnight. It was then diluted in EtOAc and the organic phase was washed with a 2% w/w citric acid (aq), brine, and then with a sat sodium NaHCO$_3$ (aq) and concentrated in vacuo. The residue obtained was dissolved in DCM (5 mL). The insolubles were filtered off, dissolved in MeOH (5 mL) and blown down overnight to give a first fraction of product. The DCM filtrate was loaded onto a 25 g silica cartridge. Purification by flash chromatography on silica gel (20-100% EtOAc in cyclohexane) gave a second fraction of product. Both fractions were combined to give (2S,3S)—$N^5$-(4,4-diethoxybutyl)-2-(fluoromethyl)-$N^7$-methyl-3-phenyl-2,3-dihydrobenzofuran-5,7-dicarboxamide (158 mg, 55%) as a white solid.

LCMS (2 min high pH): Rt 1.08 min, [M−H]$^−$=471

Intermediate 129: (2S,3S)—$N^5$-(3-((2r,5)-5-(1,3-Dioxoisoindolin-2-yl)-1,3-dioxan-2-yl)propyl)-2-(fluoromethyl)-$N^7$-methyl-3-phenyl-2,3-dihydrobenzofuran-5,7-dicarboxamide

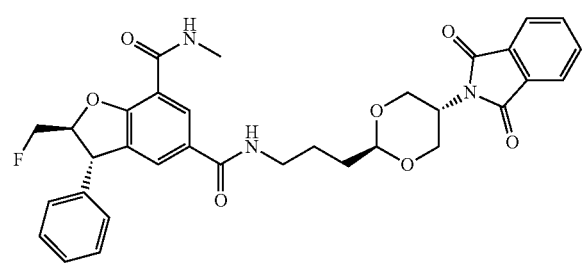 [SMILES: CNC(=O)c1cc(C(=O)NCCC[C@H]2OC[C@H](N3C(=O)c4ccccc4C3=O)CO2)cc2c1O[C@H](CF)[C@H]2c1ccccc1]

A suspension of (2S,3S)—$N^5$-(4,4-diethoxybutyl)-2-(fluoromethyl)-$N^7$-methyl-3-phenyl-2,3-dihydrobenzofuran-5,7-dicarboxamide (158 mg, 0.318 mmol), 2-(1,3-dihydroxypropan-2-yl)isoindoline-1,3-dione (70.3 mg, 0.318 mmol) and p-toluenesulfonic acid monohydrate (60.4 mg, 0.318 mmol) in toluene (6 mL) was stirred at 40° C. for 1.5 h then at 70° C. under N$_2$ for a further 4 h before being allowed to cool to rt and left to stand overnight. The solvent was then removed in vacuo. The residue obtained was partitioned between EtOAc and a 1M Na$_2$CO$_3$ (aq) and the layers were separated. The aqueous phase was extracted with EtOAc and the combined organics were dried using a hydrophobic frit. The filtrate was evaporated in vacuo. Purification of the residue by flash chromatography on silica gel (50 g column, gradient 70-100% EtOAc in cyclohexane) gave (2S,3S)—$N^5$-(3-(5-(1,3-dioxoisoindolin-2-yl)-1,3-dioxan-2-yl)propyl)-2-(fluoromethyl)-$N^7$-methyl-3-phenyl-2,3-dihydrobenzofuran-5,7-dicarboxamide (48 mg, 25%) as a yellow solid.

LCMS (2 min formic): Rt 1.12 min, [M+H]$^+$=602

Intermediate 130: (2S,3S)—$N^5$-(3,3-Diethoxypropyl)-2-(fluoromethyl)-$N^7$-methyl-3-phenyl-2,3-dihydrobenzofuran-5,7-dicarboxamide

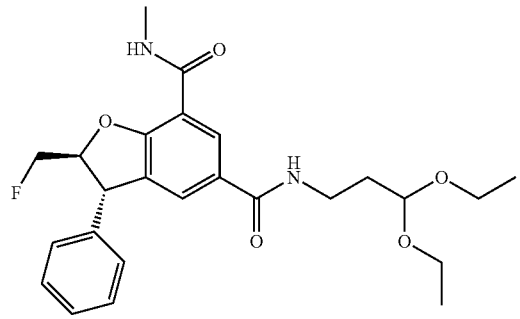 [SMILES: CCOC(CCNC(=O)c1cc(C(=O)NC)c2c(c1)[C@H](c1ccccc1)[C@@H](CF)O2)OCC]

A flask was charged with (2S,3S)-2-(fluoromethyl)-7-(methylcarbamoyl)-3-phenyl-2,3-dihydrobenzofuran-5-carboxylic acid (250 mg, 0.759 mmol) and HATU (346 mg, 0.911 mmol), then was filled with DMF (4 mL) and the resulting mixture was treated at rt with DIPEA (0.398 mL, 2.28 mmol) then was stirred at this temperature for 5 min. 3,3-Diethoxypropan-1-amine (0.147 mL, 0.911 mmol) was then added and the resulting mixture was stirred for 1 h at rt before being diluted with water (50 mL). The aqueous phase was extracted with EtOAc. The combined organics were washed with a 10% w/w LiCl (aq) and filtered through a hydrophobic frit. The solvents were evaporated in vacuo. Purification of the residue obtained by flash chromatography on silica gel (10 g column, gradient: 20 to 100% EtOAc in cyclohexane) gave (2S,3S)—$N^5$-(3,3-diethoxypropyl)-2-(fluoromethyl)-$N^7$-methyl-3-phenyl-2,3-dihydrobenzofuran-5,7-dicarboxamide (306 mg, 88%) as a yellow gum.

LCMS (2 min formic): Rt 1.05 min, [M+H]$^+$=458

Intermediate 131: (2S,3S)—N⁵-(2-((2r,5S)-5-(1,3-Dioxoisoindolin-2-yl)-1,3-dioxan-2-yl)ethyl)-2-(fluoromethyl)-N⁷-methyl-3-phenyl-2,3-dihydrobenzofuran-5,7-dicarboxamide

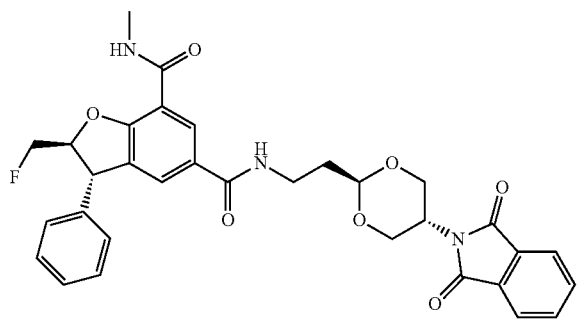 [SMILES: CNC(=O)c1cc(C(=O)NCC[C@H]2OC[C@H](N3C(=O)c4ccccc4C3=O)CO2)cc2c1O[C@H](CF)[C@H]2c1ccccc1]

A suspension of (2S,3S)—N⁵-(3,3-diethoxypropyl)-2-(fluoromethyl)-N⁷-methyl-3-phenyl-2,3-dihydrobenzofuran-5,7-dicarboxamide (306 mg, 0.668 mmol), 2-(1,3-dihydroxpropan-2-yl)isoindoline-1,3-dione (162 mg, 0.734 mmol) and p-toluenesulfonic acid monohydrate (140 mg, 0.734 mmol) in toluene (10 mL) was stirred at 70° C. under N₂ overnight then was allowed to cool to rt and concentrated in vacuo to give a brown solid. This residue was partitioned between EtOAc and a 2N Na₂CO₃ (aq) and the layers were separated. The aqueous phase was extracted with EtOAc and the combined organic phases were dried using a hydrophobic frit. The filtrate was concentrated in vacuo to give (2S,3S)—N⁵-(2-((2r,5S)-5-(1,3-Dioxoisoindolin-2-yl)-1,3-dioxan-2-yl)ethyl)-2-(fluoromethyl)-N⁷-methyl-3-phenyl-2,3-dihydrobenzofuran-5,7-dicarboxamide (144.9 mg, 37%) as a white solid.

LCMS (2 min formic): Rt 1.09 min, [M+H]⁺=588

Intermediate 132: Methyl 3-bromo-4-(cinnamyloxy)benzoate

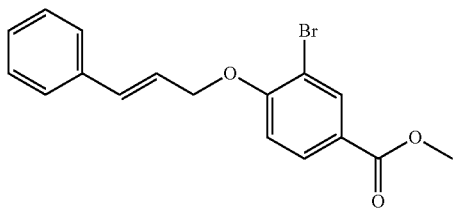 [SMILES: COC(=O)c1ccc(OC/C=C/c2ccccc2)c(Br)c1]

A flask was charged with methyl 3-bromo-4-hydroxybenzoate (40.7 g, 176 mmol), potassium carbonate (48.7 g, 352 mmol) and potassium iodide (2.047 g, 12.33 mmol) then was filled with acetone (400 mL) and the resulting suspension was treated with (E)-(3-chloroprop-1-en-1-yl)benzene (27.2 mL, 282 mmol) before being stirred at reflux for 8 h. The mixture was cooled to rt and the solid was filtered off and partitioned between EtOAc and water. The layers were sperated and the water layer further extracted with EtOAc. The acetone filtrate was concentrated in vacuo and the residue dissolved into the combined EtOAc fractions from the extraction. The EtOAc layer was washed with water and the combined phases ran through a filter to collect a solid which was washed with EtOAc and dried under vacuum at 40° C. for 2 h to give methyl 3-bromo-4-(cinnamyloxy)benzoate (7.7 g, 22.18 mmol, 13% yield). The layers were separated, the organic phase washed with brine, dried over MgSO₄ and concentrated in vacuo to give methyl 3-bromo-4-(cinnamyloxy)benzoate (47.4 g, 137 mmol, 77% yield) as a pale yellow solid.

LCMS (2 min high pH): Rt 1.46 min, [MH]⁺=does not ionise at correct m/z

Intermediate 133: Methyl 3-bromo-4-hydroxy-5-(1-phenylallyl)benzoate

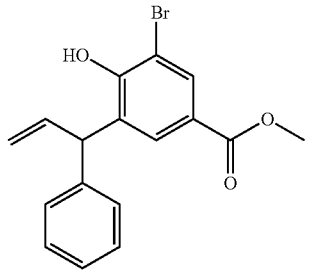 [SMILES: C=CC(c1ccccc1)c1cc(C(=O)OC)cc(Br)c1O]

A solution of methyl 3-bromo-4-(cinnamyloxy)benzoate (15 g, 43.2 mmol) in N,N-dimethyl aniline (100 mL) was stirred at 220° C. for 1 h then was cooled to rt. The mixture was poored onto an ice cold 25% w/w HCl (aq) with 300 mL of EtOAc. The layers were separated and the aqueous phase was extracted twice with EtOAc. The combined organics were washed twice with sat NaHCO₃ (aq), then brine, dried over MgSO₄ and concentrated in vacuo to give methyl 3-bromo-4-hydroxy-5-(1-phenylallyl)benzoate (15 g, 43.2 mmol, 100% yield) as a pale brown oil.

LCMS (2 min high pH): Rt 0.85 min, [MH]⁺=347

Intermediate 134: Methyl 3-bromo-4-(methoxymethoxy)-5-(1-phenylallyl)benzoate

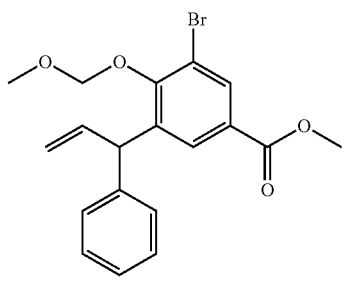

A solution of methyl 3-bromo-4-hydroxy-5-(1-phenylallyl)benzoate (15.0 g, 43.2 mmol) in DMF (100 mL) at rt was treated with K₂CO₃ (11.9 g, 86.0 mmol) then with MOM-Cl (3.94 mL, 51.8 mmol) dropwise. After 10 min, the mixture was partitioned between water and Et₂O and the layers were separated. The aqueous phase was extracted twice with Et₂O and the combined organics were washed with water then brine, dried over MgSO₄ and concentrated in vacuo. Purification of the residue by flash chromatography on silica gel (330 g column, 0 to 10% EtOAc in hexanes) gave methyl 3-bromo-4-(methoxymethoxy)-5-(1-phenylallyl)benzoate (13 g, 77%) as a pale orange oil.

Intermediate 135: 3-Bromo-4-(methoxymethoxy)-5-(1-phenylallyl)benzoic Acid

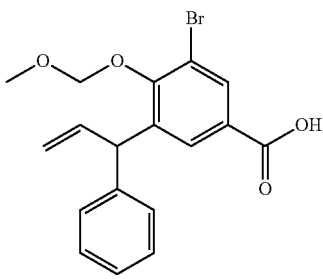 [SMILES: C=CC(c1ccccc1)c1cc(C(=O)O)cc(Br)c1OCOC]

A solution of methyl 3-bromo-4-(methoxymethoxy)-5-(1-phenylallyl)benzoate (6.00 g, 15.3 mmol) in MeOH (40 mL) and THF (20 mL) at rt was treated with NaOH (2N in water, 19.17 mL, 38.3 mmol) and the resulting mixture was stirred at 80° C. for 1.5 h, then was cooled to rt. Most of the volatiles were removed in vacuo and the residue was diluted with water. The aqueous phase was extracted with Et$_2$O then acidified with 2N HCl (aq). The suspension was extracted twice with EtOAc and the combined organics were washed with brine, dried over MgSO$_4$ and concentrated in vacuo. The residue was triturated with Et$_2$O to give 3-bromo-4-(methoxymethoxy)-5-(1-phenylallyl)benzoic acid (2.9 g, 50%) as a white solid. The Et$_2$O phase used for trituration was then concentrated in vacuo to give further 3-bromo-4-(methoxymethoxy)-5-(1-phenylallyl)benzoic acid (2.4 g, 41%) as a pale brown solid.

LCMS (2 min high pH): Rt 0.78 min, [M−H]$^-$=377 (1 Br).

Intermediate 136: N-((1R,5S,6r)-3-Oxabicyclo[3.1.0]hexan-6-yl)-3-bromo-4-(methoxymethoxy)-5-(1-phenyl)benzamide

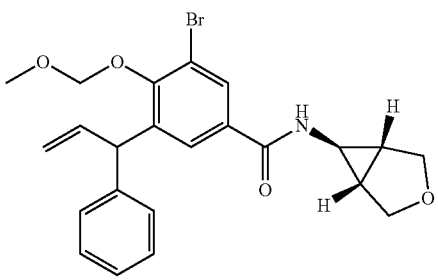 [SMILES: C=CC(c1ccccc1)c1cc(C(=O)N[C@H]2[C@@H]3COC[C@@H]32)cc(Br)c1OCOC]

A solution of 3-bromo-4-(methoxymethoxy)-5-(1-phenylallyl)benzoic acid (2.30 g, 6.10 mmol) in DMF (25 mL) at rt was treated with HATU (2.78 g, 7.32 mmol) then DIPEA (2.66 mL, 15.2 mmol) followed by (1R,5S,6r)-3-oxabicyclo[3.1.0]hexan-6-amine hydrochloride (0.992 g, 7.32 mmol) and the resulting yellow mixture was stirred at this temperature for 10 min then was diluted with water. The aqueous phase was extracted three times with EtOAc. The combined organics were washed with sat. LiCl (aq), then with brine, dried over MgSO$_4$ and concentrated in vacuo. Purification of the residue by flash chromatography on silica gel (100 g column, 40% AcOEt in hexanes) gave N-((1R,5S,6r)-3-oxabicyclo[3.1.0]hexan-6-yl)-3-bromo-4-(methoxymethoxy)-5-(1-phenylallyl)benzamide (2.45 g, 88%) as a white foam.

LCMS (2 min high pH): Rt 1.20 min, [M+H]$^+$=458 (1 Br).

Intermediate 137: (+/−)-N-((1R,5S,6r)-3-Oxabicyclo[3.1.0]hexan-6-yl)-3-bromo-4-hydroxy-5-(1-phenylallyl)benzamide

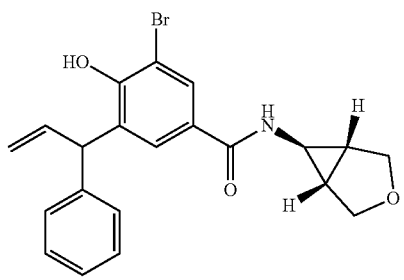 [SMILES: C=CC(c1ccccc1)c1cc(C(=O)N[C@H]2[C@@H]3COC[C@@H]32)cc(Br)c1O]

A solution of N-(1R,5S,6r)-3-oxabicyclo[3.1.0]hexan-6-yl)-3-bromo-4-(methoxymethoxy)-5-(1-phenylallyl)benzamide (2.45 g, 5.35 mmol) in DCM (15 mL) at rt was treated with HCl (4N in dioxane, 5.35 mL, 21.4 mmol) and the resulting mixture was stirred for 1 h at this temperature. The mixture was diluted with Et$_2$O and stirred for 4 min then the white precipitate which formed was filtered off, rinsed with Et$_2$O and dried under vacuum to give (+/−)-N-((1R,5S,6r)-3-oxabicyclo[3.1.0]hexan-6-yl)-3-bromo-4-hydroxy-5-(1-phenylallyl)benzamide (2.2 g, 99%) as a white solid.

LCMS (2 min formic): Rt 1.08 min, [M+H]$^+$=416 (1 Br).

Intermediate 138: (+/−)-N-((1R,5S,6r)-3-Oxabicyclo[3.1.0]hexan-6-yl)-3-bromo-4-hydroxy-5-(oxiran-2-yl(phenyl)methyl)benzamide

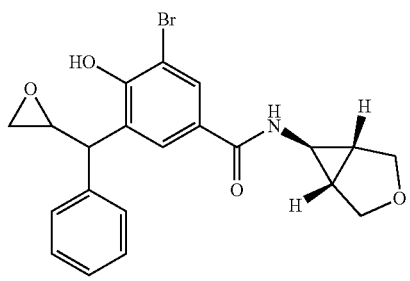 [SMILES: O=C(N[C@H]1[C@@H]2COC[C@@H]21)c1cc(Br)c(O)c(C(c2ccccc2)C2CO2)c1]

A solution of (+/−)-N-((1R,5S,6r)-3-oxabicyclo[3.1.0]hexan-6-yl)-3-bromo-4-hydroxy-5-(1-phenylallyl)benzamide (4.20 g, 10.1 mmol) in DCM (50 mL) at rt was treated with m-CPBA (<77% w/w, 5.68 g, 25.3 mmol) and the resulting mixture was stirred for 3 days at this temperature. m-CPBA (<77% w/w, 5.68 g, 25.3 mmol) was then added and the mixture was stirred at rt for two days. The mixture was then poured onto a mixture of a solution of sodium thiosulfate pentahydrate (15.1 g, 60.8 mmol) in water (100 mL) and sat. NaHCO$_3$ (aq). The biphasic mixture was stirred for 20 min at rt then the layers were separated. The aqueous phase was extracted twice with DCM and the combined organics were washed 3 times with sat. NaHCO$_3$ (aq) and then dried using a hydrophobic frit and concentrated in vacuo to give (+/−)-N-((1R,5S,6r)-3-oxabicyclo[3.1.0]

hexan-6-yl)-3-bromo-4-hydroxy-5-(oxiran-2-yl(phenyl) methyl)benzamide (4.5 g, 103%) as a very pale yellow foam (5/4 mixture of racemic diastereosiomers).

LCMS (method formic): Rt 0.88 and 0.93 min, [M+H]+=432 (1 Br)

Intermediate 139: (trans)-N-((1R,5S,6s)-3-Oxabicyclo[3.1.0]hexan-6-yl)-7-bromo-2-(hydroxymethyl)-3-phenyl-2,3-dihydrobenzofuran-5-carboxamide

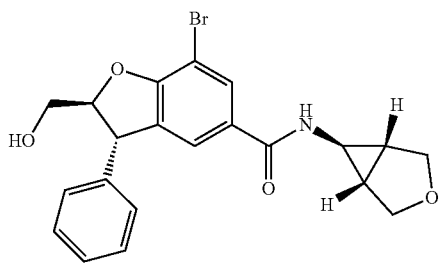 [SMILES: O=C(N[C@H]1[C@@H]2COC[C@@H]21)c1cc(Br)c2c(c1)[C@H](c1ccccc1)[C@@H](CO)O2]

A solution of N-((1R,5S,6r)-3-oxabicyclo[3.1.0]hexan-6-yl)-3-bromo-4-hydroxy-5-(oxiran-2-yl(phenyl)methyl)benzamide (4.2 g, 9.76 mmol) in water (5 mL) and DMSO (25 mL) at 0° C. was treated with KOH (1.095 g, 19.52 mmol) in water (5 mL) dropwise. The resulting mixture was stirred at this temperature for 8 h then was treated with acetic acid (1.285 mL, 22.45 mmol). 30 mL of water was added and a precipitate appeared which was vigorously stirred for 5 min then filtered off and rinsed with water. The residue obtained was dissolved in EtOAc (100 mL) and the organic phase was washed with brine, dried over MgSO4 and concentrated in vacuo to give (trans)-N-((1R,5S,6r)-3-oxabicyclo[3.1.0]hexan-6-yl)-7-bromo-2-(hydroxymethyl)-3-phenyl-2,3-dihydrobenzofuran-5-carboxamide (3.87 g, 92%) as a pale yellow foam.LCMS (2 min formic): Rt 0.93 min, [M+H]+=432 (1 Br)

Intermediate 140: (trans)-N-((1R,5S,6r)-3-Oxabicyclo[3.1.0]hexan-6-yl)-7-bromo-2-(fluoromethyl)-3-phenyl-2,3-dihydrobenzofuran-5-carboxamide

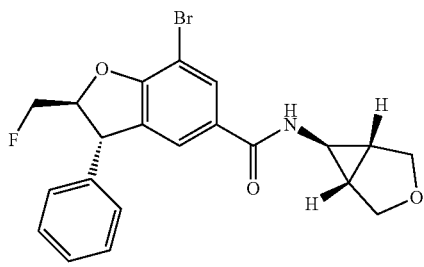 [SMILES: O=C(N[C@H]1[C@@H]2COC[C@@H]21)c1cc(Br)c2c(c1)[C@H](c1ccccc1)[C@@H](CF)O2]

A solution of (trans)-N-((1R,5S,6r)-3-oxabicyclo[3.1.0] hexan-6-yl)-7-bromo-2-(hydroxymethyl)-3-phenyl-2,3-dihydrobenzofuran-5-carboxamide (2.6 g, 6.0 mmol) in DCM (20 mL) at 0° C. was treated with deoxofluor (6.68 mL, 18.1 mmol) and the resulting solution was stirred at this temperature for 1 h, then was stirred at reflux overnight. The reaction mixture was then cooled to rt and added to sat. sodium bicarbonate (aq) (100 mL). The resulting biphasic mixture was stirred for 30 min, then the layers were separated. The organic phase was dried using a hydrophobic frit and concentrated in vacuo to give a pale yellow gum. Purification of the residue by flash chromatography on silica gel (25 g column, gradient: 0-100% EtOAc in cyclohexane) gave (trans)-N-((1R,5S,6r)-3-oxabicyclo[3.1.0]hexan-6-yl)-7-bromo-2-(fluoromethyl)-3-phenyl-2,3-dihydrobenzofuran-5-carboxamide (0.72 g, 28%) as a colourless gum.

LCMS (2 min formic): Rt 1.09 min, [M+H]+=434 (1 Br)

Intermediate 141: (trans)-Methyl 5-((1R,5S,6r)-3-oxabicyclo[3.1.0]hexan-6-ylcarbamoyl)-2-(fluoromethyl)-3-phenyl-2,3-dihydrobenzofuran-7-carboxylate

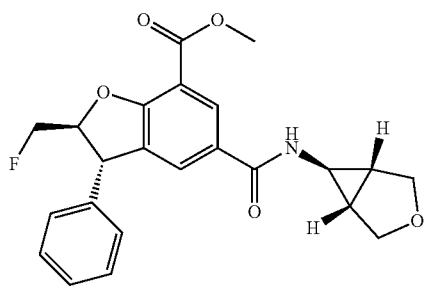 [SMILES: COC(=O)c1cc(C(=O)N[C@H]2[C@@H]3COC[C@@H]32)cc2c1O[C@H](CF)[C@H]2c1ccccc1]

(trans)-N-((1R,5S,6r)-3-Oxabicyclo[3.1.0]hexan-6-yl)-7-bromo-2-(fluoromethyl)-3-phenyl-2,3-dihydrobenzofuran-5-carboxamide (720 mg, 1.67 mmol), palladium(II) acetate (37.4 mg, 0.167 mmol) and Xantphos (96 mg, 0.17 mmol) were combined in a round bottom flask which was sealed with a suba seal and purged with nitrogen. DMF (5 mL), NEt3 (0.696 mL, 5.00 mmol) and MeOH (1.00 mL, 24.7 mmol) were added. The vessel was purged with carbon monoxide from a balloon, then stirred under a CO atmosphere (using a balloon) overnight at 70° C. The mixture was then cooled to rt and diluted with water (20 mL). The aqueous phase was extracted with EtOAc, and the organic phase was washed with a 10% w/w LiCl (aq), dried over MgSO4 and concentrated in vacuo. Purification of the residue by flash chromatography on silica gel (50 g column, gradient: 0-100% EtOAc in cyclohexane) gave methyl (trans)-5-(((1R,5S,6r)-3-oxabicyclo[3.1.0]hexan-6-yl)carbamoyl)-2-(fluoromethyl)-3-phenyl-2,3-dihydrobenzofuran-7-carboxylate (0.46 g, 67%) as a light brown solid.

LCMS (2 min formic): Rt 0.96 min, [M+H]+=412

Intermediate 142: (trans)-Methyl 5-((1R,5S,6r)-3-oxabicyclo[3.1.0]hexan-6-ylcarbamoyl)-2-(fluoromethyl)-3-phenyl-2,3-dihydrobenzofuran-7-carboxylate

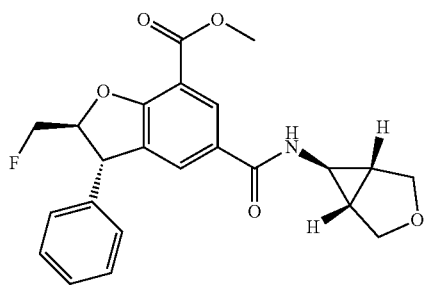 [SMILES: COC(=O)c1cc(C(=O)N[C@H]2[C@@H]3COC[C@@H]32)cc2c1O[C@H](CF)[C@H]2c1ccccc1]

(trans)-methyl 5-((1R,5S,6r)-3-oxabicyclo[3.1.0]hexan-6-ylcarbamoyl)-2-(fluoromethyl)-3-phenyl-2,3-dihydrobenzofuran-7-carboxylate (0.450 g, 1.09 mmol) was purified by chiral chromatography.

Approximatively 80 mg of racemate was dissolved in 1.5 mL EtOH and 3 mL DCM, heating the mixture until it became a solution. Injection: overall, 4.5 mL of the solution was injected onto the column (total number of injections: 6). Eluant: 40% EtOH (+0.2% isopropylamine) in heptane (+0.2% isopropylamine), flow=30 mL/min; wavelength, 215 nm. Column 30 mm×25 cm Chiralpak IC (5 μm). During this process, some mixed fractions were obtained. They were concentrated in vacuo and the residue obtained was submitted to the same process. Methyl (2S*,3S*)-5-(((1R,5S,6r)-3-oxabicyclo[3.1.0]hexan-6-yl)carbamoyl)-2-(fluoromethyl)-3-phenyl-2,3-dihydrobenzofuran-7-carboxylate was obtained as the fastest eluting isomer (201 mg, 89%).

LCMS (2 min high pH): Rt 0.97 min, [M+H]$^+$=412.

Intermediate 143: (trans)-5-(((1R,5S,6r)-3-Oxabicyclo[3.1.0]hexan-6-yl)carbamoyl)-2-(fluoromethyl)-3-phenyl-2,3-dihydrobenzofuran-7-carboxylic Acid

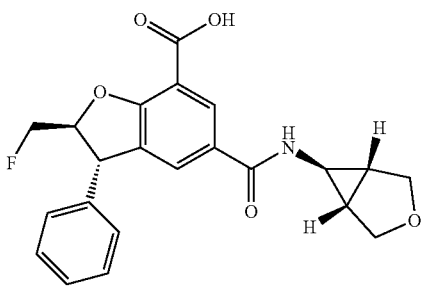 [SMILES: O=C(N[C@H]1[C@@H]2COC[C@@H]21)c1cc(C(=O)O)c2c(c1)[C@H](c1ccccc1)[C@@H](CF)O2]

NaOH (2N in water, 0.5 mL, 1 mmol) was added at rt to a solution of methyl (trans)-5-(((1R,5S,6r)-3-oxabicyclo[3.1.0]hexan-6-yl)carbamoyl)-2-(fluoromethyl)-3-phenyl-2,3-dihydrobenzofuran-7-carboxylate (200 mg, 0.486 mmol) in MeOH (10 mL) and the mixture was stirred at this temperature overnight, then was concentrated in vacuo. The residue was dissolved in water and the aqueous phase was acidified with 2N HCl aqueous solution to pH 2, giving a dense suspension. This was extracted with DCM and the combined organics were dried using a hydrophobic frit and concentrated in vacuo to give (trans)-5-(((1R,5S,6r)-3-oxabicyclo[3.1.0]hexan-6-yl)carbamoyl)-2-(fluoromethyl)-3-phenyl-2,3-dihydrobenzofuran-7-carboxylic acid (195 mg, 101%) as a colourless solid.

LCMS (2 min high pH): Rt 0.60 min, [M+H]$^+$=398

Intermediate 144: (trans)-N$^5$-((1R,5S,6r)-3,3-Difluorobicyclo[3.1.0]hexan-6-yl)-N$^7$,2-dimethyl-3-phenyl-2,3-dihydrobenzofuran-5,7-dicarboxamide

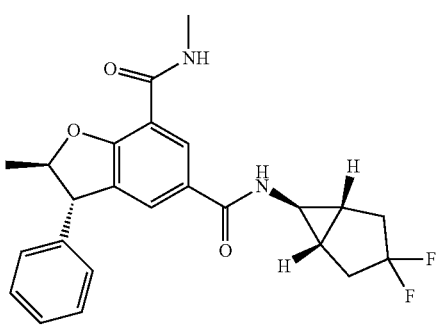 [SMILES: CNC(=O)c1cc(C(=O)N[C@H]2[C@@H]3CC(F)(F)C[C@@H]32)cc2c1O[C@H](C)[C@H]2c1ccccc1]

(trans)-2-Methyl-7-(methylcarbamoyl)-3-phenyl-2,3-dihydrobenzofuran-5-carboxylic acid (30 mg, 0.096 mmol), (1R,5S,6r)-3,3-difluorobicyclo[3.1.0]hexan-6-amine hydrochloride (21.25 mg, 0.125 mmol), HATU (55.0 mg, 0.145 mmol) and DIPEA (0.050 mL, 0.289 mmol) were dissolved in DMF (4 mL). The reaction mixture was stirred for 1 h. The reaction mixture was partitioned between EtOAc and water. The organic layer was washed with water, saturated aqueous NaHCO$_3$, passed through a hydrophobic frit and evaporated in vacuo. The sample was purified using MDAP (formic) to give (2R,3S)—N$^5$-((1R,5S,6r)-3,3-difluorobicyclo[3.1.0]hexan-6-yl)-N$^7$,2-dimethyl-3-phenyl-2,3-dihydrobenzofuran-5,7-dicarboxamide (18.2 mg, 0.041 mmol, 42% yield) as a white solid.

LCMS (2 min formic): Rt 1.11 min, [M+H]$^+$=427

Intermediate 145: (trans)-N$^7$,2-dimethyl-N$^5$-(1-methyl-1H-pyrazol-4-yl)-3-phenyl-2,3-dihydrobenzofuran-5,7-dicarboxamide

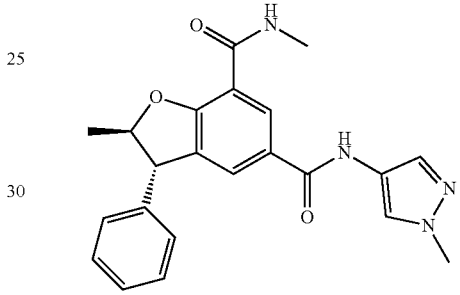

(trans)-2-methyl-7-(methylcarbamoyl)-3-phenyl-2,3-dihydrobenzofuran-5-carboxylic acid (100 mg, 0.321 mmol), HATU (147 mg, 0.385 mmol) and DIPEA (0.168 mL, 0.964 mmol) were stirred in DMF (4 mL) at rt for 5 min, 1-methyl-1H-pyrazol-4-amine (46.8 mg, 0.482 mmol) was added and the reaction stirred at rt for 1 h. The reaction was diluted with 10% aqueous citric acid and extracted with EtOAc. The organic phase was washed with 10% aqueous LiCl, dried using a hydrophobic frit and concentrated to give a yellow gum. This gum was purified using using silica gel column chromatography eluting with a gradient of 0-60% (25% EtOH in EtOAc):cyclohexane to give (trans)-N$^7$,2-dimethyl-N$^5$-(1-methyl-1H-pyrazol-4-yl)-3-phenyl-2,3-dihydrobenzofuran-5,7-dicarboxamide (65 mg, 0.166 mmol, 52% yield) as a white solid.

LCMS (2 min formic): Rt 0.95 min, [M+H]$^+$=391

Intermediate 146: tert-butyl(cyclopent-3-en-1-yloxy)dimethylsilane

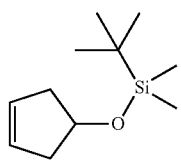

Cyclopent-3-en-1-ol (5 g, 59.4 mmol, commercially available from, for example, Astatech) was dissolved in DCM (100 mL) and TBDMS-Cl (8.96 g, 59.4 mmol) and imidazole (4.86 g, 71.3 mmol) were added, then the resulting suspension was stirred at room temperature over the weekend. The mixture was washed with water (2×100 mL), dried and evaporated in vacuo to give tert-butyl(cyclopent-3-en-1-yloxy)dimethylsilane (12.05 g, 60.7 mmol, 102% yield) as a pale yellow liquid.

$^1$H NMR (400 MHz, CHLOROFORM-d) δ ppm 5.68 (s, 2H) 4.50-4.62 (m, 1H) 2.59 (dd, J=14.9, 6.8 Hz, 2H) 2.23-2.37 (m, 2H) 0.91 (s, 9H) 0.09 (s, 6H).

Intermediate 147: (1R,5S,6r)-ethyl 3-((tert-butyldimethylsilyl)oxy)bicyclo[3.1.0]hexane-6-carboxylate

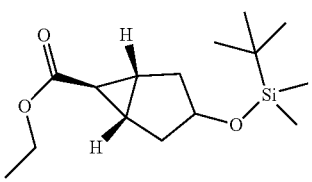 [SMILES: CCOC(=O)[C@H]1[C@@H]2CC(O[Si](C)(C)C(C)(C)C)C[C@@H]21]

Ethyl diazoacetate (6.90 mL, 66.5 mmol, commercially available from, for example, Sigma Aldrich) was dissolved in DCM (150 mL) and added dropwise over 5 h to a mixture of rhodium(II) acetate dimer (1 g, 2.263 mmol, commercially available from, for example, Sigma Aldrich) and tert-butyl(cyclopent-3-en-1-yloxy)dimethylsilane (12 g, 60.5 mmol) in DCM (150 mL) at room temperature. The resulting green solution was stirred overnight, then evaporated in vacuo to give a green liquid. This was loaded onto a 340 g silica column and eluted with 0-40% EtOAc/cyclohexane. Appropriate fractions were evaporated in vacuo to give ethyl (1R,5S,6r)-3-((tert-butyldimethylsilyl)oxy)bicyclo[3.1.0]hexane-6-carboxylate (5.5 g, 19.33 mmol, 32.0% yield) as a colourless liquid—NMR appears to be consistent with the desired product as a mixture of isomers at the silyl ether position in about 3:1 ratio and this was carried through crude to the next step.

LCMS (2 min High pH): Rt=0.96 min, [MH]$^+$=not present.

Intermediate 148: benzyl ((1R,5S,6r)-3-((tert-butyldimethylsilyl)oxy)bicyclo[3.1.0]hexan-6-yl)carbamate

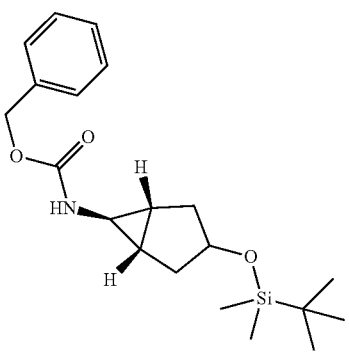 [SMILES: CC(C)(C)[Si](C)(C)OC1C[C@@H]2[C@H](C1)[C@H]2NC(=O)OCc1ccccc1]

Step 1:
Sodium hydroxide (20 mL, 40.0 mmol) was added to a solution of ethyl (1R*,5S*,6r*)-3-((tert-butyldimethylsilyl)oxy)bicyclo[3.1.0]hexane-6-carboxylate (5.0 g, 17.58 mmol) in ethanol (50 mL) at room temperature and the mixture was stirred for 3 h. TLC suggested that all the starting material had been consumed and the mixture was evaporated in vacuo to about 30 mL volume, then diluted with water (30 mL) and washed with ether (50 mL). The ether washings from the workup were dried and evaporated in vacuo to give recovered starting material (3.85 g) ethyl (1R*,5S*,6r*)-3-((tert-butyldimethylsilyl)oxy)bicyclo[3.1.0]hexane-6-carboxylate. This was dissolved in ethanol (30 mL) and 2M aqueous NaOH solution (20 mL) was added, then the mixture was heated at 70° C. for 3 h, then evaporated in vacuo. The residue was dissolved in water (50 mL) and washed with ether (50 mL), then the aqueous layer was acidified with 2M HCl (20 mL) and extracted with EtOAc (2×50 mL). The combined organics were dried and evaporated in vacuo to give (1R,5S,6r)-3-((tert-butyldimethylsilyl)oxy)bicyclo[3.1.0]hexane-6-carboxylic acid (1.9 g, 7.41 mmol, 42.2% yield) as a pale yellow solid. The product was carried through to the next step without purification.

Step 2:
(1R,5S,6r)-3-((tert-butyldimethylsilyl)oxy)bicyclo[3.1.0]hexane-6-carboxylic acid (1.8 g, 7.02 mmol) was dissolved in a mixture of toluene (20 mL) and Et$_3$N (1.957 mL, 14.04 mmol), then DPPA (1.815 mL, 8.42 mmol) was added and the mixture was stirred for 30 min at room temperature. Benzyl alcohol (1.095 mL, 10.53 mmol) was added and the mixture heated at 100° C. for 4 h, then cooled to room temperature. Ethyl acetate (100 mL) was added and the solution was washed with water (2×100 mL), then dried over sodium sulphate, filtered and the filtrate evaporated in vacuo to give a pale yellow oil. This was dissolved in DCM (10 mL) and loaded onto a 50 g silica column, then eluted with 0-30% EtOAc/cyclohexane and product-containing fractions (detected by permanganate dip) were collected and evaporated in vacuo to give benzyl ((1R,5S,6r)-3-((tert-butyldimethylsilyl)oxy)bicyclo[3.1.0]hexan-6-yl)carbamate (1.90 g, 5.26 mmol, 74.9% yield) as a pale yellow oil, NMR consistent with desired product as a mixture of isomers in approximately 2:1 ratio. The compound was taken through to the next step without further purification.

LCMS (2 min Formic): Rt=1.56 min, [MH]$^+$=362.6.

Intermediate 149: (1R,3s,5S,6r)-3-((tert-butyldimethylsilyl)oxy)bicyclo[3.1.0]hexan-6-amine (9:1 Mix of Diastereomers)

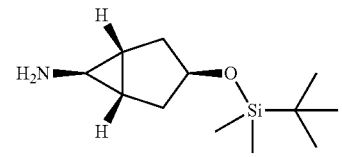

benzyl ((1R,5S,6r)-3-((tert-butyldimethylsilyl)oxy)bicyclo[3.1.0]hexan-6-yl)carbamate (0.52 g, 1.438 mmol) was dissolved in EtOH (30 mL) and hydrogenated in the H-Cube at atmospheric pressure and 1 ml/min flow rate. The eluant was evaporated in vacuo and the residue purified using silica gel column chromatography eluting with a gradient of 0-10% 2M methanolic ammonia:DCM over to give: (1R,5S,6r)-3-((tert-butyldimethylsilyl)oxy)bicyclo[3.1.0]hexan-6-amine (9:1 mix of diastereomers) (12 mg, 37%)

$^1$H NMR (400 MHz, CHLOROFORM-d)•ppm 3.79 (t, J=7.6 Hz, 1H) 2.01 (dd, 1=12.8, 7.2 Hz, 2H) 1.95 (s, 1H) 1.62-1.69 (m, 2H) 1.53 (br. s., 2H) 1.17 (dd, J=3.2, 1.7 Hz, 2H) 0.82-0.87 (m, 9H) −0.03-0.02 (m, 6H)

Intermediate 150: (2S,3S)—N$_5$-((1R,5S,6r)-3-((tert-butyldimethylsilyl)oxy)bicyclo[3.1.0]hexan-6-yl)-2-(fluoromethyl)-N7-methyl-3-phenyl-2,3-dihydrobenzofuran-5,7-dicarboxamide (9:1 Mix of Diastereomers)

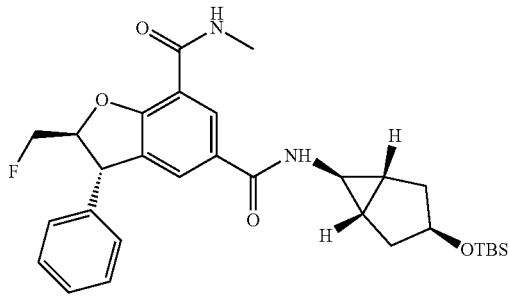 [SMILES: CNC(=O)c1cc(C(=O)N[C@H]2[C@@H]3C[C@@H](O[Si](C)(C)C(C)(C)C)C[C@@H]32)cc2c1O[C@H](CF)[C@H]2c1ccccc1]

(2S,3S)-2-(fluoromethyl)-7-(methylcarbamoyl)-3-phenyl-2,3-dihydrobenzofuran-5-carboxylic acid (101 mg, 0.308 mmol), HATU (138 mg, 0.363 mmol), DMF (5 mL) and DIPEA (0.157 mL, 0.901 mmol) were mixed into a flask and stirred for 15 minutes. Then (1R,3s,5S,6r)-3-((tert-butyldimethylsilyl)oxy)bicyclo[3.1.0]hexan-6-amine (50 mg, 0.220 mmol) was added and the reaction was stirred 3 h at rt. The reaction was diluted with water and extracted with EtOAc (3, the organics were washed with a 10% LiCl (aq), dried using a hydrophobic frit and concentrated in vacuo to a brown oil. The oil was purified using silica gel column chromatography eluting with a gradient of 0 to 60% of (25% EtOH in ethyl acetate) in cyclohexane to give (2S,3S)—N$_5$-((1R,5S,6r)-3-((tert-butyldimethylsilyl)oxy)bicyclo[3.1.0]hexan-6-yl)-2-(fluoromethyl)-N7-methyl-3-phenyl-2,3-dihydrobenzofuran-5,7-dicarboxamide (72.4 mg, 0.134 mmol, 61.1% yield) (9:1 mix of diastereomers)

LCMS (2 min Formic): Rt=1.47 min, [MH]$^+$=539

EXAMPLES

Examples 1 and 2: (2R*,3R*)—N$^5$-Cyclobutyl-N$^7$,2-dimethyl-3-phenyl-2,3-dihydrobenzofuran-5,7-dicarboxamide and (2R*,3S*)—N$^5$-cyclobutyl-N$^7$,2-dimethyl-3-phenyl-2,3-dihydrobenzofuran-5,7-dicarboxamide

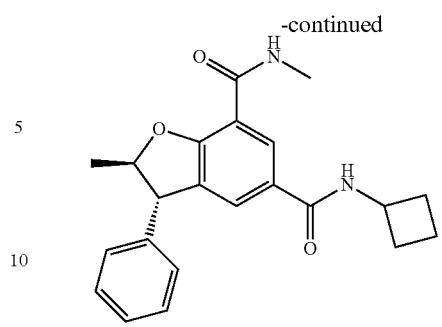

A microwave vial was charged with 5-bromo-N,2-dimethyl-3-phenyl-2,3-dihydrobenzofuran-7-carboxamide (90 mg, 0.26 mmol), dicobalt octacarbonyl (44.4 mg, 0.130 mmol), cyclobutanamine (37.0 mg, 0.520 mmol), DMAP (63.5 mg, 0.520 mmol), di((3S,5S,7S)-adamantan-1-yl)(butyl)phosphine (9.3 mg, 0.026 mmol) and Pd(OAc)$_2$ (5.8 mg, 0.026 mmol), then was filled with 2-methyltetrahydrofuran (3 mL). The resulting mixture was stirred under microwave irradiations at 100° C. for 1 h then at 120° C. for 30 min, and then was cooled to room temperature. In parallel, a second reaction was performed: a microwave vial was charged with 5-bromo-N,2-dimethyl-3-phenyl-2,3-dihydrobenzofuran-7-carboxamide (40 mg, 0.12 mmol), dicobalt octacarbonyl (9.9 mg, 0.029 mmol), cyclobutanamine (8.2 mg, 0.12 mmol), DMAP (28.2 mg, 0.231 mmol), di((3S,5S,7S)-adamantan-1-yl)(butyl)phosphine (4.1 mg, 0.012 mmol) and Pd(OAc)$_2$ (2.6 mg, 0.012 mmol), then was filled with 2-methyltetrahydrofuran (3 mL). The resulting mixture was stirred under microwave irradiations at 80° C. for 20 min, then at 120° C. for 2 h, then was cooled to room temperature. The two reaction mixtures were then combined and diluted with EtOAc (20 mL) and the organic phase was washed with a 1N HCl aqueous solution (20 mL) then with water (20 mL), and then was dried over MgSO$_4$ and concentrated in vacuo. Purification of the residue obtained by flash chromatography on silica gel (25 g column, gradient: 0-100% EtOAc in cyclohexane) gave two fractions which were individually further purified by MDAP (method high pH) to give (2R*,3R*)—N$^5$-cyclobutyl-N$^7$,2-dimethyl-3-phenyl-2,3-dihydrobenzofuran-5,7-dicarboxamide (7 mg, 5%) as a pale yellow crystalline solid (Example 1), and (2R*,3S*)—N$^5$-cyclobutyl-N$^7$,2-dimethyl-3-phenyl-2,3-dihydrobenzofuran-5,7-dicarboxamide (3 mg, 2%) as a pale yellow gum (Example 2).

LCMS (method high pH): Retention time 1.07 min, [M+H]$^+$=365 (Example 1)

LCMS (method high pH): Retention time 1.09 min, [M+H]$^+$=365 (Example 2)

Example 3: N$^5$-(2-Hydroxypropyl)-N$^7$,2-dimethyl-3-phenyl-2,3-dihydrobenzofuran-5,7-dicarboxamide

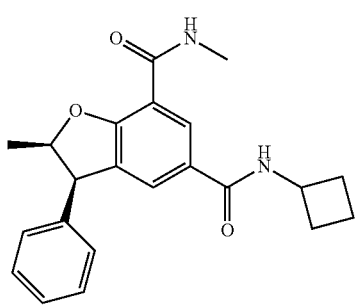

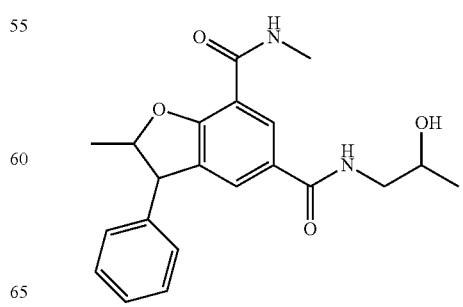

A microwave vial was charged with 5-bromo-N,2-dimethyl-3-phenyl-2,3-dihydrobenzofuran-7-carboxamide (250 mg, 0.722 mmol), dicobalt octacarbonyl (123 mg, 0.361 mmol), 3-aminopropan-1-ol (108 mg, 1.44 mmol), DMAP (176 mg, 1.44 mmol), di((3S,5S,7S)-adamantan-1-yl)(butyl) phosphine (26 mg, 0.072 mmol) and Pd(OAc)$_2$ (16 mg, 0.072 mmol) then was filled with 2-methyltetrahydrofuran (3 mL) and the resulting mixture was stirred at 100° C. under microwave irradiation for 1 h then was cooled to room temperature and diluted with a 1N HCl aqueous solution (20 mL). The aqueous phase was extracted with EtOAc (20 mL) and the organic phase was washed with water, dried over MgSO$_4$ and concentrated in vacuo to give a brown gum. Purification of the residue obtained by flash chromatography on silica gel (25 g column, gradient: 0-10% MeOH in DCM) gave $N^5$-(3-hydroxypropyl)-$N^7$,2-dimethyl-3-phenyl-2,3-dihydrobenzofuran-5,7-dicarboxamide (135 mg, 51%) as a 1:1 mixture of cis and trans isomers.

LCMS (method high pH): Retention time 0.89 min, [M+H]$^+$=369

Example 4: $N^5$-Cyclopropyl-$N^7$,2-dimethyl-3-phenyl-2,3-dihydrobenzofuran-5,7-dicarboxamide

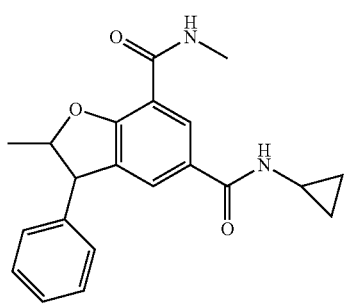 [SMILES: CNC(=O)c1cc(C(=O)NC2CC2)cc2c1OC(C)C2c1ccccc1]

A microwave vial was charged with 5-bromo-N,2-dimethyl-3-phenyl-2,3-dihydrobenzofuran-7-carboxamide (250 mg, 0.722 mmol), dicobalt octacarbonyl (123 mg, 0.361 mmol), cyclopropanamine (82 mg, 1.4 mmol), DMAP (176 mg, 1.44 mmol), di((3S,5S,7S)-adamantan-1-yl)(butyl) phosphine (26 mg, 0.072 mmol) and Pd(OAc)$_2$ (16 mg, 0.072 mmol) then was filled with 2-methyltetrahydrofuran (3 mL) and the resulting mixture was stirred at 100° C. under microwave irradiation for 1 h then was cooled to room temperature and diluted with a 1N HCl aqueous solution (20 mL). The aqueous phase was extracted with EtOAc (20 mL) and the organic phase was washed with water, dried over MgSO$_4$ and concentrated in vacuo to give a brown gum. Purification of the residue obtained by flash chromatography on silica gel (25 g column, gradient: 0-100% EtOAc in cyclohexane) gave $N^5$-cyclopropyl-$N^7$,2-dimethyl-3-phenyl-2,3-dihydrobenzofuran-5,7-dicarboxamide (1:1 mixture of cis and trans isomer, 100 mg, 39%) as a purple solid.

LCMS (method high pH): Retention time 0.99 min, [M+H]$^+$=351

Example 5: $N^5$,$N^7$,2-Trimethyl-3-phenyl-2,3-dihydrobenzofuran-5,7-dicarboxamide

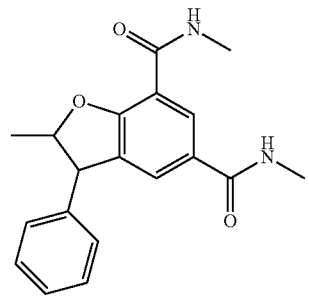

A microwave vial was charged with DMAP (141 mg, 1.15 mmol), Pd(OAc)$_2$ (13 mg, 0.058 mmol), dicobalt octacarbonyl (99 mg, 0.289 mmol), 5-bromo-N,2-dimethyl-3-phenyl-2,3-dihydrobenzofuran-7-carboxamide (200 mg, 0.578 mmol), di((3S,5S,7S)-adamantan-1-yl)(butyl)phosphine (21 mg, 0.058 mmol) and methanamine (2N in THF, 0.58 mL, 1.1 mmol) then was filled with DMF (5 mL) and the resulting mixture was stirred at 100° C. under microwave irradiations for 1 h then was cooled to room temperature and diluted with a 1N HCl aqueous solution (20 mL). The aqueous phase was extracted twice with EtOAc (20 mL) and the combined organic phases were washed with a saturated NH$_4$Cl aqueous solution, dried over MgSO$_4$ and concentrated in vacuo to give a yellow solid. Purification of the residue obtained by flash chromatography on silica gel (10 g column, gradient: 0-100% EtOAc in cyclohexane) gave $N^5$,$N^7$,2-trimethyl-3-phenyl-2,3-dihydrobenzofuran-5,7-dicarboxamide (1:1 mixture of cis and trans isomers, 78.5 mg, 42%) as a colourless oil.

LCMS (method formic): Retention time 0.90 min, [M+H]$^+$=325

Examples 6 and 7: (2R,3S)—$N^5$-(2-Hydroxypropyl)-$N^7$,2-dimethyl-3-phenyl-2,3-dihydrobenzofuran-5,7-dicarboxamide and (2S,3S)—$N^5$-(2-hydroxypropyl)-$N^7$,2-dimethyl-3-phenyl-2,3-dihydrobenzofuran-5,7-dicarboxamide

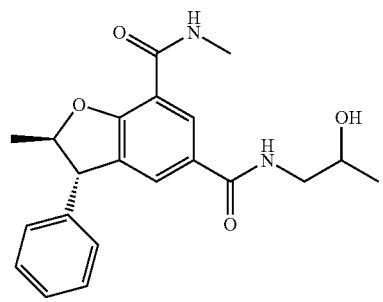

-continued

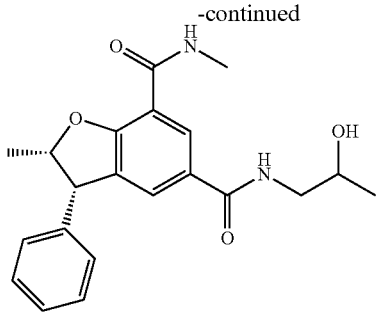

$N^5$-(2-hydroxypropyl)-$N^7$,2-dimethyl-3-phenyl-2,3-dihydrobenzofuran-5,7-dicarboxamide (Example 3, 130 mg) was submitted for chiral HPLC purification.

Analytical method: Approximatively 130 mg of material was dissolved in EtOH (4 mL); 50 uL diluted into 1 mL of EtOH and injected on column. Elution: 10% EtOH in heptane, f=1.0 mL/min, wavelength 250 nm. Column Chiralpak IA 250×4.6 mm (5 micron).

Preparative method: Approximatively 130 mg of material was dissolved in EtOH (4 mL). Injections: 0.75 mL of the solution was injected onto the column. Elution: 10% EtOH in heptane, f=42.5 mL/min, wavelength, 280 nm. Column Chiralpak IA 250×30 mm (5 um).

This gave (2R,3S)—$N^5$-(2-hydroxypropyl)-$N^7$,2-dimethyl-3-phenyl-2,3-dihydrobenzofuran-5,7-dicarboxamide (8 mg, 6%, Example 6) and (2S,3S)—$N^5$-(2-hydroxypropyl)-$N^7$,2-dimethyl-3-phenyl-2,3-dihydrobenzofuran-5,7-dicarboxamide (5 mg, 4%, Example 7).

LCMS (method high pH): Retention time 0.88 min, $[M+H]^+$=369 (Example 6)

LCMS (method high pH): Retention time 0.88 min, $[M+H]^+$=369 (Example 7).

Examples 8 and 9: (2R,3S)—$N^5$-Cyclopropyl-$N^7$,2-dimethyl-3-phenyl-2,3-dihydrobenzofuran-5,7-dicarboxamide and (2S,3S)—$N^5$-cyclopropyl-$N^7$,2-dimethyl-3-phenyl-2,3-dihydrobenzofuran-5,7-dicarboxamide

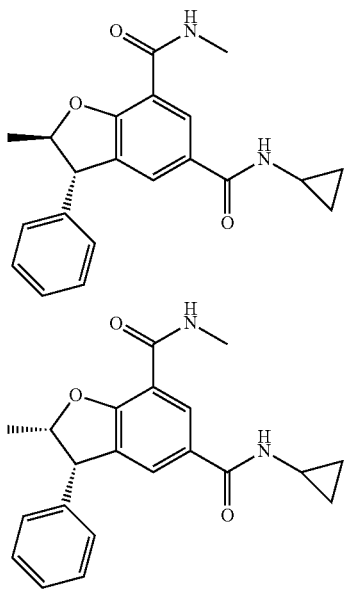

Example 4 (100 mg) was purified by chiral chromatography:

Analytical method: Approximatively 100 mg of material was dissolved in EtOH (4 mL); 50 uL diluted into 1 mL of EtOH and injected on column. Elution: 10% EtOH in heptane, f=1.0 mL/min, wavelength 250 nm. Column Chiralpak IA 250×4.6 mm (5 micron).

Preparative method: Approximatively 100 mg of material was dissolved in EtOH (4 mL). Injections: 0.75 mL of the solution was injected onto the column. Elution: 10% EtOH in heptane, f=42.5 mL/min, wavelength, 280 nm. Column Chiralpak IA 250×30 mm (5 um).

This gave (2R,3S)—$N^5$-cyclopropyl-$N^7$,2-dimethyl-3-phenyl-2,3-dihydrobenzofuran-5,7-dicarboxamide (9 mg, 9%, Example 8) as first eluting isomer and (2S,3S)—$N^5$-cyclopropyl-$N^7$,2-dimethyl-3-phenyl-2,3-dihydrobenzofuran-5,7-dicarboxamide (19 mg, 19%) contaminated with (2S,3R)—$N^5$-cyclopropyl-$N^7$,2-dimethyl-3-phenyl-2,3-dihydrobenzofuran-5,7-dicarboxamide. This mixture of cis and trans enantiomers was further purified by MDAP (method high pH) to give (2S,3S)—$N^5$-cyclopropyl-$N^7$,2-dimethyl-3-phenyl-2,3-dihydrobenzofuran-5,7-dicarboxamide (3 mg, 3%, Example 9).

LCMS (method high pH): Retention time 0.99 min, $[M+H]^+$=351 (Example 8)

LCMS (method high pH): Retention time 0.99 min, $[M+H]^+$=351 (Example 9)

Example 8: Alternative Procedure

DIPEA (0.128 mL, 0.732 mmol), 2-(3H-[1,2,3]triazolo[4,5-b]pyridin-3-yl)-1,1,3,3-tetramethylisouronium hexafluorophosphate(V) (278 mg, 0.732 mmol) and cyclopropylamine (0.052 mL, 0.73 mmol) were successively added to a solution of (2R*,3S*)-2-methyl-7-(methylcarbamoyl)-3-phenyl-2,3-dihydrobenzofuran-5-carboxylic acid (190 mg, 0.610 mmol) in DMF (2 mL). The mixture was concentrated in vacuo after 15 min. Purification of the residue obtained by flash chromatography on silica gel (10 g column, gradient: 0-50% EtOAc in cyclohexane) gave (2R*,3S*)—$N^5$-cyclopropyl-$N^7$,2-dimethyl-3-phenyl-2,3-dihydrobenzofuran-5,7-dicarboxamide (400 mg) contaminated with HATU. This material was then purified by chiral chromatography:

Analytical method: Approximatively 0.5 mg of material was dissolved in 50% EtOH/heptane (1 mL), 20 uL injected on column. Elution: 10% EtOH in heptane, f=1.0 mL/min, wavelength 215 nm. Column 4.6 mmid×25 cm Chiralpak IA.

Preparative method: Approximatively 400 mg of material was dissolved in EtOH (4 mL). Injections (2 in total): 2 mL of the solution was injected onto the column. Elution: 10% EtOH in heptane, f=30 mL/min, wavelength, 215 nm. Column 30 mm×25 cm Chiralpak IA (5 um). This gave (2R,3S)—$N^5$-Cyclopropyl-$N^7$,2-dimethyl-3-phenyl-2,3-dihydrobenzofuran-5,7-dicarboxamide (91 mg, 23%).

LCMS (method high pH): Retention time 0.99 min, $[M+H]^+$=351.

Example 10: (2S*,3S*)—N⁵-Cyclopropyl-2-(hydroxymethyl)-N⁷-methyl-3-phenyl-2,3-dihydrobenzofuran-5,7-dicarboxamide

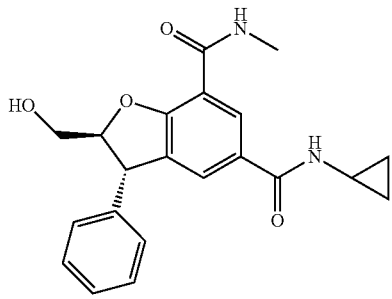 [SMILES: CNC(=O)c1cc(C(=O)NC2CC2)cc2c1O[C@H](CO)[C@H]2c1ccccc1]

A microwave vial was charged with DMAP (202 mg, 1.66 mmol), Pd(OAc)₂ (18 mg, 0.083 mmol), dicobalt octacarbonyl (142 mg, 0.414 mmol), (2S*,3S*)-5-bromo-2-(hydroxymethyl)-N-methyl-3-phenyl-2,3-dihydrobenzofuran-7-carboxamide (300 mg, 0.828 mmol), cyclopropylamine (0.070 mL, 0.99 mmol) and Xantphos (57 mg, 0.099 mmol) then was filled with THF (3 mL). The resulting mixture was stirred under microwave irradiations at 110° C. for 1 h then was cooled to room temperature and concentrated in vacuo. Purification of the residue by MDAP (method high pH) gave (2S*,3S*)—N⁵-cyclopropyl-2-(hydroxymethyl)-N⁷-methyl-3-phenyl-2,3-dihydrobenzofuran-5,7-dicarboxamide (24 mg, 8%).

LCMS (method formic): Retention time 0.78 min, [M+H]⁺=367

Example 11: (2S*,3S*)—N⁵-Cyclobutyl-2-(hydroxymethyl)-N⁷-methyl-3-phenyl-2,3-dihydrobenzofuran-5,7-dicarboxamide

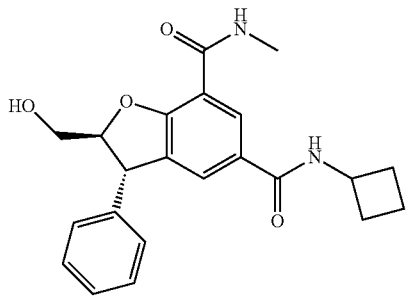 [SMILES: CNC(=O)c1cc(C(=O)NC2CCC2)cc2c1O[C@H](CO)[C@H]2c1ccccc1]

A microwave vial was charged with DMAP (67.5 mg, 0.552 mmol), Pd(OAc)₂ (6.2 mg, 0.028 mmol), dicobalt octacarbonyl (47.2 mg, 0.138 mmol), (2S,3S)-5-bromo-2-(hydroxymethyl)-N-methyl-3-phenyl-2,3-dihydrobenzofuran-7-carboxamide (100 mg, 0.276 mmol), di((3S,5S,7S)-adamantan-1-yl)(butyl)phosphine (9.9 mg, 0.028 mmol) and cyclobutanamine (39.3 mg, 0.552 mmol) then was filled with THF (3 mL). The resulting mixture was stirred under microwave irradiations at 110° C. for 1 h then was cooled to room temperature, filtered over Celite® (2.5 g pad) and concentrated in vacuo. Purification of the residue by MDAP (method high pH) gave (2S*,3S*)—N⁵-cyclobutyl-2-(hydroxymethyl)-N⁷-methyl-3-phenyl-2,3-dihydrobenzofuran-5,7-dicarboxamide (10 mg, 10%).

LCMS (method formic): Retention time 0.88 min, [M+H]⁺=381

Example 12: (2S*,3S*)-2-(Hydroxymethyl)-N⁷-methyl-3-phenyl-N⁵-propyl-2,3-dihydrobenzofuran-5,7-dicarboxamide

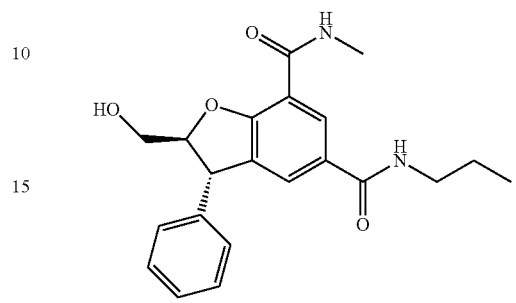

A microwave vial was charged with DMAP (67.5 mg, 0.552 mmol), Pd(OAc)₂ (6.2 mg, 0.028 mmol), dicobalt octacarbonyl (47.2 mg, 0.138 mmol), (2S*,3S*)-5-bromo-2-(hydroxymethyl)-N-methyl-3-phenyl-2,3-dihydrobenzofuran-7-carboxamide (100 mg, 0.276 mmol), di((3S,5S,7S)-adamantan-1-yl)(butyl)phosphine (9.9 mg, 0.028 mmol) and n-propylamine (0.046 mL, 0.55 mmol) then was filled with THF (2 mL). The resulting mixture was stirred under microwave irradiations at 110° C. for 1 h then was cooled to room temperature, filtered over celite (2.5 g pad) and concentrated in vacuo. Purification of the residue by MDAP (method high pH) gave (2S*,3S*)-2-(hydroxymethyl)-N⁷-methyl-3-phenyl-N⁵-propyl-2,3-dihydrobenzofuran-5,7-dicarboxamide (10 mg, 10%).

LCMS (method formic): Retention time 0.85 min, [M+H]⁺=369

Example 13: (2S*,3S*)-2-(Hydroxymethyl)-N⁷-methyl-3-phenyl-N⁵-(2-(piperidin-4-yl)ethyl)-2,3-dihydrobenzofuran-5,7-dicarboxamide

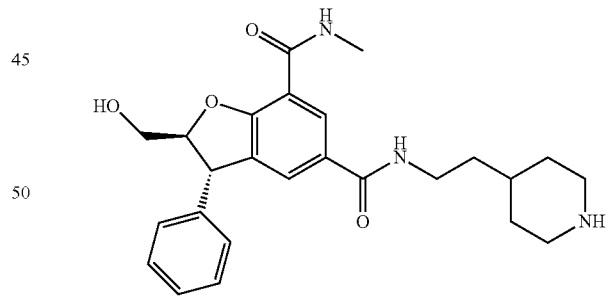

A microwave vial was charged with DMAP (54.0 mg, 0.442 mmol), Pd(OAc)₂ (5.0 mg, 0.022 mmol), dicobalt octacarbonyl (37.8 mg, 0.110 mmol), (2S*,3S*)-5-bromo-2-(hydroxymethyl)-N-methyl-3-phenyl-2,3-dihydrobenzofuran-7-carboxamide (80 mg, 0.22 mmol), di((3S,5S,7S)-adamantan-1-yl)(butyl)phosphine (7.9 mg, 0.022 mmol) and tert-butyl 4-(2-aminoethyl)piperidine-1-carboxylate (101 mg, 0.442 mmol) then was filled with THF (2 mL). The resulting mixture was stirred under microwave irradiations at 110° C. for 1 h then was cooled to room temperature and treated with TFA (1.7 mL, excess). The resulting mixture was stirred at this temperature for 20 min, then was filtered over Celite® (2.5 g pad) and concentrated in vacuo. The residue was co-evaporated with a 2N NH₃ solution in MeOH (10 mL), and then was purified by MDAP (method high pH) to give (2S*,3S*)-2-(hydroxymethyl)-N⁷-methyl-3-phenyl-N⁵-(2-(piperidin-4-yl)ethyl)-2,3-dihydrobenzofuran-5,7-dicarboxamide (40 mg, 41%).

LCMS (method formic): Retention time 0.53 min, [M+H]⁺=438

Example 14: (2S*,3S*)-2-(Hydroxymethyl)-N⁷-methyl-N⁵-(3-(4-methylpiperazin-1-yl)propyl)-3-phenyl-2,3-dihydrobenzofuran-5,7-dicarboxamide

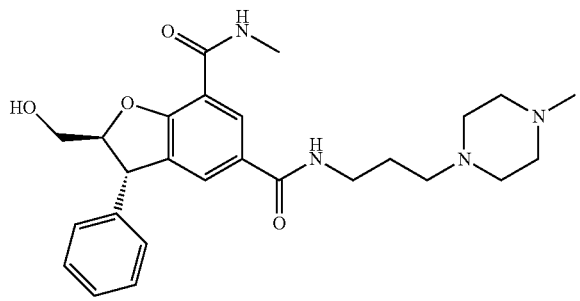 [SMILES: CNC(=O)c1cc(C(=O)NCCCN2CCN(C)CC2)cc2c1O[C@H](CO)[C@H]2c1ccccc1]

A microwave vial was charged with DMAP (33.7 mg, 0.276 mmol), Pd(OAc)₂ (3.1 mg, 0.014 mmol), dicobalt octacarbonyl (24 mg, 0.069 mmol), (2S*,3S*)-5-bromo-2-(hydroxymethyl)-N-methyl-3-phenyl-2,3-dihydrobenzofuran-7-carboxamide (50 mg, 0.14 mmol), di((3S,5S,7S)-adamantan-1-yl)(butyl)phosphine (5.0 mg, 0.014 mmol) and 3-(4-methylpiperazin-1-yl)propan-1-amine (43.4 mg, 0.276 mmol) then was filled with THF (1 mL). The resulting mixture was stirred under microwave irradiations at 110° C. for 1 h then was cooled to room temperature and concentrated in vacuo. Purification of the residue by MDAP (method high pH) gave (2S*,3S*)-2-(hydroxymethyl)-N⁷-methyl-N⁵-(3-(4-methylpiperazin-1-yl)propyl)-3-phenyl-2,3-dihydrobenzofuran-5,7-dicarboxamide (8 mg, 12%).

LCMS (method high pH): Retention time 0.75 min, [M+H]⁺=467

Example 15: (2S*,3S*)-2-(Hydroxymethyl)-N⁷-methyl-3-phenyl-N⁵-(3-(piperazin-1-yl)propyl)-2,3-dihydrobenzofuran-5,7-dicarboxamide

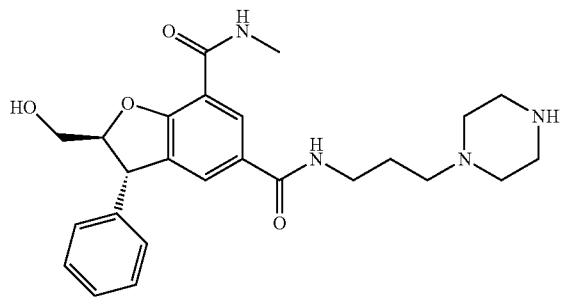 [SMILES: CNC(=O)c1cc(C(=O)NCCCN2CCNCC2)cc2c1O[C@H](CO)[C@H]2c1ccccc1]

A microwave vial was charged with DMAP (84 mg, 0.69 mmol), Pd(OAc)₂ (7.8 mg, 0.035 mmol), dicobalt octacarbonyl (59.0 mg, 0.173 mmol), (2S*,3S*)-5-bromo-2-(hydroxymethyl)-N-methyl-3-phenyl-2,3-dihydrobenzofuran-7-carboxamide (125 mg, 0.345 mmol), di((3S,5S,7S)-adamantan-1-yl)(butyl)phosphine (12 mg, 0.035 mmol) and tert-butyl 4-(3-aminopropyl)piperazine-1-carboxylate (168 mg, 0.690 mmol) then was filled with THF (2 mL). The resulting mixture was stirred under microwave irradiations at 110° C. for 1 h then was cooled to room temperature and treated with TFA (1.4 mL, excess). The resulting mixture was stirred at this temperature for 10 min, then was filtered over Celite® (2.5 g pad) and concentrated in vacuo. The residue was co-evaporated with a 2N NH₃ solution in MeOH (10 mL), and then was purified by MDAP (method high pH) to give (2S,3S)-2-(hydroxymethyl)-N⁷-methyl-3-phenyl-N⁵-(3-(piperazin-1-yl)propyl)-2,3-dihydrobenzofuran-5,7-dicarboxamide (15 mg, 10%).

LCMS (method formic): Retention time 0.39 min, [M+H]⁺=453

Example 16: (2S,3S)—N⁵-Cyclopropyl-2-(hydroxymethyl)-N⁷-methyl-3-phenyl-2,3-dihydrobenzofuran-5,7-dicarboxamide

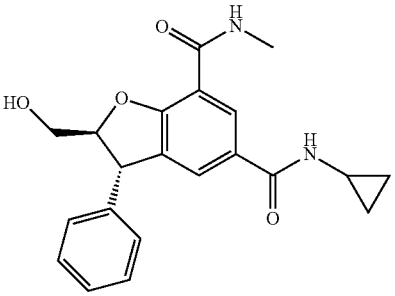 [SMILES: CNC(=O)c1cc(C(=O)NC2CC2)cc2c1O[C@H](CO)[C@H]2c1ccccc1]

A solution of (2R,3R)-2-(hydroxymethyl)-7-(methylcarbamoyl)-3-phenyl-2,3-dihydrobenzofuran-5-carboxylic acid (100 mg, 0.306 mmol) in DMF (2 mL) at room temperature was treated with DIPEA (0.064 mL, 0.37 mmol), HATU (139 mg, 0.367 mmol) and cyclopropylamine (0.043 mL, 0.61 mmol) and the resulting mixture was stirred at this temperature for 15 min then was concentrated in vacuo. Purification of the residue obtained by flash chromatography on silica gel (10 g column, gradient: 0-25% EtOH in EtOAc) gave the expected product contaminated with HATU. Further purification of this residue by flash chromatography on silica gel (10 g column, gradient: 0-25% EtOH in EtOAc) gave (2R,3R)—N⁵-cyclopropyl-2-(hydroxymethyl)-N⁷-methyl-3-phenyl-2,3-dihydrobenzofuran-5,7-dicarboxamide (14 mg, 13%).

LCMS (method formic): Retention time 0.77 min, [M+H]⁺=367

Example 17: (2R*,3S*)—N⁷,2-Dimethyl-3-phenyl-N⁵-(3-(piperidin-4-yl)propyl)-2,3-dihydrobenzofuran-5,7-dicarboxamide

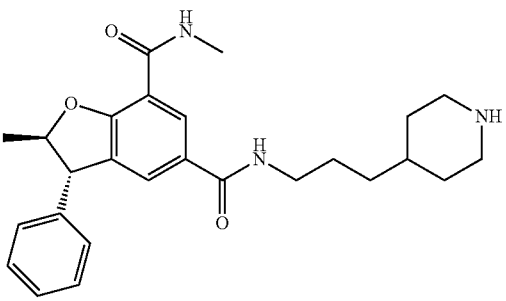 [SMILES: CNC(=O)c1cc(C(=O)NCCCC2CCNCC2)cc2c1O[C@H](C)[C@H]2c1ccccc1]

A solution of (2S*,3R*)-2-methyl-7-(methylcarbamoyl)-3-phenyl-2,3-dihydrobenzofuran-5-carboxylic acid (180 mg, 0.578 mmol) in DMF (2 mL) at room temperature was treated with DIPEA (0.121 mL, 0.694 mmol), 2-(3H-[1,2,3]triazolo[4,5-b]pyridin-3-yl)-1,1,3,3-tetramethylisouronium hexafluorophosphate(V) (264 mg, 0.694 mmol) and tert-butyl 4-(3-aminopropyl)piperidine-1-carboxylate (168 mg, 0.694 mmol) and the resulting mixture was stirred at this temperature for 15 min then was treated with TFA (0.89 mL, 12 mmol). The resulting mixture was stirred at room temperature for 20 min then was concentrated in vacuo. The residue was co-evaporated with a 2N NH$_3$ solution in MeOH (10 mL) then was loaded onto a 10 g SCX column, eluting with MeOH then with a 2N NH$_3$ solution in MeOH. The ammonia fractions were concentrated in vacuo to give (2S*,3R*)—N$^7$,2-dimethyl-3-phenyl-N$^5$-(3-(piperidin-4-yl)propyl)-2,3-dihydrobenzofuran-5,7-dicarboxamide (250 mg, 99%).

LCMS (method formic): Retention time 0.66 min, [M+H]$^+$=436.

Example 18: (2R,3S)—N$^7$,2-Dimethyl-3-phenyl-N$^5$-(3-(piperidin-4-yl)propyl)-2,3-dihydrobenzofuran-5,7-dicarboxamide

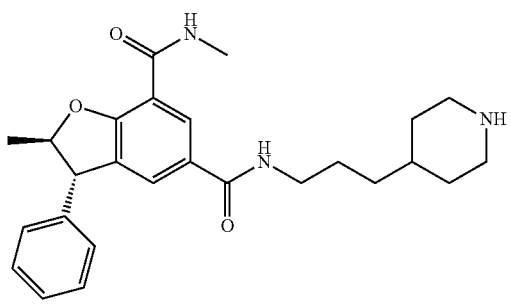 [SMILES: CNC(=O)c1cc(C(=O)NCCCC2CCNCC2)cc2c1O[C@H](C)[C@H]2c1ccccc1]

(2R*,3S*)—N$^7$,2-Dimethyl-3-phenyl-N$^5$-(3-(piperidin-4-yl)propyl)-2,3-dihydrobenzofuran-5,7-dicarboxamide (Example 17, 300 mg) was purified by chiral chromatography:

Analytical method: Approximatively 0.5 mg of material was dissolved in 50% EtOH in heptane (1 mL) and 20 uL were injected onto column. Elution: 75% EtOH (0.2% isopropylamine) in heptane, f=1.0 mL/min, wavelength 215 nm. Column 4.6 mmid×25 cm Chiralpak IC.

Preparative method: Approximatively 300 mg of material were dissolved in EtOH (3 mL). Injections (2 in total): 1.5 mL of the solution was injected onto the column. Elution: 75% EtOH (0.2% isopropylamine) in heptane, f=30 mL/min, wavelength 215 nm. Column 30 mm×25 cm Chiralpak IC The fractions containing the fast running enantiomer were concentrated in vacuo to give (2R,3S)—N$^7$,2-dimethyl-3-phenyl-N$^5$-(3-(piperidin-4-yl)propyl)-2,3-dihydrobenzofuran-5,7-dicarboxamide (104 mg, 69%).

LCMS (method formic): Retention time 0.66 min, [M+H]$^+$=436

Example 19: (2R,3S)—N$^5$-Ethyl-N$^7$,2-dimethyl-3-phenyl-2,3-dihydrobenzofuran-5,7-dicarboxamide

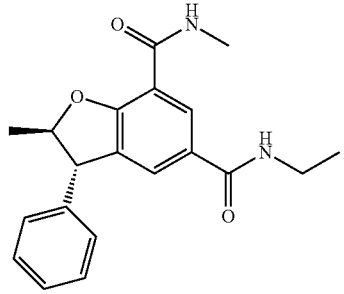 [SMILES: CCNC(=O)c1cc(C(=O)NC)c2c(c1)[C@H](c1ccccc1)[C@@H](C)O2]

A solution of (2S,3R)-2-methyl-7-(methylcarbamoyl)-3-phenyl-2,3-dihydrobenzofuran-5-carboxylic acid (50 mg, 0.16 mmol) in DMF (0.5 mL) at room temperature was treated with DIPEA (0.034 mL, 0.19 mmol), HATU (67.2 mg, 0.177 mmol) and ethanamine (2N in THF, 0.080 mL, 0.16 mmol) and the resulting mixture was stirred at this temperature for 15 min then was treated with a 2N HCl aqueous solution (5 mL). The aqueous phase was extracted with EtOAc (20 mL) and the organic phase was washed with water (4*10 mL) then with a saturated LiCl aqueous solution followed by brine. The organic phase was then dried using a phase separator and concentrated in vacuo to give (2S,3R)—N$^5$-ethyl-N$^7$,2-dimethyl-3-phenyl-2,3-dihydrobenzofuran-5,7-dicarboxamide (50 mg, 92%).

LCMS (method formic): Retention time 0.97 min, [M+H]$^+$=339

Example 20: (2R,3S)—N$^5$,N$^7$,2-Trimethyl-3-phenyl-2,3-dihydrobenzofuran-5,7-dicarboxamide

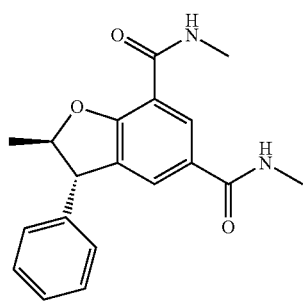

A solution of (2R,3S)-2-methyl-7-(methylcarbamoyl)-3-phenyl-2,3-dihydrobenzofuran-5-carboxylic acid (50 mg, 0.161 mmol) in DMF (2 mL) at room temperature was treated with DIPEA (0.034 mL, 0.19 mmol), HATU (67.2 mg, 0.177 mmol) and methanamine (2N in THF, 0.2 mL, 0.4 mmol) and the resulting mixture was stirred at this temperature for 15 min then was treated with a 2N HCl aqueous solution (5 mL). The aqueous phase was extracted with EtOAc (20 mL) and the organic phase was washed with water (4*10 mL) then with a saturated LiCl aqueous solution followed by brine. The organic phase was then dried using a phase separator and concentrated in vacuo to give (2R,3S)—N$^5$,N$^7$,2-trimethyl-3-phenyl-2,3-dihydrobenzofuran-5,7-dicarboxamide (40 mg, 77%).

LCMS (method formic): Retention time 0.90 min, [M+H]+=325

Example 21: (2R,3S)—N⁵-((1S*,2S*)-2-(Hydroxymethyl)cyclopropyl)-N⁷,2-dimethyl-3-phenyl-2,3-dihydrobenzofuran-5,7-dicarboxamide

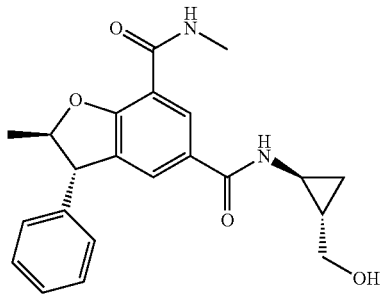 [SMILES: CNC(=O)c1cc(C(=O)N[C@H]2C[C@@H]2CO)cc2c1O[C@H](C)[C@H]2c1ccccc1]

A solution of (2S,3R)-2-methyl-7-(methylcarbamoyl)-3-phenyl-2,3-dihydrobenzofuran-5-carboxylic acid (40 mg, 0.13 mmol) in DMF (2 mL) at room temperature was treated with DIPEA (0.027 mL, 0.15 mmol), HATU (53.7 mg, 0.141 mmol) and ((1S*,2S*)-2-aminocyclopropyl)methanol (11.2 mg, 0.128 mmol) and the resulting mixture was stirred at this temperature for 15 min then was treated with a 2N HCl aqueous solution (5 mL). The aqueous phase was extracted with EtOAc (20 mL) and the organic phase was washed with water (4*10 mL) then with a saturated LiCl aqueous solution followed by brine. The organic phase was then dried using a phase separator and concentrated in vacuo to give (2S,3R)—N⁵-((1S*,2S*)-2-(hydroxymethyl)cyclopropyl)-N⁷,2-dimethyl-3-phenyl-2,3-dihydrobenzofuran-5,7-dicarboxamide (37 mg, 76%).

LCMS (method formic): Retention time 0.87 min, [M+H]+=381

Example 22: (2S*,3S*)—N⁵-Cyclopropyl-2-(fluoromethyl)-N⁷-methyl-3-phenyl-2,3-dihydrobenzofuran-5,7-dicarboxamide

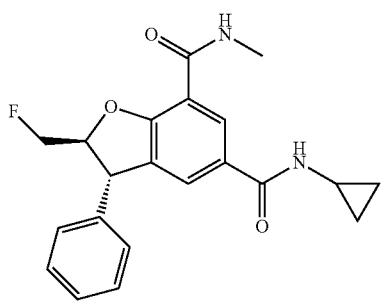 [SMILES: CNC(=O)c1cc(C(=O)NC2CC2)cc2c1O[C@H](CF)[C@H]2c1ccccc1]

A solution of (2S*,3S*)-2-(fluoromethyl)-7-(methylcarbamoyl)-3-phenyl-2,3-dihydrobenzofuran-5-carboxylic acid (65 mg, 0.20 mmol) in DMF (2 mL) at room temperature was treated with NEt₃ (0.083 mL, 0.59 mmol), HATU (150 mg, 0.395 mmol) and cyclopropylamine (0.014 mL, 0.20 mmol) and the resulting mixture was stirred at this temperature for 2 h then was directly purified by MDAP (method high pH) to give (2S*,3S*)—N⁵-cyclopropyl-2-(fluoromethyl)-N⁷-methyl-3-phenyl-2,3-dihydrobenzofuran-5,7-dicarboxamide (32 mg, 44)

LCMS (method formic): Retention time 0.94 min, [M+H]+=369

Example 23: (2S,3S)—N⁵-Cyclopropyl-2-(fluoromethyl)-N⁷-methyl-3-phenyl-2,3-dihydrobenzofuran-5,7-dicarboxamide

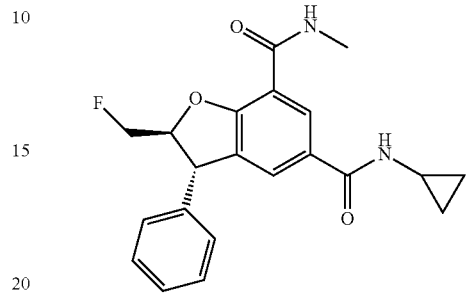

A solution of (2S,3S)-2-(fluoromethyl)-7-(methylcarbamoyl)-3-phenyl-2,3-dihydrobenzofuran-5-carboxylic acid (100 mg, 0.304 mmol) in DMF (3 mL) at room temperature was treated with Et₃N (0.085 mL, 0.61 mmol) and HATU (150 mg, 0.395 mmol). The mixture was stirred at this temperature for 30 min, then cyclopropylamine (0.028 mL, 0.40 mmol) was added and the resulting mixture was stirred at room temperature for 2 h then was concentrated in vacuo. Purification of the residue by MDAP (high pH method) gave (2S,3S)—N⁵-cyclopropyl-2-(fluoromethyl)-N⁷-methyl-3-phenyl-2,3-dihydrobenzofuran-5,7-dicarboxamide (30 mg, 27%) as a colourless solid.

LCMS (method formic): Retention time 0.94 min, [M+H]+=369

Example 24: (2S,3S)-2-(Fluoromethyl)-N⁵,N⁷-dimethyl-3-phenyl-2,3-dihydrobenzofuran-5,7-dicarboxamide

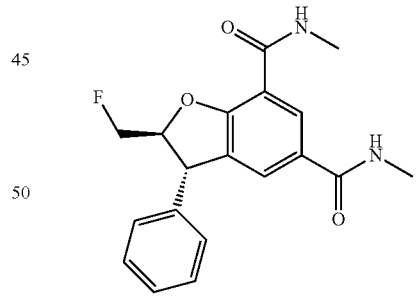

A solution of (2S,3S)-2-(fluoromethyl)-7-(methylcarbamoyl)-3-phenyl-2,3-dihydrobenzofuran-5-carboxylic acid (55 mg, 0.17 mmol) in DMF (3 mL) at room temperature was treated with Et₃N (0.047 mL, 0.33 mmol) and HATU (83 mg, 0.22 mmol) The resulting solution was stirred at this temperature for 30 min, then methanamine (2N in THF, 0.109 mL, 0.217 mmol) was added and the resulting mixture was stirred at room temperature for 2 h then was concentrated in vacuo. Purification of the residue by MDAP (method high pH) gave (2S,3S)-2-(fluoromethyl)-N⁵,N⁷-dimethyl-3-phenyl-2,3-dihydrobenzofuran-5,7-dicarboxamide (16 mg, 28%).

LCMS (method formic): Retention time 0.85 min, [M+H]$^+$=343

Example 25: (2S,3S)-2-(Fluoromethyl)-N$^7$-methyl-N$^5$-((1S,2S)-2-methylcyclopropyl)-3-phenyl-2,3-dihydrobenzofuran-5,7-dicarboxamide

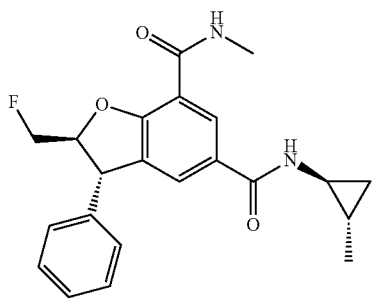 [SMILES: CNC(=O)c1cc(C(=O)N[C@H]2C[C@@H]2C)cc2c1O[C@H](CF)[C@H]2c1ccccc1]

A solution of (2S,3S)-2-(fluoromethyl)-7-(methylcarbamoyl)-3-phenyl-2,3-dihydrobenzofuran-5-carboxylic acid (100 mg, 0.304 mmol) in DMF (3 mL) at room temperature was treated with Et$_3$N (0.085 mL, 0.61 mmol) and HATU (150 mg, 0.395 mmol). The resulting solution was stirred at this temperature for 30 min, then (1S,2S)-2-methylcyclopropanamine (28.1 mg, 0.395 mmol) was added and the resulting mixture was stirred at room temperature for 2 h then was concentrated in vacuo. Purification of the residue by MDAP (method high pH) gave (2S,3S)-2-(fluoromethyl)-N$^7$-methyl-N$^5$-((1S,2S)-2-methylcyclopropyl)-3-phenyl-2,3-dihydrobenzofuran-5,7-dicarboxamide (39 mg, 34%) as a colourless solid.

LCMS (method formic): Retention time 1.00 min, [M+H]$^+$=383

Example 26: (2S,3S)—N$^5$-((1R,5S,6r)-3-oxabicyclo[3.1.0]hexan-6-yl)-2-(fluoromethyl)-N$^7$-methyl-3-phenyl-2,3-dihydrobenzofuran-5,7-dicarboxamide

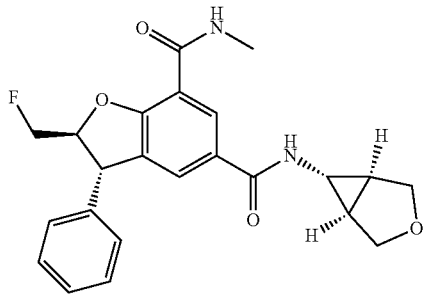 [SMILES: CNC(=O)c1cc(C(=O)N[C@H]2[C@@H]3COC[C@@H]32)cc2c1O[C@H](CF)[C@H]2c1ccccc1]

(2S,3S)-2-(Fluoromethyl)-7-(methylcarbamoyl)-3-phenyl-2,3-dihydrobenzofuran-5-carboxylic acid (1.9 g, 5.8 mmol), (1R,5S,6r)-3-oxabicyclo[3.1.0]hexan-6-amine hydrochloride (1.02 g, 7.50 mmol), HATU (2.85 g, 7.50 mmol) and Et$_3$N (2.010 mL, 14.42 mmol) were dissolved in DCM (20 mL) and the resulting mixture was stirred at room temperature for 16 h. The organic phase was then washed successively with a 0.5N HCl aqueous solution (20 mL), a 1N NaOH aqueous solution (20 mL) and brine (20 mL), dried over MgSO$_4$ and concentrated in vacuo to give a pale yellow gum. Purification of this residue by flash chromatography on silica gel (column 100 g, gradient: 0 to 80% (25% EtOH/EtOAc) in cyclohexane) gave (2S,3S)—N$^5$-((1R,5S,6r)-3-oxabicyclo[3.1.0]hexan-6-yl)-2-(fluoromethyl)-N$^7$-methyl-3-phenyl-2,3-dihydrobenzofuran-5,7-dicarboxamide (1.90 g, 80%) as a colourless solid.

LCMS (method formic): Retention time 0.88 min, [M+H]$^+$=411

$^1$H NMR (400 MHz, DMSO-d$_6$) δ ppm 8.44 (d, J=4.0 Hz, 1H), 8.22 (d, J=2.0 Hz, 1H), 7.89 (q, J=4.5 Hz, 1H), 7.59-7.57 (m, 1H), 7.42-7.36 (m, 2H), 7.35-7.30 (m, 1H), 7.30-7.26 (m, 2H), 5.17-5.04 (m, 1H), 4.97-4.80 (m, 1H), 4.85-4.67 (m, 1H), 4.68 (d, J=7.5 Hz, 1H), 3.82 (d, J=8.5 Hz, 2H), 3.61 (dd, J=3.0, 8.5 Hz, 2H), 2.87 (d, J=4.5 Hz, 3H), 2.58-2.53 (m, 1H), 1.89-1.80 (m, 2H).

Example 26 Alternative Preparation

Example 26 was also prepared by an alternative synthetic procedure. Certain intermediates in this process were prepared by methods described below.

5-Bromo-2-hydroxy-N-methyl-3-(1-phenylallyl)benzamide

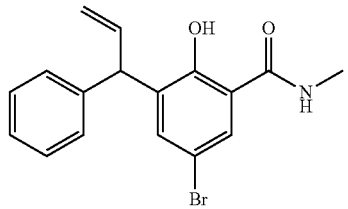 [SMILES: C=CC(c1ccccc1)c1cc(Br)cc(C(=O)NC)c1O]

5-bromo-2-(cinnamyloxy)benzoate (1 wt) was dissolved in anhydrous N-Methyl-2-pyrrolidone (NMP) (3.5 vol). The feed was pumped at 1.45 mL/min (2.76 min residence time) through a 4 mL stainless steel heated tube reactor at 250° C. with 4 barg back pressure. To the crude solution of methyl 5-bromo-2-hydroxy-3-(1-phenylallyl)benzoate was added an aqueous solution of methanamine (40% wt/wt, 3 eq). The solution was stirred for one hour. The pH was adjusted using 8M HCl (0.9 vol, 2.5 eq) to pH 5, TBME (9 vol) added and washed with water (2×9 vol). The aqueous phase was back extracted with TBME (6.5 vol), the combined organic layers were washed with water (4 vol) then brine (4 vol), dried over MgSO$_4$ and concentrated in vacuo to a brown oil. This oil was purified by silica gel column chromatography eluting with a 30% gradient (EtOAc in hexanes) to give 5-bromo-2-hydroxy-N-methyl-3-(1-phenylallyl)benzamide (58.3% yield) as a brown sticky oil (+/−)(2S,3S)-5-bromo-2-(fluoromethyl)-N-methyl-3-phenyl-2,3-dihydrobenzofuran-7-carboxamide

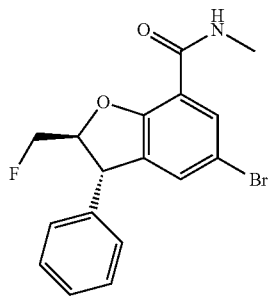

(+/−)(2S,3S)-5-bromo-2-(hydroxymethyl)-N-methyl-3-phenyl-2,3-dihydrobenzofuran-7-carboxamide (54.7 g, 151 mmol) was suspended in DCM (400 ml) and stirred under $N_2$, cooling in an ice bath. Then DIPEA (92 ml, 529 mmol) was added, followed by triethylamine trihydrofluoride (30.1 ml, 181 mmol) and Perfluoro-1-butanesulfonyl fluoride (32.5 ml, 181 mmol) and the mixture was stirred for 18 h, allowing it to warm to rt. The mixture was quenched by addition (cautiously) of sodium bicarbonate solution (500 ml) and stirred vigorously for 30 min, then the organic layer was separated and washed with 1M HCl (500 ml). The solvent was dried over sodium sulphate and evaporated in vacuo to give a pale yellow solid. The crude product was purified using silica gel column chromatography eluting with a gradient of 5-60% EtOAc/cyclohexane to give (2S,3S)-5-bromo-2-(fluoromethyl)-N-methyl-3-phenyl-2,3-dihydrobenzofuran-7-carboxamide (42.2 g, 116 mmol, 77% yield) as a colourless solid.

LCMS (method formic): Retention time 1.21 min, $[MH]^+$=364

1H NMR (600 MHz, DMSO-d6) δ ppm 2.85 (d, J=5.0 Hz, 3H) 4.68 (d, J=7.5 Hz, 1H) 4.68-4.79 (m, 1H) 4.80-4.92 (m, 1H) 5.03-5.16 (m, 1H) 7.22-7.25 (m, 1H) 7.26-7.29 (m, 2H) 7.29-7.34 (m, 1H) 7.36-7.40 (m, 2H) 7.73 (dd, J=2.5, 0.5 Hz, 1H) 7.88 (q, J=5.0 Hz, 1H)

(+/−)(2S,3S)—$N^5$-((1R,5S,6r)-3-oxabicyclo[3.1.0]hexan-6-yl)-2-(fluoromethyl)-N7-methyl-3-phenyl-2,3-dihydrobenzofuran-5,7-dicarboxamide

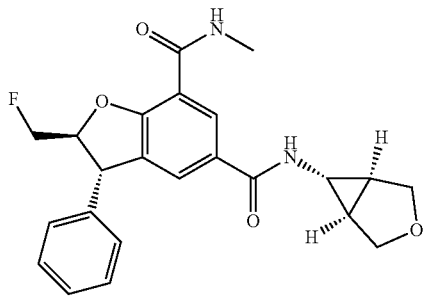 [SMILES: CNC(=O)c1cc(C(=O)N[C@H]2[C@@H]3COC[C@@H]32)cc2c1O[C@H](CF)[C@H]2c1ccccc1]

(+/−)(2S,3S)-5-bromo-2-(fluoromethyl)-N-methyl-3-phenyl-2,3-dihydrobenzofuran-7-carboxamide (44.9 g, 123 mmol), (1R,5S,6r)-3-oxabicyclo[3.1.0]hexan-6-amine, hydrochloride (21.73 g, 160 mmol), PdOAc2 (1.384 g, 6.16 mmol), xantphos (3.57 g, 6.16 mmol), 2,6-lutidine (35.9 mL, 308 mmol) and 1,4-Dioxane (500 mL) were added to a 1 litre jacketed vessel fitted with an overhead stirrer and gas intake, then the vessel was sealed and flushed with nitrogen×3, then filled with carbon monoxide and the mixture heated to 90° C. overnight with vigorous stirring. The resulting brown suspension was dispensed to a 1 litre glass bottle, the vessel washed with 2×100 ml methanol and the washings added to the reaction mixture, giving a clear, dark brown solution. The solution was evaporated to approximately half its original volume, then diluted with DCM (2 litres) and washed with 1M HCl (2×1 litre) and a mixture of saturated brine and water (500 ml of each). The organic layer was dried over sodium sulphate, filtered and evaporated in vacuo to give a brown solid. The crude product was suspended in diethyl ether (500 ml) and stirred for 30 min, then filtered and the solid dried in the vacuum oven overnight to give (2S,3S)—$N_5$-((1R,5S,6r)-3-oxabicyclo[3.1.0]hexan-6-yl)-2-(fluoromethyl)-$N^7$-methyl-3-phenyl-2,3-dihydrobenzofuran-5,7-dicarboxamide (47.9 g, 117 mmol, 95% yield) as a pale brown solid, this was combined with 70 g of the same material form other batches giving 120 g in total. The solid was dissolved in DCM and methanol. Si Thiol resin (Silicycle catalogue number R51030B) was added and the mixture was stirred at rt for 30 min, then filtered and the solid washed with 10% MeOH/DCM. The filtrate was evaporated in vacuo to give a brown solid. EtOAc was added to the evaporation flask, which was rotated at atmospheric pressure on the Buchi for 30 min, then the flask was removed and the suspension allowed to stand for 1 h. The product was collected by filtration and washed with EtOAc (500 ml) and ether (500 ml), then dried in the vacuum oven to give (+/−) (2S,3S)—$N^5$-((1R,5S,6r)-3-oxabicyclo[3.1.0]hexan-6-yl)-2-(fluoromethyl)-$N^7$-methyl-3-phenyl-2,3-dihydrobenzofuran-5,7-dicarboxamide (98.9 g, 241 mmol) as a pale beige.

LCMS (method High pH): Retention time 0.91 min, $[M+H]^+$=411

$^1$H NMR (400 MHz, DMSO-$d_6$) δ ppm 8.45 (d, J=4.2 Hz, 1H) 8.23 (d, J=1.5 Hz, 1H) 7.89 (d, J=4.6 Hz, 1H) 7.58 (d, J=1.2 Hz, 1H) 7.25-7.45 (m, 5H) 5.04-5.19 (m, 1H) 4.91-4.99 (m, 1H) 4.77-4.87 (m, 1H) 4.62-4.74 (m, 1H) 3.83 (d, J=8.6 Hz, 2H) 3.61 (dd, J=8.3, 2.7 Hz, 2H) 2.88 (d, J=4.6 Hz, 3H) 2.55 (dt, J=4.2, 2.4 Hz, 1H) 1.80-1.90 (m, 2H)

(2S,3S)—$N^5$-((1R,5S,6r)-3-oxabicyclo[3.1.0]hexan-6-yl)-2-(fluoromethyl)-$N^7$-methyl-3-phenyl-2,3-dihydrobenzofuran-5,7-dicarboxamide

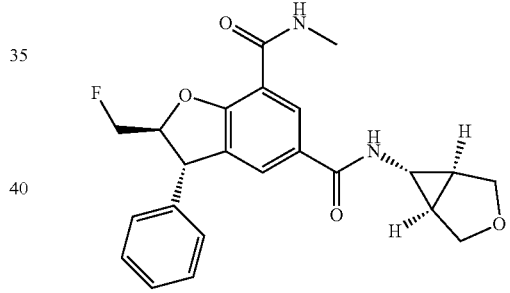

(+/−) (2S,3S)—$N^5$-((1R,5S,6r)-3-oxabicyclo[3.1.0]hexan-6-yl)-2-(fluoromethyl)-$N^7$-methyl-3-phenyl-2,3-dihydrobenzofuran-5,7-dicarboxamide (24 g) was purified by chiral HPLC. The racemate (150 mg) was dissolved in EtOH (2 mL)+DCM (1 ml) with heating. Injection: 3.5 mL of the solution was injected onto the column (75% EtOH[+0.2% isopropylamine]/heptane[+0.2% isopropylamine], flow rate=30 mL/min, detection wavelength=215 nm, 4. Ref 550, 100, Column 30 mm×25 cm Chiralcel IC (5 μm), lot no. IC10028-01).

Also the racemate (400-500 mg) was dissolved in EtOH (2 mL)+DCM (3 ml) with heating. Injection: 5 mL of the solution was injected onto the column (75% EtOH[+0.2% isopropylamine]/heptane[+0.2% isopropylamine], flow rate=60 mL/min, detection wavelength=215 nm, 4. Ref 550, 100, Column 5 cm×20 cm Chiralcel IC (20 μm), (self packed). Fractions from 11-14 min were bulked and concentrated to afford (2R,3S)—$N^5$-((1R,5S,6r)-3-oxabicyclo[3.1.0]hexan-6-yl)-3-(3-(2-hydroxyethoxy)phenyl)-$N^7$,2-dimethyl-2,3-dihydrobenzofuran-5,7-dicarboxamide, (10.88 g)

LCMS (2 min Formic): Rt=0.89 min, [MH]+=411.

$^1$H NMR (400 MHz, DMSO-d$_6$) δ ppm 8.44 (d, J=4.2 Hz, 1H) 8.22 (d, J=1.7 Hz, 1H) 7.88 (d, J=4.6 Hz, 1H) 7.57 (s, 1H) 7.24-7.43 (m, 5H) 5.02-5.18 (m, 1H) 4.90-5.00 (m, 1H) 4.77-4.87 (m, 1H) 4.63-4.74 (m, 1H) 3.82 (d, J=8.3 Hz, 2H) 3.61 (dd, J=8.3, 2.7 Hz, 2H) 2.87 (d, J=4.6 Hz, 3H) 2.55 (dt, J=4.2, 2.4 Hz, 1H) 1.80-1.89 (m, 2H)

Examples 27 and 28: (2R,3S)—N$^5$-((1S,2S)-2-(Hydroxymethyl)cyclopropyl)-N$^7$,2-dimethyl-3-phenyl-2,3-dihydrobenzofuran-5,7-dicarboxamide and (2R,3S)—N$^5$-((1R,2R)-2-(hydroxymethyl)cyclopropyl)-N$^7$,2-dimethyl-3-phenyl-2,3-dihydrobenzofuran-5,7-dicarboxamide

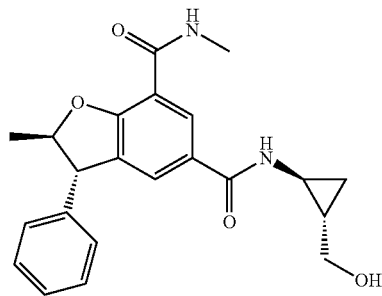

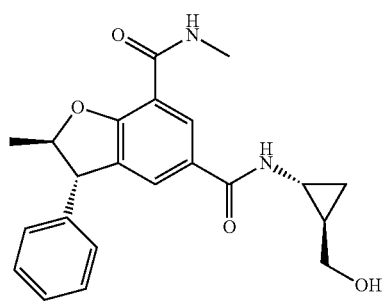

(2S,3S)—N$^5$-((1R,5S,6r)-3-oxabicyclo[3.1.0]hexan-6-yl)-2-(fluoromethyl)-N$^7$-methyl-3-phenyl-2,3-dihydrobenzofuran-5,7-dicarboxamide (35 mg) was purified by chiral chromatography:

Analytical method: Approximatively 35 mg of material was dissolved in EtOH (4 mL); 50 uL diluted into 1 mL of EtOH and injected on column. Elution: 25% EtOH (+0.2% w/w Isopropylamine) in heptane (+0.2% w/w Isopropylamine), f=1.0 mL/min, wavelength 280 nm. Column Chiralpak AD-H (250×4.6 mm).

Preparative method: Approximatively 35 mg of material was dissolved in EtOH (4 mL). Injections: 0.75 mL of the solution was injected onto the column. Elution: 25% EtOH (+0.2% w/w Isopropylamine) in heptane (+0.2% w/w Isopropylamine), f=40 mL/min, wavelength 280 nm. Column Chiralpak AD-H (250×30 mm, 5 micron).

This gave (2R,3S)—N$^5$-((1S,2S)-2-(hydroxymethyl)cyclopropyl)-N$^7$,2-dimethyl-3-phenyl-2,3-dihydrobenzofuran-5,7-dicarboxamide (5 mg, 29%) and (2R,3S)—N$^5$-((1R,2R)-2-(hydroxymethyl)cyclopropyl)-N$^7$,2-dimethyl-3-phenyl-2,3-dihydrobenzofuran-5,7-dicarboxamide (5 mg, 29%).

Example 29: (2R,3S)—N$^7$,2-dimethyl-3-phenyl-2,3-dihydrobenzofuran-5,7-dicarboxamide

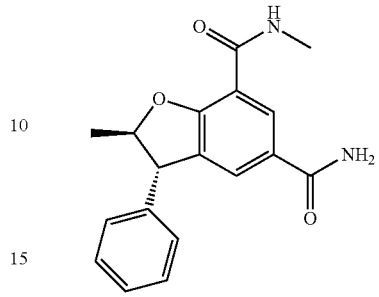

A solution of (2R,3S)-2-methyl-7-(methylcarbamoyl)-3-phenyl-2,3-dihydrobenzofuran-5-carboxylic acid (50 mg, 0.16 mmol) in DCM (5 mL) at room temperature was treated with HATU (92 mg, 0.24 mmol) and Et$_3$N (0.045 mL, 0.32 mmol). The resulting mixture was stirred for 1 h, then was treated with ammonium hydroxide (0.2 mL, 5.14 mmol). The resulting solution was stirred for a further 2 h then was concentrated in vacuo. Purification of the residue obtained by MDAP (method high pH) gave (2R,3S)—N$^7$,2-dimethyl-3-phenyl-2,3-dihydrobenzofuran-5,7-dicarboxamide (13 mg, 26%) as a colourless solid.

LCMS (method formic): Retention time 0.85 min, [M+H]$^+$=311

Example 30: (2S*,3S*)—N$^5$-Cyclopropyl-2-(hydroxymethyl)-3-(3-methoxyphenyl)-N$^7$-methyl-2,3-dihydrobenzofuran-5,7-dicarboxamide

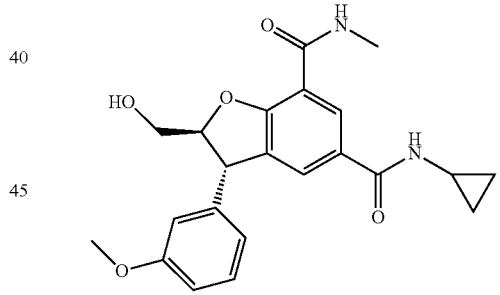

A solution of (2S*,3S*)-2-(hydroxymethyl)-3-(3-methoxyphenyl)-7-(methylcarbamoyl)-2,3-dihydrobenzofuran-5-carboxylic acid (46 mg, 0.13 mmol) in DCM (10 mL) at room temperature was treated with HATU (63.6 mg, 0.167 mmol) and NEt$_3$ (0.036 mL, 0.26 mmol) and the resulting mixture was stirred at this temperature for 20 min before being treated with cyclopropylamine (0.012 mL, 0.17 mmol). The resulting mixture was stirred at this temperature for 1 h then was washed with water, dried using an hydrophobic frit and concentrated in vacuo. Purification of the residue obtained by flash chromatography on silica gel (10 g column, gradient: 0-25% EtOH in EtOAc) gave (2S*,3S*)—N$^5$-cyclopropyl-2-(hydroxymethyl)-3-(3-methoxyphenyl)-N$^7$-methyl-2,3-dihydrobenzofuran-5,7-dicarboxamide (25 mg, 49%) as a colourless foam.

LCMS (method high pH): Retention time 0.83 min, [M+H]$^+$=397

Example 31: (2S*,3S*)-2-(Hydroxymethyl)-3-(3-methoxyphenyl)-N⁷-methyl-N⁵-((1S,2S)-2-methylcyclopropyl)-2,3-dihydrobenzofuran-5,7-dicarboxamide

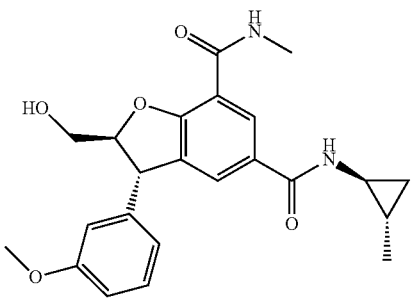 [SMILES: CNC(=O)c1cc(C(=O)N[C@H]2C[C@@H]2C)cc2c1O[C@H](CO)[C@H]2c1cccc(OC)c1]

A solution of (2S*,3S*)-2-(hydroxymethyl)-3-(3-methoxyphenyl)-7-(methylcarbamoyl)-2,3-dihydrobenzofuran-5-carboxylic acid (110 mg, 0.308 mmol) in DCM (10 mL) at room temperature was treated with HATU (152 mg, 0.400 mmol) and NEt₃ (0.086 mL, 0.62 mmol) and the resulting mixture was stirred at this temperature for 20 min before being treated with (1S,2S)-2-methylcyclopropanamine (49.7 mg, 0.462 mmol). The resulting mixture was stirred at this temperature for 1 h then was washed with water, dried using an hydrophobic frit and concentrated in vacuo. Purification of the residue obtained by flash chromatography on silica gel (10 g column, gradient: 0-25% EtOH in EtOAc) gave (2S*,3S*)-2-(hydroxymethyl)-3-(3-methoxyphenyl)-N⁷-methyl-N⁵-((1S,2S)-2-methylcyclopropyl)-2,3-dihydrobenzofuran-5,7-dicarboxamide (84 mg, 66%) as a colourless foam.

LCMS (method high pH): Retention time 0.91 min, [M+H]⁺=411

Example 32: (2S*,3S*)-2-(Hydroxymethyl)-3-(3-methoxyphenyl)-N⁵,N⁷-dimethyl-2,3-dihydrobenzofuran-5,7-dicarboxamide

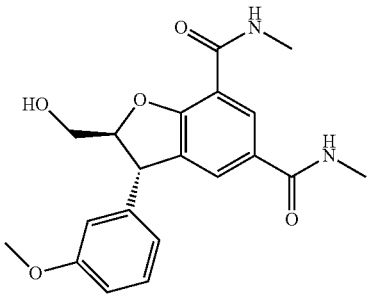

A solution of (2S*,3S*)-2-(hydroxymethyl)-3-(3-methoxyphenyl)-7-(methylcarbamoyl)-2,3-dihydrobenzofuran-5-carboxylic acid (110 mg, 0.308 mmol) in DCM (10 mL) at room temperature was treated with HATU (152 mg, 0.400 mmol) and NEt₃ (0.086 mL, 0.62 mmol) and the resulting mixture was stirred at this temperature for 20 min before being treated with methanamine (2N in THF, 0.308 mL, 0.616 mmol). The resulting mixture was stirred at this temperature for 1 h then was washed with water, dried using an hydrophobic frit and concentrated in vacuo. Purification of the residue obtained by flash chromatography on silica gel (10 g column, gradient: 0-25% EtOH in EtOAc) gave (2S*,3S*)-2-(hydroxymethyl)-3-(3-methoxyphenyl)-N⁵,N⁷-dimethyl-2,3-dihydrobenzofuran-5,7-dicarboxamide (14 mg, 12%) as a colourless foam.

LCMS (method high pH): Retention time 0.76 min, [M+H]⁺=371

Example 33: (2S*,3S*)—N⁵-Ethyl-2-(hydroxymethyl)-3-(3-methoxyphenyl)-N⁷-methyl-2,3-dihydrobenzofuran-5,7-dicarboxamide

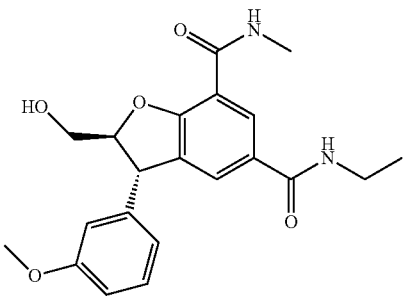 [SMILES: CCNC(=O)c1cc(C(=O)NC)c2c(c1)[C@H](c1cccc(OC)c1)[C@@H](CO)O2]

A solution of (2S,3S*)-2-(hydroxymethyl)-3-(3-methoxyphenyl)-7-(methylcarbamoyl)-2,3-dihydrobenzofuran-5-carboxylic acid (40 mg, 0.11 mmol) in DCM (10 mL) at room temperature was treated with HATU (42.6 mg, 0.112 mmol) and Et₃N (0.016 mL, 0.11 mmol) and the resulting mixture was stirred at this temperature for 20 min before being treated with ethanamine (2M in THF, 0.12 mL, 0.24 mmol). The resulting mixture was stirred at this temperature for 1 h then was washed with water (10 mL), dried using an hydrophobic frit and concentrated in vacuo. Purification of the residue obtained by flash chromatography on silica gel (10 g column, gradient: 0-25% EtOH in EtOAc) gave (2S*3S*)—N⁵-ethyl-2-(hydroxymethyl)-3-(3-methoxyphenyl)-N⁷-methyl-2,3-dihydrobenzofuran-5,7-dicarboxamide (20 mg, 47%) as a colourless gum.

LCMS (method high pH): Retention time 0.82 min, [M+H]⁺=385

Example 34 (2S*,3S*)-2-(Hydroxymethyl)-N⁵-(2-methoxyethyl)-3-(3-methoxyphenyl)-N⁷-methyl-2,3-dihydrobenzofuran-5,7-dicarboxamide

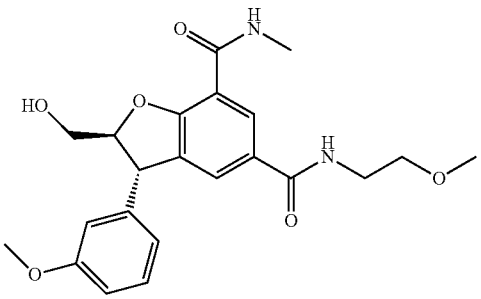

A solution of (2S*,3S*)-2-(hydroxymethyl)-3-(3-methoxyphenyl)-7-(methylcarbamoyl)-2,3-dihydrobenzofuran-5-carboxylic acid (50 mg, 0.14 mmol) in DCM (10 mL) at room temperature was treated with HATU (63.8 mg, 0.168 mmol) and Et₃N (0.039 mL, 0.28 mmol) and the resulting mixture was stirred at this temperature for 20 min before being treated with 2-methoxyethanamine (15.8 mg, 0.210 mmol). The resulting mixture was stirred at this temperature for 1 h then was washed with water (10 mL), dried using an hydrophobic frit and concentrated in vacuo. Purification of the residue obtained by flash chromatography on silica gel (10 g column, gradient: 0-25% EtOH in EtOAc) gave (2S*,3S*)-2-(hydroxymethyl)-N⁵-(2-methoxyethyl)-3-(3-methoxyphenyl)-N⁷-methyl-2,3-dihydrobenzofuran-5,7-dicarboxamide (48 mg, 83%) as a colourless gum.

LCMS (method high pH): Retention time 0.80 min, [M+H]⁺=415

Example 35: (2R,3S)—N⁵-(2-Methoxyethyl)-N⁷,2-dimethyl-3-phenyl-2,3-dihydrobenzofuran-5,7-dicarboxamide

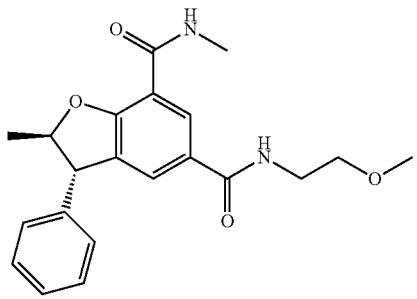

A solution of (2R,3S)-2-methyl-7-(methylcarbamoyl)-3-phenyl-2,3-dihydrobenzofuran-5-carboxylic acid (50 mg, 0.16 mmol) in DCM (5 mL) at room temperature was treated with HATU (92 mg, 0.24 mmol) and Et₃N (0.045 mL, 0.32 mmol) and the resulting mixture was stirred at this temperature for 1 h before being treated with 2-methoxyethanamine (12.1 mg, 0.161 mmol). The resulting mixture was stirred at this temperature for 2 h then was concentrated in vacuo. Purification of the residue obtained by flash chromatography on silica gel (10 g column) gave (2R,3S)—N⁵-(2-methoxyethyl)-N⁷,2-dimethyl-3-phenyl-2,3-dihydrobenzofuran-5,7-dicarboxamide (51 mg, 86%) as a colourless solid.

LCMS (method high pH): Retention time 0.97 min, [M+H]⁺=369

Example 36: (2R,3S)—N⁷,2-Dimethyl-3-phenyl-N⁵-(tetrahydro-2H-pyran-4-yl)-2,3-dihydrobenzofuran-5,7-dicarboxamide

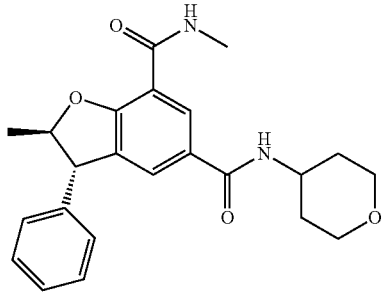 [SMILES: CNC(=O)c1cc(C(=O)NC2CCOCC2)cc2c1O[C@H](C)[C@H]2c1ccccc1]

A solution of (2R,3S)-2-methyl-7-(methylcarbamoyl)-3-phenyl-2,3-dihydrobenzofuran-5-carboxylic acid (50 mg, 0.16 mmol) in DCM (5 mL) at room temperature was treated with HATU (92 mg, 0.24 mmol) and Et₃N (0.090 mL, 0.64 mmol) and the resulting mixture was stirred at this temperature for 1 h before being treated with tetrahydro-2H-pyran-4-amine hydrochloride (44.2 mg, 0.321 mmol). The resulting mixture was stirred at this temperature for 2 h then was concentrated in vacuo. Purification of the residue obtained by flash chromatography on silica gel (10 g column) gave (2R,3S)—N⁷,2-dimethyl-3-phenyl-N⁵-(tetrahydro-2H-pyran-4-yl)-2,3-dihydrobenzofuran-5,7-dicarboxamide (30 mg, 47%) as a colourless solid.

LCMS (method high pH): Retention time 0.98 min, [M+H]⁺=395

Example 37: (2R,3S)—N⁵-(2-hydroxyethyl)-N⁷,2-Dimethyl-3-phenyl-2,3-dihydrobenzofuran-5,7-dicarboxamide

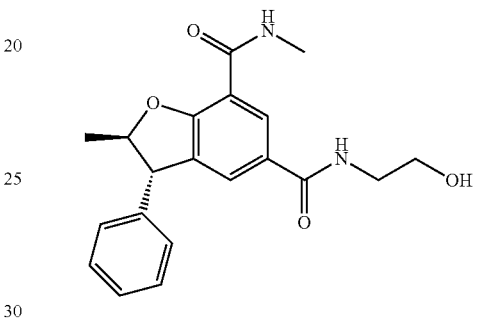

A solution of (2R,3S)-2-methyl-7-(methylcarbamoyl)-3-phenyl-2,3-dihydrobenzofuran-5-carboxylic acid (30 mg, 0.096 mmol) in DCM (5 mL) at room temperature was treated with HATU (55.0 mg, 0.145 mmol) and Et₃N (0.054 mL, 0.38 mmol) and the resulting mixture was stirred at this temperature for 1 h before being treated with 2-aminoethanol (11.8 mg, 0.193 mmol). The resulting mixture was stirred at this temperature for 2 h then was concentrated in vacuo. Purification of the residue obtained by MDAP (method high pH) gave (2R,3S)—N⁵-(2-hydroxyethyl)-N⁷,2-dimethyl-3-phenyl-2,3-dihydrobenzofuran-5,7-dicarboxamide (25 mg, 73%) as a colourless solid.

LCMS (method high pH): Retention time 0.87 min, [M+H]⁺=355

Example 38: (1R,5S,6S)-tert-Butyl 6-((2R,3S)-2-methyl-7-(methylcarbamoyl)-3-phenyl-2,3-dihydrobenzofuran-5-carboxamido)-3-azabicyclo[3.1.0]hexane-3-carboxylate

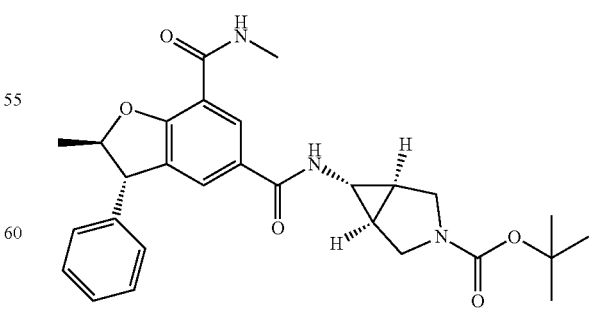

A solution of HATU (216 mg, 0.569 mmol) in DCM (5 mL) at room temperature was treated with Et₃N (0.211 mL, 1.56 mmol) and (2R,3S)-2-methyl-7-(methylcarbamoyl)-3- phenyl-2,3-dihydrobenzofuran-5-carboxylic acid (118 mg, 0.379 mmol) and the resulting mixture was stirred at this temperature for 1 h before being treated with (1R,5S,6s)-tert-butyl 6-amino-3-azabicyclo[3.1.0]hexane-3-carboxylate (98 mg, 0.49 mmol). The resulting mixture was stirred at this temperature for 2 h then was concentrated in vacuo. Purification of the residue obtained by MDAP (method high pH) gave (1R,5S,6s)-tert-butyl 6-((2R,3S)-2-methyl-7-(methylcarbamoyl)-3-phenyl-2,3-dihydrobenzofuran-5-carboxamido)-3-azabicyclo[3.1.0]hexane-3-carboxylate (175 mg, 94%) as a colourless solid.

LCMS (method high pH): Retention time 1.19 min, [M+H]⁺=492

Example 39: (2R,3S)—N⁵-((1R,5S,6s)-3-Azabicyclo[3.1.0]hexan-6-yl)-N⁷,2-dimethyl-3-phenyl-2,3-dihydrobenzofuran-5,7-dicarboxamide

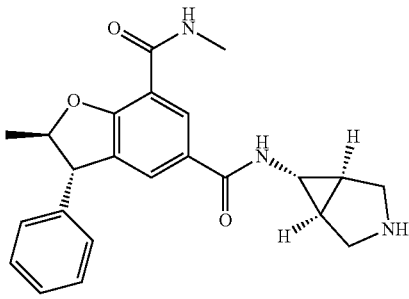 [SMILES: CNC(=O)c1cc(C(=O)N[C@H]2[C@@H]3CNC[C@@H]32)cc2c1O[C@H](C)[C@H]2c1ccccc1]

A solution of (1R,5S,6s)-tert-butyl 6-((2R,3S)-2-methyl-7-(methylcarbamoyl)-3-phenyl-2,3-dihydrobenzofuran-5-carboxamido)-3-azabicyclo[3.1.0]hexane-3-carboxylate (150 mg, 0.305 mmol) in DCM (10 mL) at room temperature was treated with TFA (5 mL) and the resulting mixture was stirred at this temperature for 2 h then was concentrated in vacuo. The residue was dissolved in MeOH (5 mL) and loaded onto a 5 g SCX2 cartridge, which was washed with MeOH (20 mL), then eluted with a 2N NH₃ solution in MeOH (20 mL). The ammonia fractions were concentrated in vacuo to give (2R,3S)—N⁵-((1R,5S,6s)-3-azabicyclo[3.1.0]hexan-6-yl)-N⁷,2-dimethyl-3-phenyl-2,3-dihydrobenzofuran-5,7-dicarboxamide (100 mg, 84%).

LCMS (method high pH): Retention time 0.89 min, [M+H]⁺=392

Example 40: (2R,3S)—N⁵-((1R,5S,6s)-3-Acetyl-3-azabicyclo[3.1.0]hexan-6-yl)-N⁷,2-dimethyl-3-phenyl-2,3-dihydrobenzofuran-5,7-dicarboxamide

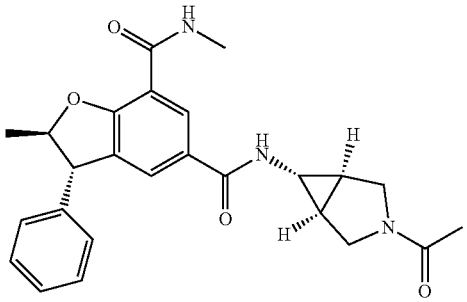 [SMILES: CNC(=O)c1cc(C(=O)N[C@H]2[C@@H]3CN(C(C)=O)C[C@@H]32)cc2c1O[C@H](C)[C@H]2c1ccccc1]

A solution of (2R,3S)—N⁵-((1R,5S,6s)-3-azabicyclo[3.1.0]hexan-6-yl)-N⁷,2-dimethyl-3-phenyl-2,3-dihydrobenzofuran-5,7-dicarboxamide (35 mg, 0.089 mmol) in DMF (1 mL) at room temperature was treated with Et₃N (0.012 mL, 0.089 mmol) and acetyl chloride (6.4 μL, 0.089 mmol) and the resulting mixture was stirred at this temperature for 1 h before being purified by MDAP (method high pH) to give (2R,3S)—N⁵-((1R,5S,6s)-3-acetyl-3-azabicyclo[3.1.0]hexan-6-yl)-N⁷,2-dimethyl-3-phenyl-2,3-dihydrobenzofuran-5,7-dicarboxamide (25 mg, 65%) as a colourless solid.

LCMS (method high pH): Retention time 0.91 min, [M+H]⁺=434

Example 41: (2R,3S)—N⁵-((1R,5S,6R)-3-Oxabicyclo[3.1.0]hexan-6-yl)-N⁷,2-dimethyl-3-phenyl-2,3-dihydrobenzofuran-5,7-dicarboxamide

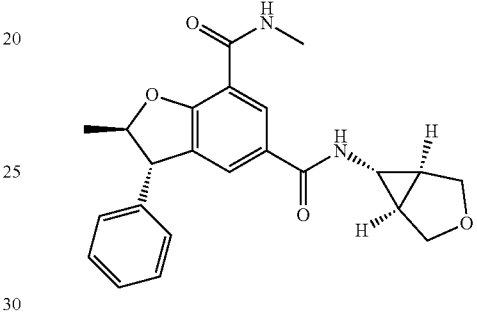

A solution of HATU (82 mg, 0.28 mmol) and Et₃N (0.081 mL, 0.58 mmol) in DCM (5 mL) at room temperature was treated with (1R,5S,6r)-3-oxabicyclo[3.1.0]hexan-6-amine, hydrochloride (25 mg, 0.18 mmol) and (2R,3S)-2-methyl-7-(methylcarbamoyl)-3-phenyl-2,3-dihydrobenzofuran-5-carboxylic acid (45 mg, 0.14 mmol). The resulting mixture was stirred at this temperature for 1 h then was concentrated in vacuo. Purification of the residue by MDAP (method high pH) gave (2R,3S)—N⁵-((1R,5S,6r)-3-oxabicyclo[3.1.0]hexan-6-yl)-N⁷,2-dimethyl-3-phenyl-2,3-dihydrobenzofuran-5,7-dicarboxamide (34 mg, 60%) as a colourless solid.

LCMS (method high pH): Retention time 0.93 min, [M+H]⁺=393

Example 42: (2R,3S)—N⁵-(2-(Dimethylamino)ethyl)-N⁷,2-dimethyl-3-phenyl-2,3-dihydrobenzofuran-5,7-dicarboxamide

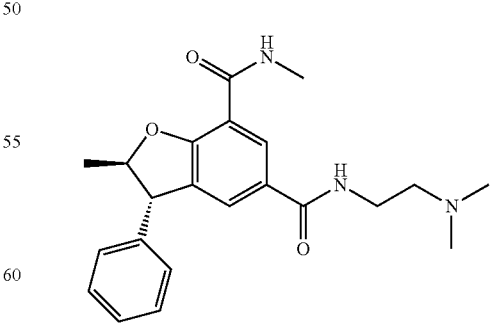

A solution of HATU (82 mg, 0.28 mmol) in DCM (5 mL) at room temperature was treated with Et₃N (0.081 mL, 0.58 mmol) and (2R,3S)-2-methyl-7-(methylcarbamoyl)-3-phenyl-2,3-dihydrobenzofuran-5-carboxylic acid (45 mg, 0.14 mmol) and the resulting mixture was stirred at this temperature for 1 h, then was treated with N¹,N¹-dimethylethane-1,2-diamine (25.5 mg, 0.289 mmol). The resulting mixture was stirred at room temperature for 2 h then was concentrated in vacuo. Purification of the residue by MDAP (method high pH) gave (2R,3S)—N⁵-(2-(dimethylamino) ethyl)-N⁷,2-dimethyl-3-phenyl-2,3-dihydrobenzofuran-5,7-dicarboxamide (25 mg, 45%).

LCMS (method high pH): Retention time 0.93 min, [M+H]⁺=382

Example 43: (2R,3S)—N⁵-(3-(Dimethylamino)propyl)-N⁷,2-dimethyl-3-phenyl-2,3-dihydrobenzofuran-5,7-dicarboxamide

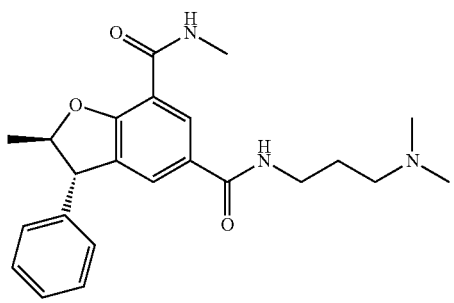

A solution of HATU (82 mg, 0.22 mmol) in DCM (5 mL) at room temperature was treated with Et₃N (0.081 mL, 0.58 mmol) and (2R,3S)-2-methyl-7-(methylcarbamoyl)-3-phenyl-2,3-dihydrobenzofuran-5-carboxylic acid (45 mg, 0.14 mmol) and the resulting mixture was stirred at this temperature for 1 h, then was treated with N¹,N¹-dimethylpropane-1,3-diamine (29.5 mg, 0.289 mmol). The resulting mixture was stirred at room temperature for 2 h then was concentrated in vacuo. Purification of the residue by MDAP (method high pH) gave (2R,3S)—N⁵-(3-(dimethylamino) propyl)-N⁷,2-dimethyl-3-phenyl-2,3-dihydrobenzofuran-5,7-dicarboxamide (25 mg, 44%).

LCMS (method high pH): Retention time 0.99 min, [M+H]⁺=396

Example 44: (2R*,3S*)—N⁵-Cyclopropyl-3-(3-methoxyphenyl)-N⁷,2-dimethyl-2,3-dihydrobenzofuran-5,7-dicarboxamide

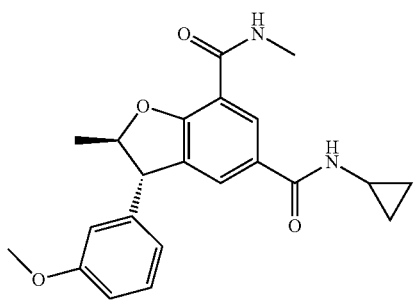 [SMILES: CNC(=O)c1cc(C(=O)NC2CC2)cc2c1O[C@H](C)[C@H]2c1cccc(OC)c1]

A solution of ((2R*,3S*)-5-(cyclopropylcarbamoyl)-3-(3-methoxyphenyl)-7-(methylcarbamoyl)-2,3-dihydrobenzofuran-2-yl)methyl methanesulfonate (90 mg, 0.19 mmol) in THF (5 mL) at 0° C. was treated with LiBH₄ (24.8 mg, 1.14 mmol) and the resulting mixture was stirred at this temperature for 2 h, then was allowed to warm to room temperature and stirred for 24 h. The mixture was left without stirring at room temperature for 10 days then was diluted with EtOAc (20 mL) and treated with a saturated NH₄Cl aqueous solution (20 mL). The biphasic mixture was stirred for 30 min, then the layers were separated. The organic phase was dried over MgSO₄ and concentrated in vacuo. Purification of the residue obtained by flash chromatography on silica gel (25 g column, gradient: 0-100% EtOAc in cyclohexane) gave (2R*,3S*))—N⁵-cyclopropyl-3-(3-methoxyphenyl)-N⁷,2-dimethyl-2,3-dihydrobenzofuran-5,7-dicarboxamide (45 mg, 62%) as a colourless foam. LCMS (method high pH): Retention time 1.01 min, [M+H]⁺=381

Example 45: (2R,3S)—N⁷,2-Dimethyl-N⁵-(oxetan-3-yl)-3-phenyl-2,3-dihydrobenzofuran-5,7-dicarboxamide

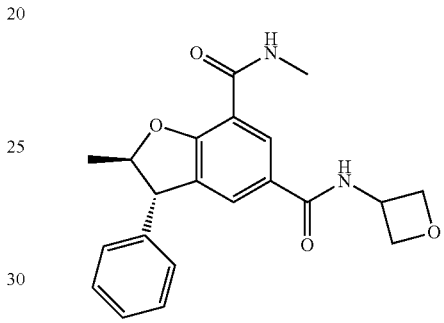

A solution of HATU (82 mg, 0.22 mmol) in DCM (5 mL) at room temperature was treated with Et₃N (0.081 mL, 0.58 mmol) and (2R,3S)-2-methyl-7-(methylcarbamoyl)-3-phenyl-2,3-dihydrobenzofuran-5-carboxylic acid (45 mg, 0.145 mmol) and the resulting mixture was stirred at this temperature for 1 h, then was treated with oxetan-3-amine (21.1 mg, 0.289 mmol). The resulting mixture was stirred at room temperature for 2 h then was concentrated in vacuo. Purification of the residue obtained by MDAP (method high pH) gave (2R,3S)—N⁷,2-dimethyl-N⁵-(oxetan-3-yl)-3-phenyl-2, 3-dihydrobenzofuran-5,7-dicarboxamide (30 mg, 57%).

LCMS (method high pH): Retention time 0.93 min, [M+H]⁺=367

Example 46: tert-Butyl 2-(2R,3S)-2-methyl-7-(methylcarbamoyl)-3-phenyl-2,3-dihydrobenzofuran-5-carboxamido)ethyl)morpholine-4-carboxylate

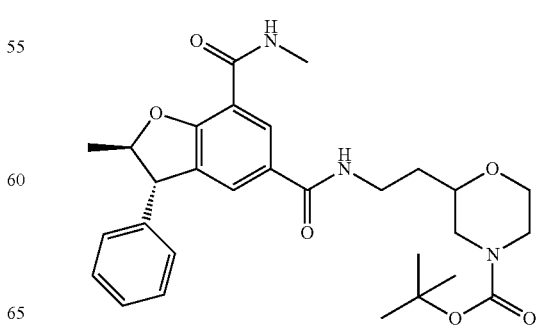

A solution of HATU (92 mg, 0.24 mmol) in DCM (5 mL) at room temperature was treated with Et$_3$N (0.090 mL, 0.64 mmol) and (2R,3S)-2-methyl-7-(methylcarbamoyl)-3-phenyl-2,3-dihydrobenzofuran-5-carboxylic acid (50 mg, 0.16 mmol) and the resulting mixture was stirred at this temperature for 1 h, then was treated with tert-butyl 2-(2-aminoethyl)morpholine-4-carboxylate (44.4 mg, 0.193 mmol, which can be obtained according to Dowle, Michael Dennis et al, PCT Int. Appl., 2003097618). The resulting mixture was stirred at room temperature for 2 h then was washed with water (10 mL), dried over sodium sulfate and concentrated in vacuo. Purification of the residue obtained by flash chromatography on silica gel (25 g column, gradient: 0-100% EtOAc in hexanes) gave tert-butyl 2-(2-((2R,3S)-2-methyl-7-(methylcarbamoyl)-3-phenyl-2,3-dihydrobenzofuran-5-carboxamido)ethyl)morpholine-4-carboxylate (50 mg, 60%) as a colourless foam.

LCMS (method high pH): Retention time 1.20 min, [M+H]$^+$=524

Example 47: (2R,3S)—N$^7$,2-Dimethyl-N$^5$-(2-(morpholin-2-yl)ethyl)-3-phenyl-2,3-dihydrobenzofuran-5,7-dicarboxamide

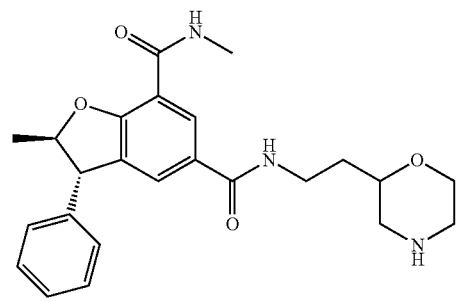 [SMILES: CNC(=O)c1cc(C(=O)NCCC2CNCCO2)cc2c1O[C@H](C)[C@H]2c1ccccc1]

A solution of tert-butyl 2-(2-((2R,3S)-2-methyl-7-(methylcarbamoyl)-3-phenyl-2,3-dihydrobenzofuran-5-carboxamido)ethyl)morpholine-4-carboxylate (45 mg, 0.086 mmol) in DCM (3 mL) at room temperature was treated with TFA (1 mL) and the resulting solution was allowed to stand still for 1 h, then was concentrated in vacuo. The residue was dissolved in MeOH (3 mL) and loaded onto a 2 g SCX cartridge, which was washed with MeOH (10 mL), then was eluted with a 2N NH$_3$ solution in MeOH. The ammonia fractions were concentrated in vacuo to give (2R,3S)—N$^7$,2-dimethyl-N$^5$-(2-(morpholin-2-yl)ethyl)-3-phenyl-2,3-dihydrobenzofuran-5,7-dicarboxamide (25 mg, 69%) as a colourless solid.

LCMS (method high pH): Retention time 1.20 min, [M+H]$^+$=424

Examples 48-52

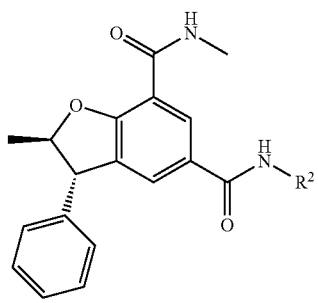

General Procedure:

A solution of (2R,3S)-2-methyl-7-(methylcarbamoyl)-3-phenyl-2,3-dihydrobenzofuran-5-carboxylic acid (30 mg, 0.096 mmol) in DMF (1 mL) at room temperature was treated with HATU (55.0 mg, 0.145 mmol) and NEt$_3$ (19.5 mg, 0.193 mmol) and the resulting solution was stirred for 20 min at this temperature, then was treated with the primary amine (0.145 mmol). The resulting mixture was stirred for 1 h at room temperature then purified directly by MDAP (method high pH) to give the corresponding example as an off white solid in all cases.

The following amines were used for examples 48 to 52, respectively:

3-aminopropan-1-ol (10.9 mg)
3-morpholinopropan-1-amine (20.8 mg)
3-methoxypropan-1-amine (12.9 mg)
tetrahydrofuran-3-amine (12.6 mg),
2,2-difluoroethanamine (11.7 mg)

| Ex. | Structure Example | Name | Mass obtained (mg), yield | Retention time (method high pH) | [M + H]+ |
|---|---|---|---|---|---|
| 48 | | (2R,3S)-N$^5$-(3-hydroxypropyl)-N$^7$,2-dimethyl-3-phenyl-2,3-dihydrobenzofuran-5,7-dicarboxamide | 23 (65%) | 0.89 | 369 |

| Ex. | Structure Example | Name | Mass obtained (mg), yield | Retention time (method high pH) | [M + H]+ |
| --- | --- | --- | --- | --- | --- |
| 49 | | (2R,3S)-N$^7$,2-dimethyl-N$^5$-(3-morpholinopropyl)-3-phenyl-2,3-dihydrobenzofuran-5,7-dicarboxamide | 18 (43%) | 0.96 | 438 |
| 50 | | (2R,3S)-N$^5$-(3-methoxypropyl)-N$^7$,2-dimethyl-3-phenyl-2,3-dihydrobenzofuran-5,7-dicarboxamide | 16 (43%) | 1.01 | 383 |
| 51 | | (2R,3S)-N$^7$,2-dimethyl-3-phenyl-N$^5$-(tetrahydrofuran-3-yl)-2,3-dihydrobenzofuran-5,7-dicarboxamide | 18 (49%) | 0.96 | 381 |
| 52 | | (2R,3S)-N$^5$-(2,2-difluoroethyl)-N$^7$,2-dimethyl-3-phenyl-2,3-dihydrobenzofuran-5,7-dicarboxamide | 22 (61%) | 1.05 | 375 |

Example 53: tert-Butyl 2-(3-((2R,3S)-2-methyl-7-(methylcarbamoyl)-3-phenyl-2,3-dihydrobenzofuran-5-carboxamido)propyl)morpholine-4-carboxylate

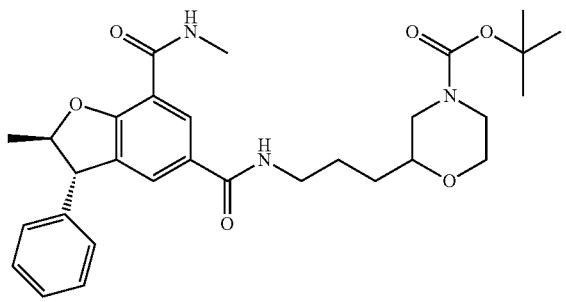 [SMILES: CNC(=O)c1cc(C(=O)NCCCC2CN(C(=O)OC(C)(C)C)CCO2)cc2c1O[C@H](C)[C@H]2c1ccccc1]

A solution of (2R,3S)-2-methyl-7-(methylcarbamoyl)-3-phenyl-2,3-dihydrobenzofuran-5-carboxylic acid (30 mg, 0.096 mmol) in DMF (1 mL) at room temperature was treated with NEt$_3$ (19.5 mg, 0.193 mmol) and HATU (55.0 mg, 0.145 mmol) and the resulting solution was stirred at this temperature for 20 min before being treated with tert-butyl 2-(3-aminopropyl)morpholine-4-carboxylate (30 mg, 0.12 mmol). The resulting mixture was stirred at room temperature for 1 h, then was purified by MDAP (method high pH) to give tert-butyl 2-(3-((2R,3S)-2-methyl-7-(methylcarbamoyl)-3-phenyl-2,3-dihydrobenzofuran-5-carboxamido)propyl)morpholine-4-carboxylate (35 mg, 68%) as a colourless solid.

LCMS (method high pH): Retention time 1.21 min, [M+H]$^+$=538

Example 54: (2R,3S)—N$^7$,2-Dimethyl-N$^5$-(3-(morpholin-2-yl)propyl)-3-phenyl-2,3-dihydrobenzofuran-5,7-dicarboxamide

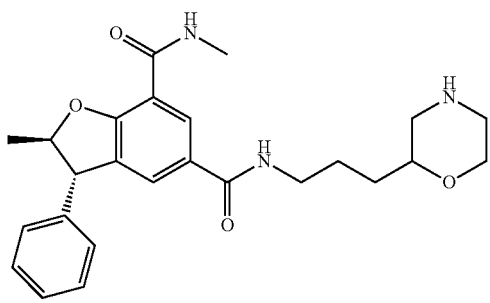 [SMILES: CNC(=O)c1cc(C(=O)NCCCC2CNCCO2)cc2c1O[C@H](C)[C@H]2c1ccccc1]

A solution of tert-butyl 2-(3-((2R,3S)-2-methyl-7-(methylcarbamoyl)-3-phenyl-2,3-dihydrobenzofuran-5-carboxamido)propyl)morpholine-4-carboxylate (30 mg, 0.056 mmol) in DCM (5 mL) at room temperature was treated with TFA (2.0 mL, 26 mmol) and the resulting mixture was stirred at room temperature for 1 h, then was concentrated in vacuo. The residue was dissolved in MeOH and loaded onto a 2 g SCX cartridge. This was washed with MeOH (10 mL), then eluted with a 2N NH$_3$ solution in MeOH. The ammonia fractions were concentrated in vacuo to give (2R,3S)—N$^7$,2-dimethyl-N$^5$-(3-(morpholin-2-yl)propyl)-3-phenyl-2,3-dihydrobenzofuran-5,7-dicarboxamide (24 mg, 98%) as a pale yellow solid.

LCMS (method formic): Retention time 0.65 min, [M+H]$^+$=438

Example 55: (2R,3S)—N$^5$-ethyl-3-(3-methoxyphenyl)-N$^7$,2-dimethyl-2,3-dihydrobenzofuran-5,7-dicarboxamide

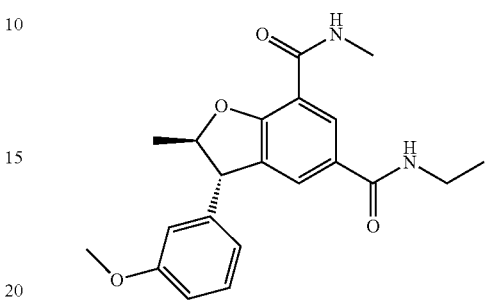

A solution of (2R,3S)-3-(3-methoxyphenyl)-2-methyl-7-(methylcarbamoyl)-2,3-dihydrobenzofuran-5-carboxylic acid (125 mg, 0.366 mmol) in DCM (10 mL) at room temperature was treated with HATU (209 mg, 0.549 mmol) and NEt$_3$ (0.102 mL, 0.732 mmol) and the resulting mixture was stirred at this temperature for 20 min, then was treated with ethanamine (2N in THF, 0.366 mL, 0.732 mmol). The resulting mixture was stirred at this temperature for 1 h then was washed with water (2*10 mL), dried using an hydrophobic frit and concentrated in vacuo to give (2R,3S)—N$^5$-ethyl-3-(3-methoxyphenyl)-N$^7$,2-dimethyl-2,3-dihydrobenzofuran-5,7-dicarboxamide (110 mg, 82%) as a colourless foam.

LCMS (method high pH): Retention time 1.00 min, [M+H]$^+$=369

Example 56: (2R,3S)—N$^5$-((1R,2R)-2-(Hydroxymethyl)cyclopropyl)-3-(3-methoxyphenyl)-N$^7$,2-dimethyl-2,3-dihydrobenzofuran-5,7-dicarboxamide

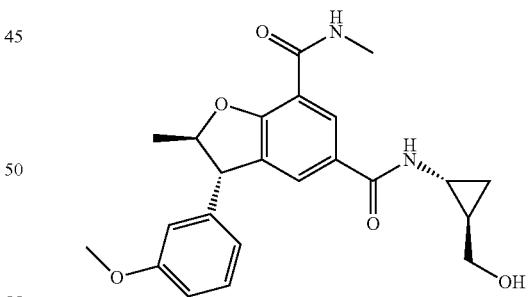

A flask was charged with (2R,3S)-3-(3-methoxyphenyl)-2-methyl-7-(methylcarbamoyl)-2,3-dihydrobenzofuran-5-carboxylic acid (40 mg, 0.12 mmol), ((1R,2R)-2-aminocyclopropyl)methanol hydrochloride (18 mg, 0.15 mmol), HATU (66.8 mg, 0.176 mmol) and Et$_3$N (0.016 mL, 0.12 mmol) then was filled with DMF (1 mL). The resulting mixture was stirred at room temperature for 1 h, then was purified directly by MDAP (high pH method) to give (2R,3S)—N$^5$-((1R,2R)-2-(hydroxymethyl)cyclopropyl)-3-(3-methoxyphenyl)-N$^7$,2-dimethyl-2,3-dihydrobenzofuran-5,7-dicarboxamide (28 mg, 58%) as a colourless gum.

LCMS (method formic): Retention time 0.89 min, [M+H]$^+$=411

Example 57: (2R,3S)—N$^5$-((1R,5S,6r)-3-Oxabicyclo[3.1.0]hexan-6-yl)-3-(3-methoxyphenyl)-N$^7$,2-dimethyl-2,3-dihydrobenzofuran-5,7-dicarboxamide

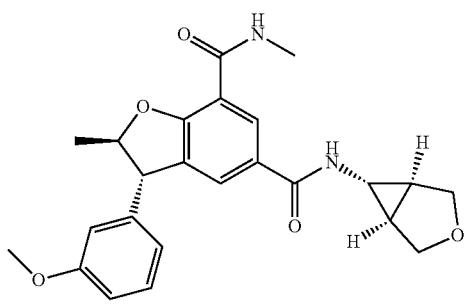 [SMILES: CNC(=O)c1cc(C(=O)N[C@H]2[C@@H]3COC[C@@H]32)cc2c1O[C@H](C)[C@H]2c1cccc(OC)c1]

A solution of HATU (75 mg, 0.20 mmol) and Et$_3$N (73.5 µL, 0.527 mmol) in DCM (5 mL) at room temperature was treated with (1R,5S,6r)-3-oxabicyclo[3.1.0]hexan-6-amine, hydrochloride (25 mg, 0.18 mmol) and (2R,3S)-3-(3-methoxyphenyl)-2-methyl-7-(methylcarbamoyl)-2,3-dihydrobenzofuran-5-carboxylic acid (45 mg, 0.13 mmol). The resulting mixture was stirred at room temperature for 1 h then was concentrated in vacuo. Purification of the residue by MDAP (method high pH) gave (2R,3S)—N$^5$-((1R,5S,6r)-3-oxabicyclo[3.1.0]hexan-6-yl)-3-(3-methoxyphenyl)-N$^7$,2-dimethyl-2,3-dihydrobenzofuran-5,7-dicarboxamide (37 mg, 66%) as a colourless solid.

LCMS (method formic): Retention time 0.93 min, [M+H]$^+$=423

Example 58: (R)-tert-Butyl 2-(3-((2R,3S)-3-(3-methoxyphenyl)-2-methyl-7-(methylcarbamoyl)-2,3-dihydrobenzofuran-5-carboxamido)propyl)morpholine-4-carboxylate

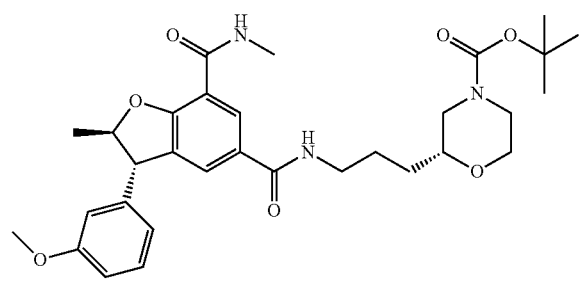 [SMILES: CNC(=O)c1cc(C(=O)NCCC[C@@H]2CN(C(=O)OC(C)(C)C)CCO2)cc2c1O[C@H](C)[C@H]2c1cccc(OC)c1]

A solution of HATU (75 mg, 0.20 mmol) and Et$_3$N (73.5 µL, 0.527 mmol) in DCM (5 mL) at room temperature was treated with (R)-tert-butyl 2-(3-aminopropyl)morpholine-4-carboxylate (41.9 mg, 0.171 mmol) and (2R,3S)-3-(3-methoxyphenyl)-2-methyl-7-(methylcarbamoyl)-2,3-dihydrobenzofuran-5-carboxylic acid (45 mg, 0.13 mmol). The resulting mixture was stirred at room temperature for 1 h then was concentrated in vacuo. Purification of the residue obtained by MDAP (method high pH) gave (R)-tert-butyl 2-(3-((2R,3S)-3-(3-methoxyphenyl)-2-methyl-7-(methylcarbamoyl)-2,3-dihydrobenzofuran-5-carboxamido)propyl) morpholine-4-carboxylate (45 mg, 60%) as a colourless gum.

LCMS (method formic): Retention time 1.19 min, [M+H]$^+$=568

Example 59: (2R,3S)-3-(3-Methoxyphenyl)-N$^7$,2-dimethyl-N$^5$-(3-((R)-morpholin-2-yl)propyl)-2,3-dihydrobenzofuran-5,7-dicarboxamide

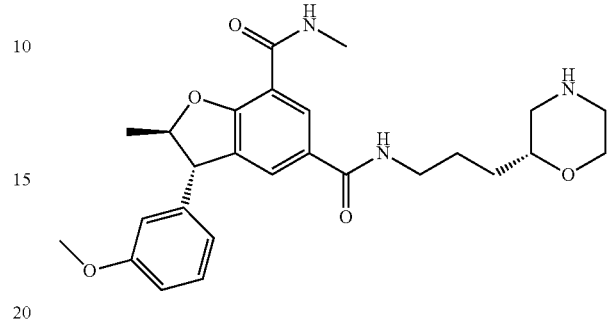

A solution of (R)-tert-butyl 2-(3-((2R,3S)-3-(3-methoxyphenyl)-2-methyl-7-(methylcarbamoyl)-2,3-dihydrobenzofuran-5-carboxamido)propyl)morpholine-4-carboxylate (40 mg, 0.071 mmol) in DCM (2 mL) at room temperature was treated with TFA (1 mL) and the resulting mixture was stirred for 2 h at room temperature then was concentrated in vacuo. The residue was dissolved in MeOH and loaded onto a 5 g SCX cartridge, which was washed with MeOH (10 mL) and then eluted with a 2N NH$_3$ in MeOH. The ammonia fractions were concentrated in vacuo to give (2R,3S)-3-(3-methoxyphenyl)-N',2-dimethyl-N$^5$-(3-((R)-morpholin-2-yl)propyl)-2,3-dihydrobenzofuran-5,7-dicarboxamide (30 mg, 91%) as a colourless gum.

LCMS (method formic): Retention time 0.63 min, [M+H]$^+$=468

Example 60: (2R,3S)-3-(3-Methoxyphenyl)-N$^7$,2-dimethyl-N$^5$-(3-((S)-morpholin-2-yl)propyl)-2,3-dihydrobenzofuran-5,7-dicarboxamide

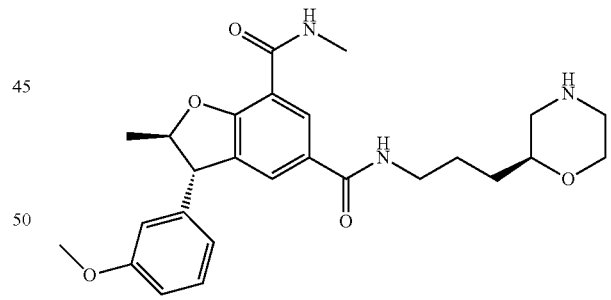

A solution of HATU (50.1 mg, 0.132 mmol) and Et$_3$N (49.0 µL, 0.352 mmol) in DCM (5 mL) at room temperature was treated with (S)-tert-butyl 2-(3-aminopropyl)morpholine-4-carboxylate (27.9 mg, 0.114 mmol) and (2R,3S)-3-(3-methoxyphenyl)-2-methyl-7-(methylcarbamoyl)-2,3-dihydrobenzofuran-5-carboxylic acid (30 mg, 0.088 mmol) and the resulting mixture was stirred for 1 h at room temperature then was concentrated in vacuo. Purification of the residue by MDAP gave a colourless solid which was dissolved in DCM (2 mL) and treated with TFA (1 mL). The resulting solution was stirred at room temperature for 2 h then was concentrated in vacuo. The residue was dissolved in MeOH then loaded onto a 5 g SCX cartridge, which was washed with MeOH (10 mL), then was eluted with a 2N NH$_3$ solution in MeOH. The ammonia fractions were concentrated in vacuo to give (2R,3S)-3-(3-methoxyphenyl)-N$^7$,2-dimethyl-N$^5$-(3-((S)-morpholin-2-yl)propyl)-2,3-dihydrobenzofuran-5,7-dicarboxamide (35 mg, 85%) as a colourless gum.

LCMS (method formic): Retention time 0.63 min, [M+H]$^+$=468

Example 61: tert-Butyl 3-fluoro-3-(3-(((2R,3S)-2-methyl-7-(methylcarbamoyl)-3-phenyl-2,3-dihydrobenzofuran-5-carboxamido)propyl)piperidine-1-carboxylate

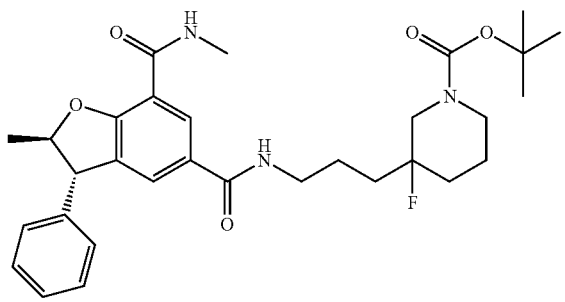 [SMILES: CNC(=O)c1cc(C(=O)NCCCC2(F)CCCN(C(=O)OC(C)(C)C)C2)cc2c1O[C@H](C)[C@H]2c1ccccc1]

A solution of (2R,3S)-2-methyl-7-(methylcarbamoyl)-3-phenyl-2,3-dihydrobenzofuran-5-carboxylic acid (80 mg, 0.26 mmol) and tert-butyl 3-(3-aminopropyl)-3-fluoropiperidine-1-carboxylate (66.9 mg, 0.257 mmol) in DCM (10 mL) at room temperature was treated with HATU (147 mg, 0.385 mmol) and Et$_3$N (0.036 mL, 0.26 mmol) and the resulting mixture was stirred at this temperature for 2 h, then was concentrated in vacuo. Purification of the residue obtained by MDAP (method high pH) gave tert-butyl 3-fluoro-3-(3-(((2R,3S)-2-methyl-7-(methylcarbamoyl)-3-phenyl-2,3-dihydrobenzofuran-5-carboxamido)propyl)piperidine-1-carboxylate (105 mg, 74%) as a colourless gum.

LCMS (method high pH): Retention time 1.27 min, [M+H-Boc]$^+$=454

Example 62: (2R,3S)—N$^5$-(3-(3-Fluoropiperidin-3-yl)propyl)-N$^7$,2-dimethyl-3-phenyl-2,3-dihydrobenzofuran-5,7-dicarboxamide

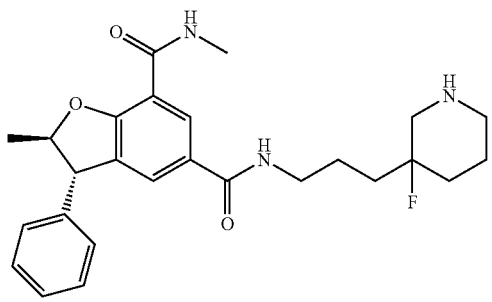 [SMILES: CNC(=O)c1cc(C(=O)NCCCC2(F)CCCNC2)cc2c1O[C@H](C)[C@H]2c1ccccc1]

A solution of tert-butyl 3-fluoro-3-(3-(((2R,3S)-2-methyl-7-(methylcarbamoyl)-3-phenyl-2,3-dihydrobenzofuran-5-carboxamido)propyl)piperidine-1-carboxylate (100 mg, 0.181 mmol) in DCM (5 mL) at room temperature was treated with TFA (1 mL) and the resulting mixture was stirred at room temperature for 2 h, then was concentrated in vacuo. The residue was dissolved in MeOH and loaded onto a 5 g SCX cartridge, which was washed with MeOH (20 mL), then was eluted with a 2N NH$_3$ solution in MeOH. The ammonia fractions were concentrated in vacuo to give (2R,3S)—N$^5$-(3-(3-fluoropiperidin-3-yl)propyl)-N$^7$,2-dimethyl-3-phenyl-2,3-dihydrobenzofuran-5,7-dicarboxamide (75 mg, 92%).

LCMS (method high pH): Retention time 1.01 min, [M+H]$^+$=454

Example 63: (2R,3S)—N$^5$-((1S*,2R*)-2-(2-Hydroxyethyl)cyclopropyl)-N$^7$,2-dimethyl-3-phenyl-2,3-dihydrobenzofuran-5,7-dicarboxamide

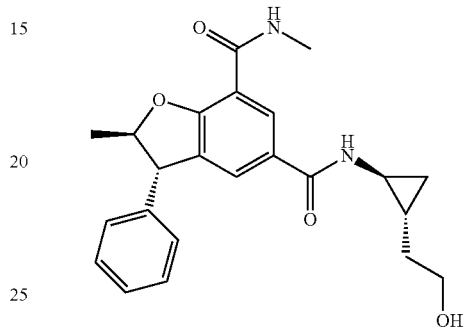

A solution of 2-((1R*,2S*)-2-aminocyclopropyl)ethanol (71.5 mg, 0.707 mmol) and (2R,3S)-2-methyl-7-(methylcarbamoyl)-3-phenyl-2,3-dihydrobenzofuran-5-carboxylic acid (110 mg, 0.353 mmol) in DCM (5 mL) at room temperature was treated with Et$_3$N (0.098 mL, 0.707 mmol) and HATU (202 mg, 0.530 mmol) and the resulting mixture was allowed to stand at this temperature for 16 h before being washed with water (2×5 mL), dried using an hydrophobic frit and concentrated in vacuo to give (2R,3S)—N$^5$-((1S*,2R*)-2-(2-Hydroxyethyl)cyclopropyl)-N$^7$,2-dimethyl-3-phenyl-2,3-dihydrobenzofuran-5,7-dicarboxamide (160 mg, 115%) as a pale yellow oil which was used in the next step without further purification.

LCMS (method high pH): Retention time 0.94 min, [M+H]$^+$=395

Example 64: (2R,3S)—N$^7$,2-Dimethyl-N$^5$-((1S*,2S*)-2-(2-morpholinoethyl)cyclopropyl)-3-phenyl-2,3-dihydrobenzofuran-5,7-dicarboxamide

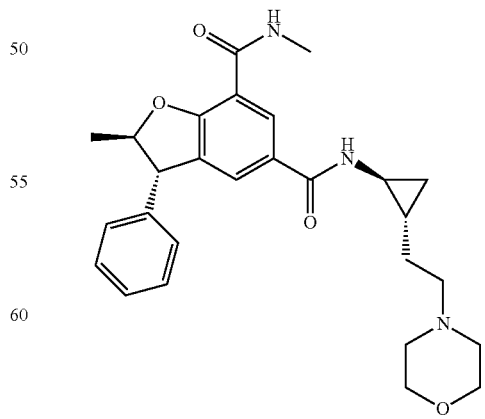

A solution of (2R,3S)—N$^5$-((1S*,2R*)-2-(2-hydroxyethyl)cyclopropyl)-N$^7$,2-dimethyl-3-phenyl-2,3-dihydrobenzofuran-5,7-dicarboxamide (100 mg, 0.254 mmol) in DCM (5 mL) at room temperature and Dess-Martin periodinane (161 mg, 0.380 mmol) was added, then the mixture was stirred for 4 h at room temperature. The mixture was washed with water (5 mL) and dried using an hydrophobic frit. The solution was then treated with morpholine (0.044 mL, 0.51 mmol) and sodium triacetoxyborohydride (215 mg, 1.01 mmol) and the mixture was stirred at room temperature for 16 h. The solution was then washed with a saturated NaHCO$_3$ aqueous solution, then dried using an hydrophobic frit and concentrated in vacuo. Purification of the residue by MDAP (method high pH) gave (2R,3S)—N$^7$, 2-dimethyl-N$^5$-((1S*,2S*)-2-(2-morpholinoethyl)cyclopropyl)-3-phenyl-2,3-dihydrobenzofuran-5,7-dicarboxamide (95 mg, 81%) as a colourless solid.

LCMS (method formic): Retention time 0.68 min, [M+H]$^+$=464

Examples 65 and 66: (2R,3S)—N$^7$,2-Dimethyl-N$^5$-((1S,2S)-2-(2-morpholinoethyl)cyclopropyl)-3-phenyl-2,3-dihydrobenzofuran-5,7-dicarboxamide and (2R,3S)—N$^7$,2-dimethyl-N$^5$-((1R,2R)-2-(2-morpholinoethyl)cyclopropyl)-3-phenyl-2,3-dihydrobenzofuran-5,7-dicarboxamide

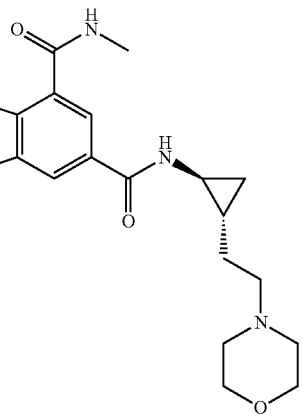

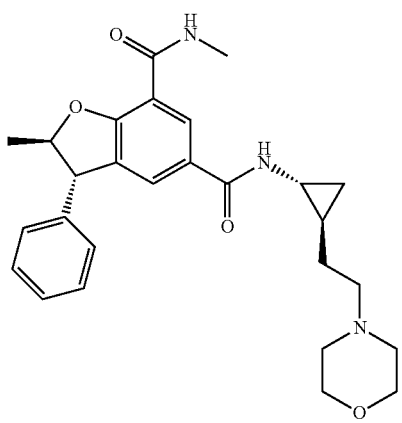 [SMILES: CNC(=O)c1cc(C(=O)N[C@H]2C[C@@H]2CCN2CCOCC2)cc2c1O[C@H](C)[C@H]2c1ccccc1]

Example 64 (60 mg) was purified by chiral chromatography as follows:

Analytical Method: Approximatively 0.5 mg of material was dissolved in 50% EtOH/heptane (1 mL) and 20 uL of the resulting solution were injected on column. Eluant: 25% EtOH(+0.2% isopropylamine)/heptane, flow=1.0 mL/min, wavelength 215 nm. Column 4.6 mmidx25 cm Chiralpak AD-H Prep Method: Approximatively 60 mg of material was dissolved in EtOH (1.5 mL). Injections (3 in total): 0.5 mL of the solution was injected onto the column. Eluant: 30% EtOH (+0.2% isopropylamine)/heptane (+0.2% isopropylamine), flow=30 mL/min, wavelength 215 nm. Column 30 mm×25 cm Chiralpak AD-H (5 um).

This purification gave (2R,3S)—N$^7$,2-dimethyl-N$^5$-((1S, 2S)-2-(2-morpholinoethyl)cyclopropyl)-3-phenyl-2,3-dihydrobenzofuran-5,7-dicarboxamide (25 mg, 83%) as fast running enantiomer and (2R,3S)—N$^7$,2-dimethyl-N$^5$-((1R,2R)-2-(2-morpholinoethyl)cyclopropyl)-3-phenyl-2,3-dihydrobenzofuran-5,7-dicarboxamide (25 mg, 83%) as slow running enantiomer.

Example 67: (2R*,3S*)-3-(3-(2-Hydroxyethoxy)phenyl)-N$^7$, 2-dimethyl-N$^5$-((1S,2S)-2-methylcyclopropyl)-2,3-dihydrobenzofuran-5,7-dicarboxamide

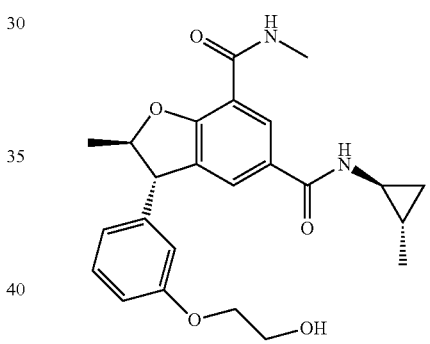

A solution of (2R*,3S*)-ethyl 3-(3-(2-hydroxyethoxy)phenyl)-2-methyl-7-(methylcarbamoyl)-2,3-dihydrobenzofuran-5-carboxylate (13 mg, 0.033 mmol) in MeOH (2 mL) at room temperature was treated with a 2N NaOH aqueous solution (0.5 mL, 1 mmol) and the resulting mixture was stirred at this temperature for 2 h, then was concentrated in vacuo. The residue was dissolved in water (2 mL) and acidified with a 2N HCl aqueous solution to pH 2. The aqueous phase was extracted with EtOAc (2×5 mL) and the combined organics were dried over MgSO$_4$ and concentrated in vacuo to give a colourless gum. This gum was dissolved in DCM (2 mL) and the resulting solution was treated with HATU (12 mg, 0.033 mmol), Et$_3$N (4.5 μL, 0.033 mmol) and (1S,2S)-2-methylcyclopropanamine hydrochloride (3.5 mg, 0.033 mmol). The resulting mixture was stirred at room temperature for 2 h, then was concentrated in vacuo. Purification of the residue obtained by MDAP (method high pH) gave (2R*,3S*)-3-(3-(2-hydroxyethoxy)phenyl)-N$^7$,2-dimethyl-N$^5$-((1S,2S)-2-methylcyclopropyl)-2,3-dihydrobenzofuran-5,7-dicarboxamide (4.4 mg, 32%) as a colourless solid.

LCMS (method high pH): Retention time 0.91 min, [M+H]$^+$=425

Example 68: (S)-tert-Butyl 3-fluoro-3-(3-((2R*,3S*)-3-(3-(2-hydroxyethoxy)phenyl)-2-methyl-7-(methylcarbamoyl)-2,3-dihydrobenzofuran-5-carboxamido)propyl)piperidine-1-carboxylate

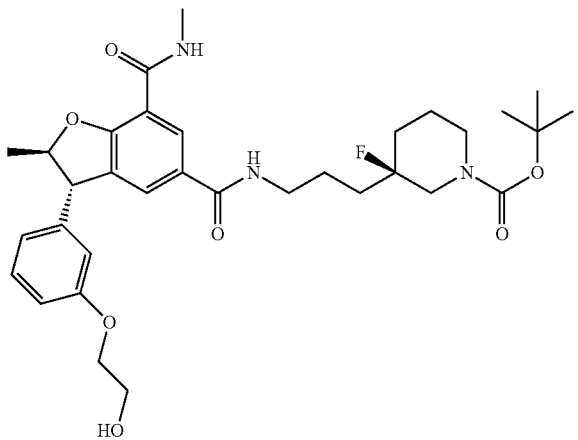 [SMILES: CNC(=O)c1cc(C(=O)NCCC[C@]2(F)CCCN(C(=O)OC(C)(C)C)C2)cc2c1O[C@H](C)[C@H]2c1cccc(OCCO)c1]

A flask was charged with (2R*,3S*)-3-(3-(2-hydroxyethoxy)phenyl)-2-methyl-7-(methylcarbamoyl)-2,3-dihydrobenzofuran-5-carboxylic acid (13 mg, 0.035 mmol), (S)-tert-butyl 3-(3-aminopropyl)-3-fluoropiperidine-1-carboxylate (12 mg, 0.046 mmol), HATU (17 mg, 0.046 mmol) then was filled with DCM (2 mL) and the resulting mixture was treated at room temperature with Et$_3$N (4.9 µL, 0.035 mmol) then was stirred at this temperature for 2 h, before being diluted with DCM, washed with water, dried using an hydrophobic frit and concentrated in vacuo to give (S)-tert-butyl 3-fluoro-3-(3-((2R*,3S*)-3-(3-(2-hydroxyethoxy)phenyl)-2-methyl-7-(methylcarbamoyl)-2,3-dihydrobenzofuran-5-carboxamido)propyl)piperidine-1-carboxylate (22 mg, 102%) as a colourless gum which was used in the next step without further purification.

LCMS (method formic): Retention time 1.10 min, [M+H]$^+$=614

Example 69: (2R*,3S*)—N$^5$-(3-((R)-3-Fluoropiperidin-3-yl)propyl)-3-(3-(2-hydroxyethoxy)phenyl)-N$^7$,2-dimethyl-2,3-dihydrobenzofuran-5,7-dicarboxamide

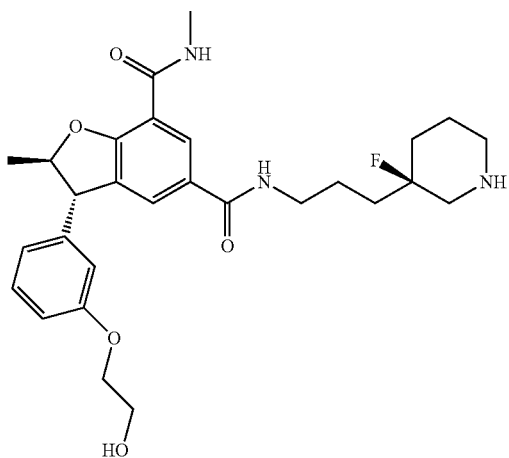 [SMILES: CNC(=O)c1cc(C(=O)NCCC[C@]2(F)CCCNC2)cc2c1O[C@H](C)[C@H]2c1cccc(OCCO)c1]

A solution of (S)-tert-butyl 3-fluoro-3-(3-((2R*3S*)-3-(3-(2-hydroxyethoxy)phenyl)-2-methyl-7-(methylcarbamoyl)-2,3-dihydrobenzofuran-5-carboxamido)propyl)piperidine-1-carboxylate (20 mg, 0.033 mmol) in DCM (2 mL) at room temperature was treated with TFA (200 µL, 2.60 mmol) and the resulting mixture was stirred for 2 h at this temperature then was concentrated in vacuo. The residue obtained was dissolved in MeOH (2 mL) and loaded onto a 5 g SCX cartridge, which was then washed with MeOH (20 mL) and then was eluted with a 2N NH$_3$ in MeOH. The ammonia fractions were concentrated in vacuo to give (2R*3S*)—N$^5$-(3-((R)-3-fluoropiperidin-3-yl)propyl)-3-(3-(2-hydroxyethoxy)phenyl)-N$^7$,2-dimethyl-2,3-dihydrobenzofuran-5,7-dicarboxamide (15 mg, 90%) as a colourless gum.

LCMS (method high pH): Retention time 0.85 min, [M+H]$^+$=514

Example 70: (R)-test-Butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate

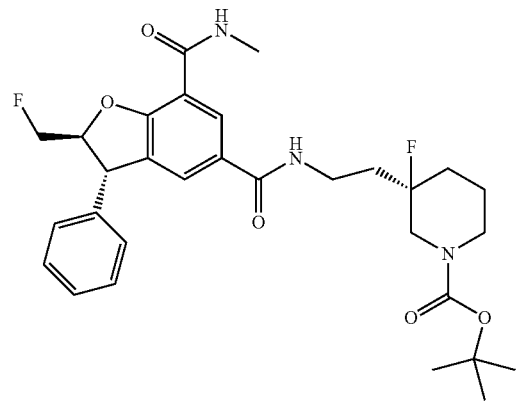 [SMILES: CNC(=O)c1cc(C(=O)NCC[C@]2(F)CCCN(C(=O)OC(C)(C)C)C2)cc2c1O[C@H](CF)[C@H]2c1ccccc1]

A solution of (2S,3S)-2-(fluoromethyl)-7-(methylcarbamoyl)-3-phenyl-2,3-dihydrobenzofuran-5-carboxylic acid (50 mg, 0.15 mmol) in DCM (5 mL) at room temperature was treated with (R)-tert-butyl 3-(2-aminoethyl)-3-fluoropiperidine-1-carboxylate (50 mg, 0.20 mmol), HATU (57.7 mg, 0.152 mmol) and Et$_3$N (0.021 mL, 0.15 mmol) and the resulting mixture was stirred at this temperature for 2 h. The mixture was then diluted with DCM, and washed successively with water, a 0.5N NaOH aqueous solution, and a 0.5N HCl aqueous solution, and then was dried using an hydrophobic frit and concentrated in vacuo to give (R)-tert-butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate (56 mg, 66%) as a colourless gum which was used in the next step without further purification.

LCMS (method formic): Retention time 1.17 min, [M+H]$^+$=558

Example 71: (2S,3S)-2-(Fluoromethyl)-N⁵-(2-((R)-3-fluoropiperidin-3-yl)ethyl)-N⁷-methyl-3-phenyl-2,3-dihydrobenzofuran-5,7-dicarboxamide

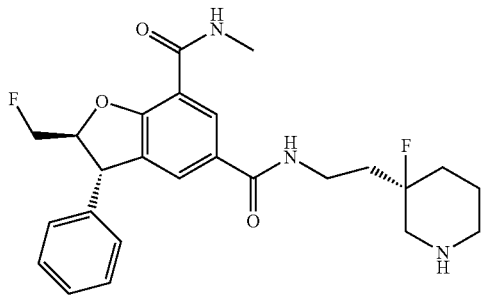 [SMILES: CNC(=O)c1cc(C(=O)NCC[C@]2(F)CCCNC2)cc2c1O[C@H](CF)[C@H]2c1ccccc1]

A solution of (R)-tert-butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate (56 mg, 0.10 mmol) in DCM (1 mL) at room temperature was treated with TFA (1.0 mL, 13 mmol) and the resulting mixture was stirred at room temperature for 2 h, then was concentrated in vacuo. Purification of the residue obtained by MDAP (method high pH) gave (2S,3S)-2-(fluoromethyl)-N⁵-(2-((R)-3-fluoropiperidin-3-yl)ethyl)-N⁷-methyl-3-phenyl-2,3-dihydrobenzofuran-5,7-dicarboxamide (35 mg, 76%) as a colourless solid.

LCMS (method formic): Retention time 0.61 min, [M+H]⁺=458

Example 72: (2S,3S)-2-(Fluoromethyl)-N⁵-(3-((R)-3-fluoropiperidin-3-yl)propyl)-N⁷-methyl-3-phenyl-2,3-dihydrobenzofuran-5,7-dicarboxamide

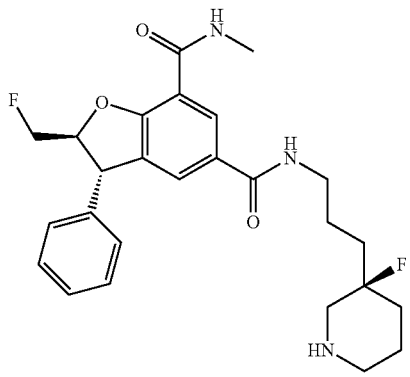 [SMILES: CNC(=O)c1cc(C(=O)NCCC[C@]2(F)CCCNC2)cc2c1O[C@H](CF)[C@H]2c1ccccc1]

A solution of (2S,3S)-2-(fluoromethyl)-7-(methylcarbamoyl)-3-phenyl-2,3-dihydrobenzofuran-5-carboxylic acid (60 mg, 0.18 mmol) in DCM (5 mL) at room temperature was treated with (S)-tert-butyl 3-(3-aminopropyl)-3-fluoropiperidine-1-carboxylate (60 mg, 0.23 mmol), HATU (69.3 mg, 0.182 mmol) and Et₃N (0.025 mL, 0.18 mmol) and the resulting mixture was stirred at this temperature for 2 h. The solution was diluted with DCM and successively washed with water, a 0.5N NaOH aqueous solution and a 0.5N HCl aqueous solution, and then was dried using an hydrophobic frit and concentrated in vacuo to give a colourless gum. This residue was dissolved in DCM (5 mL) and the resulting solution was treated with TFA (1 mL). The resulting mixture was stirred for 2 h at room temperature, then was concentrated in vacuo. Purification of the residue obtained by MDAP (method high pH) gave (2S,3S)-2-(fluoromethyl)-N⁵-(3-((R)-3-fluoropiperidin-3-yl)propyl)-N⁷-methyl-3-phenyl-2,3-dihydrobenzofuran-5,7-dicarboxamide (68 mg, 79%) as a colourless foam.

LCMS (method high pH): Retention time 0.94 min, [M+H]⁺=472

Example 73: (R)-tert-Butyl 3-fluoro-3-(2-((2R,3S)-2-methyl-7-(methylcarbamoyl)-3-phenyl-2,3-dihydrobenzofuran-5-carboxamido)ethyl)piperidine-1-carboxylate

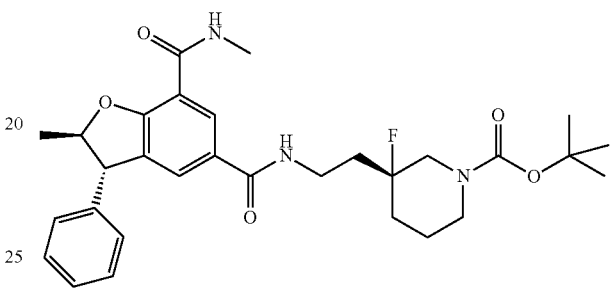

A flask was charged with (2R,3S)-2-methyl-7-(methylcarbamoyl)-3-phenyl-2,3-dihydrobenzofuran-5-carboxylic acid (80 mg, 0.26 mmol), HATU (117 mg, 0.308 mmol) and DIPEA (0.090 mL, 0.51 mmol) then was filled with DMF (2 mL) and the resulting solution was stirred at room temperature for 5 min before being treated with (R)-tert-butyl 3-(2-aminoethyl)-3-fluoropiperidine-1-carboxylate (63.3 mg, 0.257 mmol). The resulting mixture was stirred at this temperature for 1 h and then was partitioned between water and EtOAc. The layers were separated, the organic phase was washed with a 10% w/w LiCl aqueous solution, dried using a hydrophobic frit and concentrated in vacuo. Purification of the residue obtained by flash chromatography on silica gel (10 g column, gradient: 0-70% (25% EtOH: EtOAc) in DCM) gave (R)-tert-butyl 3-fluoro-3-(2-((2R,3S)-2-methyl-7-(methylcarbamoyl)-3-phenyl-2,3-dihydrobenzofuran-5-carboxamido)ethyl)piperidine-1-carboxylate (95 mg, 69%) as a white solid.

LCMS (method formic): Retention time 1.21 min, [M+H]⁺=540

Example 74: (2R,3S)—N⁵-(2-((R)-3-Fluoropiperidin-3-yl)ethyl)-N⁷,2-dimethyl-3-phenyl-2,3-dihydrobenzofuran-5,7-dicarboxamide

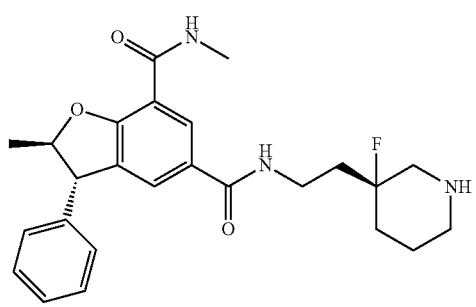 [SMILES: CNC(=O)c1cc(C(=O)NCC[C@]2(F)CCCNC2)cc2c1O[C@H](C)[C@H]2c1ccccc1]

A solution of (R)-tert-butyl 3-fluoro-3-(2-((2R,3S)-2-methyl-7-(methylcarbamoyl)-3-phenyl-2,3-dihydrobenzofuran-5-carboxamido)ethyl)piperidine-1-carboxylate (95 mg, 0.18 mmol) in DCM (2 mL) at room temperature was treated with TFA (0.014 mL, 0.18 mmol) and the resulting solution was stirred at this temperature for 18 h before being concentrated in vacuo. Purification of the residue obtained by MDAP (method high pH) gave (2R,3S)—$N^5$-(2-((R)-3-fluoropiperidin-3-yl)ethyl)-$N^7$,2-dimethyl-3-phenyl-2,3-dihydrobenzofuran-5,7-dicarboxamide (51 mg, 66%) as a white solid.

LCMS (method formic): Retention time 0.63 min, [M+H]$^+$=440

Example 75: (R)-tert-Butyl 2-(3-((2S,3S)-2-(fluoromethyl)-7-(methylcarbamoyl)-3-phenyl-2,3-dihydrobenzofuran-5-carboxamido)propyl)morpholine-4-carboxylate

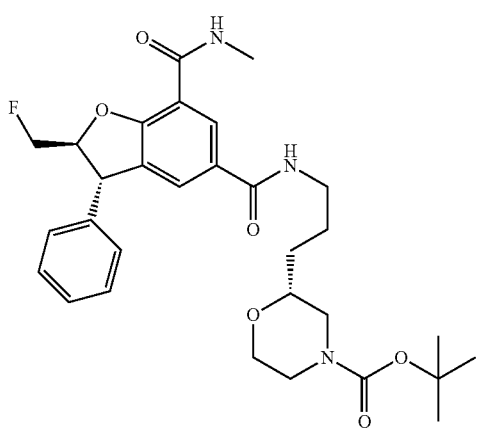 [SMILES: CNC(=O)c1cc(C(=O)NCCC[C@@H]2CN(C(=O)OC(C)(C)C)CCO2)cc2c1O[C@H](CF)[C@H]2c1ccccc1]

(2S,3S)-2-(Fluoromethyl)-7-(methylcarbamoyl)-3-phenyl-2,3-dihydrobenzofuran-5-carboxylic acid (50 mg, 0.15 mmol), HATU (69.3 mg, 0.182 mmol) and DIPEA (0.080 mL, 0.46 mmol) were dissolved in DMF (3 mL) and the resulting solution was stirred at room temperature for 10 min. (R)-Tert-butyl 2-(3-aminopropyl)morpholine-4-carboxylate (40.8 mg, 0.167 mmol) was dissolved in DMF (1 mL) and added to the reaction mixture, which was then stirred at room temperature for 2 h. (R)-tert-Butyl 2-(3-aminopropyl)morpholine-4-carboxylate (20 mg, 0.082 mmol) was dissolved in DMF (0.327 mL) and then added to the reaction mixture. The resulting solution was stirred at room temperature for 30 min then was diluted with water (10 mL). The aqueous phase was extracted with DCM (3×20 mL). The combined organics were washed twice with a 10% w/w LiCl solution, dried using a hydrophobic frit and concentrated in vacuo. Purification of the residue obtained by flash chromatography on silica gel (10 g column, gradient: 0-100% EtOAc in cyclohexane) gave (R)-tert-butyl 2-(3-((2S,3S)-2-(fluoromethyl)-7-(methylcarbamoyl)-3-phenyl-2,3-dihydrobenzofuran-5-carboxamido)propyl)morpholine-4-carboxylate (68 mg, 81%) as a yellow oil.

LCMS (method formic): Retention time 1.15 min, [M+H-Boc]$^+$=456

Example 76: (2S,3S)-2-(Fluoromethyl)-$N^7$-methyl-$N^5$-(3-((R)-morpholin-2-yl)propyl)-3-phenyl-2,3-dihydrobenzofuran-5,7-dicarboxamide

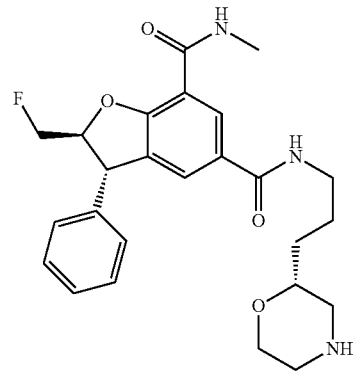 [SMILES: CNC(=O)c1cc(C(=O)NCCC[C@@H]2CNCCO2)cc2c1O[C@H](CF)[C@H]2c1ccccc1]

A solution of (R)-tert-butyl 2-(3-((2S,3S)-2-(fluoromethyl)-7-(methylcarbamoyl)-3-phenyl-2,3-dihydrobenzofuran-5-carboxamido)propyl)morpholine-4-carboxylate (68 mg, 0.12 mmol) in DCM (5 mL) at room temperature was treated with TFA (0.5 mL, 6.49 mmol) and the resulting solution was stirred at this temperature for 1 h then was treated with a saturated NaHCO$_3$ aqueous solution (10 mL). The biphasic mixture was stirred for 30 min then was diluted with water (5 mL) and extracted with DCM (3×20 mL). The combined organics were washed twice with a 10% w/w LiCl aqueous solution, dried using a hydrophobic frit and concentrated in vacuo. The residue was taken up in MeOH (3 mL) and eluted through a 500 mg NH$_2$ isolute column with MeOH (the column was prewashed with MeOH (~10 mL)). The relevant fractions were combined and concentrated in vacuo to give (2S,3S)-2-(fluoromethyl)-$N^7$-methyl-$N^5$-(3-((R)-morpholin-2-yl)propyl)-3-phenyl-2,3-dihydrobenzofuran-5,7-dicarboxamide (25 mg, 45%) as an off white gum.

LCMS (method high pH): Retention time 0.86 min, [M+H]$^+$=456

Example 77: (2R*,3S*)—$N^5$-((1R,5S,6R)-3-Oxabicyclo[3.1.0]hexan-6-yl)-3-(3-(2-hydroxyethoxy)phenyl)-$N^7$,2-dimethyl-2,3-dihydrobenzofuran-5,7-dicarboxamide

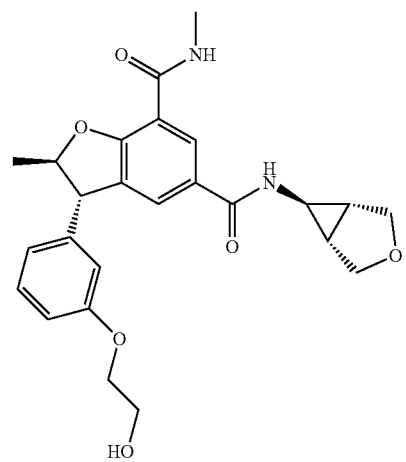 [SMILES: CNC(=O)c1cc(C(=O)N[C@H]2[C@@H]3COC[C@@H]32)cc2c1O[C@H](C)[C@H]2c1cccc(OCCO)c1]

A flask was charged with (2R*,3S*)-3-(3-(2-hydroxyethoxy)phenyl)-2-methyl-7-(methylcarbamoyl)-2,3-dihydrobenzofuran-5-carboxylic acid (67 mg, 0.090 mmol), HATU (41.2 mg, 0.108 mmol) and DIPEA (0.047 mL, 0.27 mmol) then was filled with DMF (4 mL) and the resulting mixture was stirred at room temperature for 5 min before being treated with (1R,5S,6r)-3-oxabicyclo[3.1.0]hexan-6-amine hydrochloride (12 mg, 0.090 mmol) in DMF (1 mL). The resulting mixture was stirred at room temperature for 1 h and then was diluted with water (10 mL). The aqueous phase was extracted with DCM (3×30 mL) and the combined organics were washed twice with a 10% w/w LiCl aqueous solution, dried using a hydrophobic frit and concentrated in vacuo. Purification of the residue by flash chromatography on silica gel (10 g column, gradient: 0-25% (2N $NH_3$ in MeOH) in DCM) gave (2R*,3S*)—$N^5$-((1R,5S,6r)-3-oxabicyclo[3.1.0]hexan-6-yl)-3-(3-(2-hydroxyethoxy)phenyl)-$N^7$,2-dimethyl-2,3-dihydrobenzofuran-5,7-dicarboxamide (50 mg, 61%) a white solid.

LCMS (method high pH): Retention time 0.82 min, [M+H]$^+$=453

Example 78: (R)-tert-Butyl 2-(2-((2S,3S)-2-(fluoromethyl)-7-(methylcarbamoyl)-3-phenyl-2,3-dihydrobenzofuran-5-carboxamido)ethyl)morpholine-4-carboxylate

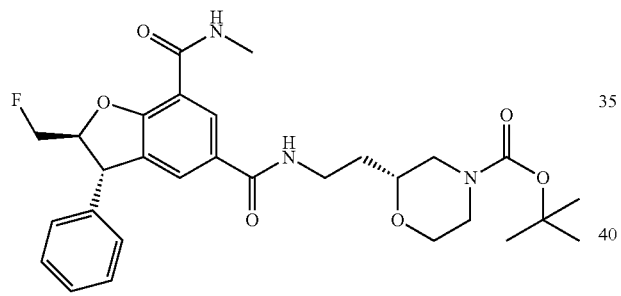

(2S,3S)-2-(Fluoromethyl)-7-(methylcarbamoyl)-3-phenyl-2,3-dihydrobenzofuran-5-carboxylic acid (55 mg, 0.17 mmol), HATU (76 mg, 0.20 mmol) and DIPEA (0.088 mL, 0.50 mmol) were dissolved in DMF (4 mL) and the resulting mixture was stirred at room temperature for 10 min before being treated with (R)-tert-butyl 2-(2-aminoethyl)morpholine-4-carboxylate (42.3 mg, 0.184 mmol) DMF (1 mL). The resulting solution was stirred at this temperature for 1 h then was diluted with water (10 mL). The aqueous phase was extracted with EtOAc (3×30 mL) and the combined organics were washed twice with a 10% w/w LiCl aqueous solution, dried via a hydrophobic frit and concentrated in vacuo. Purification of the residue by flash chromatography on silica gel (10 g column, gradient: 0-100% EtOAc in cyclohexane) gave (R)-tert-butyl 2-(2-((2S,3S)-2-(fluoromethyl)-7-(methylcarbamoyl)-3-phenyl-2,3-dihydrobenzofuran-5-carboxamido)ethyl)morpholine-4-carboxylate (21 mg, 23%) as a colourless oil.

LCMS (method formic): Retention time 1.12 min, [M+H]$^+$=542

Example 79: (2S,3S)-2-(Fluoromethyl)-$N^7$-methyl-$N^5$-(2-((R)-morpholin-2-yl)ethyl)-3-phenyl-2,3-dihydrobenzofuran-5,7-dicarboxamide

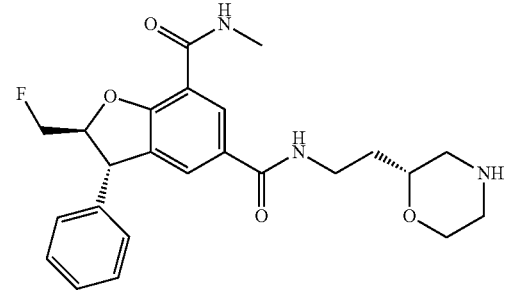 [SMILES: CNC(=O)c1cc(C(=O)NCC[C@@H]2CNCCO2)cc2c1O[C@H](CF)[C@H]2c1ccccc1]

A solution of (R)-tert-butyl 2-(2-((2S,3S)-2-(fluoromethyl)-7-(methylcarbamoyl)-3-phenyl-2,3-dihydrobenzofuran-5-carboxamido)ethyl)morpholine-4-carboxylate (21 mg, 0.039 mmol) in DCM (5 mL) at room temperature was treated with TFA (0.5 mL) and the resulting solution was stirred at this temperature for 1 h then was treated with a saturated $NaHCO_3$ aqueous solution (10 mL). The biphasic mixture was stirred 20 min at room temperature then was diluted with water and extracted with DCM (3×20 mL). The combined organics were washed twice with a 10% LiCl aqueous solution, dried via a hydrophobic frit and concentrated in vacuo. The residue was taken up in MeOH (3 mL) and eluted through a 500 mg $NH_2$ isolute column with MeOH (the column was prewashed with MeOH (~10 mL)). The relevant fractions were combined and concentrated in vacuo to give (2S,3S)-2-(fluoromethyl)-$N^7$-methyl-$N^5$-(2-((R)-morpholin-2-yl)ethyl)-3-phenyl-2,3-dihydrobenzofuran-5,7-dicarboxamide (6 mg, 35%) as an off white gum.

LCMS (method high pH): Retention time 0.84 min, [M+H]$^+$=442

Example 80: (2R,3S)—$N^5$-(2-(4,4-Difluoropiperidin-3-yl)ethyl)-$N^7$,2-dimethyl-3-phenyl-2,3-dihydrobenzofuran-5,7-dicarboxamide

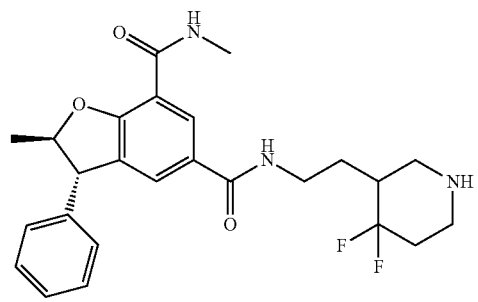 [SMILES: CNC(=O)c1cc(C(=O)NCCC2CNCCC2(F)F)cc2c1O[C@H](C)[C@H]2c1ccccc1]

A solution of tert-butyl 4,4-difluoro-3-(2-((2R,3S)-2-methyl-7-(methylcarbamoyl)-3-phenyl-2,3-dihydrobenzofuran-5-carboxamido)ethyl)piperidine-1-carboxylate (79 mg, 0.14 mmol) in DCM (5 mL) at room temperature was treated with TFA (0.5 mL, 6.49 mmol). The resulting mixture was stirred at room temperature for 1 h, then was treated with a saturated $NaHCO_3$ aqueous solution. The resulting mixture was stirred for 30 min at room temperature then was diluted with water and extracted with DCM. The organics were washed with a 10% w/w LiCl aqueous solution, dried via a hydrophobic frit and concentrated in vacuo. The residue was taken up in MeOH (3 mL) and eluted through NH$_2$ isolute column (500 mg). The relevant fractions were combined and concentrated in vacuo to give (2R,3S)—N$^5$-(2-(4,4-difluoropiperidin-3-yl)ethyl)-N$^7$,2-dimethyl-3-phenyl-2,3-dihydrobenzofuran-5,7-dicarboxamide (31 mg, 48%) as an off white gum.

LCMS (method high pH): Retention time 1.01 min, [M+H]$^+$=458.

Example 81: tert-Butyl 4,4-difluoro-3-(2-((2R,3S)-2-methyl-7-(methylcarbamoyl)-3-phenyl-2,3-dihydrobenzofuran-5-carboxamido)ethyl)piperidine-1-carboxylate

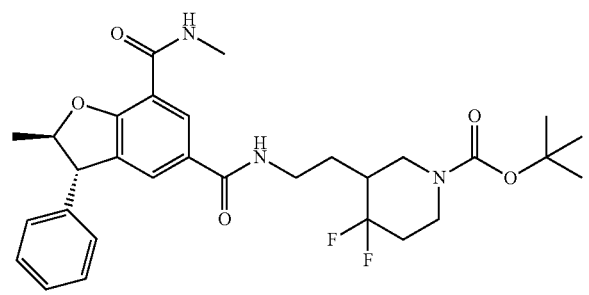 [SMILES: CNC(=O)c1cc(C(=O)NCCC2CN(C(=O)OC(C)(C)C)CCC2(F)F)cc2c1O[C@H](C)[C@H]2c1ccccc1]

(2R,3S)-2-Methyl-7-(methylcarbamoyl)-3-phenyl-2,3-dihydrobenzofuran-5-carboxylic acid (50 mg, 0.16 mmol), HATU (73.3 mg, 0.193 mmol) and DIPEA (0.084 mL, 0.48 mmol) were dissolved in DMF (3 mL) with stirring at room temperature for 5 min. Tert-butyl 3-(2-aminoethyl)-4,4-difluoropiperidine-1-carboxylate (59.4 mg, 0.225 mmol) was dissolved in DMF (1 mL) and added to the reaction mixture, which was then stirred at room temperature for 2 h. Tert-butyl 3-(2-aminoethyl)-4,4-difluoropiperidine-1-carboxylate (20 mg, 0.076 mmol) was added. The reaction mixture was stirred at room temperature for 1 h. The reaction mixture was diluted with water and extracted with DCM. The organics were washed with a 10% w/w LiCl aqueous solution The organic layers were dried via a hydrophobic frit and concentrated in vacuo. The residue was purified using silica gel column chromatography (10 g SNAP Si column) eluting with a gradient of 0-25% 2N NH$_3$ in 20:80 MeOH:DCM in DCM to give tert-butyl 4,4-difluoro-3-(2-((2R,3S)-2-methyl-7-(methylcarbamoyl)-3-phenyl-2,3-dihydrobenzofuran-5-carboxamido)ethyl)piperidine-1-carboxylate (79 mg, 88%), as a yellow oil.

LCMS (method high pH): Retention time 1.28 min, [M+H]$^+$=558

Example 82: (2R,3S)—N$^5$-(2-(3,3-Difluoropiperidin-4-yl)ethyl)-N$^7$,2-dimethyl-3-phenyl-2,3-dihydrobenzofuran-5,7-dicarboxamide

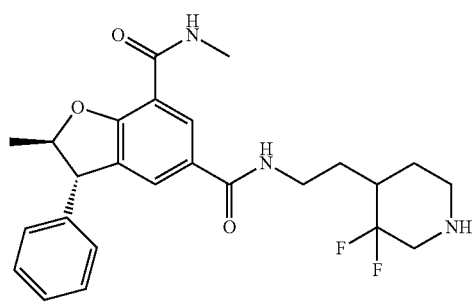 [SMILES: CNC(=O)c1cc(C(=O)NCCC2CCNCC2(F)F)cc2c1O[C@H](C)[C@H]2c1ccccc1]

A solution of tert-butyl 3,3-difluoro-4-(2-((2R,3S)-2-methyl-7-(methylcarbamoyl)-3-phenyl-2,3-dihydrobenzofuran-5-carboxamido)ethyl)piperidine-1-carboxylate (75 mg, 0.13 mmol) in DCM (5 mL) at room temperature was treated with TFA (0.5 mL, 6.49 mmol). The resulting mixture was stirred at room temperature for 1 h then was treated with a saturated NaHCO$_3$ aqueous solution. The resulting mixture was stirred for 30 min then was diluted with water and extracted with DCM. The organics were washed with a 10% w/w LiCl aqueous solution, dried via a hydrophobic frit and concentrated in vacuo. The residue was taken up in MeOH and eluted through 500 mg NH$_2$ isolute column. The relevant fractions were combined and concentrated in vacuo to give (2R,3S)—N$^5$-(2-(3,3-difluoropiperidin-4-yl)ethyl)-N$^7$,2-dimethyl-3-phenyl-2,3-dihydrobenzofuran-5,7-dicarboxamide (32 mg, 52%) as an off white gum.

LCMS (method high pH): Retention time 0.99 min, [M+H]$^+$=458

Example 83: tert-Butyl 3,3-difluoro-4-(2-((2R,3S)-2-methyl-7-(methylcarbamoyl)-3-phenyl-2,3-dihydrobenzofuran-5-carboxamido)ethyl)piperidine-1-carboxylate

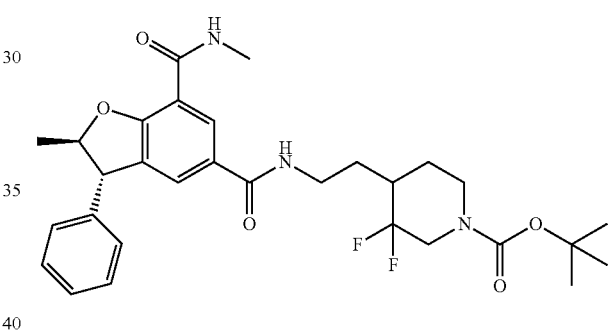

(2R,3S)-2-Methyl-7-(methylcarbamoyl)-3-phenyl-2,3-dihydrobenzofuran-5-carboxylic acid (50 mg, 0.16 mmol), HATU (73.3 mg, 0.193 mmol) and DIPEA (0.084 mL, 0.48 mmol) were dissolved in DMF (3 mL) with stirring at room temperature for 5 min. Tert-butyl 4-(2-aminoethyl)-3,3-difluoropiperidine-1-carboxylate (59.4 mg, 0.225 mmol) was dissolved in DMF (1 mL) and added to the reaction mixture, which was then stirred at room temperature for 2 h. Tert-butyl 4-(2-aminoethyl)-3,3-difluoropiperidine-1-carboxylate (30 mg, 0.11 mmol) was added and the reaction mixture was stirred at room temperature for 1 h, then was diluted with water and extracted with DCM. The organics were washed with a 10% w/w LiCl aqueous solution then were dried via a hydrophobic frit and concentrated in vacuo. The residue was purified using silica gel column chromatography (10 g SNAP column) eluting with a gradient of 0-25% 2N NH$_3$ in 20:80 MeOH:DCM in DCM to give tert-butyl 3,3-difluoro-4-(2-((2R,3S)-2-methyl-7-(methylcarbamoyl)-3-phenyl-2,3-dihydrobenzofuran-5-carboxamido)ethyl)piperidine-1-carboxylate (75 mg, 84%) as a yellow oil.

LCMS (method high pH): Retention time 1.27 min, [M+H]$^+$=558

Example 84: (2S*,3S*)-2-(Fluoromethyl)-N⁵-((1R,4S)-4-hydroxycyclohexyl)-N⁷-methyl-3-phenyl-2,3-dihydrobenzofuran-5,7-dicarboxamide

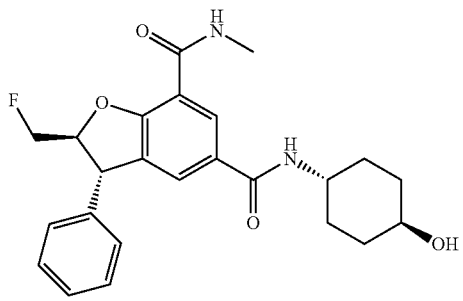 [SMILES: CNC(=O)c1cc(C(=O)N[C@H]2CC[C@H](O)CC2)cc2c1O[C@H](CF)[C@H]2c1ccccc1]

(2S*,3S*)-2-(Fluoromethyl)-7-(methylcarbamoyl)-3-phenyl-2,3-dihydrobenzofuran-5-carboxylic acid (50 mg, 0.15 mmol), HATU (69.3 mg, 0.182 mmol) and DIPEA (0.080 mL, 0.45 mmol) were stirred in DMF (2 mL) at room temperature for 5 min, trans amino cyclohexanol (21.0 mg, 0.182 mmol) was added and the resulting mixture was stirred at room temperature for 30 min. The reaction was then diluted with water and extracted with EtOAc. The organic phase was washed with a 10% w/w LiCl aqueous solution, dried using a hydrophobic frit and concentrated in vacuo to give a white solid. This solid was purified using silica gel column chromatography (SNAP10 Si column) eluting with a gradient of 0-100% (25% EtOH:EtOAc):DCM to give (2S*,3S*)-2-(fluoromethyl)-N⁵-((1S*,4S*)-4-hydroxycyclohexyl)-N⁷-methyl-3-phenyl-2,3-dihydrobenzofuran-5,7-dicarboxamide (51 mg, 79%) as a white solid.

LCMS (method formic): Retention time 0.86 min, [M+H]⁺=427

Example 85: (2R,3S)—N⁵-((1R,5S,6R)-3-Oxabicyclo[3.1.0]hexan-6-yl)-3-(3-(2-hydroxyethoxy)phenyl)-N⁷,2-dimethyl-2,3-dihydrobenzofuran-5,7-dicarboxamide

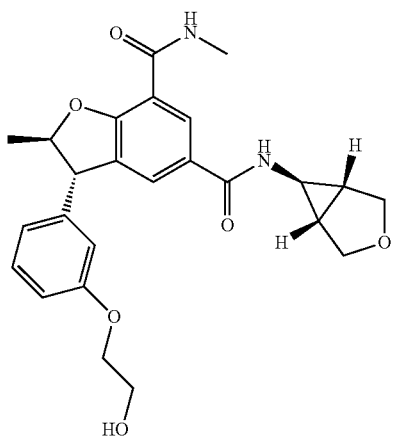 [SMILES: CNC(=O)c1cc(C(=O)N[C@H]2[C@@H]3COC[C@@H]32)cc2c1O[C@H](C)[C@H]2c1cccc(OCCO)c1]

(2R*,3S*)-3-(3-(2-Hydroxyethoxy)phenyl)-2-methyl-7-(methylcarbamoyl)-2,3-dihydrobenzofuran-5-carboxylic acid (67 mg, 0.090 mmol), HATU (41.2 mg, 0.108 mmol) and DIPEA (0.047 mL, 0.27 mmol) were dissolved in DMF (4 mL) with stirring at room temperature for 5 min. (1R,5S,6r)-3-Oxabicyclo[3.1.0]hexan-6-amine hydrochloride (12 mg, 0.090 mmol) was dissolved in DMF (1 mL) and added to the reaction mixture, which was then stirred at room temperature for 1 h. The reaction mixture was then diluted with water and extracted with DCM. The organics were washed with a 10% w/w LiCl aqueous solution, dried via a hydrophobic frit and concentrated in vacuo. The residue was purified using silica gel column chromatography (10 g SNAP Si column) eluting with a gradient of 0-25% 2N NH₃ in 20:80 MeOH:DCM.to give (2R*,3S*)—N⁵-((1R,5S,6r)-3-oxabicyclo[3.1.0]hexan-6-yl)-3-(3-(2-hydroxyethoxy)phenyl)-N⁷,2-dimethyl-2,3-dihydrobenzofuran-5,7-dicarboxamide (50 mg, 61%). (2R*,3S*)—N⁵-((1R,5S,6r)-3-oxabicyclo[3.1.0]hexan-6-yl)-3-(3-(2-hydroxyethoxy)phenyl)-N⁷,2-dimethyl-2,3-dihydrobenzofuran-5,7-dicarboxamide (47 mg, 0.10 mmol) was purified by chiral chromatography using a 4.6 mmid×25 cm Chiralcel OD-H column and eluting with Heptane:EtOH 70:30 to give (2R,3S)—N⁵-((1R,5S,6r)-3-oxabicyclo[3.1.0]hexan-6-yl)-3-(3-(2-hydroxyethoxy)phenyl)-N⁷,2-dimethyl-2,3-dihydrobenzofuran-5,7-dicarboxamide (8.5 mg, 18%) as a white solid.

LCMS (method high pH): Retention time 0.82 min, [M+H]⁺=453

Example 86: (2S*,3S*)-2-(Fluoromethyl)-N⁵-((1R,3S)-3-hydroxycyclobutyl)-N⁷-methyl-3-phenyl-2,3-dihydrobenzofuran-5,7-dicarboxamide

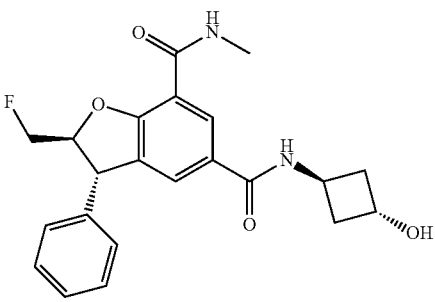 [SMILES: CNC(=O)c1cc(C(=O)N[C@H]2C[C@H](O)C2)cc2c1O[C@H](CF)[C@H]2c1ccccc1]

(2S*,3S*)-2-(Fluoromethyl)-7-(methylcarbamoyl)-3-phenyl-2,3-dihydrobenzofuran-5-carboxylic acid (50 mg, 0.15 mmol), HATU (69.3 mg, 0.182 mmol) and DIPEA (0.080 mL, 0.45 mmol) were stirred in DMF (2 mL) at room temperature for 5 min before being treated with (1r,3r)-3-aminocyclobutanol hydrochloride (22.5 mg, 0.182 mmol). The resulting mixture was stirred at room temperature for 30 min then was diluted with water and extracted with EtOAc. The organic phase was washed with a 10% w/w LiCl aqueous solution, dried using a hydrophobic frit and concentrated in vacuo to give a white solid. This solid was purified using silica gel column chromatography (SNAP10 Si column) eluting with a gradient of 0-100% (25% EtOH:EtOAc):DCM to give (2S,3S)-2-(fluoromethyl)-N⁵-((1r,3S)-3-hydroxycyclobutyl)-N⁷-methyl-3-phenyl-2,3-dihydrobenzofuran-5,7-dicarboxamide (52 mg, 86%) as a white solid.

LCMS (method formic): Retention time 0.82 min, [M+H]⁺=399

Example 87: (2S,3S)-2-(Fluoromethyl)-N⁵-((1R,2R)-2-(hydroxymethyl)cyclopropyl)-N⁷-methyl-3-phenyl-2,3-dihydrobenzofuran-5,7-dicarboxamide

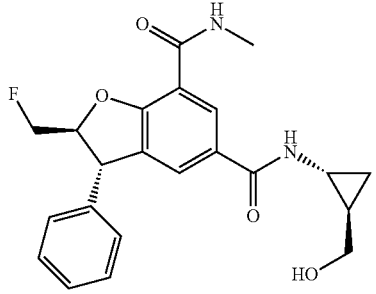 [SMILES: CNC(=O)c1cc(C(=O)N[C@@H]2C[C@H]2CO)cc2c1O[C@H](CF)[C@H]2c1ccccc1]

(2S,3S)-2-(Fluoromethyl)-7-(methylcarbamoyl)-3-phenyl-2,3-dihydrobenzofuran-5-carboxylic acid (50 mg, 0.15 mmol), HATU (69.3 mg, 0.182 mmol) and DIPEA (0.080 mL, 0.45 mmol) were dissolved in DMF (4 mL) with stirring at room temperature for 5 min. ((1R,2R)-2-Aminocyclopropyl)methanol hydrochloride (22.5 mg, 0.182 mmol) was added and the mixture was stirred at room temperature for 1.5 h then was diluted with water and extracted with DCM. The organics were washed with a 10% w/w LiCl aqueous solution, were dried via a hydrophobic frit and concentrated in vacuo. The residue was purified using silica gel column chromatography (10 g SNAP Si column) eluting with a gradient of 0-100% EtOAc in cyclohexane followed by 0-25% 2N NH₃ in 20:80 MeOH:DCM in DCM to give (2S,3S)-2-(fluoromethyl)-N⁵-((1R,2R)-2-(hydroxymethyl)cyclopropyl)-N⁷-methyl-3-phenyl-2,3-dihydrobenzofuran-5,7-dicarboxamide (33 mg 55%) as an off white solid.

LCMS (method high pH): Retention time 0.85 min, [M+H]⁺=399

Example 88: (2S,3S)—N⁵-((1R,5S,6S)-3-azabicyclo[3.1.0]hexan-6-yl)-2-(fluoromethyl)-N⁷-methyl-3-phenyl-2,3-dihydrobenzofuran-5,7-dicarboxamide

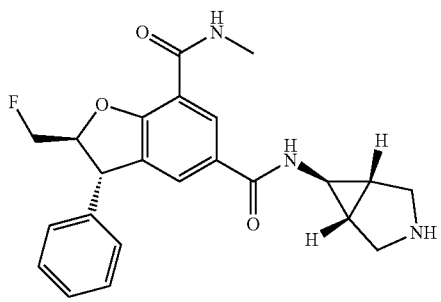 [SMILES: CNC(=O)c1cc(C(=O)N[C@H]2[C@@H]3CNC[C@@H]32)cc2c1O[C@H](CF)[C@H]2c1ccccc1]

A solution of (1R,5S,6S)-tert-butyl 6-((2S,3S)-2-(fluoromethyl)-7-(methylcarbamoyl)-3-phenyl-2,3-dihydrobenzofuran-5-carboxamido)-3-azabicyclo[3.1.0]hexane-3-carboxylate (140 mg, 0.275 mmol) in DCM (5 mL) at room temperature was treated with TFA (0.5 mL) and the resulting mixture was stirred at this temperature for 1 h then was treated with a saturated NaHCO₃ aqueous solution. The mixture was stirred at room temperature for 20 min then was diluted with water and extracted with DCM. The organics were washed with a 10% w/w LiCl aqueous solution, dried via a hydrophobic frit and concentrated in vacuo. The residue was taken up in MeOH and eluted through 500 mg NH₂ isolute column with MeOH. The relevant fractions were combined and concentrated in vacuo. The residue was purified by MDAP (high pH method) to give (2S,3S)—N⁵-((1R,5S,6s)-3-azabicyclo[3.1.0]hexan-6-yl)-2-(fluoromethyl)-N⁷-methyl-3-phenyl-2,3-dihydrobenzofuran-5,7-dicarboxamide (53 mg, 47%) as a white solid.

LCMS (method high pH): Retention time 0.84 min, [M+H]⁺=410

Example 89: (1R,5S,6S)-tert-butyl 6-((2S,3S)-2-(fluoromethyl)-7-(methylcarbamoyl)-3-phenyl-2,3-dihydrobenzofuran-5-carboxamido)-3-azabicyclo[3.1.0]hexane-3-carboxylate

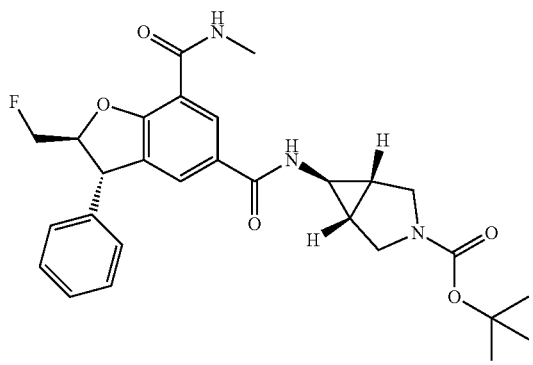 [SMILES: CNC(=O)c1cc(C(=O)N[C@H]2[C@@H]3CN(C(=O)OC(C)(C)C)C[C@@H]32)cc2c1O[C@H](CF)[C@H]2c1ccccc1]

(2S,3S)-2-(Fluoromethyl)-7-(methylcarbamoyl)-3-phenyl-2,3-dihydrobenzofuran-5-carboxylic acid (100 mg, 0.304 mmol), HATU (139 mg, 0.364 mmol) and DIPEA (0.159 mL, 0.911 mmol) were dissolved in DMF (4 mL) with stirring at room temperature for 5 min. (1R,5S,6s)-Tert-butyl 6-amino-3-azabicyclo[3.1.0]hexane-3-carboxylate (72.2 mg, 0.364 mmol) was dissolved in DMF (1 mL) and added to the reaction mixture, which was then stirred at room temperature for 1 h before being diluted with water and extracted with DCM. The organics were washed with a 10% w/w LiCl aqueous solution, dried via a hydrophobic frit and concentrated in vacuo. The residue was purified using silica gel column chromatography (25 g SNAP Si column) eluting with a gradient of 0-25% 2N NH₃ in 20:80 MeOH:DCM in DCM to give (1R,5S,6s)-tert-butyl 6-((2S,3S)-2-(fluoromethyl)-7-(methylcarbamoyl)-3-phenyl-2,3-dihydrobenzofuran-5-carboxamido)-3-azabicyclo[3.1.0]hexane-3-carboxylate (140 mg, 90%) as a yellow oil.

LCMS (method high pH): Retention time 1.13 min, [M+H]⁺=510

Example 90: (2S,3S)-2-(Fluoromethyl)-N⁷-methyl-3-phenyl-N⁵-(tetrahydrofuran-3-yl)-2,3-dihydrobenzofuran-5,7-dicarboxamide

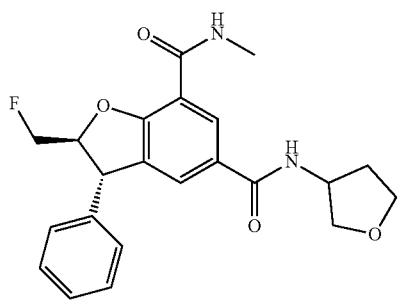 [SMILES: CNC(=O)c1cc(C(=O)NC2CCOC2)cc2c1O[C@H](CF)[C@H]2c1ccccc1]

(2S,3S)-2-(Fluoromethyl)-7-(methylcarbamoyl)-3-phenyl-2,3-dihydrobenzofuran-5-carboxylic acid (50 mg, 0.15 mmol), HATU (69.3 mg, 0.182 mmol) and DIPEA (0.080 mL, 0.45 mmol) were dissolved in DMF (4 mL) with stirring at room temperature for 5 min. Tetrahydrofuran-3-amine (17.2 mg, 0.197 mmol) was dissolved in DMF (1 mL) and added to the reaction mixture, which was then stirred at room temperature for 1 h before being diluted with water and extracted with DCM. The organics were washed with a 10% w/w LiCl aqueous solution, dried via a hydrophobic frit and concentrated in vacuo. The residue was purified using silica gel column chromatography (10 g SNAP Si column) eluting with a gradient of 0-25% 2N NH$_3$ in 20:80 MeOH:DCM in DCM to give crude material. The crude was purified by MDAP (method high pH) to give (2S,3S)-2-(fluoromethyl)-N$^7$-methyl-3-phenyl-N$^5$-(tetrahydrofuran-3-yl)-2,3-dihydrobenzofuran-5,7-dicarboxamide (30 mg, 50%) as a white solid.

LCMS (method high pH): Retention time 0.90 min, [M+H]$^+$=399

Example 91: (2S,3S)-2-(Fluoromethyl)-N$^5$-(2-hydroxyethyl)-N$^7$-methyl-3-phenyl-2,3-dihydrobenzofuran-5,7-dicarboxamide

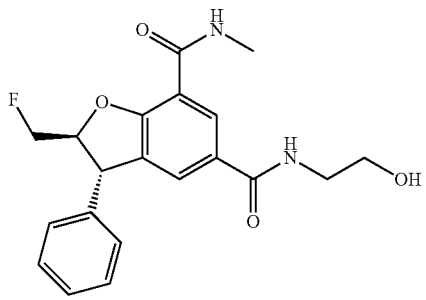 [SMILES: CNC(=O)c1cc(C(=O)NCCO)cc2c1O[C@H](CF)[C@H]2c1ccccc1]

(2S,3S)-2-(Fluoromethyl)-7-(methylcarbamoyl)-3-phenyl-2,3-dihydrobenzofuran-5-carboxylic acid (43 mg, 0.13 mmol), HATU (59.6 mg, 0.157 mmol) and DIPEA (0.068 mL, 0.39 mmol) were dissolved in DMF (4 mL) with stirring at room temperature for 5 min. 2-Aminoethanol (9.46 µL, 0.157 mmol) was added and the reaction mixture was stirred at room temperature for 2 h before being diluted with water and extracted with DCM. The organics were washed with a 10% w/w LiCl aqueous solution, dried via a hydrophobic frit and concentrated in vacuo. The residue was purified using silica gel column chromatography (10 g SNAP Si column) eluting with a gradient of 0-25% 2N NH$_3$ in 20:80 MeOH:DCM in DCM to give crude material. The crude was purified by MDAP (method high pH) to give (2S,3S)-2-(fluoromethyl)-N$^5$-(2-hydroxyethyl)-N$^7$-methyl-3-phenyl-2,3-dihydrobenzofuran-5,7-dicarboxamide (23 mg, 47%) as a white solid.

LCMS (method high pH): Retention time 0.81 min, [M+H]$^+$=373

Example 92: (2S*,3S*)—N$^5$-((1R,5S,6S)-3-Acetyl-3-azabicyclo[3.1.0]hexan-6-yl)-2-(fluoromethyl)-N$^7$-methyl-3-phenyl-2,3-dihydrobenzofuran-5,7-dicarboxamide

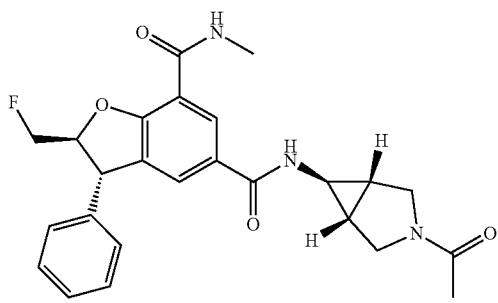 [SMILES: CNC(=O)c1cc(C(=O)N[C@H]2[C@@H]3CN(C(C)=O)C[C@@H]32)cc2c1O[C@H](CF)[C@H]2c1ccccc1]

(2S,3S*)—N$^5$-((1R,5S,6S)-3-Azabicyclo[3.1.0]hexan-6-yl)-2-(fluoromethyl)-N$^7$-methyl-3-phenyl-2,3-dihydrobenzofuran-5,7-dicarboxamide (35 mg, 0.085 mmol) was dissolved in acetic anhydride (1.00 mL, 10.6 mmol) and the reaction mixture was stirred at room temperature under nitrogen for 1.5 h then was concentrated in vacuo. The residue was co-evaporated in toluene (4 mL) then was purified using silica gel column chromatography (10 g SNAP Si column) eluting with a gradient of 0-25% 2N NH$_3$ in 20:80 MeOH:DCM in DCM to give (2S*,3S*)—N$^5$-((1R,5S,6s)-3-acetyl-3-aza bicyclo[3.1.0]hexan-6-yl)-2-(fluoromethyl)-N$^7$-methyl-3-phenyl-2,3-dihydrobenzofuran-5,7-dicarboxamide (19 mg, 49%) as a white solid.

LCMS (method high pH): Retention time 0.85 min, [M+H]$^+$=452

Example 93: (2R,3S)-3-(3-(2-Hydroxyethoxy)phenyl)-N$^7$,2-dimethyl-N$^5$-(2-(pyridin-3-yl)ethyl)-2,3-dihydrobenzofuran-5,7-dicarboxamide

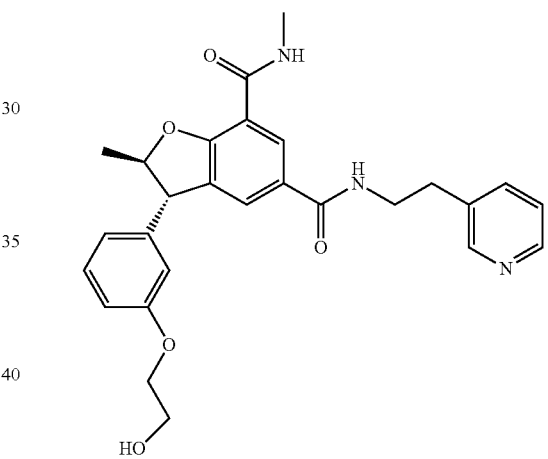

(2R,3S)-3-(3-(2-Hydroxyethoxy)phenyl)-2-methyl-7-(methylcarbamoyl)-2,3-dihydrobenzofuran-5-carboxylic acid (50 mg, 0.13 mmol), HATU (61.4 mg, 0.162 mmol) and DIPEA (0.071 mL, 0.40 mmol) were dissolved in DMF (4 mL) with stirring at room temperature for 5 min. 2-(Pyridin-3-yl)ethanamine (19.7 mg, 0.162 mmol) was dissolved in DMF (1 mL) and added to the reaction mixture, which was then stirred at room temperature for 2 h before being diluted with water and extracted with DCM. The organics were washed with a 10% w/w LiCl aqueous solution, dried via a hydrophobic frit and concentrated in vacuo. The residue was purified using silica gel column chromatography (10 g SNAP Si column) eluting with a gradient of 0-25% 2N NH$_3$ in 20:80 MeOH:DCM in DCM to give (2R,3S)-3-(3-(2-hydroxyethoxy)phenyl)-N$^7$,2-dimethyl-N$^5$-(2-(pyridin-3-yl)ethyl)-2,3-dihydrobenzofuran-5,7-dicarboxamide (33 mg, 51%) as an off white gum.

LCMS (method high pH): Retention time 0.83 min, [M+H]$^+$=476

Example 94: (2R*,3S*)—N⁵-((1R,5S,6S)-3-Acetyl-3-azabicyclo[3.1.0]hexan-6-yl)-3-(3-(2-hydroxyethoxy)phenyl)-N⁷,2-dimethyl-2,3-dihydrobenzofuran-5,7-dicarboxamide

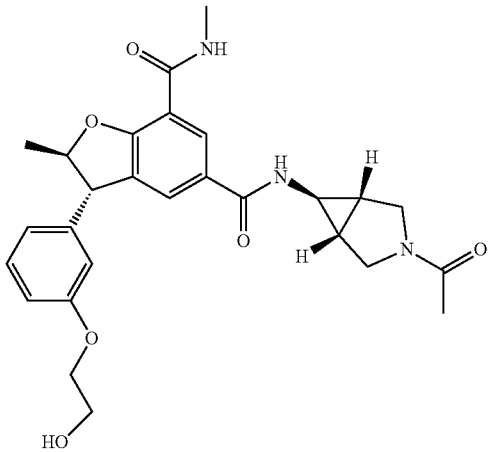 [SMILES: CNC(=O)c1cc(C(=O)N[C@H]2[C@@H]3CN(C(C)=O)C[C@@H]32)cc2c1O[C@H](C)[C@H]2c1cccc(OCCO)c1]

(2R*,3S*)—N⁵-((1R,5S,6S)-3-azabicyclo[3.1.0]hexan-6-yl)-3-(3-(2-hydroxyethoxy)phenyl)-N⁷,2-dimethyl-2,3-dihydrobenzofuran-5,7-dicarboxamide (32 mg, 0.071 mmol) was dissolved in acetic anhydride (1.00 mL, 10.6 mmol) and the reaction mixture was stirred at room temperature under nitrogen for 1 h, and then was concentrated in vacuo. The residue was co-evaporated with toluene then was purified using silica gel column chromatography (10 g SNAP Si column) eluting with a gradient of 0-25% 2N NH₃ in 20:80 MeOH:DCM in DCM to give (2R*,3S*)—N⁵-((1R,5S,6s)-3-acetyl-3-azabicyclo[3.1.0]hexan-6-yl)-3-(3-(2-hydroxyethoxy)phenyl)-N',2-dimethyl-2,3-dihydrobenzofuran-5,7-dicarboxamide (6 mg, 17%) as a white solid.

LCMS (method high pH): Retention time 0.78 min, [M+H]⁺=494

Example 95: (2R*,3S*)—N⁵-((1R,5S,6S)-3-azabicyclo[3.1.0]hexan-6-yl)-3-(3-(2-hydroxyethoxy)phenyl)-N⁷,2-dimethyl-2,3-dihydrobenzofuran-5,7-dicarboxamide

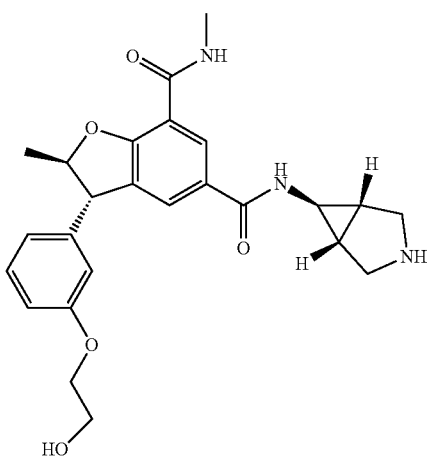 [SMILES: CNC(=O)c1cc(C(=O)N[C@H]2[C@@H]3CNC[C@@H]32)cc2c1O[C@H](C)[C@H]2c1cccc(OCCO)c1]

A solution of (1R,5S,6S)-tert-butyl 6-((2R*,3S*)-3-(3-(2-hydroxyethoxy)phenyl)-2-methyl-7-(methylcarbamoyl)-2,3-dihydrobenzofuran-5-carboxamido)-3-azabicyclo[3.1.0]hexane-3-carboxylate (60 mg, 0.109 mmol) in DCM (5 mL) at room temperature was treated with TFA (0.50 mL, 6.5 mmol) and the resulting mixture was stirred at this temperature for 1 h then was treated with a saturated NaHCO₃ aqueous solution. The mixture was stirred for 20 min then was diluted with water and extracted with DCM. The organics were dried using a hydrophobic frit and concentrated in vacuo. The residue was purified by MDAP (method high pH) to give (2R*,3S*)—N⁵-((1R,5S,6s)-3-azabicyclo[3.1.0]hexan-6-yl)-3-(3-(2-hydroxyethoxy)phenyl)-N⁷,2-dimethyl-2,3-dihydrobenzofuran-5,7-dicarboxamide (32 mg, 65%) as a white solid.

LCMS (method high pH): Retention time 0.75 min, [M+H]⁺=452

Example 96: (1R,5S,6S)-tert-Butyl 6-((2R*,3S*)-3-(3-(2-hydroxyethoxy)phenyl)-2-methyl-7-(methylcarbamoyl)-2,3-dihydrobenzofuran-5-carboxamido)-3-azabicyclo[3.1.0]hexane-3-carboxylate

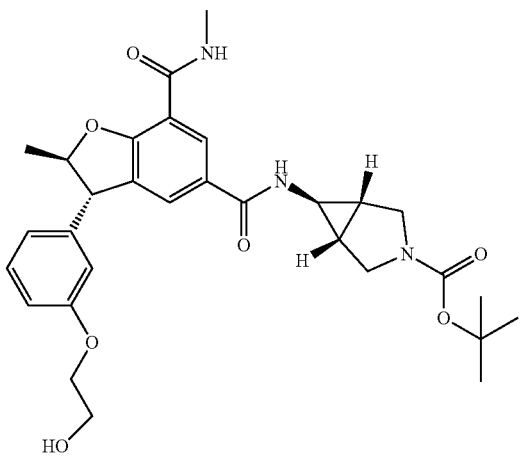 [SMILES: CNC(=O)c1cc(C(=O)N[C@H]2[C@@H]3CN(C(=O)OC(C)(C)C)C[C@@H]32)cc2c1O[C@H](C)[C@H]2c1cccc(OCCO)c1]

(2R*,3S*)-3-(3-(2-Hydroxyethoxy)phenyl)-2-methyl-7-(methylcarbamoyl)-2,3-dihydrobenzofuran-5-carboxylic acid (50 mg, 0.13 mmol), HATU (61.4 mg, 0.162 mmol) and DIPEA (0.071 mL, 0.40 mmol) were dissolved in DMF (4 mL) with stirring at room temperature for 5 min. (1R,5S,6s)-tert-butyl 6-amino-3-azabicyclo[3.1.0]hexane-3-carboxylate (32.0 mg, 0.162 mmol) was dissolved in DMF (1 mL) and added to the reaction mixture, which was then stirred at room temperature for 2 h, and then was diluted with water and extracted with DCM. The organics were washed with a 10% w/w LiCl aqueous solution, dried via a hydrophobic frit and concentrated in vacuo. The residue obtained was purified using silica gel column chromatography (10 g SNAP Si column) eluting with a gradient of 0-25% 2N NH₃ in 20:80 MeOH:DCM in DCM to give (1R,5S,6s)-tert-butyl 6-((2R*,3S*)-3-(3-(2-hydroxyethoxy)phenyl)-2-methyl-7-(methylcarbamoyl)-2,3-dihydrobenzofuran-5-carboxamido)-3-azabicyclo[3.1.0]hexane-3-carboxylate (60 mg, 81%) as a orange/yellow oil.

LCMS (method high pH): Retention time 1.02 min, [M+H]⁺=552

Example 97: (R)-tert-Butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate

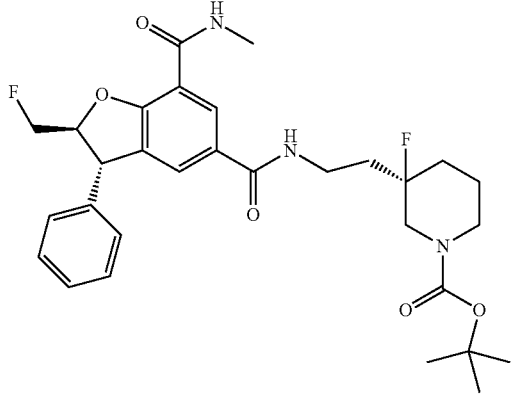 [SMILES: CNC(=O)c1cc(C(=O)NCC[C@]2(F)CCCN(C(=O)OC(C)(C)C)C2)cc2c1O[C@H](CF)[C@H]2c1ccccc1]

A solution of (2S,3S)-2-(fluoromethyl)-7-(methylcarbamoyl)-3-phenyl-2,3-dihydrobenzofuran-5-carboxylic acid (50 mg, 0.15 mmol) in DCM (5 mL) at room temperature was treated with (R)-tert-butyl 3-(2-aminoethyl)-3-fluoropiperidine-1-carboxylate (50 mg, 0.20 mmol), HATU (57.7 mg, 0.152 mmol) and Et₃N (0.021 mL, 0.15 mmol) and the resulting mixture was stirred at this temperature for 2 h then was washed successively with water, a 0.5N NaOH aqueous solution, and a 0.5N HCl aqueous solution, and then was dried and evaporated in vacuo to give (R)-tert-butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate (56 mg, 66%) as a colourless gum which was used in the next step without further purification LCMS (method formic): Retention time 1.18 min, [M+H]⁺=558

Example 98: (2S,3S)-2-(Fluoromethyl)-N⁵-(2-((R)-3-fluoropiperidin-3-yl)ethyl)-N⁷-methyl-3-phenyl-2,3-dihydrobenzofuran-5,7-dicarboxamide

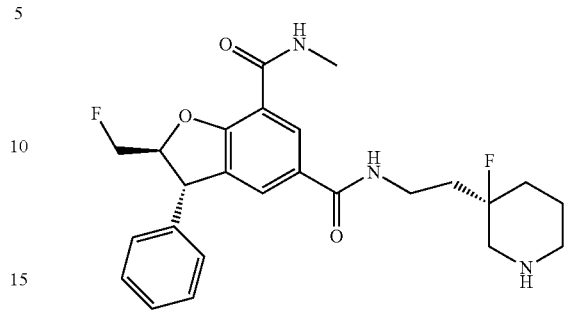

A solution of (R)-tert-butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate (56 mg, 0.10 mmol) in DCM (1 mL) at room temperature was treated with TFA (1.0 mL, 13 mmol) and the mixture was stirred at this temperature for 2 h, then was concentrated in vacuo. The residue was purified by MDAP (method high pH) to give (2S,3S)-2-(fluoromethyl)-N⁵-(2-((R)-3-fluoropiperidin-3-yl)ethyl)-N⁷-methyl-3-phenyl-2,3-dihydrobenzofuran-5,7-dicarboxamide (35 mg, 76%) as a colourless solid LCMS (method formic): Retention time 0.61 min, [M+H]⁺=458

Examples 99-108

The following examples have been either the least active of the two enantiomers obtained following chiral purification of a racemic mixture, or have been synthesised from a chiral intermediate of the stereochemistry shown below:

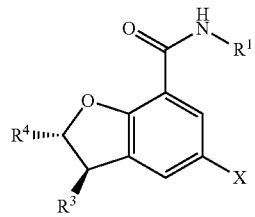

X = Br, COORy, Ry = C₁₋₂ alkyl

| Ex. | Structure Example | Name | Retention time (method high pH) | [M + H]+ |
|---|---|---|---|---|
| 99 | | (2S,3R)-N⁷,2-dimethyl-3-phenyl-N⁵-(3-(piperidin-4-yl)propyl)-2,3-dihydrobenzofuran-5,7-dicarboxamide | 1.03 | 436 |

-continued

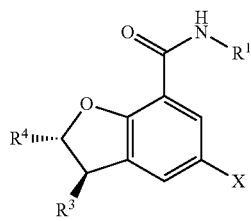

X = Br, COORy, Ry = C$_{1-2}$ alkyl

| Ex. | Structure Example | Name | Retention time (method high pH) | [M + H]+ |
|---|---|---|---|---|
| 100 | | (2S,3R)-N$^5$,N$^7$,2-trimethyl-3-phenyl-2,3-dihydrobenzofuran-5,7-dicarboxamide | 0.9* | 325 |
| 101 | | (2S,3R)-N$^5$-ethyl-N$^7$,2-dimethyl-3-phenyl-2,3-dihydrobenzofuran-5,7-dicarboxamide | 0.97* | 339 |
| 102 | | (2S,3R)-N$^5$-cyclopropyl-N$^7$,2-dimethyl-3-phenyl-2,3-dihydrobenzofuran-5,7-dicarboxamide | 0.99 | 351 |
| 103 | | (2R,3R)-N$^5$-cyclopropyl-N$^7$,2-dimethyl-3-phenyl-2,3-dihydrobenzofuran-5,7-dicarboxamide | 0.98* | 351 |

-continued

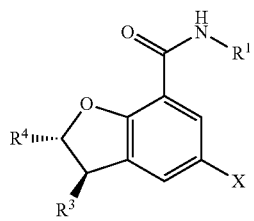

X = Br, COORy, Ry = C$_{1-2}$ alkyl

| Ex. | Structure Example | Name | Retention time (method high pH) | [M + H]+ |
|---|---|---|---|---|
| 104 | | (2R,3R)-N$^5$-cyclopropyl-2-(hydroxymethyl)-N$^7$-methyl-3-phenyl-2,3-dihydrobenzofuran-5,7-dicarboxamide | 0.79 | 367 |
| 105 | | (2R,3R)-N$^5$-((1R,5S,6R)-3-oxabicyclo[3.1.0]hexan-6-yl)-2-(fluoromethyl)-N$^7$-methyl-3-phenyl-2,3-dihydrobenzofuran-5,7-dicarboxamide | 0.88* | 411 |
| 106 | | (2R,3R)-N$^5$-cyclopropyl-2-(hydroxymethyl)-N$^7$-methyl-3-phenyl-2,3-dihydrobenzofuran-5,7-dicarboxamide | 0.79* | 367 |
| 107 | | (2S,3R)-N$^5$-(2-hydroxypropyl)-N$^7$,2-dimethyl-3-phenyl-2,3-dihydrobenzofuran-5,7-dicarboxamide | 0.88 | 369 |

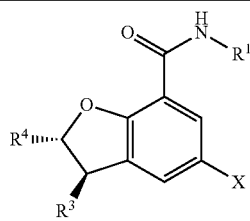

X = Br, COORy, Ry = $C_{1-2}$ alkyl

| Ex. | Structure Example | Name | Retention time (method high pH) | [M + H]+ |
|---|---|---|---|---|
| 108 |  | (2S,3S)-$N^5$-(2-hydroxypropyl)-$N^7$,2-dimethyl-3-phenyl-2,3-dihydrobenzofuran-5,7-dicarboxamide | 0.88 | 369 |

*method formic

Example 109: (Trans)-$N^5$-(2-(4,4-difluoropiperidin-3-yl)ethyl)-$N^7$,2-dimethyl-3-phenyl-2,3-dihydrobenzofuran-5,7-dicarboxamide (Diastereomeric Mixture)

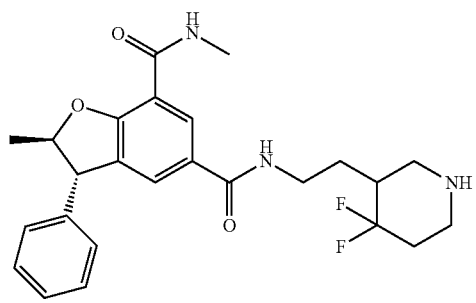 [SMILES: CNC(=O)c1cc(C(=O)NCCC2CNCCC2(F)F)cc2c1O[C@H](C)[C@H]2c1ccccc1]

Tert-butyl 4,4-difluoro-3-(2-((trans)-2-methyl-7-(methylcarbamoyl)-3-phenyl-2,3-dihydrobenzofuran-5-carboxamido)ethyl)piperidine-1-carboxylate (diastereomeric mixture)(79 mg, 0.14 mmol) was dissolved in DCM (5 mL) and TFA (0.50 mL, 6.5 mmol) was added. The reaction mixture was stirred at rt for 1 h, sat. $NaHCO_3$ (aq) (10 mL) was added and the mixture was stirred for 30 min. The reaction mixture was diluted with water and extracted with DCM. The organics were washed with 10% w/w LiCl (aq), dried via a hydrophobic frit and concentrated in vacuo. The residue was taken up in MeOH and eluted through 500 mg $NH_2$ isolute column, eluting with further MeOH. The fractions were combined and concentrated in vacuo to give the product (trans)-$N^5$-(2-(4,4-difluoropiperidin-3-yl)ethyl)-$N^7$,2-dimethyl-3-phenyl-2,3-dihydrobenzofuran-5,7-dicarboxamide (diastereomeric mixture) (31 mg, 0.068 mmol, 47.8% yield), as an off white gum.

LCMS (high pH method): Retention time 1.01 min, $[M+H]^+$=458

Example 111: (2S,3S)-2-(Fluoromethyl)-$N^5$-((1r,4S)-4-hydroxycyclohexyl)-$N^7$-methyl-3-phenyl-2,3-dihydrobenzofuran-5,7-dicarboxamidedicarboxamide

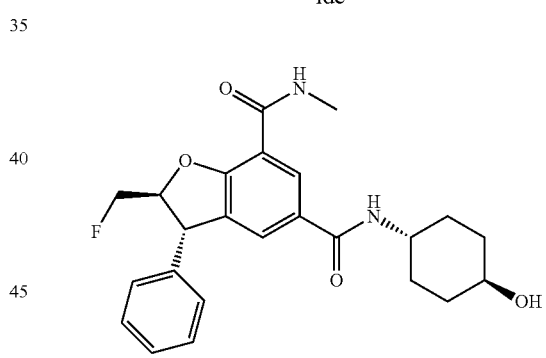

(2S,3S)-2-(Fluoromethyl)-7-(methylcarbamoyl)-3-phenyl-2,3-dihydrobenzofuran-5-carboxylic acid (50 mg, 0.15 mmol), HATU (69.3 mg, 0.182 mmol) and DIPEA (0.080 mL, 0.45 mmol) were stirred in DMF (2 mL) at rt for 5 mins, trans amino cyclohexanol (21.0 mg, 0.182 mmol) was added and the reaction was stirred at rt for 30 mins. The reaction was diluted with water and extracted with EtOAc, the organic phase was washed with 10% w/w LiCl (aq), dried using a hydrophobic frit and concentrated to give a white solid, this solid was purified using silica gel column chromatography eluting with a gradient of 0-100% (25% EtOH:EtOAc):DCM to give (2S,3S)-2-(fluoromethyl)-$N^5$-((1r,4S)-4-hydroxycyclohexyl)-$N^7$-methyl-3-phenyl-2,3-dihydrobenzofuran-5,7-dicarboxamide (51 mg, 0.120 mmol, 79% yield) as a white solid.

LCMS (formic method): Retention time 0.86 min, $[M+H]^+$=427

Example 112: (2R,3S)—N⁵-((1R,5S,6r)-3-oxabicyclo[3.1.0]hexan-6-yl)-3-(3-(2-hydroxyethoxy)phenyl)-N⁷,2-dimethyl-2,3-dihydrobenzofuran-5,7-dicarboxamide

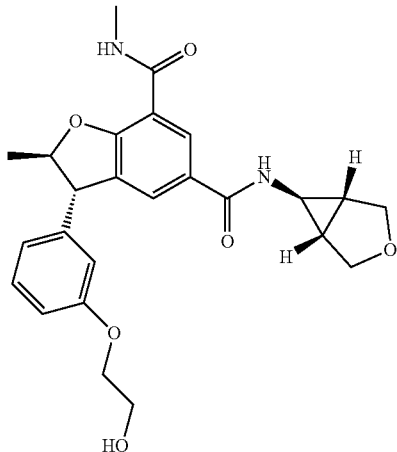 [SMILES: CNC(=O)c1cc(C(=O)N[C@H]2[C@@H]3COC[C@@H]32)cc2c1O[C@H](C)[C@H]2c1cccc(OCCO)c1]

(+/−)(2R,3S)—N⁵-((1R,5S,6r)-3-oxabicyclo[3.1.0]hexan-6-yl)-3-(3-(2-hydroxyethoxy)phenyl)-N⁷,2-dimethyl-2,3-dihydrobenzofuran-5,7-dicarboxamide (60 mg) was purified by chiral HPLC. The racemate was dissolved in EtOH (2 mL) with heating. Injection: 1 mL of the solution was injected onto the column (30% EtOH/heptane, flow rate=30 mL/min, detection wavelength=215 nm, 4. Ref 550, 100, Column 30 mm×25 cm Chiralcel OD-H (5 μm), lot no. ODH11158-01). Total number of injections=4. Fractions from 12-14 min were bulked and labelled peak 2.

The fractions corresponding to peak 2 were collected to afford (2R,3S)—N⁵-((1R,5S,6r)-3-oxabicyclo[3.1.0]hexan-6-yl)-3-(3-(2-hydroxyethoxy)phenyl)-N⁷,2-dimethyl-2,3-dihydrobenzofuran-5,7-dicarboxamide (yield 25 mg)

LCMS (2 min Formic): Rt=0.83 min, [MH]+=453.

Example 113: (2S,3S)-2-(Fluoromethyl)-N⁵-((1r,3S)-3-hydroxycyclobutyl)-N⁷-methyl-3-phenyl-2,3-dihydrobenzofuran-5,7-dicarboxamide

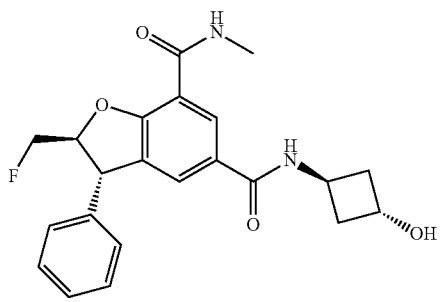 [SMILES: CNC(=O)c1cc(C(=O)N[C@H]2C[C@H](O)C2)cc2c1O[C@H](CF)[C@H]2c1ccccc1]

(2S,3S)-2-(Fluoromethyl)-7-(methylcarbamoyl)-3-phenyl-2,3-dihydrobenzofuran-5-carboxylic acid (50 mg, 0.15 mmol), HATU (69.3 mg, 0.182 mmol) and DIPEA (0.080 mL, 0.45 mmol) were stirred in DMF (2 mL) at rt for 5 mins, (1r,3r)-3-aminocyclobutanol hydrochloride (22.5 mg, 0.182 mmol) was added and the reaction was stirred at rt for 30 mins. The reaction was diluted with water and extracted with EtOAc, the organic phase was washed with 10% w/w LiCl (aq), dried using a hydrophobic frit and concentrated to give a white solid. This solid was purified using silica gel column chromatography eluting with a gradient of 0-100% (25% EtOH:EtOAc):DCM to give (2S,3S)-2-(fluoromethyl)-N⁵-((1r,3S)-3-hydroxycyclobutyl)-N⁷-methyl-3-phenyl-2,3-dihydrobenzofuran-5,7-dicarboxamide (52 mg, 0.131 mmol, 86% yield) as a white solid.

LCMS (formic method): Retention time 0.82 min, [M+H]+=399

Example 114: (2S,3S)-2-(Fluoromethyl)-N⁷-methyl-3-phenyl-N⁵-(tetrahydrofuran-3-yl)-2,3-dihydrobenzofuran-5,7-dicarboxamide (Mix of Diastereomers)

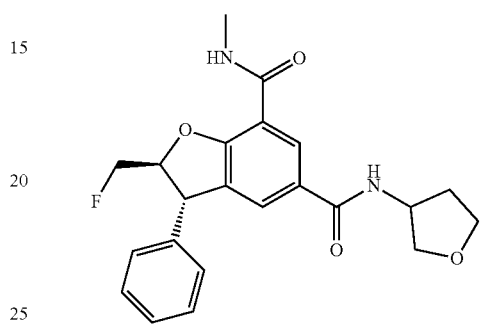

(2S,3S)-2-(Fluoromethyl)-7-(methylcarbamoyl)-3-phenyl-2,3-dihydrobenzofuran-5-carboxylic acid (50 mg, 0.15 mmol), HATU (69.3 mg, 0.182 mmol) and DIPEA (0.080 mL, 0.45 mmol) were dissolved in DMF (4 mL) with stirring at rt for 5 min. Tetrahydrofuran-3-amine (17.2 mg, 0.197 mmol) was dissolved in DMF (1 mL) and added to the reaction mixture, which was then stirred at rt for 1 h. The reaction mixture was diluted with water, extracted with DCM and brine was added. The organics were washed with 10% w/w LiCl (aq) solution and brine was added. The organic layers were dried via a hydrophobic frit and concentrated in vacuo. The residue was purified using silica gel column chromatography eluting with a gradient of 0-20% 2M NH₃ in MeOH:DCM to give crude title compound. This was further purified using a MDAP (high pH method) to give (2S,3S)-2-(fluoromethyl)-N⁷-methyl-N⁵-(tetrahydrofuran-3-yl)-2,3-dihydrobenzofuran-5,7-dicarboxamide (mix of diasteromers) (30 mg, 0.075 mmol, 50% yield), as a white solid.

LCMS (2 min High pH): Rt=0.90 min, [MH]+=399.

Example 115: (2S,3S)-2-(Fluoromethyl)-N⁵-(2-hydroxyethyl)-N⁷-methyl-3-phenyl-2,3-dihydrobenzofuran-5,7-dicarboxamide

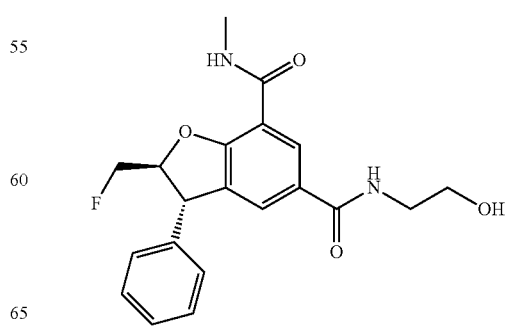

(2S,3S)-2-(Fluoromethyl)-7-(methylcarbamoyl)-3-phenyl-2,3-dihydrobenzofuran-5-carboxylic acid (43 mg, 0.13 mmol), HATU (59.6 mg, 0.157 mmol) and DIPEA (0.068 mL, 0.39 mmol) were dissolved in DMF (4 mL) with stirring at rt for 5 min. 2-Aminoethanol (9.46 µl, 0.157 mmol) was added and the reaction mixture was stirred at rt for 2 h. The reaction mixture was diluted with water and extracted with DCM. The organics were washed with 10% w/w LiCl (aq) and brine. The organic layers were dried via a hydrophobic frit and concentrated in vacuo. The residue was purified using silica gel column chromatography eluting with a gradient of 0-10% 2M $NH_3$ in MeOH:DCM to give crude title compound. The crude was further purified using a MDAP (high pH method) to give (2S,3S)-2-(fluoromethyl)-$N^5$-(2-hydroxyethyl)-$N^7$-methyl-3-phenyl-2,3-dihydrobenzofuran-5,7-dicarboxamide (23 mg, 0.062 mmol, 47.3% yield) as a white solid.

LCMS (2 min High pH): Rt=0.81 min, [MH]+=373.

Example 116: (Trans)-$N^5$-((1R,5S,6s)-3-acetyl-3-azabicyclo[3.1.0]hexan-6-yl)-3-(3-(2-hydroxyethoxy)phenyl)-$N^7$,2-dimethyl-2,3-dihydrobenzofuran-5,7-dicarboxamide

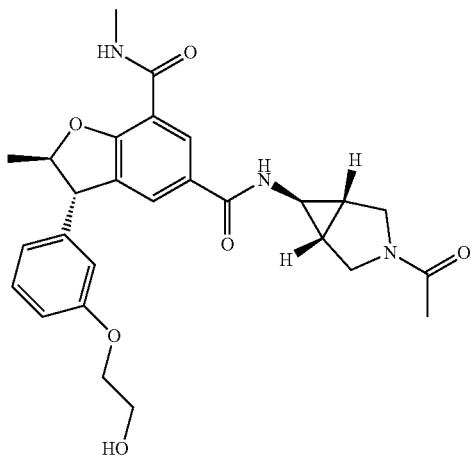 [SMILES: CNC(=O)c1cc(C(=O)N[C@H]2[C@@H]3CN(C(C)=O)C[C@@H]32)cc2c1O[C@H](C)[C@H]2c1cccc(OCCO)c1]

(Trans)-$N^5$-((1R,5S,6s)-3-azabicyclo[3.1.0]hexan-6-yl)-3-(3-(2-hydroxyethoxy)phenyl)-$N^7$,2-dimethyl-2,3-dihydrobenzofuran-5,7-dicarboxamide (32 mg, 0.071 mmol)(example 95) was dissolved in acetic anhydride (1 mL, 10.60 mmol) and the reaction mixture was stirred at rt under $N_2$ for 1 h. The reaction mixture was concentrated in vacuo. The residue was dissolved in toluene (5 mL) and concentrated in vacuo. The residue was taken up in DCM and purified using silica gel column chromatography eluting with a gradient of 0-5% MeOH:DCM to give (trans)-$N^5$-((1R,5S,6s)-3-acetyl-3-azabicyclo[3.1.0]hexan-6-yl)-3-(3-(2-hydroxyethoxy)phenyl)-$N^7$,2-dimethyl-2,3-dihydrobenzofuran-5,7-dicarboxamide (6.0 mg, 0.012 mmol, 17% yield) as a white solid.

LCMS (2 min High pH): Rt=0.78 min, [MH]+=494

Example 117: (Trans)-3-(3-(2-hydroxyethoxy)phenyl)-$N^7$,2-dimethyl-$N^5$-(2-(pyridin-3-yl)ethyl)-2,3-dihydrobenzofuran-5,7-dicarboxamide

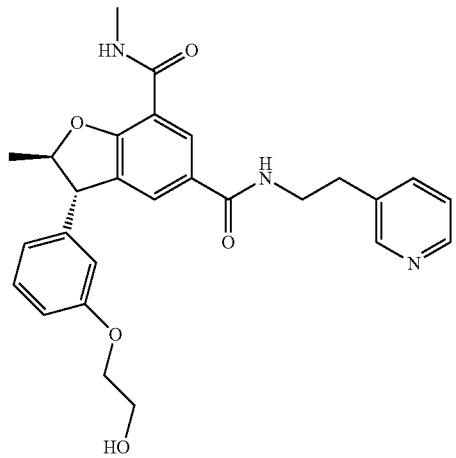 [SMILES: CNC(=O)c1cc(C(=O)NCCc2cccnc2)cc2c1O[C@H](C)[C@H]2c1cccc(OCCO)c1]

(Trans)-3-(3-(2-hydroxyethoxy)phenyl)-2-methyl-7-(methylcarbamoyl)-2,3-dihydrobenzofuran-5-carboxylic acid (50 mg, 0.13 mmol), HATU (61.4 mg, 0.162 mmol) and DIPEA (0.071 mL, 0.40 mmol) were dissolved in DMF (4 mL) with stirring at rt for 5 min. 2-(Pyridin-3-yl)ethanamine (19.7 mg, 0.162 mmol) was dissolved in DMF (1 mL) and added to the reaction mixture, which was then stirred at rt for 2 h. The reaction mixture was diluted with water and extracted with DCM. The organics were washed with 10% w/w LiCl (aq) and brine was added. The organic layers were dried via a hydrophobic frit and concentrated in vacuo. The residue was purified using silica gel column chromatography eluting with a gradient of 0-5% MeOH:DCM to give (trans)-3-(3-(2-hydroxyethoxy)phenyl)-$N^7$,2-dimethyl-$N^5$-(2-(pyridin-3-yl)ethyl)-2,3-dihydrobenzofuran-5,7-dicarboxamide (33 mg, 0.069 mmol, 51% yield), an off white gum.

LCMS (2 min High pH): Rt=0.83 min, [MH]+=476

Example 118: (Trans)-2-(fluoromethyl)-$N^7$-methyl-$N^5$-(1-methyl-1H-pyrazol-4-yl)-3-phenyl-2,3-dihydrobenzofuran-5,7-dicarboxamide

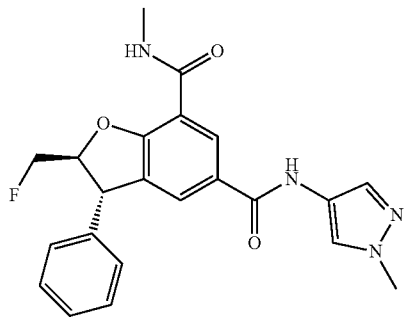 [SMILES: CNC(=O)c1cc(C(=O)Nc2cnn(C)c2)cc2c1O[C@H](CF)[C@H]2c1ccccc1]

(Trans)-2-(fluoromethyl)-7-(methylcarbamoyl)-3-phenyl-2,3-dihydrobenzofuran-5-carboxylic acid (150 mg, 0.455 mmol), HATU (208 mg, 0.547 mmol) and DIPEA (0.239 mL, 1.37 mmol) were dissolved in DMF (5 mL) with stirring at rt for 5 min. 1-Methyl-1H-pyrazol-4-amine (53.1 mg, 0.547 mmol) was added and the reaction mixture was stirred at rt for 3 h. Further HATU (87 mg, 0.23 mmol) and 1-methyl-1H-pyrazol-4-amine (22.1 mg, 0.228 mmol) were added and the reaction mixture was stirred at rt for 30 mins. The reaction mixture was diluted with water and extracted with DCM. The organics were washed with 10% w/w LiCl solution (aq), dried via a hydrophobic frit and concentrated in vacuo. The residue was purified using silica gel column chromatography eluting with a gradient of 0-7% (2M NH$_3$ in MeOH):DCM to give (trans)-2-(fluoromethyl)-N$^7$-methyl-N$^5$-(1-methyl-1H-pyrazol-4-yl)-3-phenyl-2,3-dihydrobenzofuran-5,7-dicarboxamide (131 mg, 0.321 mmol, 70% yield) as an off white solid.

LCMS (2 min High pH): Rt=0.92 min, [MH]+=409

Example 119: (2S,3S)-2-(Fluoromethyl)-N$^7$-methyl-N$^5$-(1-methyl-1H-pyrazol-4-yl)-3-phenyl-2,3-dihydrobenzofuran-5,7-dicarboxamide

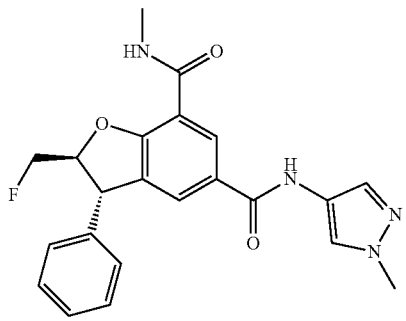 [SMILES: CNC(=O)c1cc(C(=O)Nc2cnn(C)c2)cc2c1O[C@H](CF)[C@H]2c1ccccc1]

(Trans)-2-(fluoromethyl)-N$^7$-methyl-N$^5$-(1-methyl-1H-pyrazol-4-yl)-3-phenyl-2,3-dihydrobenzofuran-5,7-dicarboxamide (126 mg) was purified by chiral HPLC. The racemate was dissolved in EtOH (10 mL) with heating. Injection: 0.5 mL of the solution was injected onto the column; isocratic method 50:50 Heptane:Ethanol flow rate=20 mL/min, detection wavelength=280 nm. Ref 400 nm, 100 nm, Column 250 mm×20 cm Regis Whekl-O1[R,R] (5 μm). Total number of injections=20. Fractions from 16-19.5 min were bulked and concentrated to afford (2R, 3S)-3-(3-(2-hydroxyethoxy)phenyl)-N$^7$,2-dimethyl-N$^5$-(2-(pyridin-3-yl)ethyl)-2,3-dihydrobenzofuran-5,7-dicarboxamide (yield 39 mg)

LCMS (2 min High pH): Rt=0.92 min, [MH]+=409

Example 120: (Trans)-2-(fluoromethyl)-N$^7$-methyl-3-phenyl-N$^5$-(1H-pyrazol-4-yl)-2,3-dihydrobenzofuran-5,7-dicarboxamide

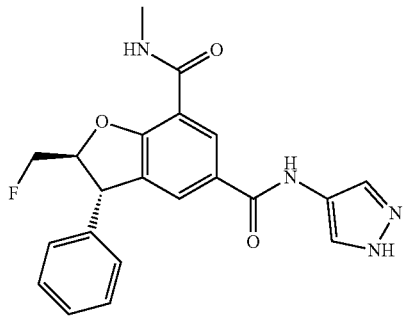 [SMILES: CNC(=O)c1cc(C(=O)Nc2cn[nH]c2)cc2c1O[C@H](CF)[C@H]2c1ccccc1]

(Trans)-2-(fluoromethyl)-7-(methylcarbamoyl)-3-phenyl-2,3-dihydrobenzofuran-5-carboxylic acid (150 mg, 0.455 mmol), HATU (208 mg, 0.547 mmol), DIPEA (0.239 mL, 1.37 mmol) were dissolved in DMF (5 mL) with stirring at rt for 5 min. 1H-Pyrazol-4-amine (45.4 mg, 0.547 mmol) was added and the reaction mixture was stirred at rt for 2 h. The reaction mixture was diluted with water and extracted with DCM. The organics were washed with 10% w/w LiCl (aq), dried via a hydrophobic frit and concentrated in vacuo. The residue was purified using silica gel column chromatography eluting with a gradient of 0-7% 2M NH$_3$ in MeOH:DCM to give (trans)-2-(fluoromethyl)-N$^7$-methyl-3-phenyl-N$^5$-(1H-pyrazol-4-yl)-2,3-dihydrobenzofuran-5,7-dicarboxamide (65 mg, 0.16 mmol, 36% yield) as an off white gum.

LCMS (2 min High pH): Rt=0.87 min, [MH]+=395

Example 121: (2S,3S)-2-(Fluoromethyl)-N$^7$-methyl-3-phenyl-N$^5$-(1H-pyrazol-4-yl)-2,3-dihydrobenzofuran-5,7-dicarboxamide

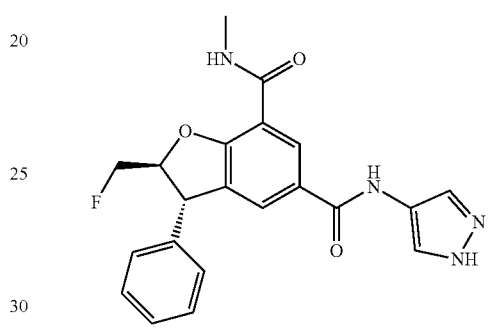

(Trans)-2-(fluoromethyl)-N$^7$-methyl-N$^5$-(1-methyl-1H-pyrazol-4-yl)-3-phenyl-2,3-dihydrobenzofuran-5,7-dicarboxamide (62 mg) was purified by chiral HPLC. The racemate was dissolved in EtOH (2 mL). Injection: 1 mL of the solution was injected onto the column; isocratic method 15% Ethanol:Heptane; flow rate=20 mL/min, detection wavelength=215 nm. Ref 550 nm, 100 nm, Column 2 cm×25 cm Chiralcel OJ (10 μm). Total number of injections=2. Fractions from 10-14 min were bulked and concentrated to afford (2S,3S)-2-(fluoromethyl)-N$^7$-methyl-3-phenyl-N$^5$-(1H-pyrazol-4-yl)-2,3-dihydrobenzofuran-5,7-dicarboxamide (yield 25 mg)

LCMS (2 min High pH): Rt=0.87 min, [MH]+=395

Example 122: (Trans)-N$^5$-((1R,5S,6r)-3-oxabicyclo[3.1.0]hexan-6-yl)-2-(fluoromethyl)-N$^7$-trideuteromethyl-3-phenyl-2,3-dihydrobenzofuran-5,7-dicarboxamide

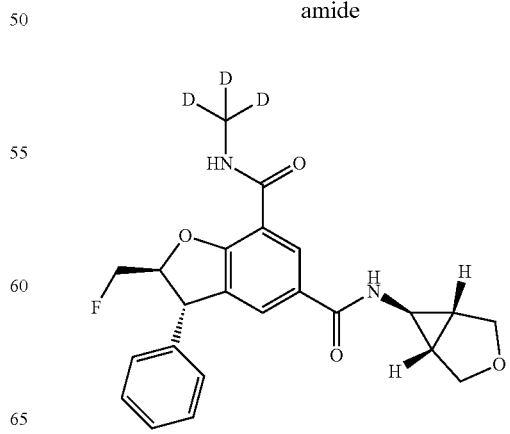

(Trans)-5-bromo-2-(fluoromethyl)-N-trideuteromethyl-3-phenyl-2,3-dihydrobenzofuran-7-carboxamide (100 mg, 0.272 mmol), xantphos (16 mg, 0.027 mmol), palladium(II) acetate (6.1 mg, 0.027 mmol), DMAP (100 mg, 0.817 mmol), cobalt carbonyl (100 mg, 0.272 mmol) and (1R,5S,6r)-3-oxabicyclo[3.1.0]hexan-6-amine hydrochloride (55.4 mg, 0.408 mmol) were combined in a microwave vial, which was sealed and flushed with nitrogen, then 1,4-Dioxane (3 mL) was added and the mixture was irradiated at 100° C. in the microwave reactor for 1 h. The vial contents were diluted with 0.5 M HCl (aq) and extracted with EtOAc. The combined organics were washed with 0.5 M HCl (aq) and then dried and evaporated in vacuo to give a brown residue. This residue was purified by silica gel column chromatography eluting with a gradient of 0-25% EtOH/EtOAc to give (trans)-$N^5$-((1R,5S,6r)-3-oxabicyclo[3.1.0]hexan-6-yl)-2-(fluoromethyl)-$N^7$-trideuteromethyl-3-phenyl-2,3-dihydrobenzofuran-5,7-dicarboxamide (70.2 mg, 0.170 mmol, 62% yield) as a pale yellow foam.

LCMS (2 min Formic): Rt=0.88 min, [MH]+=414

Example 123: (Trans)-$N^5$-(2-(1H-pyrazol-4-yl)ethyl)-2-(fluoromethyl)-$N^7$-methyl-3-phenyl-2,3-dihydrobenzofuran-5,7-dicarboxamide

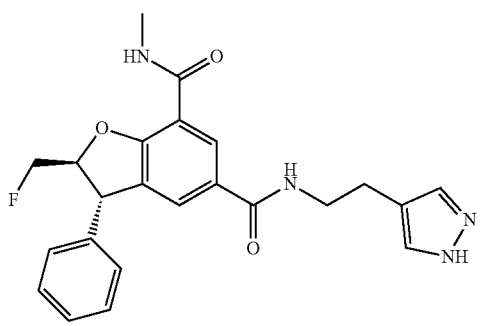 [SMILES: CNC(=O)c1cc(C(=O)NCCc2cn[nH]c2)cc2c1O[C@H](CF)[C@H]2c1ccccc1]

2-(1H-pyrazol-4-yl)ethanamine hydrochloride (122 mg, 0.824 mmol), (trans)-5-bromo-2-(fluoromethyl)-N-methyl-3-phenyl-2,3-dihydrobenzofuran-7-carboxamide (100 mg, 0.275 mmol), palladium(II) acetate (30.8 mg, 0.137 mmol), xantphos (79 mg, 0.14 mmol), DMAP (50.3 mg, 0.412 mmol) and cobalt carbonyl (46.9 mg, 0.137 mmol) were placed in a microwaveable vial and the cap added. 1,4-Dioxane (4 mL) was added and the reaction was irradiated in a biotage microwave at 90° C. for 60 mins. The reaction was diluted with water and was extracted with EtOAc. The organic layer was dried using a hydrophobic frit and concentrated to a purple oil. This oil was purified using a MDAP (formic method) to give (trans)-$N^5$-(2-(1H-pyrazol-4-yl)ethyl)-2-(fluoromethyl)-$N^7$-methyl-3-phenyl-2,3-dihydrobenzofuran-5,7-dicarboxamide (4.0 mg, 9.5 μmol, 3% yield) as a white solid LCMS (2 min Formic): Rt=0.83 min, [MH]+=423

Example 124: (Trans)-2-(fluoromethyl)-$N^7$-methyl-$N^5$-((1-methyl-1H-pyrazol-4-yl)methyl)-3-phenyl-2,3-dihydrobenzofuran-5,7-dicarboxamide

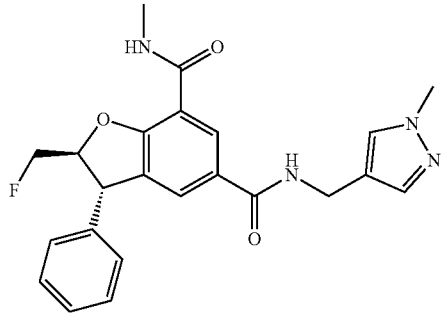 [SMILES: CNC(=O)c1cc(C(=O)NCc2cnn(C)c2)cc2c1O[C@H](CF)[C@H]2c1ccccc1]

(1-Methyl-1H-pyrazol-4-yl)methanamine, Hydrochloride (122 mg, 0.824 mmol), (trans)-5-bromo-2-(fluoromethyl)-N-methyl-3-phenyl-2,3-dihydrobenzofuran-7-carboxamide (100 mg, 0.275 mmol), palladium(II) acetate (30.8 mg, 0.137 mmol), xantphos (79 mg, 0.14 mmol), DMAP (50.3 mg, 0.412 mmol) and cobalt carbonyl (46.9 mg, 0.137 mmol) were placed in a microwaveable vial and capped. 1,4-Dioxane (4 mL) was added and the reaction was irradiated in a biotage microwave at 90° C. for 1 h. The reaction was partitioned between water and EtOAc. The organic layer was washed with brine, dried using a hydrophobic frit and concentrated to a orange gum. This gum was purified using silica gel column chromatography eluting with a gradient of 0-100% (25% EtOH in EtOAc):cyclohexane to give (trans)-2-(fluoromethyl)-$N^7$-methyl-$N^5$-((1-methyl-1H-pyrazol-4-yl)methyl)-3-phenyl-2,3-dihydrobenzofuran-5,7-dicarboxamide (46 mg, 0.11 mmol, 40% yield) as a yellow solid.

LCMS (2 min Formic): Rt=0.86 min, [MH]+=423

Example 125: (Trans)-2-(fluoromethyl)-$N^7$-methyl-$N^5$-(2-(1-methyl-1H-pyrazol-4-yl)ethyl)-3-phenyl-2,3-dihydrobenzofuran-5,7-dicarboxamide

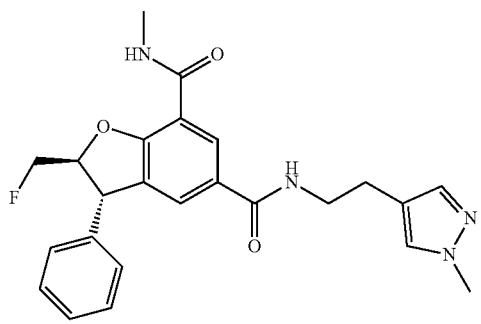 [SMILES: CNC(=O)c1cc(C(=O)NCCc2cnn(C)c2)cc2c1O[C@H](CF)[C@H]2c1ccccc1]

2-(1-Methyl-1H-pyrazol-4-yl)ethanamine (34.4 mg, 0.275 mmol), (trans)-5-bromo-2-(fluoromethyl)-N-methyl-3-phenyl-2,3-dihydrobenzofuran-7-carboxamide (100 mg, 0.275 mmol), palladium(II) acetate (30.8 mg, 0.137 mmol), xantphos (79 mg, 0.14 mmol), DMAP (50.3 mg, 0.412 mmol) and cobalt carbonyl (46.9 mg, 0.137 mmol) were placed in a microwaveable vial and the cap added. 1,4-Dioxane (4 mL) was added and the reaction irradiated in a biotage microwave at 90° C. for 60 mins. The reaction was diluted with water and 10% w/w citric acid (aq) and extracted with EtOAc, the organic phase was washed with sat NaHCO₃ (aq) dried using a hydrophobic frit and concentrated to a brown gum. This gum was purified using silica gel column chromatography eluting with a gradient of 0-100% (25% EtOH: EtOAc):cylohexane to give (trans)-2-(fluoromethyl)-N⁷-methyl-N⁵-(2-(1-methyl-1H-pyrazol-4-yl)ethyl)-3-phenyl-2,3-dihydrobenzofuran-5,7-dicarboxamide (32 mg, 0.073 mmol, 27% yield) as a brown solid.

LCMS (2 min Formic): Rt=0.88 min, [MH]+=437

Example 126: (2S,3S)-2-(Fluoromethyl)-N⁵-((1R,2R)-2-(hydroxymethyl)cyclopropyl)-N⁷-methyl-3-phenyl-2,3-dihydrobenzofuran-5,7-dicarboxamide

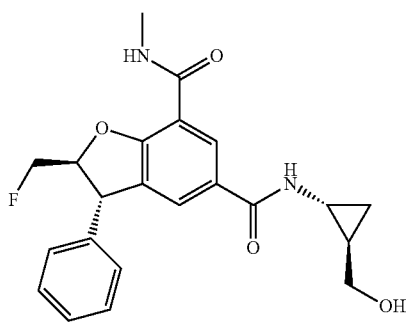 [SMILES: CNC(=O)c1cc(C(=O)N[C@@H]2C[C@H]2CO)cc2c1O[C@H](CF)[C@H]2c1ccccc1]

(Trans)-2-(fluoromethyl)-N⁵-((1R,2R)-2-(hydroxymethyl)cyclopropyl)-N⁷-methyl-3-phenyl-2,3-dihydrobenzofuran-5,7-dicarboxamide (200 mg) was purified by chiral HPLC. The racemate was dissolved in EtOH (4 mL) with heating. Injection: 1 mL of the solution was injected onto the column; isocratic method 30% Ethanol:Heptane; flow rate=30 mL/min, detection wavelength=215 nm. Ref 550 nm, 100 nm, Column 30 mm×25 cm Chiralcel AD-H (5 μm). Total number of injections=4. Fractions from 15-18 min were bulked and concentrated to afford (2S,3S)-2-(fluoromethyl)-N⁵-((1R,2R)-2-(hydroxymethyl)cyclopropyl)-N⁷-methyl-3-phenyl-2,3-dihydrobenzofuran-5,7-dicarboxamide (99 mg, 0.25 mmol, 50% yield) as a yellow solid.

LCMS (2 min High pH): Rt=0.82 min, [MH]+=399

Example 127 and 128: (2R,3S)—N⁵-(2-((R*)-4,4-difluoropiperidin-3-yl)ethyl)-N⁷,2-dimethyl-3-phenyl-2,3-dihydrobenzofuran-5,7-dicarboxamide and (2R,3S)—N⁵-(2-((S*)-4,4-difluoropiperidin-3-yl)ethyl)-N⁷,2-dimethyl-3-phenyl-2,3-dihydrobenzofuran-5,7-dicarboxamide

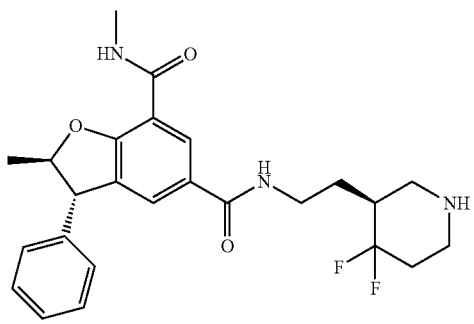

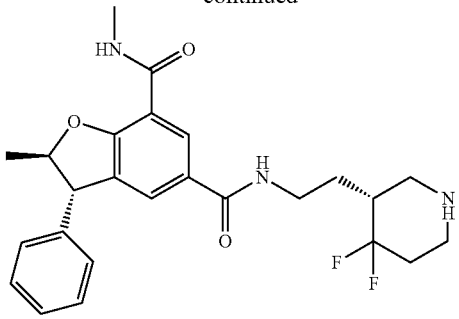

(2R,3S)—N⁵-(2-((+/−)(R)-4,4-difluoropiperidin-3-yl)ethyl)-N⁷,2-dimethyl-3-phenyl-2,3-dihydrobenzofuran-5,7-dicarboxamide (21 mg) was purified by chiral HPLC. The racemate was dissolved in EtOH (1 mL) with heating. Injection: 1 mL of the solution was injected onto the column; isocratic method 25% Ethanol (+0.2% isopropylamine): Heptane (+0.2% isopropylamine); flow rate=30 mL/min, detection wavelength=215 nm. Ref 550 nm, 100 nm, Column 30 mm×25 cm Chiralcel OJ-H (5 μm). Fractions from 7-10 min were bulked and concentrated to afford (2R,3S)—N⁵-(2-((R*)-4,4-difluoropiperidin-3-yl)ethyl)-N⁷,2-dimethyl-3-phenyl-2,3-dihydrobenzofuran-5,7-dicarboxamide (6.0 mg, 29% yield).

LCMS (2 min High pH): Rt=1.01 min, [MH]+=458

Fractions from 14-22 min were bulked and concentrated to afford (2R,3S)—N⁵-(2-((S*)-4,4-difluoropiperidin-3-yl)ethyl)-N⁷,2-dimethyl-3-phenyl-2,3-dihydrobenzofuran-5,7-dicarboxamide (7 mg, 33% yield).

LCMS (2 min High pH): Rt=1.01 min, [MH]+=458

Example 129: (Trans)-2-(fluoromethyl)-N⁷-methyl-3-phenyl-2,3-dihydrobenzofuran-5,7-dicarboxamide

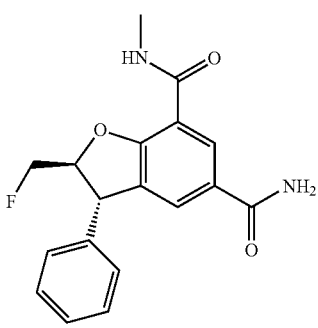 [SMILES: CNC(=O)c1cc(C(N)=O)cc2c1O[C@H](CF)[C@H]2c1ccccc1]

(Trans)-2-(fluoromethyl)-7-(methylcarbamoyl)-3-phenyl-2,3-dihydrobenzofuran-5-carboxylic acid (200 mg, 0.607 mmol), HATU (254 mg, 0.668 mmol) and DIPEA (0.318 mL, 1.82 mmol) were stirred in DMF (4 mL) at rt for 5 mins, NH₄Cl (97 mg, 1.8 mmol) was added and the reaction stirred at rt for 5 mins. The reaction was diluted with 10% w/w citric acid (aq) and was extracted with EtOAc. The organic phase was washed with 10% w/w LiCl (aq) dried using a hydrophobic frit and concentrated to give a yellow solid. This solid was purified using silica gel column chromatography eluting with gradient of 0-12% EtOH:EtOAc to give (trans)2-(fluoromethyl)-N⁷-methyl-3- phenyl-2,3-dihydrobenzofuran-5,7-dicarboxamide (125 mg, 0.381 mmol, 63% yield) as a white solid.

LCMS (2 min Formic): Rt=0.81 min, [MH]+=329

Example 130: (2S,3S)-2-(Fluoromethyl)-$N^7$-methyl-3-phenyl-2,3-dihydrobenzofuran-5,7-dicarboxamide

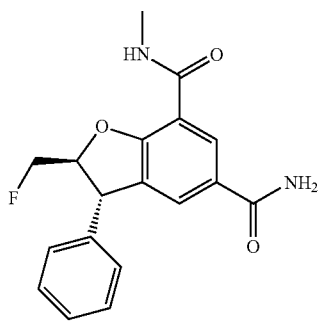 [SMILES: CNC(=O)c1cc(C(N)=O)cc2c1O[C@H](CF)[C@H]2c1ccccc1]

(Trans)-2-(fluoromethyl)-$N^7$-methyl-3-phenyl-2,3-dihydrobenzofuran-5,7-dicarboxamide (90 mg) was purified by chiral HPLC. The racemate was dissolved in EtOH (4 mL). Injection: 2 mL of the solution was injected onto the column; isocratic method 30% Ethanol:Heptane; flow rate=30 mL/min, detection wavelength=215 nm. Ref 550 nm, 100 nm, Column 30 mm×25 cm Chiralpak AD-H (5 µm). Total number of injections=2. Fractions from 12.5-14.5 min were bulked and concentrated to afford (2S,3S)-2-(fluoromethyl)-$N^7$-methyl-3-phenyl-2,3-dihydrobenzofuran-5,7-dicarboxamide (27 mg, 0.082 mmol, 30% yield) as a white solid.

LCMS (2 min Formic): Rt=0.80 min, [MH]+=329

Example 131: (2S,3S)-2-(Fluoromethyl)-$N^5$-((1R,2R)-2-(hydroxymethyl)cyclopropyl)-$N^7$-methyl-3-phenyl-2,3-dihydrobenzofuran-5,7-dicarboxamide

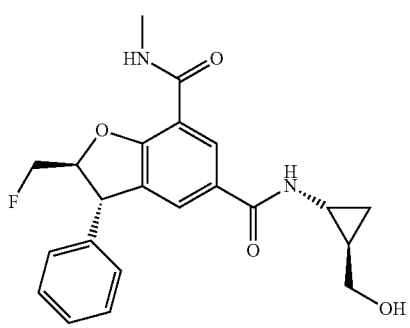

(Trans)-2-(fluoromethyl)-7-(methylcarbamoyl)-3-phenyl-2,3-dihydrobenzofuran-5-carboxylic acid (220 mg, 0.668 mmol) and HATU (305 mg, 0.802 mmol) were dissolved in DMF (2 mL), DIPEA (0.350 mL, 2.00 mmol) was added and the reaction mixture left to stir at rt for 5 mins. ((1R,2R)-2-Aminocyclopropyl)methanol (58.2 mg, 0.668 mmol) was added and the reaction left to stir for 1 h at rt. The reaction mixture was diluted in EtOAc (30 mL) and washed twice with 2% w/w aq citric acid (30 mL) and then the organic layer washed again with brine (15 mL) and then with sat. NaHCO$_3$ (aq) (30 mL) and passed through a hydrophobic frit. The filtrate was concentrated and purified using silica gel column chromatography eluting with a gradient of 70-100% EtOAc:cyclohexane to give (trans)-2-(fluoromethyl)-$N^5$-((1R,2R)-2-(hydroxymethyl)cyclopropyl)-$N^7$-methyl-3-phenyl-2,3-dihydrobenzofuran-5,7-dicarboxamide (149 mg, 0.374 mmol, 56% yield) as a yellow gum.

LCMS (2 min Formic): Rt=0.81 min, [MH]+=399

(Trans)-2-(fluoromethyl)-$N^5$-((1R,2R)-2-(hydroxymethyl)cyclopropyl)-$N^7$-methyl-3-phenyl-2,3-dihydrobenzofuran-5,7-dicarboxamide (149 mg) was purified by chiral HPLC. The racemate was dissolved in EtOH (4 mL). Injection: 0.5 mL of the solution was injected onto the column (10% EtOH/heptane, flow rate=20 mL/min, detection wavelength=215 nm, 4. Ref 550, 100, Column 30 mm×25 cm Chiralcel OJ-C (5 µm), lot no. ODH11158-01). Total number of injections=8. Fractions from 10-10.5 min were bulked and concentrated to afford (2R,3S)—$N^5$-((1R,5S,6r)-3-oxabicyclo[3.1.0]hexan-6-yl)-3-(3-(2-hydroxyethoxy)phenyl)-$N^7$,2-dimethyl-2,3-dihydrobenzofuran-5,7-dicarboxamide (yield 25 mg)

LCMS (2 min Formic): Rt=0.82 min, [MH]+=399.

Example 132: (2S,3S)-2-(Fluoromethyl)-$N^5$-((trans)-2-(2-hydroxyethyl)cyclopropyl)-$N^7$-methyl-3-phenyl-2,3-dihydrobenzofuran-5,7-dicarboxamide

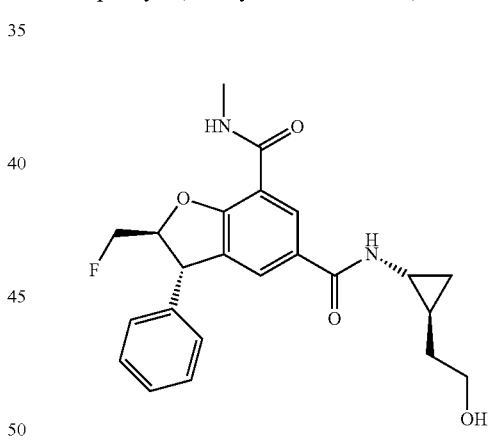

(2S,3S)-2-(Fluoromethyl)-7-(methylcarbamoyl)-3-phenyl-2,3-dihydrobenzofuran-5-carboxylic acid (200 mg, 0.607 mmol) was taken up in DMF (5 mL). DIPEA (0.318 mL, 1.82 mmol), HATU (346 mg, 0.911 mmol) and trans 2-(2-aminocyclopropyl)ethan-1-ol (132 mg, 0.911 mmol) were added and the reaction left to stir at rt overnight. The reaction was concentrated in vacuo. The residue was taken up in EtOAc and washed with sat. NaHCO$_3$ (aq.) and brine. The organic phase was dried over sodium sulphate, filtered through a hydrophobic frit and concentrated in vacuo. The residue was purified using silica gel column chromatography eluting with a gradient of 5-100% EtOAc:cyclohexane to give (2S,3S)-2-(fluoromethyl)-$N^5$-((trans)-2-(2-hydroxyethyl)cyclopropyl)-$N^7$-methyl-3-phenyl-2,3-dihydrobenzofuran-5,7-dicarboxamide (200 mg, 0.485 mmol, 80% yield).

LCMS (2 min High pH): Rt=0.91 min, [MH]+=413

Example 133: (Trans)-N⁵-(2-(4H-1,2,4-triazol-4-yl)ethyl)-2-(fluoromethyl)-N⁷-methyl-3-phenyl-2,3-dihydrobenzofuran-5,7-dicarboxamide

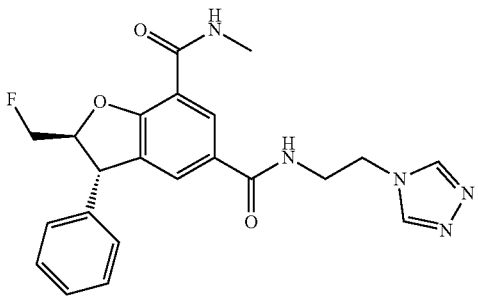 [SMILES: CNC(=O)c1cc(C(=O)NCCn2cnnc2)cc2c1O[C@H](CF)[C@H]2c1ccccc1]

To a solution of (trans)-2-(fluoromethyl)-7-(methylcarbamoyl)-3-phenyl-2,3-dihydrobenzofuran-5-carboxylic acid (0.033 g, 0.10 mmol) and HATU (38 mg) in DMF (0.5 mL) was added DIPEA (63 uL). The solution was treated with the amine (0.120 mmol). The reaction was then shaken and then stood at rt for 23 h. The reaction was directly purified by MDAP (High pH method) to give (trans) N⁵-(2-(4H-1,2,4-triazol-4-yl)ethyl)-2-(fluoromethyl)-N⁷-methyl-3-phenyl-2,3-dihydrobenzofuran-5,7-dicarboxamide (18 mg, 32%)

LCMS (method formic): RT=0.83 min, [MH]⁺=423

Similarly prepared were the following Examples:

| Ex. | Structure Example | Name | Mass obtained (mg), yield | Rt (method high pH) | [MH]+ |
|---|---|---|---|---|---|
| 134 | | (Trans)-2-(fluoromethyl)-N⁷-methyl-N⁵-(oxetan-3-yl)-3-phenyl-2,3-dihydrobenzofuran-5,7-dicarboxmide | 19.7 (38%) | 0.96 | 438 |
| 135 | | (Trans)-2-(fluoromethyl)-N⁷-methyl-3-phenyl-N⁵-(2-(pyridin-4-yl)ethyl)-2,3-dihydrobenzofuran-5,7-dicarboxmide | 11 (19%) | 0.60 | 433 |
| 136 | | (Trans)-2-(fluoromethyl)-N⁷-methyl-N⁵-(1-(methylsulfonyl)azetidin-3-yl)-3-phenyl-2,3-dihydrobenzofuran-5,7-dicarboxmide | 24 (40%) | 0.88 | 461 |

-continued

| Ex. | Structure Example | Name | Mass obtained (mg), yield | Rt (method high pH) | [MH]+ |
|---|---|---|---|---|---|
| 137 | | (Trans)-2-(fluoromethyl)-N⁷-methyl-3-phenyl-N⁵-(2-(pyridin-3-yl)ethyl)-2,3-dihydrobenzofuran-5,7-dicarboxmide | 19 (32%) | 0.61 | 433 |
| 138 | | (Trans)-N⁵-(2-(1H-imidazol-4-yl)ethyl)-2-(fluoromethyl)-N⁷-methyl-3-phenyl-2,3-dihydrobenzofuran-5,7-dicarboxamide | 23 (41%) | 0.57 | 423 |
| 139 | | (Trans)-2-(fluoromethyl)-N⁷-methyl-3-phenyl-N⁵-(2-(pyridin-3-yl)ethyl)-2,3-dihydrobenzofuran-5,7-dicarboxamide | 10 (21%) | 0.90 | 357 |
| 140 | | (Trans)-2-(fluoromethyl)-N⁵-(2-methoxycyclopropyl)-N⁷-methyl-3-phenyl-2,3-dihydrobenzofuran-5,7-dicarboxamide (mix of diastereomers) | 11.5 (22%) | 0.91 | 399 |
| 141 | | (Trans) tert-butyl 3,3-difluoro-4-(2-2-(fluoromethyl)-7-(methylcarbamoyl)-3-phenyl-2,3-dihydrobenzofuran-5-carboxamido)ethyl)piperidine-1-carboxylate (mix of diastereomers) | 15.2 (24%) | 0.62 | 476 |

| Ex. | Structure Example | Name | Mass obtained (mg), yield | Rt (method high pH) | [MH]+ |
|---|---|---|---|---|---|
| 142 | | (Trans) tert-butyl 3,3-difluoro-4-(3-2-(fluoromethyl)-7-(methylcarbamoyl)-3-phenyl-2,3-dihydrobenzofuran-5-carboxamido)propyl)piperidine-1-carboxylate (mix of diastereonners) | 16.3 (25%) | 0.64 | 490 |
| 143 | | (Trans)-2-(fluoromethyl)-N⁷-methyl-3-phenyl-N⁵-((tetrahydrofuran-3-yl)methyl)-2,3-dihydrobenzofuran-5,7-dicarboxamide (mix of diastereomers) | 19.7 (36%) | 0.82 | 413 |

Example 144: (Trans)(2R,3S)—N$^5$-(2-(3,3-difluoropiperidin-4-yl)ethyl)-N$^7$,2-dimethyl-3-phenyl-2,3-dihydrobenzofuran-5,7-dicarboxamide (Mix of Diastereomers)

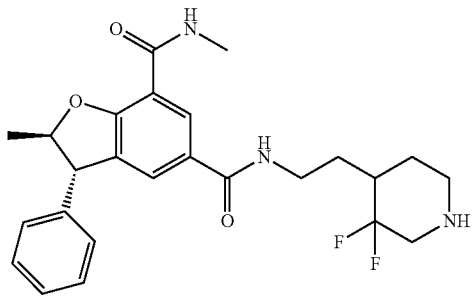 [SMILES: CNC(=O)c1cc(C(=O)NCCC2CCNCC2(F)F)cc2c1O[C@H](C)[C@H]2c1ccccc1]

(Trans) tert-butyl 3,3-difluoro-4-(2-((2R,3S)-2-methyl-7-(methylcarbamoyl)-3-phenyl-2,3-dihydrobenzofuran-5-carboxamido)ethyl)piperidine-1-carboxylate (mix of diastereomers) (75 mg, 0.13 mmol) was dissolved in DCM (5 mL) and TFA (0.50 mL, 6.5 mmol) was added. The reaction mixture was stirred at rt for 1 h. Sat. NaHCO₃ (aq) (10 mL) was added and the mixture was stirred for 30 min. The reaction mixture was diluted with water and extracted with DCM. The organics were washed with 10% w/w LiCl (aq), dried via a hydrophobic frit and concentrated in vacuo. The residue was taken up in MeOH (3 mL) and eluted through 500 mg NH₂ isolute column. The column was prewashed with MeOH (~10 mL). The relevant fractions were combined and concentrated in vacuo to give (trans)-N$^5$-(2-(3,3-difluoropiperidin-4-yl)ethyl)-N$^7$,2-dimethyl-3-phenyl-2,3-dihydrobenzofuran-5,7-dicarboxamide (mix of diastereomers) (32 mg, 0.070 mmol, 52% yield) as an off white gum.

LCMS (method formic): Rt=0.99 min, [MH]⁺=458

Example 145 (Trans) 2-(fluoromethyl)-N$^7$-methyl-3-phenyl-N$^5$-(2-(pyridin-2-yl)ethyl)-2,3-dihydrobenzofuran-5,7-dicarboxamide

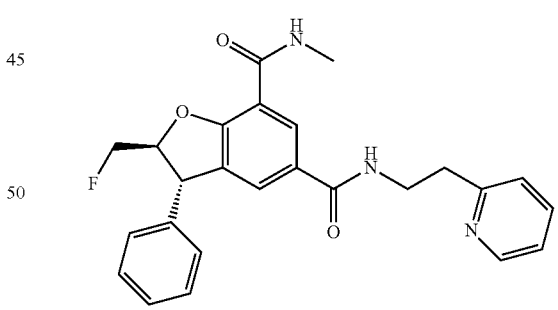

2-(2-Aminoethyl)-pyridine (50.3 mg, 0.412 mmol), (trans) 5-bromo-2-(fluoromethyl)-N-methyl-3-phenyl-2,3-dihydrobenzofuran-7-carboxamide (100 mg, 0.275 mmol), palladium(II) acetate (30.8 mg, 0.137 mmol), xantphos (79 mg, 0.14 mmol), DMAP (50.3 mg, 0.412 mmol) and cobalt carbonyl (46.9 mg, 0.137 mmol) were placed in a microwaveable vial and the cap added. 1,4-Dioxane (4 mL) was added and the reaction was irradiated in a biotage microwave at 90° C. for 60 mins. The reaction was diluted with water and extracted with EtOAc, the organic phase was washed with water, dried using a hydrophobic frit and concentrated to give a black gum. This gum was purified using silica gel column chromatography eluting with a gradient of 0-25% EtOH:EtOAc to give a yellow solid. This was further purified by MDAP (High pH method) to give (trans) 2-(fluoromethyl)-$N^7$-methyl-3-phenyl-$N^5$-(2-(pyridin-2-yl)ethyl)-2,3-dihydrobenzofuran-5,7-dicarboxamide (34 mg, 0.078 mmol, 29% yield) as a yellow solid LCMS (method High pH): Rt=0.64 mins, [MH]⁺=434

Example 146 and Example 147: (2R,3S)—$N^5$-(2-((R*)-3,3-difluoropiperidin-4-yl)ethyl)-$N^7$,2-dimethyl-3-phenyl-2,3-dihydrobenzofuran-5,7-dicarboxamide and (2R,3S)—$N^5$-(2-((S*)-3,3-difluoropiperidin-4-yl)ethyl)-$N^7$,2-dimethyl-3-phenyl-2,3-dihydrobenzofuran-5,7-dicarboxamide

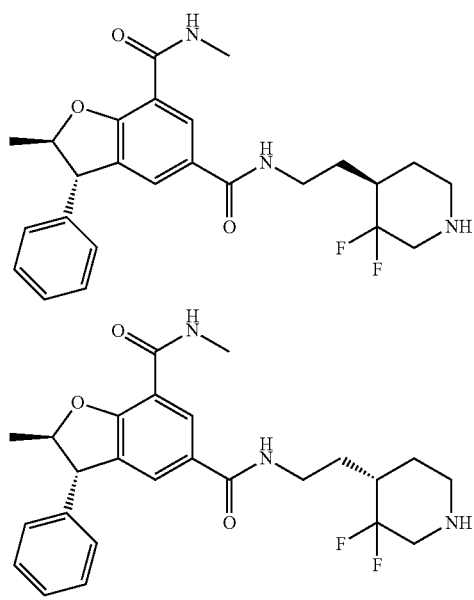

(2R,3S)—$N^5$-(2-(3,3-difluoropiperidin-4-yl)ethyl)-$N^7$,2-dimethyl-3-phenyl-2,3-dihydrobenzofuran-5,7-dicarboxamide (mix of diastereomers) (23 mg) was purified by chiral HPLC. The racemate was dissolved in EtOH (3 mL) with heating. Injection: 1 mL of the solution was injected onto the column (20% EtOH/heptane, flow rate=30 mL/min, detection wavelength=215 nm, 4. Ref 550, 100, Column 30 mm×25 cm Chiralpak IC (5 um), lot No. IC10028-01

Total number of injections=1. Fractions from 64-69 min were bulked and labelled peak 1. Fractions from 72-80 min were bulked and labelled peak 2.

The fractions corresponding to peak 1 were collected to afford (2R,3S)—$N^5$-(2-((R*)-3,3-difluoropiperidin-4-yl)ethyl)-$N^7$,2-dimethyl-3-phenyl-2,3-dihydrobenzofuran-5,7-dicarboxamide (9 mg)

LCMS (2 min Formic): Rt=0.99 min, [MH]+=458

The fractions corresponding to peak 2 were collected to afford and (2R,3S)—$N^5$-(2-((S*)-3,3-difluoropiperidin-4-yl)ethyl)-$N^7$,2-dimethyl-3-phenyl-2,3-dihydrobenzofuran-5,7-dicarboxamide (10 mg)

LCMS (2 min Formic): Rt=0.99 min, [MH]+=458

Example 148: (Trans) $N^7$,2-dimethyl-$N^5$-(1-methyl-1H-pyrazol-4-yl)-3-phenyl-2,3-dihydrobenzofuran-5,7-dicarboxamide

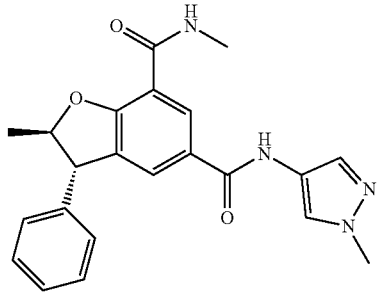

(Trans) 2-methyl-7-(methylcarbamoyl)-3-phenyl-2,3-dihydrobenzofuran-5-carboxylic acid (100 mg, 0.321 mmol), HATU (147 mg, 0.385 mmol) and DIPEA (0.168 mL, 0.964 mmol) were stirred in DMF (4 mL) at rt for 5 mins. 1-Methyl-1H-pyrazol-4-amine (46.8 mg, 0.482 mmol) (commercially available eg from Fluorochem) was added and the reaction stirred at rt for 1 h. The reaction was diluted with 10% w/w citric acid (aq) and extracted with EtOAc. The organic phase was washed with 10% w/w LiCl (aq) dried using a hydrophobic frit and concentrated to give a yellow gum. This gum was purified using silica gel column chromatography eluting with a gradient of 0-60% (25% EtOH in EtOAc):Cyclohexane to give (trans) $N^7$,2-dimethyl-$N^5$-(1-methyl-1H-pyrazol-4-yl)-3-phenyl-2,3-dihydrobenzofuran-5,7-dicarboxamide (65 mg, 0.17 mmol, 52% yield) as a white solid.

LCMS (2 min Formic): Rt=0.95 min, [MH]+=391

Example 149 (Trans)-$N^7$,2-dimethyl-$N^5$-(2-(1-methyl-1H-pyrazol-4-yl)ethyl)-3-phenyl-2,3-dihydrobenzofuran-5,7-dicarboxamide

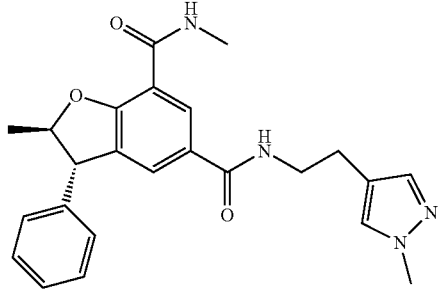 [SMILES: CNC(=O)c1cc(C(=O)NCCc2cnn(C)c2)cc2c1O[C@H](C)[C@H]2c1ccccc1]

(Trans)-2-methyl-7-(methylcarbamoyl)-3-phenyl-2,3-dihydrobenzofuran-5-carboxylic acid (100 mg, 0.321 mmol), HATU (147 mg, 0.385 mmol) and DIPEA (0.168 mL, 0.964 mmol) were stirred in DMF (4 mL) at rt for 5 mins. 2-(1-Methyl-1H-pyrazol-4-yl)ethanamine (40.2 mg, 0.321 mmol) (commercially available from eg Fluorochem) was added and the reaction stirred at rt for 1 h. The reaction was diluted with 10% w/w citric acid (aq) and extracted with EtOAc. The organic phase was washed with 10% w/w LiCl (aq) dried using a hydrophobic frit and concentrated to give a yellow gum. This gum was purified using silica gel column chromatography eluting with a gradient of 0-60% (25% EtOH in EtOAc):Cyclohexane to give (trans)-$N^7$,2-dimethyl-$N^5$-(2-(1-methyl-1H-pyrazol-4-yl)ethyl)-3-phenyl-2,3-dihydrobenzofuran-5,7-dicarboxamide (114 mg, 0.272 mmol, 85% yield) as a white solid.

LCMS (2 min Formic): Rt=0.93 min, [MH]+=419.3

Example 150: (Trans)-2-(fluoromethyl)-N⁵-((trans)-2-(2-hydroxyethyl)cyclopropyl)-N⁷-methyl-3-phenyl-2,3-dihydrobenzofuran-5,7-dicarboxamide

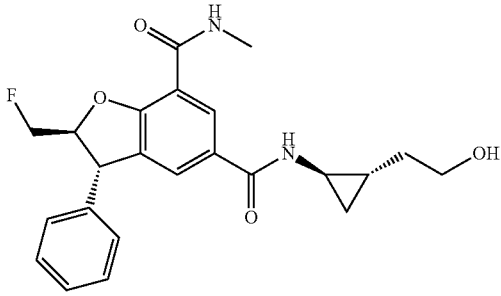 [SMILES: CNC(=O)c1cc(C(=O)N[C@@H]2C[C@H]2CCO)cc2c1O[C@H](CF)[C@H]2c1ccccc1]

(Trans) 2-(fluoromethyl)-7-(methylcarbamoyl)-3-phenyl-2,3-dihydrobenzofuran-5-carboxylic acid (100 mg, 0.304 mmol), HATU (139 mg, 0.364 mmol) and DIPEA (0.159 mL, 0.911 mmol) were stirred in DMF (4 mL) at rt for 5 mins. 2-((Trans)-2-aminocyclopropyl)ethanol (39.9 mg, 0.395 mmol) was added and the reaction stirred at rt for 2 h. The reaction was diluted with EtOAc and was washed with 10% w/w citric acid (aq) and 10% w/w LiCl (aq), dried using a hydrophobic frit and concentrated to give a brown oil. This oil was purified using silica gel column chromatography eluting with a gradient of 0-12% EtOH:EtOAc to give (trans)-2-(fluoromethyl)-N⁵-((trans)-2-(2-hydroxyethyl)cyclopropyl)-N⁷-methyl-3-phenyl-2,3-dihydrobenzofuran-5,7-dicarboxamide (70 mg, 0.17 mmol, 56% yield) as a colourless gum.

LCMS (2 min Formic): Rt=0.91 min, [MH]+=413

Example 151: (Trans)-2-(fluoromethyl)-N⁵-((1R,2S)-2-(2-hydroxyethyl)cyclopropyl)-N⁷-methyl-3-phenyl-2,3-dihydrobenzofuran-5,7-dicarboxamide

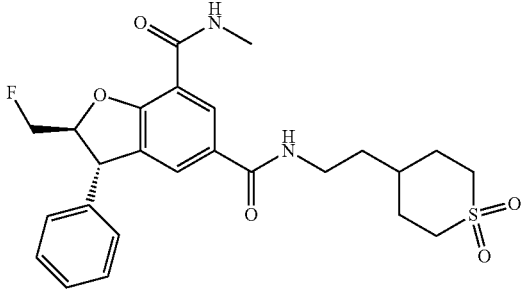 [SMILES: CNC(=O)c1cc(C(=O)NCCC2CCS(=O)(=O)CC2)cc2c1O[C@H](CF)[C@H]2c1ccccc1]

(Trans)-2-(fluoromethyl)-7-(methylcarbamoyl)-3-phenyl-2,3-dihydrobenzofuran-5-carboxylic acid (100 mg, 0.304 mmol), HATU (139 mg, 0.364 mmol) and DIPEA (0.159 mL, 0.911 mmol) were stirred in DMF (4 mL) at rt for 5 mins. 4-(2-Aminoethyl)tetrahydro-2H-thiopyran 1,1-dioxide (70.0 mg, 0.395 mmol) (commercially available, e.g. from Enamine) was added and the reaction stirred at rt for 1 h. The reaction was diluted with EtOAc and was washed with 10% w/w citric acid (aq) and 10% w/w LiCl (aq) dried using a hydrophobic frit and concentrated to a yellow gum. This gum was purified using silica gel column chromatography eluting with a gradient of 0-12% EtOH:EtOAc to give (trans)-N⁵-(2-(1,1-dioxidotetrahydro-2H-thiopyran-4-yl)ethyl)-2-(fluoromethyl)-N⁷-methyl-3-phenyl-2,3-dihydrobenzofuran-5,7-dicarboxamide (97 mg, 0.20 mmol, 65% yield) as a white solid.

LCMS (2 min Formic): Rt=0.89 min, [MH]+=489

Example 152: (2R,3S)—N⁷,2-dimethyl-N⁵-(2-(1-methyl-1H-pyrazol-4-yl)ethyl)-3-phenyl-2,3-dihydrobenzofuran-5,7-dicarboxamide

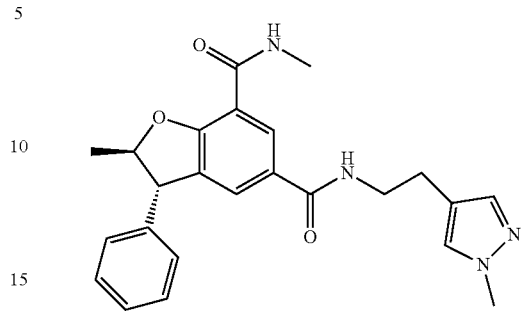

(Trans)-N⁷,2-dimethyl-N⁵-(2-(1-methyl-1H-pyrazol-4-yl)ethyl)-3-phenyl-2,3-dihydrobenzofuran-5,7-dicarboxamide (96 mg, 0.23 mmol) was purified by chiral HPLC. Analytical Method: Approx 0.5 mg was dissolved in 50% EtOH/Heptane (1 mL) and 20 uL injected on column, eluting with 30% EtOH/Heptane; flow=1.0 ml/min, wavelength 215 nm, 4. Column 4.6 mmid×25 cm Chiralcel OJ-H.

Preparative method: Approx 96 mg was dissolved in 2 mL EtOH. 2 mL of the solution was injected onto the column and eluted with 30% EtOH/Heptane; flow=30 mL/min, wavelength, 215 nm, 4. Column 30 mm×25 cm Chiralcel OJ-H (5 um). The fractions eluting between 9.5 and 14 mins were summed and concentrated to give (2S,3R)—N⁷,2-dimethyl-N⁵-(2-(1-methyl-1H-pyrazol-4-yl)ethyl)-3-phenyl-2,3-dihydrobenzofuran-5,7-dicarboxamide (48 mg, 0.12 mmol, 50% yield) as a white solid.

LCMS (method high pH): Rt 0.93 min, [MH]+=419

Example 153: (2R,3S)—N⁵-((1R,5S,6r)-3,3-difluorobicyclo[3.1.0]hexan-6-yl)-N⁷,2-dimethyl-3-phenyl-2,3-dihydrobenzofuran-5,7-dicarboxamide

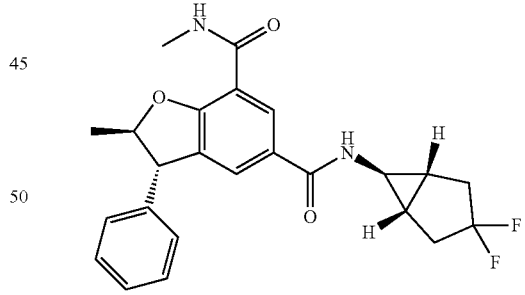

(Trans)-N⁵-((1R,5S,6r)-3,3-difluorobicyclo[3.1.0]hexan-6-yl)-N⁷,2-dimethyl-3-phenyl-2,3-dihydrobenzofuran-5,7-dicarboxamide (18 mg) was purified by chiral HPLC. The racemate was dissolved in EtOH (1.5 mL) with heating. Injection: 1.5 mL of the solution was injected onto the column (25% EtOH/heptane, flow rate=30 mL/min, detection wavelength=215 nm, 4. Ref 550, 100, Column 3 cm×25 cm Chiralpak AD-H (5 um), lot no. ADH13231). Total number of injections=1. Fractions from 14-17 min were bulked and labelled peak 1. The bulked pure fractions were concentrated in vacuo and then transferred to weighed flasks.

The fractions corresponding to peak 1 were collected to afford (2R,3S)—N⁵-((1R,5S,6r)-3,3-difluorobicyclo[3.1.0]hexan-6-yl)-N⁷,2-dimethyl-3-phenyl-2,3-dihydrobenzofuran-5,7-(6 mg)

LCMS (2 min Formic): Rt=1.10 min, [MH]+=427.

Example 154: (2S,3R)—N⁷,2-dimethyl-N⁵-(1-methyl-1H-pyrazol-4-yl)-3-phenyl-2,3-dihydrobenzofuran-5,7-dicarboxamide

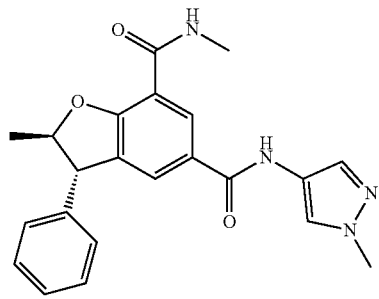

(trans)-N⁷,2-dimethyl-N⁵-(1-methyl-1H-pyrazol-4-yl)-3-phenyl-2,3-dihydrobenzofuran-5,7-dicarboxamide (54 mg) was purified by chiral HPLC. The racemate was dissolved in EtOH (7 mL). Injection: 0.5 mL of the solution was injected onto the column (50% EtOH/heptane, flow rate=20 mL/min, detection wavelength=280 nm, 4. Ref 400, 100, Column 2 cm×25 cm Regis Whekl-O1 [R,R] (5 um). Fractions from 15-19 min were bulked and concentrated to give: (2S,3R)—N⁷,2-dimethyl-N⁵-(1-methyl-1H-pyrazol-4-yl)-3-phenyl-2,3-dihydrobenzofuran-5,7-dicarboxamide (21 mg)

LCMS (2 min Formic): Rt=0.95 min, [MH]+=391.

Example 155: (2R,3S)—N⁵-(2-((S*)-4,4-difluoropiperidin-3-yl)ethyl)-N⁷,2-dimethyl-3-phenyl-2,3-dihydrobenzofuran-5,7-dicarboxamide

Example 156: (2R,3S)—N⁵-(2-((R*)-4,4-difluoropiperidin-3-yl)ethyl)-N⁷,2-dimethyl-3-phenyl-2,3-dihydrobenzofuran-5,7-dicarboxamide

Example 157: (2S,3R)—N⁵-(2-((S*)-4,4-difluoropiperidin-3-yl)ethyl)-N⁷,2-dimethyl-3-phenyl-2,3-dihydrobenzofuran-5,7-dicarboxamide

Example 158: (2S,3R)—N⁵-(2-((R*)-4,4-difluoropiperidin-3-yl)ethyl)-N⁷,2-dimethyl-3-phenyl-2,3-dihydrobenzofuran-5,7-dicarboxamide

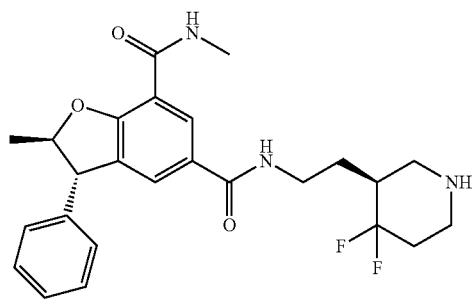

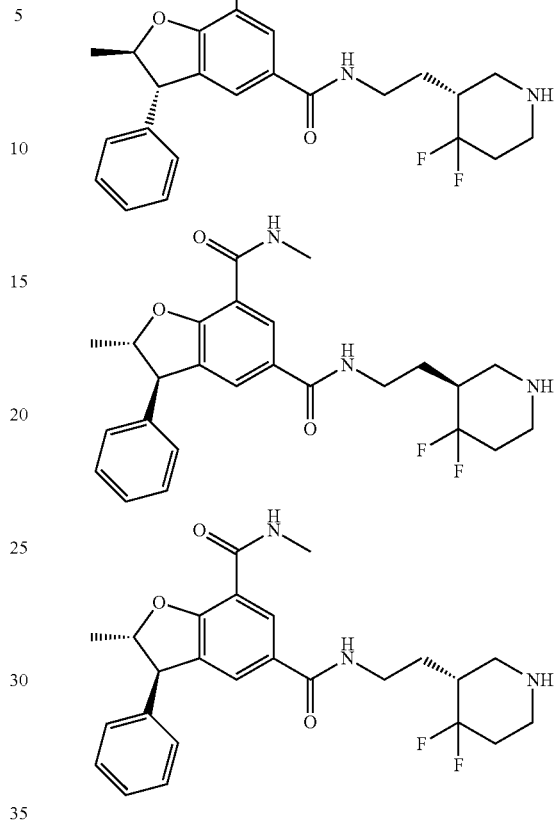

(Trans)-N⁵-(2-((+/−)-4,4-difluoropiperidin-3-yl)ethyl)-N⁷,2-dimethyl-3-phenyl-2,3-dihydrobenzofuran-5,7-dicarboxamide (30 mg) was purified by chiral HPLC. The racemate was dissolved in EtOH (1 mL). Injection: 1 mL of the solution was injected onto the column (50% EtOH/heptane+0.2% isopropylamine, flow rate=30 mL/min, detection wavelength=215 nm, 4. Ref 550, 100, Column 3 cm×25 cm Chiralpak IC Lot No IC10028-01 (5 um). Total injections=2. Fractions from 14-16 min were bulked and labelled peak 1. Fractions from 20-22 min were bulked and labelled peak 2. Fractions from 24-25.5 min were bulked and labelled peak 3. Fractions from 25.5-27 min were bulked and labelled mix. Fractions from 27-29 min were bulked and labelled peak 4. The bulked mixed fractions were concentrated in vacuo and reprocessed using the above method.

The fractions corresponding to peak 1 were collected and purified by MDAP (High pH) to afford (2R,3S)—N⁵-(2-((S*)-4,4-difluoropiperidin-3-yl)ethyl)-N⁷,2-dimethyl-3-phenyl-2,3-dihydrobenzofuran-5,7-dicarboxamide (6 mg)

LCMS (2 min High pH): Rt=0.98 min, [MH]+=458.

The fractions corresponding to peak 2 were collected to afford (2R,3S)—N⁵-(2-((R*)-4,4-difluoropiperidin-3-yl)ethyl)-N⁷,2-dimethyl-3-phenyl-2,3-dihydrobenzofuran-5,7-dicarboxamide (6 mg)

LCMS (2 min High pH): Rt=0.98 min, [MH]+=458.

The fractions corresponding to peak 1 were collected to afford (2S,3R)—N⁵-(2-((R*)-4,4-difluoropiperidin-3-yl)ethyl)-N⁷,2-dimethyl-3-phenyl-2,3-dihydrobenzofuran-5,7-dicarboxamide (7 mg)

LCMS (2 min High pH): Rt=0.98 min, [MH]+=458.

The fractions corresponding to peak 2 were collected to afford (2S,3R)—N⁵-(2-((R*)-4,4-difluoropiperidin-3-yl)ethyl)-N⁷,2-dimethyl-3-phenyl-2,3-dihydrobenzofuran-5,7-dicarboxamide (7 mg)

LCMS (2 min High pH): Rt=0.98 min, [MH]+=458

Example 159: (2S,3S)-2-(Fluoromethyl)-N⁵-((1S,2S)-2-(hydroxymethyl)cyclopropyl)-N⁷-methyl-3-phenyl-2,3-dihydrobenzofuran-5,7-dicarboxamide

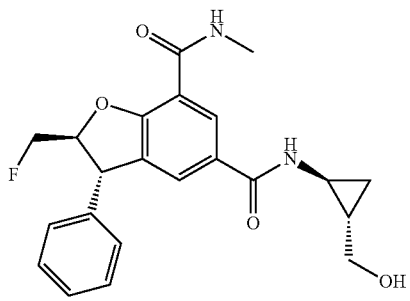 [SMILES: CNC(=O)c1cc(C(=O)N[C@H]2C[C@@H]2CO)cc2c1O[C@H](CF)[C@H]2c1ccccc1]

A solution of (2S,3S)-2-(fluoromethyl)-7-(methylcarbamoyl)-3-phenyl-2,3-dihydrobenzofuran-5-carboxylic acid (80 mg, 0.24 mmol) in DMF (5 mL) at rt was treated with ((1S,2S)-2-aminocyclopropyl)methanol hydrochloride (45.0 mg, 0.36 mmol), HATU (139 mg, 0.364 mmol) and DIPEA (0.127 mL, 0.729 mmol) and the resulting mixture was stirred at this temperature for 2 h then was concentrated in vacuo. The residue was taken up in EtOAc (10 mL) and the organic phase was washed with water then brine. The organic phase was dried over sodium sulphate, filtered through a hydrophobic frit and concentrated in vacuo. Purification of the residue by flash chromatography on silica gel (10 g column, gradient 5-100% (3:1 EtOAc:EtOH) in cyclohexane) gave (2S,3S)-2-(fluoromethyl)-N⁵-((1S,2S)-2-(hydroxymethyl)cyclopropyl)-N⁷-methyl-3-phenyl-2,3-dihydrobenzofuran-5,7-dicarboxamide (70 mg, 72%). The sample was purified by MDAP (formic method) to give (2S,3S)-2-(fluoromethyl)-N⁵-((1S,2S)-2-(hydroxymethyl)cyclopropyl)-N⁷-methyl-3-phenyl-2,3-dihydrobenzofuran-5,7-dicarboxamide (49 mg, 45%) as a cream solid.

LCMS (method high pH): Rt=0.83 min, [MH]+=399

Example 160: (2S,3S)-2-(Fluoromethyl)-N⁷-methyl-3-phenyl-N⁵-((1R,5S,6s)-3-propionyl-3-azabicyclo[3.1.0]hexan-6-yl)-2,3-dihydrobenzofuran-5,7-dicarboxamide

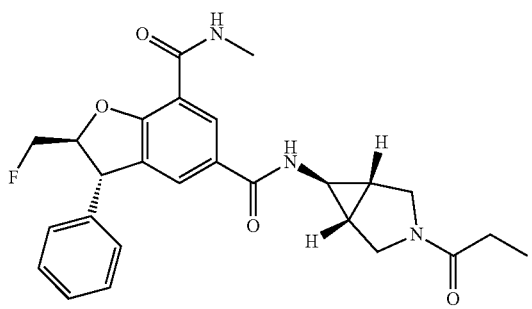 [SMILES: CCC(=O)N1C[C@@H]2[C@H](C1)[C@H]2NC(=O)c1cc(C(=O)NC)c2c(c1)[C@H](c1ccccc1)[C@@H](CF)O2]

A solution of (2S,3S)—N⁵-((1R,5S,6s)-3-azabicyclo[3.1.0]hexan-6-yl)-2-(fluoromethyl)-N⁷-methyl-3-phenyl-2,3-dihydrobenzofuran-5,7-dicarboxamide (132 mg, 0.323 mmol) in DCM (5 mL) was treated at rt with DIPEA (0.113 mL, 0.646 mmol) then propionyl chloride (0.056 mL, 0.65 mmol). The resulting solution was stirred 1h at this temperature then was treated with water. The layers were separated and the aqueous phase was extracted twice with DCM. The combined organics were filtered through a hydrophobic frit and concentrated in vacuo. Purification of the residue by flash chromatography on silica gel (10 g column, gradient: 0 to 70% of [25% (v/v) EtOH in ethyl acetate] in cyclohexane) gave (2S,3S)-2-(fluoromethyl)-N⁷-methyl-3-phenyl-N⁵-((1R,5S,6s)-3-propionyl-3-azabicyclo[3.1.0]hexan-6-yl)-2,3-dihydrobenzofuran-5,7-dicarboxamide (91 mg, 61%) as a white solid.

LCMS (method formic): Retention time 0.89 min, [M+H]+=466

Example 161: (Trans)-N⁵-((1R,5S,6s)-3-Oxabicyclo[3.1.0]hexan-6-yl)-3-(3-(2-methoxyethoxy)phenyl)-N⁷,2-dimethyl-2,3-dihydrobenzofuran-5,7-dicarboxamide

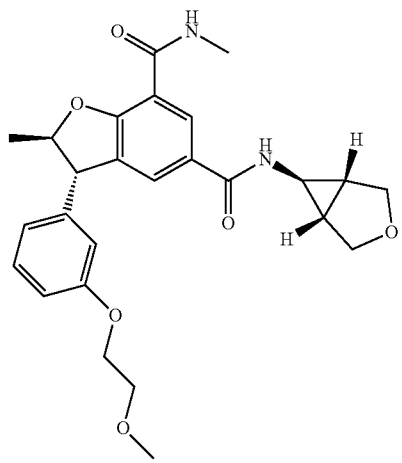 [SMILES: CNC(=O)c1cc(C(=O)N[C@H]2[C@@H]3COC[C@@H]32)cc2c1O[C@H](C)[C@H]2c1cccc(OCCOC)c1]

A microwave vial was charged with (trans)-N⁵-((1R,5S,6r)-3-oxabicyclo[3.1.0]hexan-6-yl)-3-(3-(2-methoxyethoxy)phenyl)-N⁷,2-dimethyl-2,3-dihydrobenzofuran-5,7-dicarboxamide (198 mg, 0.424 mmol), DBU (0.128 mL, 0.849 mmol) then was filled with DMF (2 mL) and the resulting mixture was stirred under microwave irradiation at 100° C. for 1 h, then was cooled to rt. The reaction was treated with further DBU (0.128 mL, 0.849 mmol), was stirred under microwave irradiations at 120° C. for 1 h, then was cooled to rt. The reaction mixture was diluted with water and was extracted with EtOAc. The organic layer was washed with a 10% w/w LiCl (aq), dried using a hydrophobic frit and concentrated in vacuo. Purification of the residue by MDAP (formic method) gave (trans)-N⁵-((1R,5S,6r)-3-oxabicyclo[3.1.0]hexan-6-yl)-3-(3-(2-methoxyethoxy)phenyl)-N⁷,2-dimethyl-2,3-dihydrobenzofuran-5,7-dicarboxamide (32 mg, 16%) as a white solid.

LCMS (method formic): Retention time 0.93 min, [M+H]+=467

Example 162 and 163: (2R,3S)—N⁵-(3-((S*)-3,3-difluoropiperidin-4-yl)propyl)-N⁷,2-dimethyl-3-phenyl-2,3-dihydrobenzofuran-5,7-dicarboxamide and (2R,3S)—N⁵-(3-((R*)-3,3-difluoropiperidin-4-yl)propyl)-N⁷,2-dimethyl-3-phenyl-2,3-dihydrobenzofuran-5,7-dicarboxamide

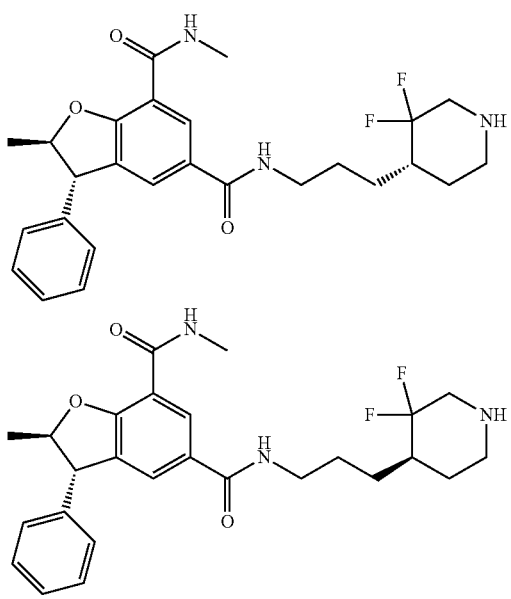

(+/−)(2R,3S)—N⁵-(3-(3,3-difluoropiperidin-4-yl)propyl)-N⁷,2-dimethyl-3-phenyl-2,3-dihydrobenzofuran-5,7-dicarboxamide (75 mg, 0.16 mmol) was purified by chiral chromatography.

Preparative method: This was done in two stages: Two pairs of isomers were isolated using chiralpak IC then individual mixtures were purified in a second round of chromatography using chiralpak IE and IF. Method 1 (Resolution of pair of isomers) used Chiralpak IC (250×4.6 mm, 5 micron) at a flow of 1 mL/min. Detection was performed using UV diode array at 250 nm (bandwidth 40 nm, reference 400 nm bandwidth 100 nm). Eluant consisted of mobile phase A: heptane (containing 0.2% v/v isopropylamine) and mobile phase B: EtOH (containing 0.2% v/v isopropylamine). The isocratic method used a 50:50 mobile phase A: mobile phase B with a runtime of 30 min. The fastest running pair of isomers were then further separated using Method 2: the chiral column used was Chiralpak IE (250×4.6 mm, 5 micron) at a flowrate of 1 mL/min. Detection was performed using UV diode array at 250 nm (bandwidth 40 nm, reference 400 nm bandwidth 100 nm). Eluant consisted of mobile phase A: heptane (containing 0.2% v/v isopropylamine) and mobile phase B: EtOH (containing 0.2% v/v isopropylamine). The isocratic method used a 50:50 mobile phase A: mobile phase B with a runtime of 50 min. (2R,3S)—N⁵-(3-((S*)-3,3-difluoropiperidin-4-yl)propyl)-N⁷,2-dimethyl-3-phenyl-2,3-dihydrobenzofuran-5,7-dicarboxamide was the slowest running enantiomer obtained—as a white solid—from this second purification (13 mg, 69%).

LCMS (method formic): Retention time 0.70 min, [M+H]⁺=472

(2R,3S)—N⁵-(3-((S*)-3,3-difluoropiperidin-4-yl)propyl)-N⁷,2-dimethyl-3-phenyl-2,3-dihydrobenzofuran-5,7-dicarboxamide was the fastest running enantiomer obtained—as a white solid—from this second purification (11 mg, 59%).

LCMS (method formic): Retention time 0.70 min, [M+H]⁺=472

Example 164: (2R,3R)-2-(Fluoromethyl)-N⁷-methyl-3-phenyl-N⁵-((1R,5S,6s)-3-propionyl-3-azabicyclo[3.1.0]hexan-6-yl)-2,3-dihydrobenzofuran-5,7-dicarboxamide

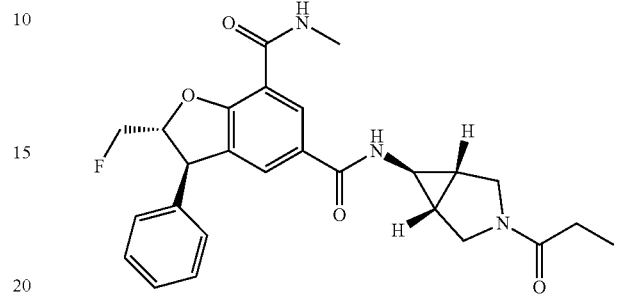

(2R,3R)—N⁵-((1R,5S,6s)-3-azabicyclo[3.1.0]hexan-6-yl)-2-(fluoromethyl)-N⁷-methyl-3-phenyl-2,3-dihydrobenzofuran-5,7-dicarboxamide (95 mg, 0.23 mmol) and propionic anhydride (500 µL, 0.232 mmol) were stirred at rt for 1 h. The reaction was diluted with water and extracted with EtOAc. The organic layer was washed with brine and dried using a hydrophobic frit and concentrated to give a colourless oil. This oil was purified using silica gel column chromatography eluting with a gradient of 0-12% EtOH:EtOAc to give (2R,3R)-2-(fluoromethyl)-N⁷-methyl-3-phenyl-N⁵-((1R,5S,6s)-3-propionyl-3-azabicyclo[3.1.0]hexan-6-yl)-2,3-dihydrobenzofuran-5,7-dicarboxamide (75 mg, 0.161 mmol, 69.4% yield) as a white solid.

Example 165: (2R,3S)—N⁵-((1R,5S,6r)-3-oxabicyclo[3.1.0]hexan-6-yl)-3-(3-(2-hydroxyethoxy)phenyl)-N⁷,2-dimethyl-2,3-dihydrobenzofuran-5,7-dicarboxamide

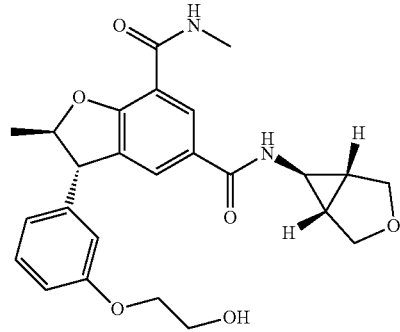 [SMILES: CNC(=O)c1cc(C(=O)N[C@H]2[C@@H]3COC[C@@H]32)cc2c1O[C@H](C)[C@H]2c1cccc(OCCO)c1]

(Trans)-2-(fluoromethyl)-N⁷-methyl-3-phenyl-N⁵-(pyrimidin-5-yl)-2,3-dihydrobenzofuran-5,7-dicarboxamide (37 mg, 0.082 mmol) was purified by chiral chromatography.

Analytical Method: Approximatively 0.5 mg of material was dissolved in 50% EtOH in heptane (1 mL) and 20 uL were injected onto the column, eluting with 30% EtOH (+0.2% isopropylamine) in heptane at a flow f=1.0 mL/min; Detection method: wavelength 215 nm. Column 4.6 mmid×25 cm Chiralcel OD-H Preparative Method: Approximatively 37 mg of material were dissolved in 1 mL of EtOH. This solution was injected onto the column, eluting with 30% EtOH (+0.2% isopropylamine) in heptane (+0.2% isopropylamine), at a flow f=30 mL/min, wavelength, 215 nm. Column used was 30 mm×25 cm Chiralcel OD-H (5 um). The same purification process was performed twice for the slowest isomer (2R,3R)-2-(Fluoromethyl)-N$^7$-methyl-3-phenyl-N$^5$-(pyrimidin-5-yl)-2,3-dihydrobenzofuran-5,7-dicarboxamide to increase enantiomeric excess, giving 10 mg (54%) of white solid.

LCMS (method formic): Retention time 0.80 min, [M+H]$^+$=453

Example 166: (2S,3S)-2-(Fluoromethyl)-N$^7$-methyl-N$^5$-(1-methyl-1H-1,2,4-triazol-3-yl)-3-phenyl-2,3-dihydrobenzofuran-5,7-dicarboxamide

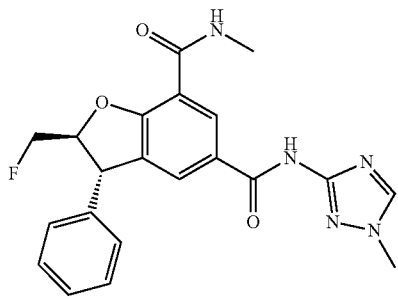 [SMILES: CNC(=O)c1cc(C(=O)Nc2ncn(C)n2)cc2c1O[C@H](CF)[C@H]2c1ccccc1]

(2S,3S)-2-(Fluoromethyl)-7-(methylcarbamoyl)-3-phenyl-2,3-dihydrobenzofuran-5-carboxylic acid (80 mg, 0.24 mmol) and HATU (111 mg, 0.292 mmol) were dissolved in DMSO (0.85 mL), and the resulting solution was treated with DIPEA (0.127 mL, 0.729 mmol) and the reaction mixture was left to stir at rt for 5 min. 1-Methyl-1H-1,2,4-triazol-3-amine (23.8 mg, 0.243 mmol) was added and the reaction was left to stir for 1 h at rt. Further HATU (111 mg, 0.292 mmol) and DIPEA (0.127 mL, 0.729 mmol) were added and the reaction mixture was left to stir for 5 min then 1-methyl-1H-1,2,4-triazol-3-amine (23.8 mg, 0.243 mmol) was added and reaction mixture stirred for 2 h at rt. Further HATU (111 mg, 0.292 mmol) and DIPEA (0.127 mL, 0.729 mmol) were added and the reaction mixture was left to stir for 5 min then 1-methyl-1H-1,2,4-triazol-3-amine (23.8 mg, 0.243 mmol) was added and reaction mixture stirred for 2 h at rt and was then left to stand overnight. HATU (111 mg, 0.292 mmol) and DIPEA (0.127 mL, 0.729 mmol) were again added and the reaction mixture was left to stir for 5 min then 1-methyl-1H-1,2,4-triazol-3-amine (23.8 mg, 0.243 mmol) was added and reaction mixture stirred for 3 h then left to stand over the weekend. The reaction mixture had separated and become solid and not all of the reactants seemed to have gone into solution therefore further DMSO (1 mL) was added to the reaction mixture and it was left to stir at rt for 3 h. 1-Methyl-1H-1,2,4-triazol-3-amine (23.8 mg, 0.243 mmol) was added and the reaction mixture was left to stir at rt for 1 h then left to stand overnight. Further HATU (111 mg, 0.292 mmol), DIPEA (0.127 mL, 0.729 mmol) and 1-methyl-1H-1,2,4-triazol-3-amine (23.8 mg, 0.243 mmol) were added and the reaction left to stir at rt for 1 h. Further HATU (111 mg, 0.292 mmol), DIPEA (0.127 mL, 0.729 mmol) and 1-methyl-1H-1,2,4-triazol-3-amine (23.8 mg, 0.243 mmol) were added and the reaction left to stir at rt for 1 h. The reaction mixture was then purified by MDAP (method high pH) to give (2S,3S)-2-(fluoromethyl)-N$^7$-methyl-N$^5$-(1-methyl-1H-1,2,4-triazol-3-yl)-3-phenyl-2,3-dihydrobenzofuran-5,7-dicarboxamide (24.8 mg 25%) as a white solid.

LCMS (method formic): Retention time 0.79 min, [M+H]$^+$=410

Example 167: (2S,3S)—N$^5$-(3-((2r,5S)-5-Amino-1,3-dioxan-2-yl)propyl)-2-(fluoromethyl)-N$^7$-methyl-3-phenyl-2,3-dihydrobenzofuran-5,7-dicarboxamide

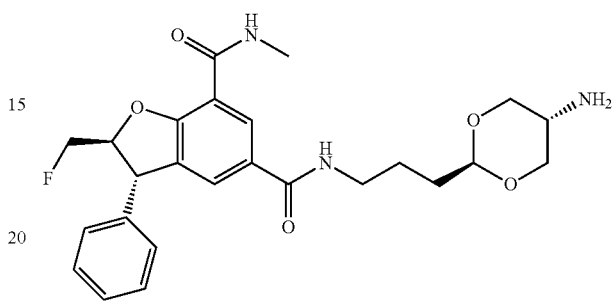

To a suspension of (2S,3S)—N$^5$-(3-((2r,5S)-5-(1,3-dioxoisoindolin-2-yl)-1,3-dioxan-2-yl)propyl)-2-(fluoromethyl)-N$^7$-methyl-3-phenyl-2,3-dihydrobenzofuran-5,7-dicarboxamide (48 mg, 0.080 mmol) in EtOH (2 mL) was added hydrazine hydrate (3.9 μL, 0.080 mmol) and the resulting suspension was stirred at 50° C. for 23 h. Further EtOH (1 mL) was added and the reaction was left to stir at 50° C. for a further 24 h. Hydrazine hydrate (3.9 μL, 0.080 mmol) was added and the reaction left to stir at 50° C. over the weekend. Further hydrazine hydrate (39 μL, 0.80 mmol) were added to the reaction mixture and the temperature lowered to 40° C. The reaction mixture was stirred for 8 h then was allowed to cool to rt and left to stand overnight. The volatiles were evaporated under a stream of N$_2$. The residue was purified by MDAP (high pH) to give (2S,3S)—N$^5$-(3-((2r,5S)-5-Amino-1,3-dioxan-2-yl)propyl)-2-(fluoromethyl)-N$^7$-methyl-3-phenyl-2,3-dihydrobenzofuran-5,7-dicarboxamide (21.8 mg, 58%) as a beige solid.

LCMS (method formic): Retention time 0.63 min, [M+H]$^+$=472

Example 168: (2S,3S)-2-(Fluoromethyl)-N$^7$-methyl-N$^5$-(1-methyl-1H-1,2,3-triazol-4-yl)-3-phenyl-2,3-dihydrobenzofuran-5,7-dicarboxamide

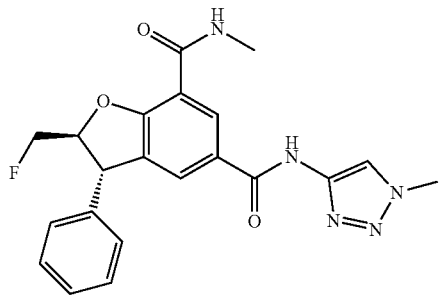 [SMILES: CNC(=O)c1cc(C(=O)Nc2cn(C)nn2)cc2c1O[C@H](CF)[C@H]2c1ccccc1]

A solution of (2S,3S)-2-(fluoromethyl)-7-(methylcarbamoyl)-3-phenyl-2,3-dihydrobenzofuran-5-carboxylic acid (80 mg, 0.24 mmol) and HATU (111 mg, 0.292 mmol) in DMSO (0.85 mL) was treated at rt with DIPEA (0.127 mL, 0.729 mmol) and the reaction mixture was stirred at this temperature for 5 min then was treated with 1-methyl-1H-1,2,3-triazol-4-amine (23.8 mg, 0.243 mmol). The resulting mixture was stirred for 1 h at rt. Further HATU (111 mg, 0.292 mmol) and DIPEA (0.127 mL, 0.729 mmol) were then added and the reaction mixture left to stir at rt for 5 min before being treated with 1-methyl-1H-1,2,3-triazol-4-amine (23.8 mg, 0.243 mmol). The reaction mixture was then stirred for 1 h at rt then was left to stand over the weekend. It was then purified by MDAP (method high pH) to give (2S,3S)-2-(fluoromethyl)-$N^7$-methyl-$N^5$-(1-methyl-1H-1,2,3-triazol-4-yl)-3-phenyl-2,3-dihydrobenzofuran-5,7-dicarboxamide (69.5 mg, 70%) as a yellow solid.

LCMS (method formic): Retention time 0.89 min, [M+H]$^+$=410

Example 169: (2S,3S)—$N^5$-(2-((2r,5S)-5-amino-1,3-dioxan-2-yl)ethyl)-2-(fluoromethyl)-$N^7$-methyl-3-phenyl-2,3-dihydrobenzofuran-5,7-dicarboxamide

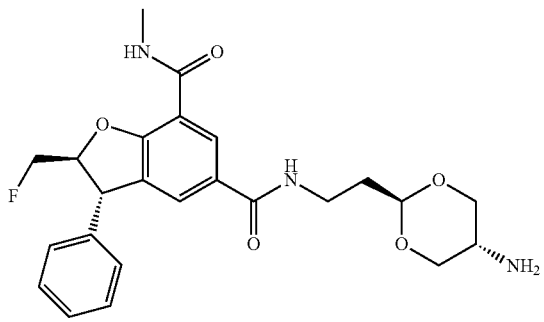 [SMILES: CNC(=O)c1cc(C(=O)NCC[C@H]2OC[C@H](N)CO2)cc2c1O[C@H](CF)[C@H]2c1ccccc1]

To a suspension of (2S,3S)—$N^5$-(2-(5-(1,3-dioxoisoindolin-2-yl)-1,3-dioxan-2-yl)ethyl)-2-(fluoromethyl)-$N^7$-methyl-3-phenyl-2,3-dihydrobenzofuran-5,7-dicarboxamide (145 mg, 0.247 mmol) in EtOH (10 mL) was added hydrazine hydrate (0.120 mL, 2.47 mmol) and the resulting solution was stirred at 50° C. for 20 h then was allowed to cool to rt. The reaction was concentrated to give a sticky yellow solid which was purified by MDAP (method formic) to give (2S,3S)—$N^5$-(2-((2r,5S)-5-amino-1,3-dioxan-2-yl)ethyl)-2-(fluoromethyl)-$N^7$-methyl-3-phenyl-2,3-dihydrobenzofuran-5,7-dicarboxamide (32.4 mg, 29%) as a colourless gum.

LCMS (method formic): Retention time 0.61 min, [M+H]$^+$=458

Example 170: (2S,3S)-2-(Fluoromethyl)-$N^7$-methyl-3-phenyl-$N^5$-(pyridazin-4-yl)-2,3-dihydrobenzofuran-5,7-dicarboxamide

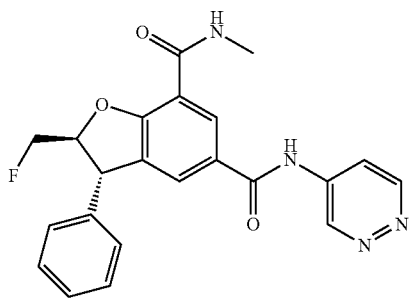 [SMILES: CNC(=O)c1cc(C(=O)Nc2ccnnc2)cc2c1O[C@H](CF)[C@H]2c1ccccc1]

A solution of (2S,3S)-2-(fluoromethyl)-7-(methylcarbamoyl)-3-phenyl-2,3-dihydrobenzofuran-5-carboxylic acid (80 mg, 0.24 mmol) and HATU (111 mg, 0.292 mmol) in DMSO (0.85 mL) was treated at rt with DIPEA (0.127 mL, 0.729 mmol) and the reaction mixture was stirred at this temperature for 5 min. Pyridazin-4-amine (23.1 mg, 0.243 mmol) was then added and the reaction was stirred 1 h at rt. Further HATU (111 mg, 0.292 mmol) and DIPEA (0.127 mL, 0.729 mmol) were then added to the reaction and the resulting mixture was left to stir at rt for 5 min. Pyridazin-4-amine (23.1 mg, 0.243 mmol) was then added and the reaction mixture was stirred 1 h at rt. The mixture was then purified by MDAP (method high pH) to give (2S,3S)-2-(fluoromethyl)-$N^7$-methyl-3-phenyl-$N^5$-(pyridazin-4-yl)-2,3-dihydrobenzofuran-5,7-dicarboxamide (65.2 mg, 66%) as an orange gum LCMS (method formic): Retention time 0.83 min, [M+H]$^+$=407

Example 171: (2R,3S)—$N^5$-((1R,5S,6r)-3-oxabicyclo[3.1.0]hexan-6-yl)-3-(3-(2-methoxyethoxy)phenyl)-$N^7$,2-dimethyl-2,3-dihydrobenzofuran-5,7-dicarboxamide

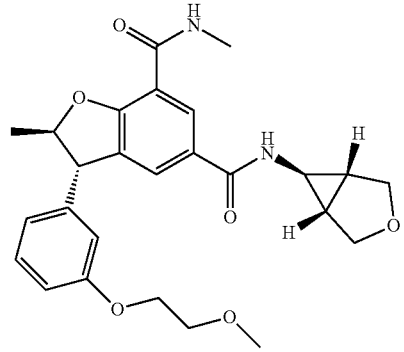 [SMILES: CNC(=O)c1cc(C(=O)N[C@H]2[C@@H]3COC[C@@H]32)cc2c1O[C@H](C)[C@H]2c1cccc(OCCOC)c1]

(trans)-$N^5$-((1R,5S,6r)-3-oxabicyclo[3.1.0]hexan-6-yl)-3-(3-(2-methoxyethoxy)phenyl)-$N^7$,2-dimethyl-2,3-dihydrobenzofuran-5,7-dicarboxamide (30 mg, 0.064 mmol) was submitted for chiral separation:

Analytical Method: Approx 0.5 mg of substance were dissolved in 50% EtOH in heptane (1 mL) and 20 uL were injected on column. Eluant: 30% EtOH in Heptane, flow=1.0 mL/min, wavelength 215 nm; Column 4.6 mmid×25 cm Chiralcel OD-H Preparative Method: Approx 30 mg of substance were dissolved in 1 mL EtOH and this was injected onto the column. Eluant: 30% EtOH in heptane, flow=30 mL/min, wavelength 215 nm; Column 30 mm×25 cm Chiralcel OD-H (5 um).

(2R,3S)—$N^5$-((1R,5S,6r)-3-oxabicyclo[3.1.0]hexan-6-yl)-3-(3-(2-methoxyethoxy)phenyl)-$N^7$,2-dimethyl-2,3-dihydrobenzofuran-5,7-dicarboxamide was the fastest eluting isomer and 15 mg (100%) were obtained as white solid.

LCMS (method formic): Retention time 0.93 min, [M+H]$^+$=467

Example 172: (2S,3S)-2-(Fluoromethyl)-N⁷-methyl-N⁵-(4-methyl-4H-1,2,4-triazol-3-yl)-3-phenyl-2,3-dihydrobenzofuran-5,7-dicarboxamide

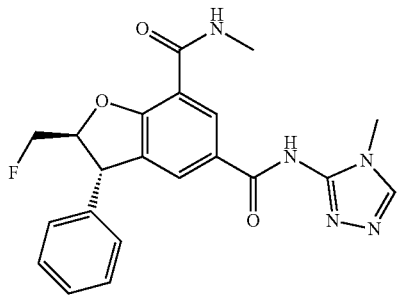 [SMILES: CNC(=O)c1cc(C(=O)Nc2nncn2C)cc2c1O[C@H](CF)[C@H]2c1ccccc1]

A solution of (2S,3S)-2-(fluoromethyl)-7-(methylcarbamoyl)-3-phenyl-2,3-dihydrobenzofuran-5-carboxylic acid (80 mg, 0.24 mmol) and HATU (111 mg, 0.292 mmol) in DMSO (0.85 mL) was treated at rt with DIPEA (0.127 mL, 0.729 mmol) and the reaction mixture was stirred at rt for 5 min before 4-methyl-4H-1,2,4-triazol-3-amine (23.8 mg, 0.243 mmol) was added. The resulting mixture was stirred at rt for 1 h. Further HATU (111 mg, 0.292 mmol) and DIPEA (0.127 mL, 0.729 mmol) were added and the reaction mixture left to stir at rt for 5 min then 4-methyl-4H-1,2,4-triazol-3-amine (23.8 mg, 0.243 mmol) was added and the reaction left to stir at rt for 1 h. The reaction mixture was then diluted with water and the aqueous phase was washed with DCM. The organics were dried using an hydrophobic frit and concentrated in vacuo. Purification of the residue by MDAP (method high pH) gave (2S,3S)-2-(fluoromethyl)-N⁷-methyl-N⁵-(4-methyl-4H-1,2,4-triazol-3-yl)-3-phenyl-2,3-dihydrobenzofuran-5,7-dicarboxamide (5.8 mg, 6%) as a pale orange solid.

LCMS (method formic): Retention time 0.81 min, [M+H]⁺=410

Example 173: (2S,3S)—N⁵-((1R,5S,6r)-3-oxabicyclo[3.1.0]hexan-6-yl)-N⁷-ethyl-2-(fluoromethyl)-3-phenyl-2,3-dihydrobenzofuran-5,7-dicarboxamide

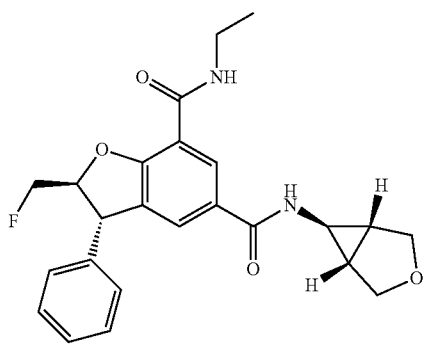 [SMILES: CCNC(=O)c1cc(C(=O)N[C@H]2[C@@H]3COC[C@@H]32)cc2c1O[C@H](CF)[C@H]2c1ccccc1]

A suspension of (2S,3S)-5-(((1R,5S,6r)-3-oxabicyclo[3.1.0]hexan-6-yl)carbamoyl)-2-(fluoromethyl)-3-phenyl-2,3-dihydrobenzofuran-7-carboxylic acid (21 mg, 0.053 mmol) in DCM (10 mL) was treated at rt with NEt₃ (0.015 mL, 0.11 mmol) and HATU (26 mg, 0.069 mmol), followed by ethanamine (0.053 mL, 0.11 mmol) and the resulting mixture was stirred for 2 h at this temperature, then was washed with water, dried using an hydrophobic frit and concentrated in vacuo. Purification of the residue by MDAP (method formic) gave (2S*,3S*)—N⁵-((1R,5S,6r)-3-oxabicyclo[3.1.0]hexan-6-yl)-N⁷-ethyl-2-(fluoromethyl)-3-phenyl-2,3-dihydrobenzofuran-5,7-dicarboxamide (14 mg, 62%) as a colourless solid.

LCMS (method high pH): Retention time 0.97 min, [M+H]⁺=425

Example 174: (2S,3S)-2-(Fluoromethyl)-N⁷-methyl-N⁵-(2-methyl-2H-tetrazol-5-yl)-3-phenyl-2,3-dihydrobenzofuran-5,7-dicarboxamide

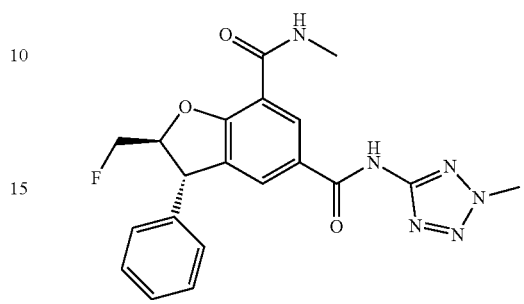

A solution of (2S,3S)-2-(fluoromethyl)-7-(methylcarbamoyl)-3-phenyl-2,3-dihydrobenzofuran-5-carboxylic acid (80 mg, 0.24 mmol) in DCM (1 mL) was treated at rt with thionyl chloride (28.9 mg, 0.243 mmol) and the resulting mixture was stirred at 50° C. for 4 h. Further thionyl chloride (28.9 mg, 0.243 mmol) was then added and the reaction was stirred at 70° C. for 2 h then was cooled to rt and concentrated in vacuo. The residue was co-evaporated with toluene. The residue was then dissolved in DMF (1 mL) and the solution was treated at rt with 2-methyl-2H-tetrazol-5-amine (24.1 mg, 0.243 mmol) and DIPEA (0.042 mL, 0.24 mmol) then was stirred overnight at this temperature. Further 2-methyl-2H-tetrazol-5-amine (48.1 mg, 0.486 mmol) and DIPEA (0.084 mL, 0.486 mmol) were added and the resulting mixture was stirred at 50° C. for 2 h then was cooled to rt and concentrated in vacuo. The residue was purified by MDAP (method formic) to give (2S,3S)-2-(fluoromethyl)-N⁷-methyl-N⁵-(2-methyl-2H-tetrazol-5-yl)-3-phenyl-2,3-dihydrobenzofuran-5,7-dicarboxamide (80 mg, 80%) as a white solid.

LCMS (method formic): Retention time 0.75 min, [M+H]⁺=411

Example 175: (2S,3S)—N⁵-((1R,5S,6r)-3-oxabicyclo[3.1.0]hexan-6-yl)-N⁷-cyclopropyl-2-(fluoromethyl)-3-phenyl-2,3-dihydrobenzofuran-5,7-dicarboxamide

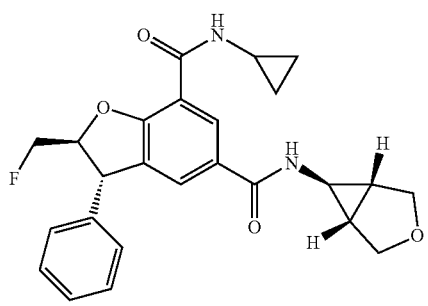 [SMILES: O=C(N[C@H]1[C@@H]2COC[C@@H]21)c1cc(C(=O)NC2CC2)c2c(c1)[C@H](c1ccccc1)[C@@H](CF)O2]

(2S,3S)-5-((1R,5S,6r)-3-oxabicyclo[3.1.0]hexan-6-ylcarbamoyl)-2-(fluoromethyl)-3-phenyl-2,3-dihydrobenzofuran-7-carboxylic acid (50 mg, 0.13 mmol) in DMF (1 mL) at rt was treated with DIPEA (0.066 mL, 0.38 mmol), then HATU (71.8 mg, 0.189 mmol) and the reaction was stirred at this temperature for 5 min then was treated with cyclopropylamine (9.76 µL, 0.138 mmol). The mixture was stirred at rt for 1 h then was concentrated in vacuo. The residue was partitioned between ethyl acetate and sat. NaHCO₃ (aq) and the layers were separated. The organic phase was washed with a 2N HCl (aq) then brine, was dried with Na₂SO₄, and concentrated in vacuo. Purification of the residue obtained by MDAP (method formic) gave (2S,3S)—$N^5$-((1R,5S,6r)-3-oxabicyclo[3.1.0]hexan-6-yl)-$N^7$-cyclopropyl-2-(fluoromethyl)-3-phenyl-2,3-dihydrobenzofuran-5,7-dicarboxamide (34.7 mg, 60%) as a white solid.

LCMS (method formic): Retention time 0.96 min, [M+H]⁺=437

Example 176: (2R,3S)—$N^5$-((1R,5S,6r)-3-oxabicyclo[3.1.0]hexan-6-yl)-3-(3-(2-hydroxyethoxy)phenyl)-$N^7$,2-dimethyl-2,3-dihydrobenzofuran-5,7-dicarboxamide

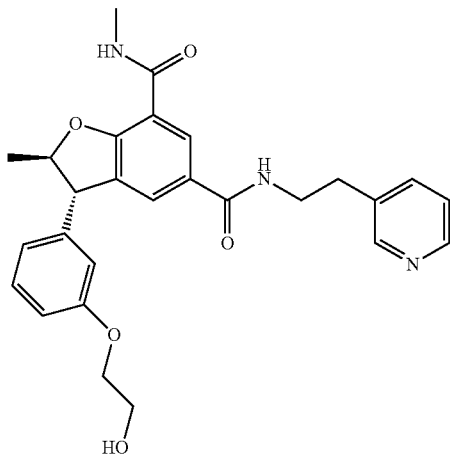 [SMILES: CNC(=O)c1cc(C(=O)NCCc2cccnc2)cc2c1O[C@H](C)[C@H]2c1cccc(OCCO)c1]

(Trans)-3-(3-(2-hydroxyethoxy)phenyl)-$N^7$,2-dimethyl-$N^5$-(2-(pyridin-3-yl)ethyl)-2,3-dihydrobenzofuran-5,7-dicarboxamide (25 mg) was purified by chiral HPLC. The racemate was dissolved in EtOH (1 mL) with heating. Injection: 1 mL of the solution was injected onto the column (50% EtOH [+0.2% isopropylamine]/heptane [+0.2% isopropylamine], flow rate=30 mL/min, detection wavelength=215 nm, 4. Ref 550, 100, Column 30 mm×25 cm Chiralcpak AD-H (5 μm), lot no. ADH13231). Fractions from 23-31 min were bulked to afford (2R,3S)-3-(3-(2-hydroxyethoxy)phenyl)-$N^7$,2-dimethyl-$N^5$-(2-(pyridin-3-yl)ethyl)-2,3-dihydrobenzofuran-5,7-dicarboxamide (7.0 mg, 0.015 mmol, 28% yield)

LCMS (2 min High pH): Rt=0.83 min, [MH]+=476.

Example 177: (Trans)-$N^5$-((1R,5S,6r)-3,3-difluorobicyclo[3.1.0]hexan-6-yl)-2-(fluoromethyl)-N7-methyl-3-phenyl-2,3-dihydrobenzofuran-5,7-dicarboxamide

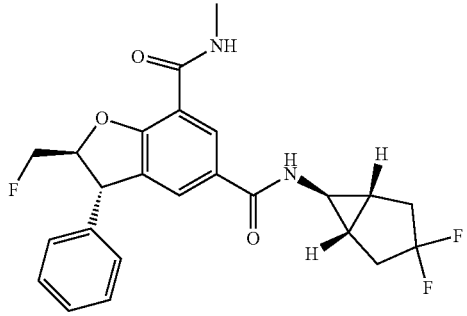 [SMILES: CNC(=O)c1cc(C(=O)N[C@H]2[C@@H]3CC(F)(F)C[C@@H]32)cc2c1O[C@H](CF)[C@H]2c1ccccc1]

(Trans)-2-(Fluoromethyl)-7-(methylcarbamoyl)-3-phenyl-2,3-dihydrobenzofuran-5-carboxylic acid (50 cmg, 0.15 mmol) was dissolved in DCM (10 mL) and Et₃N (0.042 mL, 0.30 mmol) and HATU (69.3 mg, 0.182 mmol) were added, followed by (1R,5S,6r)-3,3-difluorobicyclo[3.1.0]hexan-6-amine hydrochloride (30 mg, 0.18 mmol). The mixture was stirred for 1 h at rt, then washed with water, dried and evaporated in vacuo and the resulting pale yellow gum was purified using silica gel column chromatography eluting with a gradient of 0-100% EtOAc:cyclohexane to give (trans)-$N^5$-((1R,5S,6r)-3,3-difluorobicyclo[3.1.0]hexan-6-yl)-2-(fluoromethyl)-$N^7$-methyl-3-phenyl-2,3-dihydrobenzofuran-5,7-dicarboxamide (43 mg, 0.097 mmol, 64% yield) as a colourless foam.

LCMS (method formic): Rt=1.05 min, [MH]⁺=445

Example 178: (Trans)-2-(fluoromethyl)-$N^7$-methyl-$N^5$-((trans)-2-(2-morpholinoethyl)cyclopropyl)-3-phenyl-2,3-dihydrobenzofuran-5,7-dicarboxamide

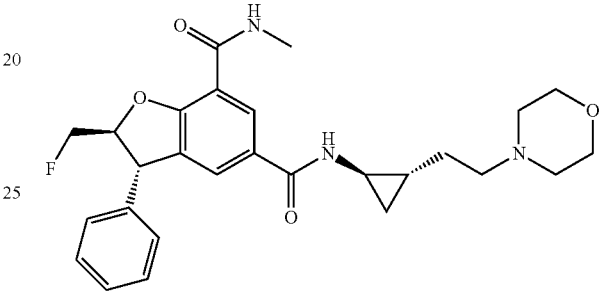

2-(Fluoromethyl)-$N^5$-((1R,2S)-2-(2-hydroxyethyl)cyclopropyl)-$N^7$-methyl-3-phenyl-2,3-dihydrobenzofuran-5,7-dicarboxamide (70 mg, 0.17 mmol) and dess-martin periodinane (144 mg, 0.339 mmol) were stirred in DCM (5 mL) at rt for 16 h. The reaction was washed with sat NaHCO₃ (aq) dried using a hydrophobic frit and concentrated to a yellow solid. The solid was diluted with DCM (5 mL) and treated with morpholine (0.030 mL, 0.34 mmol) and sodium triacetoxyborohydride (180 mg, 0.849 mmol) and stirred at rt for 1 h. The reaction was stood at rt for 9 days. The reaction was treated with water and extracted with EtOAc, the organic layer was washed with brine, dried using a hydrophobic frit and concentrated to brown oil. This oil was purified using a MDAP (formic) to give (2S,3S)-2-(fluoromethyl)-$N^7$-methyl-$N^5$-((1R,2R)-2-(2-morpholinoethyl)cyclopropyl)-3-phenyl-2,3-dihydrobenzofuran-5,7-dicarboxamide (5 mg, 6% yield) as a yellow oil.

LCMS (method formic): Rt 0.63 min, [MH]⁺=482

Example 179: (Trans)-2-(fluoromethyl)-$N^7$-methyl-$N^5$-(1S,2S)-2-methylcyclopropyl)-3-phenyl-2,3-dihydrobenzofuran-5,7-dicarboxamide

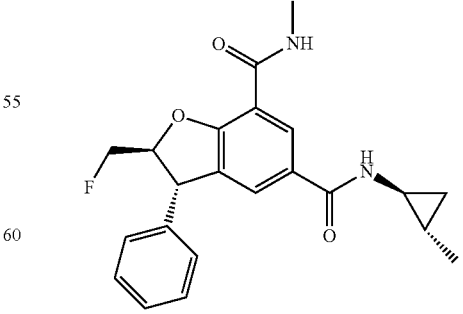

(Trans)-5-bromo-2-(fluoromethyl)-N-methyl-3-phenyl-2,3-dihydrobenzofuran-7-carboxamide (0.200 g, 0.549 mmol), (1S,2S)-2-methylcyclopropan-1-amine hydrochloride (0.089 g, 0.82 mmol), xantphos (0.016 g, 0.027 mmol), palladium(II) acetate (6.16 mg, 0.0270 mmol) and sodium carbonate (0.175 g, 1.65 mmol) were combined in a 50 mL RBF and the flask was flushed with nitrogen, then toluene (8 mL) was added, the solvent was sparged with nitrogen, then with carbon monoxide for 10 min. A balloon containing carbon monoxide was fitted and the mixture was heated at 80° C. over the weekend, giving a black suspension. This was diluted with DCM (20 mL) and washed with water. The organic layer was washed with water (10 mL) and dried through a hydrophobic frit, then evaporated in vacuo. The residue was purified using silica gel column chromatography eluting with a gradient of 0-100% EtOAc/cyclohexane to give (trans)-2-(fluoromethyl)-$N^7$-methyl-$N^5$-((1S,2S)-2-methylcyclopropyl)-3-phenyl-2,3-dihydrobenzofuran-5,7-dicarboxamide (0.132 g, 0.345 mmol, 63% yield) as a colourless solid.

LCMS (method formic): Rt 1.01 min, $[MH]^+$=383

Example 180: (2S,3S)-2-(Fluoromethyl)-$N^7$-methyl-3-phenyl-$N^5$-(pyrimidin-5-yl)-2,3-dihydrobenzofuran-5,7-dicarboxamide Dicarboxamide

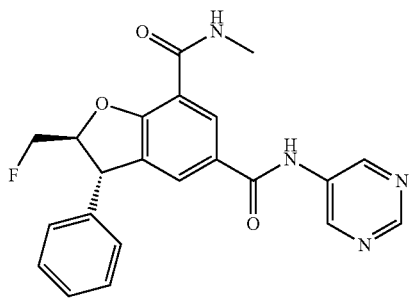 [SMILES: CNC(=O)c1cc(C(=O)Nc2cncnc2)cc2c1O[C@H](CF)[C@H]2c1ccccc1]

(2S,3S)-2-(Fluoromethyl)-7-(methylcarbamoyl)-3-phenyl-2,3-dihydrobenzofuran-5-carboxylic acid (80 mg, 0.24 mmol) and HATU (111 mg, 0.292 mmol) were dissolved in DMSO (0.9 mL), DIPEA (0.127 mL, 0.729 mmol) was added and the reaction mixture left to stir at rt for 5 mins. Pyrimidin-5-amine (23.1 mg, 0.243 mmol) was added and the reaction left to stir for 30 min at rt. The reaction mixture was left to stand overnight. HATU (111 mg, 0.292 mmol) and DIPEA (0.127 ml, 0.729 mmol) were added and the reaction mixture was left to stir for 5 min then pyrimidin-5-amine (23.1 mg, 0.243 mmol) was added and reaction mixture stirred for 1 h at rt. Pyrimidin-5-amine (23.1 mg, 0.243 mmol) was added and left to stir for 1 h at rt. The reaction was diluted to 3 mL of DMSO and purified by MDAP (high pH) to give (2S,3S)-2-(fluoromethyl)-$N^7$-methyl-3-phenyl-$N^5$-(pyrimidin-5-yl)-2,3-dihydrobenzofuran-5,7-dicarboxamide (32 mg, 0.079 mmol, 32% yield) as a white solid.

LCMS (method formic): Retention time 0.90 min, $[M+H]^+$=407

Examples 181-202

The following examples have been either the least active of the two enantiomers obtained following chiral purification of a racemic mixture or have been synthesised form a chiral intermediate of the stereochemistry shown below:

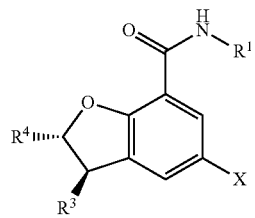

X = Br, COORy, Ry = $C_{1-2}$ alkyl

| Ex. | Structure Example | Name | Retention time (method Formic) | [M + H]+ |
|---|---|---|---|---|
| 181 | ![structure] | (2S,3R)-$N^5$-((1R,5S,6r)-3-oxabicyclo[3.1.0]hexan-6-yl)-3-(3-(2-hydroxyethoxy)phenyl)-$N^7$,2-dimethyl-2,3-dihydrobenzofuran-5,7-dicarboxamide | 0.80 | 453 |

-continued

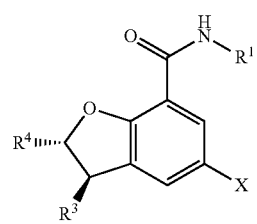

X = Br, COORy, Ry = C$_{1-2}$ alkyl

| Ex. | Structure Example | Name | Retention time (method Formic) | [M + H]+ |
|---|---|---|---|---|
| 182 | | (2S,3R)-N$^5$-((1R,5S,6r)-3-oxabicyclo[3.1.0]hexan-6-yl)-2-(fluoromethyl)-N$^7$-methyl-3-phenyl-2,3-dihydrobenzofuran-5,7-dicarboxamide | 0.87 | 411 |
| 183 | | (2S,3R)-3-(3-(2-hydroxyethoxy)phenyl)-N$^7$,2-dimethyl-N$^5$-(2-(pyridin-3-yl)ethyl)-2,3-dihydrobenzofuran-5,7-dicarboxamide | 0.83 | 476 |
| 184 | | (2R,3R)-2-(fluoromethyl)-N$^5$-((1R,2R)-2-(hydroxymethyl)cyclopropyl)-N$^7$-methyl-3-phenyl-2,3-dihydrobenzofuran-5,7-dicarboxamide | 0.82 | 399 |

-continued

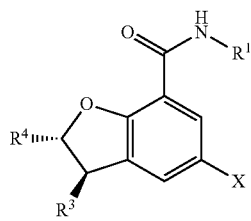

X = Br, COORy, Ry = C$_{1-2}$ alkyl

| Ex. | Structure Example | Name | Retention time (method Formic) | [M + H]+ |
|---|---|---|---|---|
| 185 | | (2R,3R)-2-(fluoromethyl)-N$^7$-methyl-3-phenyl-2,3-dihydrobenzofuran-5,7-dicarboxamide | 0.80 | 329 |
| 186 | | (2R,3R)-2-(fluoromethyl)-N$^7$-methyl-3-phenyl-N$^5$-(1H-pyrazol-4-yl)-2,3-dihydrobenzofuran-5,7-dicarboxamide | 0.86 | 395 |
| 187 | | (2R,3R)-2-(fluoromethyl)-N$^7$-methyl-N$^5$-(1-methyl-1H-pyrazol-4-yl)-3-phenyl-2,3-dihydrobenzofuran-5,7-dicarboxamide | 0.92 | 409 |
| 188 | | (2S,3R)-N$^7$,2-dimethyl-N$^5$-(2-(1-methyl-1H-pyrazol-4-yl)ethyl)-3-phenyl-2,3-dihydrobenzofuran-5,7-dicarboxamide | 0.93 | 419 |

-continued

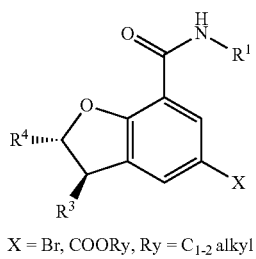

X = Br, COORy, Ry = C$_{1-2}$ alkyl

| Ex. | Structure Example | Name | Retention time (method Formic) | [M + H]+ |
|---|---|---|---|---|
| 189 | | (2S,3R)-N$^5$-((1R,5S,6s)-3-acetyl-3-azabicyclo[3.1.0]hexan-6-yl)-N$^7$,2-dimethyl-3-phenyl-2,3-dihydrobenzofuran-5,7-dicarboxamide | 0.87 | 434 |
| 190 | | (2R,3R)-N$^5$-((1R,5S,6s)-3-acetyl-3-azabicyclo[3.1.0]hexan-6-yl)-2-(fluoromethyl)-N$^7$-methyl-3-phenyl-2,3-dihydrobenzofuran-5,7-dicarboxamide | 0.83 | 452 |
| 191 | | (2R*,3R*)-N$^5$-((1R,5S,6r)-3,3-difluorobicyclo[3.1.0]hexan-6-yl)-N$^7$,2-dimethyl-3-phenyl-2,3-dihydrobenzofuran-5,7-dicarboxamide | 1.11 | 427 |
| 192 | | (2R,3R)-2-(fluoromethyl)-N$^7$-methyl-N$^5$-(1-methyl-1H-1,2,4-triazol-3-yl)-3-phenyl-2,3-dihydrobenzofuran-5,7-dicarboxamide | 0.78 | 410 |

-continued

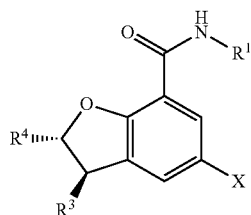

X = Br, COORy, Ry = C$_{1-2}$ alkyl

| Ex. | Structure Example | Name | Retention time (method Formic) | [M + H]+ |
|---|---|---|---|---|
| 193 | | (2R,3R)-2-(fluoromethyl)-N$^7$-methyl-3-phenyl-N$^5$-(pyridazin-4-yl)-2,3-dihydrobenzofuran-5,7-dicarboxamide | 0.82 | 407 |
| 194 | | (2R,3R)-2-(fluoromethyl)-N$^7$-methyl-N$^5$-(1-methyl-1H-1,2,3-triazol-4-yl)-3-phenyl-2,3-dihydrobenzofuran-5,7-dicarboxamide | 0.88 | 410 |
| 195 | | (2R,3R)-2-(fluoromethyl)-N$^7$-methyl-N$^5$-(4-methyl-4H-1,2,4-triazol-3-yl)-3-phenyl-2,3-dihydrobenzofuran-5,7-dicarboxamide | 0.80 | 410 |
| 196 | | (2R,3R)-2-(fluoromethyl)-N$^5$-((trans)-2-(2-hydroxyethyl)cyclopropyl)-N$^7$-methyl-3-phenyl-2,3-dihydrobenzofuran-5,7-dicarboxamide (diastereomeric mixture) | 0.91 | 413 |

-continued

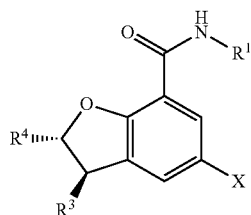

X = Br, COORy, Ry = C$_{1-2}$ alkyl

| Ex. | Structure Example | Name | Retention time (method Formic) | [M + H]+ |
|---|---|---|---|---|
| 197 | | 2R,3R)-2-(fluoromethyl)-N$^5$-((trans)-2-(2-hydroxyethyl)cyclopropyl)-N$^7$-methyl-3-phenyl-2,3-dihydrobenzofuran-5,7-dicarboxamide (diastereomeric mixture) | 0.91 | 413 |
| 198 | | (2S,3R)-N5-(3-((S*)-3,3-difluoropiperidin-4-yl)propyl)-N7,2-dimethyl-3-phenyl-2,3-dihydrobenzofuran-5,7-dicarboxamide | 0.70 | 472 |
| 199 | | (2S,3R)-N$^5$-(3-((R*)-3,3-difluoropiperidin-4-yl)propyl)-N$^7$,2-dimethyl-3-phenyl-2,3-dihydrobenzofuran-5,7-dicarboxamide | 0.70 | 472 |
| 200 | | (2R,3R)-2-(Fluoromethyl)-N$^7$-methyl-3-phenyl-N$^5$-(pyrimidin-5-yl)-2,3-dihydrobenzofuran-5,7-dicarboxamide | 0.89 | 407 |

-continued

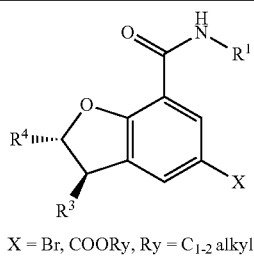

X = Br, COORy, Ry = C$_{1-2}$ alkyl

| Ex. | Structure Example | Name | Retention time (method Formic) | [M + H]+ |
|---|---|---|---|---|
| 201 | | (2S,3R)-N$^5$-((1R,5S,6r)-3-oxabicyclo[3.1.0]hexan-6-yl)-3-(3-(2-methoxyethoxy)phenyl)-N$^7$,2-dimethyl-2,3-dihydrobenzofuran-5,7-dicarboxamide | 0.93 | 467 |
| 202 | | (2S,3R)-N$^5$-((1R,5S,6r)-3-oxabicyclo[3.1.0]hexan-6-yl)-N$^7$,2-dimethyl-3-phenyl-2,3-dihydrobenzofuran-5,7-dicarboxamide | 0.94 | 393 |

Example 203: (2S,3S)-2-(Fluoromethyl)-N$^5$-((1R,3R,5S,6r)-3-hydroxybicyclo[3.1.0]hexan-6-yl)-N$^7$-methyl-3-phenyl-2,3-dihydrobenzofuran-5,7-dicarboxamide Example 204: (2S,3S)-2-(Fluoromethyl)-N$^5$-((1R,3S,5S,6r)-3-hydroxybicyclo[3.1.0]hexan-6-yl)-N$^7$-methyl-3-phenyl-2,3-dihydrobenzofuran-5,7-dicarboxamide

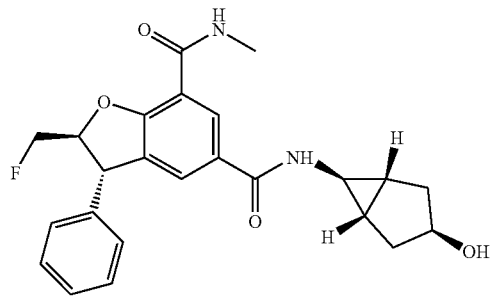

-continued

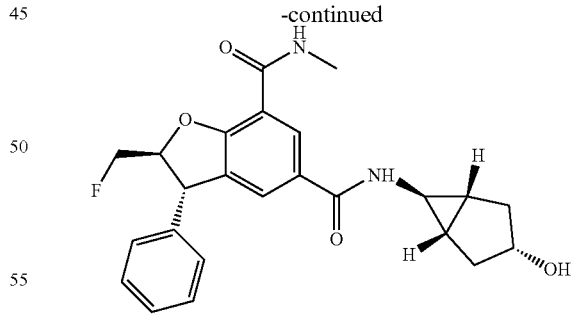

(2S,3S)—N$^5$-((1R,3R,5S,6r)-3-((tert-butyldimethylsilyl)oxy)bicyclo[3.1.0]hexan-6-yl)-2-(fluoromethyl)-N$^7$-methyl-3-phenyl-2,3-dihydrobenzofuran-5,7-dicarboxamide (72.4 mg, 0.134 mmol) (9:1 mix of diastereoisomers) was taken up in DCM (3 mL) and 4M HCl in dioxane (0.084 mL, 0.37 mmol) was added. The reaction was stirred 30 min at rt. The reaction mixture was diluted with water and extracted with EtOAc, the combined organics were filtered through a hydrophobic frit and concentrated in vacuo to a yellow solid. The solid was purified using silica gel column chromatography eluting with a gradient of 10 to 100% (25% EtOH in ethyl acetate): cyclohexane and then by MDAP (High pH method) to give (2S,3S)-2-(fluoromethyl)-$N^5$-((1R,3R,5S,6r)-3-hydroxybicyclo[3.1.0]hexan-6-yl)-$N^7$-methyl-3-phenyl-2,3-dihydrobenzofuran-5,7-dicarboxamide (31.6 mg, 55% yield) as a white solid LCMS (2 min High pH): Rt=0.86 min, $[MH]^+$=425 and (2S,3S)-2-(fluoromethyl)-$N^5$-((1R,3S,5S,6r)-3-hydroxybicyclo[3.1.0]hexan-6-yl)-$N^7$-methyl-3-phenyl-2,3-dihydrobenzofuran-5,7-dicarboxamide (4.3 mg, 8% yield) as a white solid LCMS (2 min High pH): Rt=0.90 min, $[MH]^+$=425

BET tandem bromodomain protein constructs used in this study. A TR-FRET signal is generated when the donor and acceptor fluorophores are in close proximity, between 20-80 Å, which is enabled in this assay by binding of Reference Compound X to the bromodomain protein.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

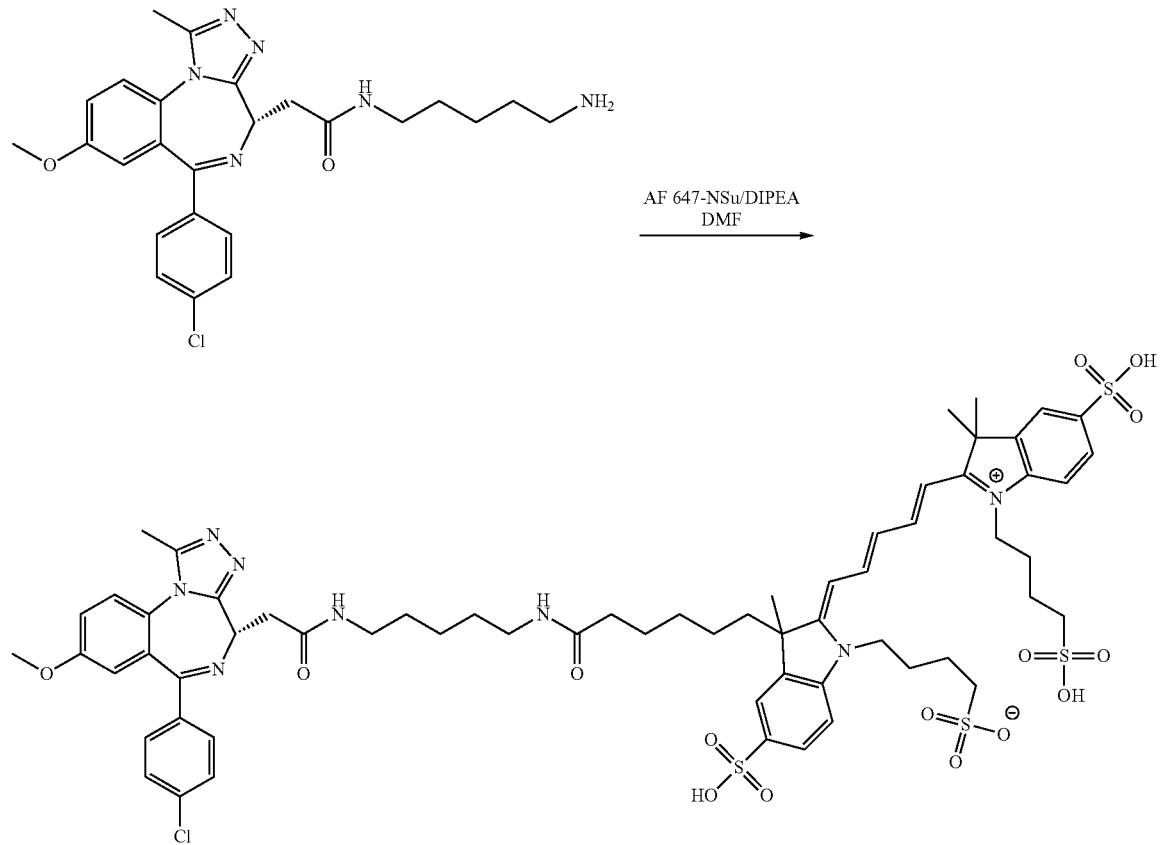

Biological Data

The compounds of formula (I) may be tested in one or more of the following assays:

Time Resolved Fluorescence Resonance Energy Transfer (TR-FRET) Assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 µmol) in DMF (40 µl) was added a solution of AlexaFluor647-ONSu (2.16 mg, 1.97 µmol) also in DMF (100 µl). The mixture was basified with DIPEA (1 µl, 5.73 µmol) and agitated overnight on a vortex mixer.

The reaction mixture was evaporated to dryness. The solid was dissolved in acetonitrile/water/acetic acid (5/4/1, <1 ml) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: [M+H]$^+$ (obs): 661.8/– corresponding with M-29. This equates to [(M+2H)/2]$^+$ for a calculated mass of 1320.984 which is M-29. This is a standard occurrence with the Alexa Fluor 647 dye and represents a theoretical loss of two methylene groups under the conditions of the mass spectrometer.

Assay Principle:

In order to generate a TR-FRET signal, donor fluorophore is excited by a laser at λ337 nm, which subsequently leads to emission at λ618 nm. If the acceptor fluorophore is in close proximity then energy transfer can occur, which leads to emission of Alexa Fluor® 647 at λ665 nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at λ665 nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly greatly reduced in comparison to the non mutated, wild type tandem BET proteins (>1000 fold reduction in Kd). The affinities of the single mutated bromdomain tandem proteins for Reference Compound X were equi-potent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein Production:

Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in E. coli cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 µl/ml protease inhibitor cocktail and extracted from the E. coli cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant TR-FRET Competition Assays:

All assay components were dissolved in an assay buffer composing of 50 mM HEPES pH7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at room temperature. An equal volume of 3 nM of anti-6*His Europium chelate was added to all wells, followed by a further 30 minute incubation at room temperature. TR-FRET was detected using a Perkin Elmer Multimode plate reader, by exciting the donor fluorophore at λ337 nm and subsequently, after a delay of 50 µsecs, measuring emission of the donor and acceptor fluorophores at λ615 nm and λ665 nm, respectively. In order to control these assays, 16 replicates each of uninhibited (DMSO vehicle) and inhibited (10*IC$_{50}$ concentrations of Example 11 of WO 2011/054846A1) TR-FRET assays were included on every microtitre plate.

cA four parameter curve fit of the following form was then applied:

$$y=a+((b-a)/(1+(10^{\wedge}x/10^{\wedge}c)^{\wedge}d)$$

Where 'a' is the minimum, 'b' is the Hill slope, 'c' is the pIC$_{50}$ and 'd' is the maximum.

With the exception of Examples 17, 28, 63, 70, 73 and 77 and 108 all Examples were each tested in the BRD4 BD1 and the BRD4 BD2 TR-FRET assays essentially as described above. Those of skill in the art will recognise that in vitro binding assays and cell-based assays for functional activity are subject to experimental variability. Accordingly, it is to be understood that the pIC$_{50}$ values given below are exemplary only. pIC$_{50}$ values are expressed as log$_{10}$ units.

All tested compounds were found to have a pIC$_{50}$≥4.0 in at least one assay described above.

Examples 6, 7, 34, 85, 100-107, 132, 133, 164, 172, 174, 181-190 and 192-201 were found to have a pIC$_{50}$≥4.0 and <6.0 in the BRD4 BD2 assay.

All other tested compounds were found to have a pIC$_{50}$≥6.0 in the BRD4 BD2 assay.

Example 26 had a mean pIC$_{50}$ of 7.8 (n=16) in the the BRD4 BD2 TR-FRET assay described above, and a mean pIC$_{50}$ of 4.7 (n=16) in the BRD4 BD1 TR-FRET assay described above.

Example 38 had a mean pIC$_{50}$ of 8 (n=2) in the the BRD4 BD2 TR-FRET assay described above, and a mean pIC$_{50}$ of 4.7 (n=2) in the BRD4 BD1 TR-FRET assay described above.

Example 54 had a mean pIC$_{50}$ of 7.8 (n=7) in the the BRD4 BD2 TR-FRET assay described above, and a mean pIC$_{50}$ of 4.6 (n=9) in the BRD4 BD1 TR-FRET assay described above.

Calculation of Selectivity for BRD4 BD2 over BRD4 BD1

Selectivity for BRD4 BD2 over BRD4 BD1 was calculated as follows:

Selectivity=BRD4 BD2 $pIC_{50}$–BRD4 BD1 $pIC_{50}$

With the exception of Examples 101-107, 132, 174, 183, 185, 187, 188, 192, and 194-198 all tested compounds were found to have selectivity for BRD4 BD2 over BRD4 BD1 of ≥1 log unit in at least one of the TR-FRET assays described above, and hence are at least 10 fold selective for BRD4 BD2 over BRD4 BD1.

Examples 1, 2, 4, 5, 8-16, 18-27, 29-33, 35-41, 43-62, 64-69, 72, 74, 76, 79-84, 86-99, 109-131, 134-158, 160-163, 165-171, 173, 175-180 and 202 were found to have selectivity for BRD4 BD2 over BRD4 BD1 of ≥2 log unit in at least one of the TR-FRET assays described above, and hence are at least 100 fold selective for BRD4 BD2 over BRD4 BD1.

Example 26 was found to have selectivity for BRD4 BD2 over BRD4 BD1 of 3.1 log units in at least one of the TR-FRET assays described above, and hence is at least 1000-fold selective for BRD4 BD2 over BRD4 BD1.

Example 38 was found to have a selectivity for BRD4 BD2 over BRD4 BD1 of 3.3 log units in at least one of the TR-FRET assays described above, and hence is at least 100-fold selective for BRD4 BD2 over BRD4 BD1.

Example 54 was found to have a selectivity for BRD4 BD2 over BRD4 BD1 of 3.2 log units in at least one of the TR-FRET assays described above, and hence is at least 1000-fold selective for BRD4 BD2 over BRD4 BD1.

The invention claimed is:
1. A compound of formula (I)

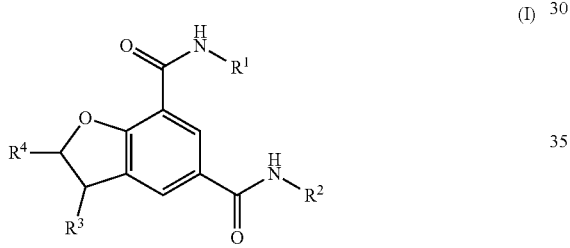

(I)

or a pharmaceutically acceptable salt thereof wherein:
$R^1$ is —$C_{1-3}$alkyl or cyclopropyl;
$R^2$ is —$C_{0-3}$alkyl-cycloalkyl, wherein the cycloalkyl group is optionally substituted with one, two, or three $R^5$ groups which may be the same or different;
$R^2$ is —$C_{0-4}$alkyl-heterocyclyl or —$(CH_2)_pO$-heterocyclyl wherein each heterocyclyl is optionally substituted by one or two $R^9$ groups which may be the same or different; or
$R^2$ is H, —$CH_3$, $C_{2-6}$alkyl optionally substituted by up to five fluoro, —$C_{2-6}$alkylOR$^{13}$, —$C_{2-6}$alkylNR$^{11}$R$^{12}$, —$(CH_2)_mSO_2C_{1-3}$alkyl, —$(CH_2)_mSO_2NR^{11}R^{12}$, —$(CH_2)_mC(O)NR^{11}R^{12}$, —$(CH_2)_mCN$, —$(CH_2)_mCO_2R^{13}$, —$(CH_2)_mNHCO_2C_{1-4}$alkyl —$(CH_2)_mNHC(O)C_{1-4}$alkyl, or —$(CH_2)_n$heteroaryl, wherein heteroaryl is optionally substituted by one or two $R^{14}$ groups which may be the same or different;
$R^3$ is phenyl optionally substituted with one, two, or three $R^7$ groups which may be the same or different;
$R^4$ is —$C_{1-3}$alkyl, —$CH_2OR^6$, or —$CH_2F$;
each $R^5$ is independently halo, —$C_{0-6}$alkyl-$R^8$, —O—$C_{2-6}$alkyl-$R^8$, —CN, or —$SO_2C_{1-3}$alkyl;
$R^6$ is —H or $C_{1-3}$alkyl;
each $R^7$ is independently -halo, —$C_{1-4}$alkyl, —$C_{0-3}$alkyl-OR$^{10}$, —$C_{0-3}$alkyl-NR$^{15}$R$^{16}$, —$C_{0-3}$alkyl-CONR$^{15}$R$^{16}$, CN, or —$SO_2R^{17}$;

$R^8$ is —H, —OR$^{10a}$, —NR$^{18}$R$^{19}$, or heteroaryl;
each $R^9$ is independently halo, $C_{1-4}$alkyl, cyclopropyl, cyclobutyl, —$CH_2CF_3$, —$CH_2CHF_2$, —$CH_2CH_2F$, —$OCH_2CH_2OR^{13}$, —$C_{0-3}$alkylOR$^{13}$, —$C_{0-3}$alkylNR$^{11}$R$^{12}$, —NHCH$_2$CH$_2$OR$^{13}$, —NHCO$_2$R$^{13}$, oxo, —C(O)R$^{13}$, —C(O)OR$^{13}$, or —C(O)NR$^{11}$R$^{12}$;
$R^{10a}$ is —H, —$C_{1-3}$alkyl, —$C_{2-3}$alkylNR$^{11}$R$^{12}$, or —$C_{2-3}$alkylOH;
$R^{10}$ is —H, —$C_{1-3}$alkyl, —$C_{2-3}$alkylNR$^{15}$R$^{16}$, or —$C_{2-3}$alkylOH;
$R^{11}$ and $R^{12}$ are each independently selected from —H and —$C_{1-3}$alkyl;
or $R^{11}$ and $R^{12}$ may join together with the nitrogen to which they are attached to form a 4 to 7-membered heterocyclyl group optionally substituted by one or two substituents independently selected from —$C_{1-3}$alkyl, —OH, and F;
$R^{13}$ is —H or $C_{1-4}$alkyl;
each $R^{14}$ is independently halo, $C_{1-4}$alkyl, cyclopropyl, cyclobutyl, or —OR$^{13}$;
$R^{15}$ and $R^{16}$ are each independently selected from —H and —$C_{1-3}$alkyl;
or $R^{15}$ and $R^{16}$ may join together with the nitrogen to which they are attached to form a 4 to 7-membered heterocyclyl group optionally substituted by one or two substituents independently selected from —$C_{1-3}$alkyl, —OH, and F;
$R^{17}$ is —$C_{1-3}$alkyl or —NR$^{15}$R$^{16}$;
$R^{18}$ and $R^{19}$ are each independently selected from —H, —C(O)OC(CH$_3$)$_3$, —$C_{1-6}$alkyl, cycloalkyl, heterocyclyl, —$C_{2-3}$alkylNR$^{13}$COC$_{1-3}$alkyl, $C_{2-3}$alkylNR$^{15}$R$^{16}$, and —$C_{2-3}$alkyl-O—$C_{1-3}$alkyl, wherein the —$C_{1-6}$alkyl and cycloalkyl may be optionally substituted by one, two, or three fluoro;
or $R^{18}$ and $R^{19}$ may join together with the nitrogen to which they are attached to form a 4 to 7-membered heterocyclyl group optionally substituted by one or two substituents independently selected from —$C_{1-3}$alkyl, —OH, and F;
m is an integer selected from 2, 3, and 4;
p is an integer selected from 2, 3, and 4;
n is an integer selected from 0, 1, 2, 3, and 4.

2. The compound or pharmaceutically acceptable salt thereof according to claim 1, wherein the compound of formula (I) is a compound of formula (IA):

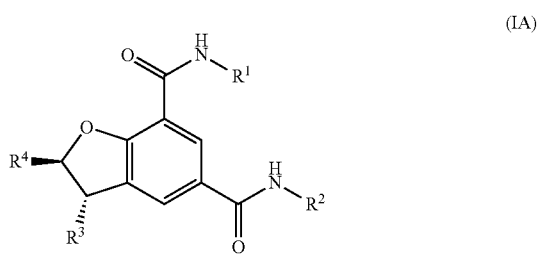

(IA)

wherein $R^1$, $R^2$, $R^3$, and $R^4$ are defined according to formula (I).

3. The compound or pharmaceutically acceptable salt thereof according to claim 1, wherein $R^1$ is methyl.

4. The compound or pharmaceutically acceptable salt thereof according to claim 1, wherein $R^2$ is —$C_{0-3}$alkyl-$C_{3-7}$cycloalkyl, wherein the $C_{3-7}$cycloalkyl group is optionally substituted with one, two, or three $R^5$ groups which may be the same or different.

5. The compound or pharmaceutically acceptable salt thereof according to claim 4, wherein $R^2$ is cyclopropyl, cyclobutyl, or cyclohexyl optionally substituted with one, two or three $R^5$ groups which may be the same or different.

6. The compound or pharmaceutically acceptable salt thereof according to claim 5, wherein $R^5$ is —$C_{0-6}$alkyl-$R^8$.

7. The compound or pharmaceutically acceptable salt thereof according to claim 6, wherein $R^5$ is selected from methyl, —$CH_2OH$, —OH, and —$CH_2CH_2$morpholinyl.

8. The compound or pharmaceutically acceptable salt thereof according to claim 1, wherein $R^2$ is —$C_{0-4}$alkyl-heterocyclyl or —$(CH_2)_p$O-heterocyclyl, wherein each heterocyclyl is optionally substituted by one or two $R^9$ groups which may be the same or different.

9. The compound or pharmaceutically acceptable salt thereof according to claim 8, wherein $R^2$ is —$C_{0-4}$alkyl-heterocyclyl, wherein the heterocyclyl is optionally substituted by one or two $R^9$ groups which may be the same or different.

10. The compound or pharmaceutically acceptable salt thereof according to claim 9, wherein —$C_{0-4}$alkyl-heterocyclyl is selected from heterocyclyl, —$CH_2CH_2$-heterocyclyl, and —$CH_2CH_2CH_2$-heterocyclyl.

11. The compound or pharmaceutically acceptable salt thereof according to claim 8, wherein the $C_{4-10}$heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl, and (1r,5s)-3-azabicyclo[3.1.0]hexanyl optionally substituted by one or two $R^9$ groups which may be the same or different.

12. The compound or pharmaceutically acceptable salt thereof according to claim 11, wherein the heterocyclyl is optionally substituted by one or two $R^9$ groups selected from methyl —C(O)$CH_3$ and fluoro.

13. The compound or pharmaceutically acceptable salt thereof according to claim 12, wherein the heterocyclyl optionally substituted by one or two $R^9$ groups is selected from:

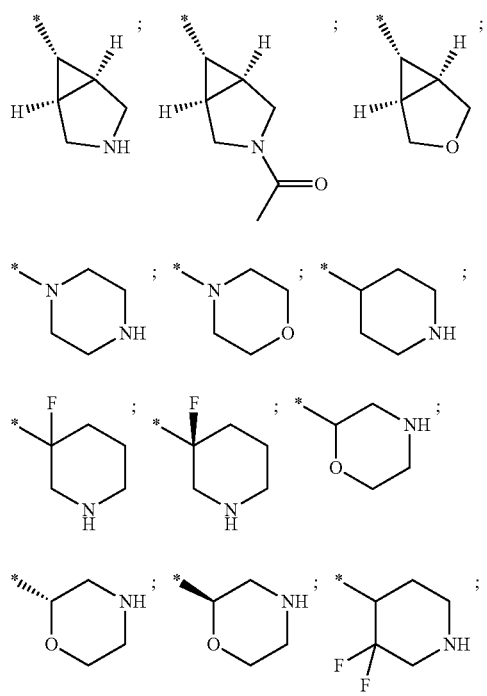

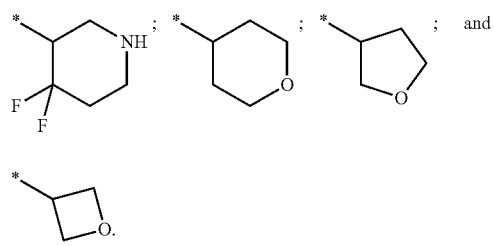

*denotes point of attachment

14. The compound or pharmaceutically acceptable salt thereof according to claim 1, wherein $R^2$ is —H, —$CH_3$, $C_{2-6}$alkyl optionally substituted by up to five fluoro, —$C_{2-6}$alkylOR$^{13}$, —$C_{2-6}$alkylNR$^{11}$R$^{12}$, —$(CH_2)_mSO_2C_{1-3}$alkyl, —$(CH_2)_mC(O)NR^{11}R^{12}$, —$(CH_2)_mCN$, —$(CH_2)_mCO_2R^{13}$, —$(CH_2)_mNHCO_2C(CH_3)_3$, or —$(CH_2)_nC_{5-6}$heteroaryl, wherein $C_{5-6}$heteroaryl is optionally substituted by one or two $R^{14}$ groups which may be the same or different.

15. The compound or pharmaceutically acceptable salt thereof according to claim 14, wherein $R^2$ is —H, —$CH_3$, $C_{2-6}$alkyl, —$C_{2-6}$alkylOR$^{13}$, —$C_{2-6}$alkylNR$^{11}$R$^{12}$, or —$(CH_2)_nC_{5-6}$heteroaryl.

16. The compound or pharmaceutically acceptable salt thereof according to claim 15, wherein $R^2$ is —H, methyl, ethyl, propyl, —$CH_2CH_2OH$, —$CH_2CH_2CH_2OH$, —$CH_2CH(CH_3)OH$, —$CH_2CH_2OCH_3$, —$CH_2CH_2CH_2OCH_3$, —$CH_2CH_2N(CH_3)_2$, —$CH_2CH_2CH_2N(CH_3)_2$, —$CH_2CHF_2$, or —$CH_2CH_2$pyridinyl.

17. The compound or pharmaceutically acceptable salt thereof according to claim 1, wherein $R^3$ is phenyl optionally substituted by —$OCH_3$ or —$OCH_2CH_2OH$.

18. The compound or pharmaceutically acceptable salt thereof according to claim 1, wherein $R^4$ is methyl, —$CH_2F$, or —$CH_2OH$.

19. The compound according to claim 1 which is:
(2R*,3R*)—$N^5$-Cyclobutyl-$N^7$,2-dimethyl-3-phenyl-2,3-dihydrobenzofuran-5,7-dicarboxamide;
(2R*,3S*)—$N^5$-cyclobutyl-$N^7$,2-dimethyl-3-phenyl-2,3-dihydrobenzofuran-5,7-dicarboxamide;
$N^5$-(2-Hydroxypropyl)-$N^7$,2-dimethyl-3-phenyl-2,3-dihydrobenzofuran-5,7-dicarboxamide;
$N^5$-Cyclopropyl-$N^7$,2-dimethyl-3-phenyl-2,3-dihydrobenzofuran-5,7-dicarboxamide;
$N^5$,$N^7$,2-Trimethyl-3-phenyl-2,3-dihydrobenzofuran-5,7-dicarboxamide;
(2R,3S)—$N^5$-(2-Hydroxypropyl)-$N^7$,2-dimethyl-3-phenyl-2,3-dihydrobenzofuran-5,7-dicarboxamide;
(2S,3S)—$N^5$-(2-hydroxypropyl)-$N^7$,2-dimethyl-3-phenyl-2,3-dihydrobenzofuran-5,7-dicarboxamide;
(2R,3S)—$N^5$-Cyclopropyl-$N^7$,2-dimethyl-3-phenyl-2,3-dihydrobenzofuran-5,7-dicarboxamide;
(2S,3S)—$N^5$-cyclopropyl-$N^7$,2-dimethyl-3-phenyl-2,3-dihydrobenzofuran-5,7-dicarboxamide;
(2S*,3S*)—$N^5$-Cyclopropyl-2-(hydroxymethyl)-$N^7$-methyl-3-phenyl-2,3-dihydrobenzofuran-5,7-dicarboxamide;
(2S*,3S*)—$N^5$-Cyclobutyl-2-(hydroxymethyl)-$N^7$-methyl-3-phenyl-2,3-dihydrobenzofuran-5,7-dicarboxamide;
(2S*,3S*)-2-(Hydroxymethyl)-$N^7$-methyl-3-phenyl-$N^5$-propyl-2,3-dihydrobenzofuran-5,7-dicarboxamide;

(2S*,3S*)-2-(Hydroxymethyl)-N⁷-methyl-3-phenyl-N⁵-(2-(piperidin-4-yl)ethyl)-2,3-dihydrobenzofuran-5,7-dicarboxamide;

(2S*,3S*)-2-(Hydroxymethyl)-N⁷-methyl-N⁵-(3-(4-methylpiperazin-1-yl)propyl)-3-phenyl-2,3-dihydrobenzofuran-5,7-dicarboxamide;

(2S*,3S*)-2-(Hydroxymethyl)-N⁷-methyl-3-phenyl-N⁵-(3-(piperazin-1-yl)propyl)-2,3-dihydrobenzofuran-5,7-dicarboxamide;

(2S,3S)—N⁵-Cyclopropyl-2-(hydroxymethyl)-N⁷-methyl-3-phenyl-2,3-dihydrobenzofuran-5,7-dicarboxamide;

(2R*,3S*)—N⁷,2-Dimethyl-3-phenyl-N⁵-(3-(piperidin-4-yl)propyl)-2,3-dihydrobenzofuran-5,7-dicarboxamide;

(2R,3S)—N⁷,2-Dimethyl-3-phenyl-N⁵-(3-(piperidin-4-yl)propyl)-2,3-dihydrobenzofuran-5,7-dicarboxamide;

(2R,3S)—N⁵-Ethyl-N⁷,2-dimethyl-3-phenyl-2,3-dihydrobenzofuran-5,7-dicarboxamide;

(2R,3S)—N⁵,N⁷,2-Trimethyl-3-phenyl-2,3-dihydrobenzofuran-5,7-dicarboxamide;

(2R,3S)—N⁵-((1S*,2S*)-2-(Hydroxymethyl)cyclopropyl)-N⁷,2-dimethyl-3-phenyl-2,3-dihydrobenzofuran-5,7-dicarboxamide;

(2S*,3S*)—N⁵-Cyclopropyl-2-(fluoromethyl)-N⁷-methyl-3-phenyl-2,3-dihydrobenzofuran-5,7-dicarboxamide;

(2S,3S)—N⁵-Cyclopropyl-2-(fluoromethyl)-N⁷-methyl-3-phenyl-2,3-dihydrobenzofuran-5,7-dicarboxamide;

(2S,3S)-2-(Fluoromethyl)-N⁵,N⁷-dimethyl-3-phenyl-2,3-dihydrobenzofuran-5,7-dicarboxamide;

(2S,3S)-2-(Fluoromethyl)-N⁷-methyl-N⁵-((1S,2S)-2-methylcyclopropyl)-3-phenyl-2,3-dihydrobenzofuran-5,7-dicarboxamide;

(2S,3S)—N⁵-((1R,5S,6r)-3-oxabicyclo[3.1.0]hexan-6-yl)-2-(fluoromethyl)-N⁷-methyl-3-phenyl-2,3-dihydrobenzofuran-5,7-dicarboxamide;

(2R,3S)—N⁵-((1S,2S)-2-(Hydroxymethyl)cyclopropyl)-N⁷,2-dimethyl-3-phenyl-2,3-dihydrobenzofuran-5,7-dicarboxamide;

(2R,3S)—N⁵-((1R,2R)-2-(hydroxymethyl)cyclopropyl)-N⁷,2-dimethyl-3-phenyl-2,3-dihydrobenzofuran-5,7-dicarboxamide;

(2R,3S)—N⁷,2-dimethyl-3-phenyl-2,3-dihydrobenzofuran-5,7-dicarboxamide;

(2S*,3S*)—N⁵-Cyclopropyl-2-(hydroxymethyl)-3-(3-methoxyphenyl)-N⁷-methyl-2,3-dihydrobenzofuran-5,7-dicarboxamide;

(2S*,3S*)-2-(Hydroxymethyl)-3-(3-methoxyphenyl)-N⁷-methyl-N⁵-((1S,2S)-2-methylcyclopropyl)-2,3-dihydrobenzofuran-5,7-dicarboxamide;

(2S*,3S*)-2-(Hydroxymethyl)-3-(3-methoxyphenyl)-N⁵,N⁷-dimethyl-2,3-dihydrobenzofuran-5,7-dicarboxamide;

(2S*,3S*)—N⁵-Ethyl-2-(hydroxymethyl)-3-(3-methoxyphenyl)-N⁷-methyl-2,3-dihydrobenzofuran-5,7-dicarboxamide;

(2S*,3S*)-2-(Hydroxymethyl)-N⁵-(2-methoxyethyl)-3-(3-methoxyphenyl)-N⁷-methyl-2,3-dihydrobenzofuran-5,7-dicarboxamide;

(2R,3S)—N⁵-(2-Methoxyethyl)-N⁷,2-dimethyl-3-phenyl-2,3-dihydrobenzofuran-5,7-dicarboxamide;

(2R,3S)—N⁷,2-Dimethyl-3-phenyl-N⁵-(tetrahydro-2H-pyran-4-yl)-2,3-dihydrobenzofuran-5,7-dicarboxamide;

(2R,3S)—N⁵-(2-hydroxyethyl)-N⁷,2-Dimethyl-3-phenyl-2,3-dihydrobenzofuran-5,7-dicarboxamide;

(1R,5S,6S)-tert-Butyl 6-((2R,3S)-2-methyl-7-(methylcarbamoyl)-3-phenyl-2,3-dihydrobenzofuran-5-carboxamido)-3-azabicyclo[3.1.0]hexane-3-carboxylate;

(2R,3S)—N⁵-((1R,5S,6s)-3-Azabicyclo[3.1.0]hexan-6-yl)-N⁷,2-dimethyl-3-phenyl-2,3-dihydrobenzofuran-5,7-dicarboxamide;

(2R,3S)—N⁵-((1R,5S,6s)-3-Acetyl-3-azabicyclo[3.1.0]hexan-6-yl)-N⁷,2-dimethyl-3-phenyl-2,3-dihydrobenzofuran-5,7-dicarboxamide;

(2R,3S)—N⁵-((1R,5S,6R)-3-Oxabicyclo[3.1.0]hexan-6-yl)-N⁷,2-dimethyl-3-phenyl-2,3-dihydrobenzofuran-5,7-dicarboxamide;

(2R,3S)—N⁵-(2-(Dimethylamino)ethyl)-N⁷,2-dimethyl-3-phenyl-2,3-dihydrobenzofuran-5,7-dicarboxamide;

(2R,3S)—N⁵-(3-(Dimethylamino)propyl)-N⁷,2-dimethyl-3-phenyl-2,3-dihydrobenzofuran-5,7-dicarboxamide;

(2R*,3S*)—N⁵-Cyclopropyl-3-(3-methoxyphenyl)-N⁷,2-dimethyl-2,3-dihydrobenzofuran-5,7-dicarboxamide;

(2R,3S)—N⁷,2-Dimethyl-N⁵-(oxetan-3-yl)-3-phenyl-2,3-dihydrobenzofuran-5,7-dicarboxamide;

tert-Butyl 2-(2-((2R,3S)-2-methyl-7-(methylcarbamoyl)-3-phenyl-2,3-dihydrobenzofuran-5-carboxamido)ethyl)morpholine-4-carboxylate;

(2R,3S)—N⁷,2-Dimethyl-N⁵-(2-(morpholin-2-yl)ethyl)-3-phenyl-2,3-dihydrobenzofuran-5,7-dicarboxamide;

(2R,3S)—N⁵-(3-hydroxypropyl)-N⁷,2-dimethyl-3-phenyl-2,3-dihydrobenzofuran-5,7-dicarboxamide;

(2R,3S)—N⁷,2-dimethyl-N⁵-(3-morpholinopropyl)-3-phenyl-2,3-dihydrobenzofuran-5,7-dicarboxamide;

(2R,3S)—N⁵-(3-methoxypropyl)-N⁷,2-dimethyl-3-phenyl-2,3-dihydrobenzofuran-5,7-dicarboxamide;

(2R,3S)—N⁷,2-dimethyl-3-phenyl-N⁵-(tetrahydrofuran-3-yl)-2,3-dihydrobenzofuran-5,7-dicarboxamide;

(2R,3S)—N⁵-(2,2-difluoroethyl)-N⁷,2-dimethyl-3-phenyl-2,3-dihydrobenzofuran-5,7-dicarboxamide;

tert-Butyl 2-(3-((2R,3S)-2-methyl-7-(methylcarbamoyl)-3-phenyl-2,3-dihydrobenzofuran-5-carboxamido)propyl)morpholine-4-carboxylate;

(2R,3S)—N⁷,2-Dimethyl-N⁵-(3-(morpholin-2-yl)propyl)-3-phenyl-2,3-dihydrobenzofuran-5,7-dicarboxamide;

(2R,3S)—N⁵-ethyl-3-(3-methoxyphenyl)-N⁷,2-dimethyl-2,3-dihydrobenzofuran-5,7-dicarboxamide;

(2R,3S)—N⁵-((1R,2R)-2-(Hydroxymethyl)cyclopropyl)-3-(3-methoxyphenyl)-N⁷,2-dimethyl-2,3-dihydrobenzofuran-5,7-dicarboxamide;

(2R,3S)—N⁵-((1R,5S,6r)-3-Oxabicyclo[3.1.0]hexan-6-yl)-3-(3-methoxyphenyl)-N⁷,2-dimethyl-2,3-dihydrobenzofuran-5,7-dicarboxamide;

(R)-tert-Butyl 2-(3-((2R,3S)-3-(3-methoxyphenyl)-2-methyl-7-(methylcarbamoyl)-2,3-dihydrobenzofuran-5-carboxamido)propyl)morpholine-4-carboxylate;

(2R,3S)-3-(3-Methoxyphenyl)-N⁷,2-dimethyl-N⁵-(3-((R)-morpholin-2-yl)propyl)-2,3-dihydrobenzofuran-5,7-dicarboxamide;

(2R,3S)-3-(3-Methoxyphenyl)-N⁷,2-dimethyl-N⁵-(3-((S)-morpholin-2-yl)propyl)-2,3-dihydrobenzofuran-5,7-dicarboxamide;

tert-Butyl 3-fluoro-3-(3-((2R,3S)-2-methyl-7-(methylcarbamoyl)-3-phenyl-2,3-dihydrobenzofuran-5-carboxamido)propyl)piperidine-1-carboxylate;

(2R,3S)—N⁵-(3-(3-Fluoropiperidin-3-yl)propyl)-N⁷,2-dimethyl-3-phenyl-2,3-dihydrobenzofuran-5,7-dicarboxamide;

(2R,3S)—N$^5$-((1S*,2R*)-2-(2-Hydroxyethyl)cyclopropyl)-N$^7$,2-dimethyl-3-phenyl-2,3-dihydrobenzofuran-5,7-dicarboxamide;
(2R,3S)—N$^7$,2-Dimethyl-N$^5$-((1S*,2S*)-2-(2-morpholinoethyl)cyclopropyl)-3-phenyl-2,3-dihydrobenzofuran-5,7-dicarboxamide;
(2R,3S)—N$^7$,2-Dimethyl-N$^5$-((1S,2S)-2-(2-morpholinoethyl)cyclopropyl)-3-phenyl-2,3-dihydrobenzofuran-5,7-dicarboxamide;
(2R,3S)—N$^7$,2-dimethyl-N$^5$-((1R,2R)-2-(2-morpholinoethyl)cyclopropyl)-3-phenyl-2,3-dihydrobenzofuran-5,7-dicarboxamide;
(2R*,3S*)-3-(3-(2-Hydroxyethoxy)phenyl)-N$^7$,2-dimethyl-N$^5$-((1S,2S)-2-methylcyclopropyl)-2,3-dihydrobenzofuran-5,7-dicarboxamide;
(S)-tert-Butyl 3-fluoro-3-(3-((2R*,3S*)-3-(3-(2-hydroxyethoxy)phenyl)-2-methyl-7-(methylcarbamoyl)-2,3-dihydrobenzofuran-5-carboxamido)propyl)piperidine-1-carboxylate;
(2R*,3S*)—N$^5$-(3-((R)-3-Fluoropiperidin-3-yl)propyl)-3-(3-(2-hydroxyethoxy)phenyl)-N$^7$,2-dimethyl-2,3-dihydrobenzofuran-5,7-dicarboxamide;
(R)-tert-Butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate;
(2S,3S)-2-(Fluoromethyl)-N$^5$-(2-((R)-3-fluoropiperidin-3-yl)ethyl)-N$^7$-methyl-3-phenyl-2,3-dihydrobenzofuran-5,7-dicarboxamide;
(2S,3S)-2-(Fluoromethyl)-N$^5$-(3-((R)-3-fluoropiperidin-3-yl)propyl)-N$^7$-methyl-3-phenyl-2,3-dihydrobenzofuran-5,7-dicarboxamide;
(R)-tert-Butyl 3-fluoro-3-(2-((2R,3S)-2-methyl-7-(methylcarbamoyl)-3-phenyl-2,3-dihydrobenzofuran-5-carboxamido)ethyl)piperidine-1-carboxylate;
(2R,3S)—N$^5$-(2-((R)-3-Fluoropiperidin-3-yl)ethyl)-N$^7$,2-dimethyl-3-phenyl-2,3-dihydrobenzofuran-5,7-dicarboxamide;
(R)-tert-Butyl 2-(3-((2S,3S)-2-(fluoromethyl)-7-(methylcarbamoyl)-3-phenyl-2,3-dihydrobenzofuran-5-carboxamido)propyl)morpholine-4-carboxylate;
(2S,3S)-2-(Fluoromethyl)-N$^7$-methyl-N$^5$-(3-((R)-morpholin-2-yl)propyl)-3-phenyl-2,3-dihydrobenzofuran-5,7-dicarboxamide;
(2R*,3S*)—N$^5$-((1R,5S,6R)-3-Oxabicyclo[3.1.0]hexan-6-yl)-3-(3-(2-hydroxyethoxy)phenyl)-N$^7$,2-dimethyl-2,3-dihydrobenzofuran-5,7-dicarboxamide;
(R)-tert-Butyl 2-(2-((2S,3S)-2-(fluoromethyl)-7-(methylcarbamoyl)-3-phenyl-2,3-dihydrobenzofuran-5-carboxamido)ethyl)morpholine-4-carboxylate;
(2S,3S)-2-(Fluoromethyl)-N$^7$-methyl-N$^5$-(2-((R)-morpholin-2-yl)ethyl)-3-phenyl-2,3-dihydrobenzofuran-5,7-dicarboxamide;
(2R,3S)—N$^5$-(2-(4,4-Difluoropiperidin-3-yl)ethyl)-N$^7$,2-dimethyl-3-phenyl-2,3-dihydrobenzofuran-5,7-dicarboxamide;
tert-Butyl 4,4-difluoro-3-(2-((2R,3S)-2-methyl-7-(methylcarbamoyl)-3-phenyl-2,3-dihydrobenzofuran-5-carboxamido)ethyl)piperidine-1-carboxylate;
(2R,3S)—N$^5$-(2-(3,3-Difluoropiperidin-4-yl)ethyl)-N$^7$,2-dimethyl-3-phenyl-2,3-dihydrobenzofuran-5,7-dicarboxamide;
tert-Butyl 3,3-difluoro-4-(2-((2R,3S)-2-methyl-7-(methylcarbamoyl)-3-phenyl-2,3-dihydrobenzofuran-5-carboxamido)ethyl)piperidine-1-carboxylate;
(2S*,3S*)-2-(Fluoromethyl)-N$^5$-((1R,4S)-4-hydroxycyclohexyl)-N$^7$-methyl-3-phenyl-2,3-dihydrobenzofuran-5,7-dicarboxamide;
(2R,3S)—N$^5$-((1R,5S,6R)-3-Oxabicyclo[3.1.0]hexan-6-yl)-3-(3-(2-hydroxyethoxy)phenyl)-N$^7$,2-dimethyl-2,3-dihydrobenzofuran-5,7-dicarboxamide;
(2S*,3S*)-2-(Fluoromethyl)-N$^5$-((1R,3S)-3-hydroxycyclobutyl)-N$^7$-methyl-3-phenyl-2,3-dihydrobenzofuran-5,7-dicarboxamide;
(2S,3S)-2-(Fluoromethyl)-N$^5$-((1R,2R)-2-(hydroxymethyl)cyclopropyl)-N$^7$-methyl-3-phenyl-2,3-dihydrobenzofuran-5,7-dicarboxamide;
(2S,3S)—N$^5$-((1R,5S,6S)-3-azabicyclo[3.1.0]hexan-6-yl)-2-(fluoromethyl)-N$^7$-methyl-3-phenyl-2,3-dihydrobenzofuran-5,7-dicarboxamide;
(1R,5S,6S)-tert-butyl 6-((2S,3S)-2-(fluoromethyl)-7-(methylcarbamoyl)-3-phenyl-2,3-dihydrobenzofuran-5-carboxamido)-3-azabicyclo[3.1.0]hexane-3-carboxylate;
(2S,3S)-2-(Fluoromethyl)-N$^7$-methyl-3-phenyl-N$^5$-(tetrahydrofuran-3-yl)-2,3-dihydrobenzofuran-5,7-dicarboxamide;
(2S,3S)-2-(Fluoromethyl)-N$^5$-(2-hydroxyethyl)-N$^7$-methyl-3-phenyl-2,3-dihydrobenzofuran-5,7-dicarboxamide;
(2S*,3S*)—N$^5$-((1R,5S,6S)-3-Acetyl-3-azabicyclo[3.1.0]hexan-6-yl)-2-(fluoromethyl)-N$^7$-methyl-3-phenyl-2,3-dihydrobenzofuran-5,7-dicarboxamide;
(2R,3S)-3-(3-(2-Hydroxyethoxy)phenyl)-N$^7$,2-dimethyl-N$^5$-(2-(pyridin-3-yl)ethyl)-2,3-dihydrobenzofuran-5,7-dicarboxamide;
(2R*,3S*)—N$^5$-((1R,5S,6S)-3-Acetyl-3-azabicyclo[3.1.0]hexan-6-yl)-3-(3-(2-hydroxyethoxy)phenyl)-N$^7$,2-dimethyl-2,3-dihydrobenzofuran-5,7-dicarboxamide;
(2R*,3S*)—N$^5$-((1R,5S,6S)-3-azabicyclo[3.1.0]hexan-6-yl)-3-(3-(2-hydroxyethoxy)phenyl)-N$^7$,2-dimethyl-2,3-dihydrobenzofuran-5,7-dicarboxamide;
(1R,5S,6S)-tert-Butyl 6-((2R*,3S*)-3-(3-(2-hydroxyethoxy)phenyl)-2-methyl-7-(methylcarbamoyl)-2,3-dihydrobenzofuran-5-carboxamido)-3-azabcyclo[3.1.0]hexane-3-carboxylate;
(R)-tert-Butyl 3-fluoro-3-(2-((2S,3S)-2-(fluoromethyl)-7-(methylcarbamoyl)-3-phenyl-2,3-dihydrobenzofuran-5-carboxamido)ethyl)piperidine-1-carboxylate;
(2S,3S)-2-(Fluoromethyl)-N$^5$-(2-((R)-3-fluoropiperidin-3-yl)ethyl)-N$^7$-methyl-3-phenyl-2,3-dihydrobenzofuran-5,7-dicarboxamide;
(2S,3R)—N$^7$,2-dimethyl-3-phenyl-N$^5$-(3-(piperidin-4-yl)propyl)-2,3-dihydrobenzofuran-5,7-dicarboxamide;
(2S,3R)—N$^5$,N$^7$,2-trimethyl-3-phenyl-2,3-dihydrobenzofuran-5,7-dicarboxamide;
(2S,3R)—N$^5$-ethyl-N$^7$,2-dimethyl-3-phenyl-2,3-dihydrobenzofuran-5,7-dicarboxamide;
(2S,3R)—N$^5$-cyclopropyl-N$^7$,2-dimethyl-3-phenyl-2,3-dihydrobenzofuran-5,7-dicarboxamide;
(2R,3R)—N$^5$-cyclopropyl-N$^7$,2-dimethyl-3-phenyl-2,3-dihydrobenzofuran-5,7-dicarboxamide;
(2R,3R)—N$^5$-cyclopropyl-2-(hydroxymethyl)-N$^7$-methyl-3-phenyl-2,3-dihydrobenzofuran-5,7-dicarboxamide;
(2R,3R)—N$^5$-((1R,5S,6R)-3-oxabicyclo[3.1.0]hexan-6-yl)-2-(fluoromethyl)-N$^7$-methyl-3-phenyl-2,3-dihydrobenzofuran-5,7-dicarboxamide;
(2R,3R)—N$^5$-cyclopropyl-2-(hydroxymethyl)-N$^7$-methyl-3-phenyl-2,3-dihydrobenzofuran-5,7-dicarboxamide;
(2S,3R)—N$^5$-(2-hydroxypropyl)-N$^7$,2-dimethyl-3-phenyl-2,3-dihydrobenzofuran-5,7-dicarboxamide;

(2S,3S)—N$^5$-(2-hydroxypropyl)-N$^7$,2-dimethyl-3-phenyl-2,3-dihydrobenzofuran-5,7-dicarboxamide;
(Trans)-N$^5$-(2-(4,4-difluoropiperidin-3-yl)ethyl)-N$^7$,2-dimethyl-3-phenyl-2,3-dihydrobenzofuran-5,7-dicarboxamide (diastereomeric mixture);
(2S,3S)-2-(Fluoromethyl)-N$^5$-((1r,4S)-4-hydroxycyclohexyl)-N$^7$-methyl-3-phenyl-2,3-dihydrobenzofuran-5,7-dicarboxamidedicarboxamide;
(2R,3S)—N$^5$-((1R,5S,6r)-3-oxabicyclo[3.1.0]hexan-6-yl)-3-(3-(2-hydroxyethoxy)phenyl)-N$^7$,2-dimethyl-2,3-dihydrobenzofuran-5,7-dicarboxamide;
(2S,3S)-2-(Fluoromethyl)-N$^5$-((1r,3S)-3-hydroxycyclobutyl)-N$^7$-methyl-3-phenyl-2,3-dihydrobenzofuran-5,7-dicarboxamide;
(2S,3S)-2-(Fluoromethyl)-N$^7$-methyl-3-phenyl-N$^5$-(tetrahydrofuran-3-yl)-2,3-dihydrobenzofuran-5,7-dicarboxamide (mix of diastereomers);
(2S,3S)-2-(Fluoromethyl)-N$^5$-(2-hydroxyethyl)-N$^7$-methyl-3-phenyl-2,3-dihydrobenzofuran-5,7-dicarboxamide;
(Trans)-N$^5$-((1R,5S,6s)-3-acetyl-3-azabicyclo[3.1.0]hexan-6-yl)-3-(3-(2-hydroxyethoxy)phenyl)-N$^7$,2-dimethyl-2,3-dihydrobenzofuran-5,7-dicarboxamide;
(Trans)-3-(3-(2-hydroxyethoxy)phenyl)-N$^7$,2-dimethyl-N$^5$-(2-(pyridin-3-yl)ethyl)-2,3-dihydrobenzofuran-5,7-dicarboxamide;
(Trans)-2-(fluoromethyl)-N$^7$-methyl-N$^5$-(1-methyl-1H-pyrazol-4-yl)-3-phenyl-2,3-dihydrobenzofuran-5,7-dicarboxamide;
(2S,3S)-2-(Fluoromethyl)-N$^7$-methyl-N$^5$-(1-methyl-1H-pyrazol-4-yl)-3-phenyl-2,3-dihydrobenzofuran-5,7-dicarboxamide;
(Trans)-2-(fluoromethyl)-N$^7$-methyl-3-phenyl-N$^5$-(1H-pyrazol-4-yl)-2,3-dihydrobenzofuran-5,7-dicarboxamide;
(2S,3S)-2-(Fluoromethyl)-N$^7$-methyl-3-phenyl-N$^5$-(1H-pyrazol-4-yl)-2,3-dihydrobenzofuran-5,7-dicarboxamide;
(Trans)-N$^5$-((1R,5S,6r)-3-oxabicyclo[3.1.0]hexan-6-yl)-2-(fluoromethyl)-N$^7$-trideuteromethyl-3-phenyl-2,3-dihydrobenzofuran-5,7-dicarboxamide;
(Trans)-N$^5$-(2-(1H-pyrazol-4-yl)ethyl)-2-(fluoromethyl)-N$^7$-methyl-3-phenyl-2,3-dihydrobenzofuran-5,7-dicarboxamide;
(Trans)-2-(fluoromethyl)-N$^7$-methyl-N$^5$-((1-methyl-1H-pyrazol-4-yl)methyl)-3-phenyl-2,3-dihydrobenzofuran-5,7-dicarboxamide;
(Trans)-2-(fluoromethyl)-N$^7$-methyl-N$^5$-(2-(1-methyl-1H-pyrazol-4-yl)ethyl)-3-phenyl-2,3-dihydrobenzofuran-5,7-dicarboxamide;
(2S,3S)-2-(Fluoromethyl)-N$^5$-((1R,2R)-2-(hydroxymethyl)cyclopropyl)-N$^7$-methyl-3-phenyl-2,3-dihydrobenzofuran-5,7-dicarboxamide;
(2R,3S)—N$^5$-(2-((R*)-4,4-difluoropiperidin-3-yl)ethyl)-N$^7$,2-dimethyl-3-phenyl-2,3-dihydrobenzofuran-5,7-dicarboxamide;
(2R,3S)—N$^5$-(2-((S*)-4,4-difluoropiperidin-3-yl)ethyl)-N$^7$,2-dimethyl-3-phenyl-2,3-dihydrobenzofuran-5,7-dicarboxamide;
(Trans)-2-(fluoromethyl)-N$^7$-methyl-3-phenyl-2,3-dihydrobenzofuran-5,7-dicarboxamide;
(2S,3S)-2-(Fluoromethyl)-N$^7$-methyl-3-phenyl-2,3-dihydrobenzofuran-5,7-dicarboxamide;
(2S,3S)-2-(Fluoromethyl)-N$^5$-((1R,2R)-2-(hydroxymethyl)cyclopropyl)-N$^7$-methyl-3-phenyl-2,3-dihydrobenzofuran-5,7-dicarboxamide;
(2S,3S)-2-(Fluoromethyl)-N$^5$-((trans)-2-(2-hydroxyethyl)cyclopropyl)-N$^7$-methyl-3-phenyl-2,3-dihydrobenzofuran-5,7-dicarboxamide;
(Trans)-N$^5$-(2-(4H-1,2,4-triazol-4-yl)ethyl)-2-(fluoromethyl)-N$^7$-methyl-3-phenyl-2,3-dihydrobenzofuran-5,7-dicarboxamide;
(Trans)-2-(fluoromethyl)-N$^7$-methyl-N$^5$-(oxetan-3-yl)-3-phenyl-2,3-dihydrobenzofuran-5,7-dicarboxamide;
(Trans)-2-(fluoromethyl)-N$^7$-methyl-3-phenyl-N$^5$-(2-(pyridin-4-yl)ethyl)-2,3-dihydrobenzofuran-5,7-dicarboxamide;
(Trans)-2-(fluoromethyl)-N$^7$-methyl-N$^5$-(1-(methyl sulfonyl)azetidin-3-yl)-3-phenyl-2,3-dihydrobenzofuran-5,7-dicarboxamide;
(Trans)-2-(fluoromethyl)-N$^7$-methyl-3-phenyl-N$^5$-(2-(pyridin-3-yl)ethyl)-2,3-dihydrobenzofuran-5,7-dicarboxamide;
(Trans)-N$^5$-(2-(1H-imidazol-4-yl)ethyl)-2-(fluoromethyl)-N$^7$-methyl-3-phenyl-2,3-dihydrobenzofuran-5,7-dicarboxamide;
(Trans)-2-(fluoromethyl)-N$^7$-methyl-3-phenyl-N$^5$-(2-(pyridin-3-yl)ethyl)-2,3-dihydrobenzofuran-5,7-dicarboxamide;
(Trans)-2-(fluoromethyl)-N$^5$-(2-methoxycyclopropyl)-N$^7$-methyl-3-phenyl-2,3-dihydrobenzofuran-5,7-dicarboxamide (mix of diastereomers);
(Trans) tert-butyl 3,3-difluoro-4-(2-2-(fluoromethyl)-7-(methylcarbamoyl)-3-phenyl-2,3-dihydrobenzofuran-5-carboxamido)ethyl)piperidine-1-carboxylate (mix of diastereomers);
(Trans) tert-butyl 3,3-difluoro-4-(3-2-(fluoromethyl)-7-(methylcarbamoyl)-3-phenyl-2,3-dihydrobenzofuran-5-carboxamido)propyl)piperidine-1-carboxylate (mix of diastereomers);
(Trans)-2-(fluoromethyl)-N$^7$-methyl-3-phenyl-N$^5$-((tetrahydrofuran-3-yl)methyl)-2,3-dihydrobenzofuran-5,7-dicarboxamide (mix of diastereomers);
(Trans)(2R,3S)—N$^5$-(2-(3,3-difluoropiperidin-4-yl)ethyl)-N$^7$,2-dimethyl-3-phenyl-2,3-dihydrobenzofuran-5,7-dicarboxamide (mix of diastereomers);
(Trans) 2-(fluoromethyl)-N$^7$-methyl-3-phenyl-N$^5$-(2-(pyridin-2-yl)ethyl)-2,3-dihydrobenzofuran-5,7-dicarboxamide;
(2R,3S)—N$^5$-(2-((R*)-3,3-difluoropiperidin-4-yl)ethyl)-N$^7$,2-dimethyl-3-phenyl-2,3-dihydrobenzofuran-5,7-dicarboxamide;
(2R,3S)—N$^5$-(2-((S*)-3,3-difluoropiperidin-4-yl)ethyl)-N$^7$,2-dimethyl-3-phenyl-2,3-dihydrobenzofuran-5,7-dicarboxamide;
(Trans) N$^7$,2-dimethyl-N$^5$-(1-methyl-1H-pyrazol-4-yl)-3-phenyl-2,3-dihydrobenzofuran-5,7-dicarboxamide;
(Trans)-N$^7$,2-dimethyl-N$^5$-(2-(1-methyl-1H-pyrazol-4-yl)ethyl)-3-phenyl-2,3-dihydrobenzofuran-5,7-dicarboxamide;
(Trans)-2-(fluoromethyl)-N$^5$-((trans)-2-(2-hydroxyethyl)cyclopropyl)-N$^7$-methyl-3-phenyl-2,3-dihydrobenzofuran-5,7-dicarboxamide;
(Trans)-2-(fluoromethyl)-N$^5$-((1R,2S)-2-(2-hydroxyethyl)cyclopropyl)-N$^7$-methyl-3-phenyl-2,3-dihydrobenzofuran-5,7-dicarboxamide;
(2R,3S)—N$^7$,2-dimethyl-N$^5$-(2-(1-methyl-1H-pyrazol-4-yl)ethyl)-3-phenyl-2,3-dihydrobenzofuran-5,7-dicarboxamide;
(2R,3S)—N$^5$-((1R,5S,6r)-3,3-difluorobicyclo[3.1.0]hexan-6-yl)-N$^7$,2-dimethyl-3-phenyl-2,3-dihydrobenzofuran-5,7-dicarboxamide;

(2S,3R)—N$^7$,2-dimethyl-N$^5$-(1-methyl-1H-pyrazol-4-yl)-3-phenyl-2,3-dihydrobenzofuran-5,7-dicarboxamide;

(2R,3S)—N$^5$-(2-((S*)-4,4-difluoropiperidin-3-yl)ethyl)-N$^7$,2-dimethyl-3-phenyl-2,3-dihydrobenzofuran-5,7-dicarboxamide;

(2R,3S)—N$^5$-(2-((R*)-4,4-difluoropiperidin-3-yl)ethyl)-N$^7$,2-dimethyl-3-phenyl-2,3-dihydrobenzofuran-5,7-dicarboxamide;

(2S,3R)—N$^5$-(2-((S*)-4,4-difluoropiperidin-3-yl)ethyl)-N$^7$,2-dimethyl-3-phenyl-2,3-dihydrobenzofuran-5,7-dicarboxamide;

(2S,3R)—N$^5$-(2-((R*)-4,4-difluoropiperidin-3-yl)ethyl)-N$^7$,2-dimethyl-3-phenyl-2,3-dihydrobenzofuran-5,7-dicarboxamide;

(2S,3S)-2-(Fluoromethyl)-N$^5$-((1S,2S)-2-(hydroxymethyl)cyclopropyl)-N$^7$-methyl-3-phenyl-2,3-dihydrobenzofuran-5,7-dicarboxamide;

(2S,3S)-2-(Fluoromethyl)-N$^7$-methyl-3-phenyl-N$^5$-((1R,5S,6s)-3-propionyl-3-azabicyclo[3.1.0]hexan-6-yl)-2,3-dihydrobenzofuran-5,7-dicarboxamide;

(Trans)-N$^5$-((1R,5S,6r)-3-Oxabicyclo[3.1.0]hexan-6-yl)-3-(3-(2-methoxyethoxy)phenyl)-N$^7$,2-dimethyl-2,3-dihydrobenzofuran-5,7-dicarboxamide;

(2R,3S)—N$^5$-(3-((S*)-3,3-difluoropiperidin-4-yl)propyl)-N$^7$,2-dimethyl-3-phenyl-2,3-dihydrobenzofuran-5,7-dicarboxamide;

(2R,3S)—N$^5$-(3-((R*)-3,3-difluoropiperidin-4-yl)propyl)-N$^7$,2-dimethyl-3-phenyl-2,3-dihydrobenzofuran-5,7-dicarboxamide;

(2R,3R)-2-(Fluoromethyl)-N$^7$-methyl-3-phenyl-N$^5$-((1R,5S,6s)-3-propionyl-3-azabicyclo[3.1.0]hexan-6-yl)-2,3-dihydrobenzofuran-5,7-dicarboxamide;

(2R,3S)—N$^5$-((1R,5S,6r)-3-oxabicyclo[3.1.0]hexan-6-yl)-3-(3-(2-hydroxyethoxy)phenyl)-N$^7$,2-dimethyl-2,3-dihydrobenzofuran-5,7-dicarboxamide;

(2S,3S)-2-(Fluoromethyl)-N$^7$-methyl-N$^5$-(1-methyl-1H-1,2,4-triazol-3-yl)-3-phenyl-2,3-dihydrobenzofuran-5,7-dicarboxamide;

(2S,3S)—N$^5$-(3-((2r,5S)-5-Amino-1,3-dioxan-2-yl)propyl)-2-(fluoromethyl)-N$^7$-methyl-3-phenyl-2,3-dihydrobenzofuran-5,7-dicarboxamide;

(2S,3S)-2-(Fluoromethyl)-N$^7$-methyl-N$^5$-(1-methyl-1H-1,2,3-triazol-4-yl)-3-phenyl-2,3-dihydrobenzofuran-5,7-dicarboxamide;

(2S,3S)—N$^5$-(2-((2r,5S)-5-amino-1,3-dioxan-2-yl)ethyl)-2-(fluoromethyl)-N$^7$-methyl-3-phenyl-2,3-dihydrobenzofuran-5,7-dicarboxamide;

(2S,3S)-2-(Fluoromethyl)-N$^7$-methyl-3-phenyl-N$^5$-(pyridazin-4-yl)-2,3-dihydrobenzofuran-5,7-dicarboxamide;

(2R,3S)—N$^5$-((1R,5S,6r)-3-oxabicyclo[3.1.0]hexan-6-yl)-3-(3-(2-methoxyethoxy)phenyl)-N$^7$,2-dimethyl-2,3-dihydrobenzofuran-5,7-dicarboxamide;

(2S,3S)-2-(Fluoromethyl)-N$^7$-methyl-N$^5$-(4-methyl-4H-1,2,4-triazol-3-yl)-3-phenyl-2,3-dihydrobenzofuran-5,7-dicarboxamide;

(2S,3S)—N$^5$-((1R,5S,6r)-3-oxabicyclo[3.1.0]hexan-6-yl)-N$^7$-ethyl-2-(fluoromethyl)-3-phenyl-2,3-dihydrobenzofuran-5,7-dicarboxamide;

(2S,3S)-2-(Fluoromethyl)-N$^7$-methyl-N$^5$-(2-methyl-2H-tetrazol-5-yl)-3-phenyl-2,3-dihydrobenzofuran-5,7-dicarboxamide;

(2S,3S)—N$^5$-((1R,5S,6r)-3-oxabicyclo[3.1.0]hexan-6-yl)-N$^7$-cyclopropyl-2-(fluoromethyl)-3-phenyl-2,3-dihydrobenzofuran-5,7-dicarboxamide;

(2R,3S)—N$^5$-((1R,5S,6r)-3-oxabicyclo[3.1.0]hexan-6-yl)-3-(3-(2-hydroxyethoxy)phenyl)-N$^7$,2-dimethyl-2,3-dihydrobenzofuran-5,7-dicarboxamide;

(Trans)-N$^5$-((1R,5S,6r)-3,3-difluorobicyclo[3.1.0]hexan-6-yl)-2-(fluoromethyl)-N7-methyl-3-phenyl-2,3-dihydrobenzofuran-5,7-dicarboxamide;

(Trans)-2-(fluoromethyl)-N$^7$-methyl-N$^5$-((trans)-2-(2-morpholinoethyl)cyclopropyl)-3-phenyl-2,3-dihydrobenzofuran-5,7-dicarboxamide;

(Trans)-2-(fluoromethyl)-N$^7$-methyl-N$^5$-(1S,2S)-2-methylcyclopropyl)-3-phenyl-2,3-dihydrobenzofuran-5,7-dicarboxamide;

(2S,3S)-2-(Fluoromethyl)-N$^7$-methyl-3-phenyl-N$^5$-(pyrimidin-5-yl)-2,3-dihydrobenzofuran-5,7-dicarboxamide dicarboxamide;

(2S,3R)—N$^5$-((1R,5S,6r)-3-oxabicyclo[3.1.0]hexan-6-yl)-3-(3-(2-hydroxyethoxy)phenyl)-N$^7$,2-dimethyl-2,3-dihydrobenzofuran-5,7-dicarboxamide;

(2S,3R)—N$^5$-((1R,5S,6r)-3-oxabicyclo[3.1.0]hexan-6-yl)-2-(fluoromethyl)-N$^7$-methyl-3-phenyl-2,3-dihydrobenzofuran-5,7-dicarboxamide;

(2S,3R)-3-(3-(2-hydroxyethoxy)phenyl)-N$^7$,2-dimethyl-N$^5$-(2-(pyridin-3-yl)ethyl)-2,3-dihydrobenzofuran-5,7-dicarboxamide;

(2R,3R)-2-(fluoromethyl)-N$^5$-((1R,2R)-2-(hydroxymethyl)cyclopropyl)-N$^7$-methyl-3-phenyl-2,3-dihydrobenzofuran-5,7-dicarboxamide;

(2R,3R)-2-(fluoromethyl)-N$^7$-methyl-3-phenyl-2,3-dihydrobenzofuran-5,7-dicarboxamide;

(2R,3R)-2-(fluoromethyl)-N$^7$-methyl-3-phenyl-N$^5$-(1H-pyrazol-4-yl)-2,3-dihydrobenzofuran-5,7-dicarboxamide;

(2R,3R)-2-(fluoromethyl)-N$^7$-methyl-N$^5$-(1-methyl-1H-pyrazol-4-yl)-3-phenyl-2,3-dihydrobenzofuran-5,7-dicarboxamide;

(2S,3R)—N$^7$,2-dimethyl-N$^5$-(2-(1-methyl-1H-pyrazol-4-yl)ethyl)-3-phenyl-2,3-dihydrobenzofuran-5,7-dicarboxamide;

(2S,3R)—N$^5$-((1R,5S,6s)-3-acetyl-3-azabicyclo[3.1.0]hexan-6-yl)-N$^7$,2-dimethyl-3-phenyl-2,3-dihydrobenzofuran-5,7-dicarboxamide;

(2R,3R)—N$^5$-((1R,5S,6s)-3-acetyl-3-azabicyclo[3.1.0]hexan-6-yl)-2-(fluoromethyl)-N$^7$-methyl-3-phenyl-2,3-dihydrobenzofuran-5,7-dicarboxamide;

(2R*,3R*)—N$^5$-((1R,5S,6r)-3,3-difluorobicyclo[3.1.0]hexan-6-yl)-N$^7$,2-dimethyl-3-phenyl-2,3-dihydrobenzofuran-5,7-dicarboxamide;

(2R,3R)-2-(fluoromethyl)-N$^7$-methyl-N$^5$-(1-methyl-1H-1,2,4-triazol-3-yl)-3-phenyl-2,3-dihydrobenzofuran-5,7-dicarboxamide;

(2R,3R)-2-(fluoromethyl)-N$^7$-methyl-3-phenyl-N$^5$-(pyridazin-4-yl)-2,3-dihydrobenzofuran-5,7-dicarboxamide;

(2R,3R)-2-(fluoromethyl)-N$^7$-methyl-N$^5$-(1-methyl-1H-1,2,3-triazol-4-yl)-3-phenyl-2,3-dihydrobenzofuran-5,7-dicarboxamide;

(2R,3R)-2-(fluoromethyl)-N$^7$-methyl-N$^5$-(4-methyl-4H-1,2,4-triazol-3-yl)-3-phenyl-2,3-dihydrobenzofuran-5,7-dicarboxamide;

(2R,3R)-2-(fluoromethyl)-N$^5$-((trans)-2-(2-hydroxyethyl)cyclopropyl)-N$^7$-methyl-3-phenyl-2,3-dihydrobenzofuran-5,7-dicarboxamide (diastereomeric mixture);

(2R,3R)-2-(fluoromethyl)-N$^5$-((trans)-2-(2-hydroxyethyl)cyclopropyl)-N$^7$-methyl-3-phenyl-2,3-dihydrobenzofuran-5,7-dicarboxamide (diastereomeric mixture);

(2S,3R)—N5-(3-((S*)-3,3-difluoropiperidin-4-yl)propyl)-N7,2-dimethyl-3-phenyl-2,3-dihydrobenzofuran-5,7-dicarboxamide;

(2S,3R)—$N^5$-(3-((R*)-3,3-difluoropiperidin-4-yl)propyl)-$N^7$,2-dimethyl-3-phenyl-2,3-dihydrobenzofuran-5,7-dicarboxamide;

(2R,3R)-2-(Fluoromethyl)-$N^7$-methyl-3-phenyl-$N^5$-(pyrimidin-5-yl)-2,3-dihydrobenzofuran-5,7-dicarboxamide;

(2S,3R)—$N^5$-((1R,5S,6r)-3-oxabicyclo[3.1.0]hexan-6-yl)-3-(3-(2-methoxyethoxy)phenyl)-$N^7$,2-dimethyl-2,3-dihydrobenzofuran-5,7-dicarboxamide;

(2S,3R)—$N^5$-((1R,5S,6r)-3-oxabicyclo[3.1.0]hexan-6-yl)-$N^7$,2-dimethyl-3-phenyl-2,3-dihydrobenzofuran-5,7-dicarboxamide;

(2S,3S)-2-(Fluoromethyl)-$N^5$-((1R,3R,5S,6r)-3-hydroxybicyclo[3.1.0]hexan-6-yl)-$N^7$-methyl-3-phenyl-2,3-dihydrobenzofuran-5,7-dicarboxamide; or (2S,3S)-2-(Fluoromethyl)-$N^5$-((1R,3S,5S,6r)-3-hydroxybicyclo[3.1.0]hexan-6-yl)-$N^7$-methyl-3-phenyl-2,3-dihydrobenzofuran-5,7-dicarboxamide;

or a pharmaceutically acceptable salt thereof.

20. A compound which is

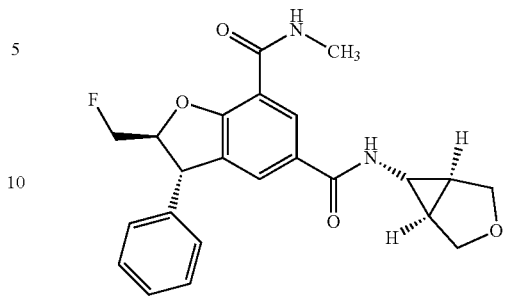

or pharmaceutically acceptable salt thereof.

21. A pharmaceutical composition comprising the compound or a pharmaceutically acceptable salt thereof according to claim 1 and one or more pharmaceutically acceptable excipients.

22. A combination comprising a compound or a pharmaceutically acceptable salt thereof according to claim 1 together with one or more other therapeutically active agents.

* * * * *